US012741957B2

(12) United States Patent
Cheruvallath et al.

(10) Patent No.: US 12,741,957 B2
(45) Date of Patent: Sep. 22, 2026

(54) N-HETEROARYLALKYL-2-(HETEROCYCLYL AND HETEROCYCLYLMETHYL) ACETAMIDE DERIVATIVES AS SSTR4 AGONISTS

(71) Applicant: Takeda Pharmaceutical Company Limited, Osaka (JP)

(72) Inventors: Zacharia Cheruvallath, San Diego, CA (US); Jason Green, San Diego, CA (US); Ben Johnson, San Diego, CA (US); Benjamin Jones, San Diego, CA (US); Kristin Schleicher, San Diego, CA (US); Huikai Sun, San Diego, CA (US); Mingnam Tang, San Diego, CA (US)

(73) Assignee: Takeda Pharmaceutical Company Limited, Osaka (JP)

( * ) Notice: Subject to any disclaimer, the term of this patent is extended or adjusted under 35 U.S.C. 154(b) by 756 days.

(21) Appl. No.: 17/916,467

(22) PCT Filed: Mar. 31, 2021

(86) PCT No.: PCT/US2021/025231
§ 371 (c)(1),
(2) Date: Sep. 30, 2022

(87) PCT Pub. No.: WO2021/202781
PCT Pub. Date: Oct. 7, 2021

(65) Prior Publication Data

US 2023/0150981 A1 May 18, 2023

Related U.S. Application Data

(60) Provisional application No. 63/002,727, filed on Mar. 31, 2020.

(51) Int. Cl.

| | |
|---|---|
| ***C07D 403/12*** | (2006.01) |
| ***A61K 45/06*** | (2006.01) |
| ***C07D 205/04*** | (2006.01) |
| ***C07D 207/09*** | (2006.01) |
| ***C07D 211/34*** | (2006.01) |
| ***C07D 217/14*** | (2006.01) |
| ***C07D 217/16*** | (2006.01) |
| ***C07D 295/15*** | (2006.01) |
| ***C07D 401/12*** | (2006.01) |
| ***C07D 405/12*** | (2006.01) |
| ***C07D 413/12*** | (2006.01) |
| ***C07D 471/04*** | (2006.01) |
| ***C07D 487/04*** | (2006.01) |
| ***C07D 491/048*** | (2006.01) |

(52) U.S. Cl.
CPC ............ *C07D 403/12* (2013.01); *A61K 45/06* (2013.01); *C07D 205/04* (2013.01); *C07D 207/09* (2013.01); *C07D 211/34* (2013.01); *C07D 217/14* (2013.01); *C07D 217/16* (2013.01); *C07D 295/15* (2013.01); *C07D 401/12* (2013.01); *C07D 405/12* (2013.01); *C07D 413/12* (2013.01); *C07D 471/04* (2013.01); *C07D 487/04* (2013.01); *C07D 491/048* (2013.01)

(58) Field of Classification Search
None
See application file for complete search history.

(56) References Cited

U.S. PATENT DOCUMENTS

| | | | | |
|---|---|---|---|---|
| 6,106,864 | A | 8/2000 | Dolan et al. | |
| 11,045,457 | B2 * | 6/2021 | Cheruvallath | C07D 403/12 |
| 12,005,054 | B2 * | 6/2024 | Cheruvallath | A61K 31/40 |
| 2023/0021834 | A1 | 1/2023 | Cheruvallath et al. | |

(Continued)

FOREIGN PATENT DOCUMENTS

| | | | |
|---|---|---|---|
| CN | 1960970 | A | 5/2007 |
| CN | 101277695 | A | 10/2008 |

(Continued)

OTHER PUBLICATIONS

CAS# 1511266-62-8 CAS Registry File Accessed Oct. 14, 2025 from STN, entered into STN Jan. 5, 2014. (Year: 2014).*
CAS# 1776608-78-6 CAS Registry File Accessed Oct. 14, 2025 from STN, entered into STN Jun. 9, 2015 (Year: 2015).*
Rouvier Emile et al., "Etude en Spectrometrie de Masse: VI-Evaluation de l'Induction de la Fragmentation dans les amines [beta] Fonctionnelles", Apr. 1, 1974 (Apr. 1, 1974), vol. 9, No. 4, p. 453-458 with English Translation.
Almarsson et al. Crystal engineering of the composition of pharmaceutical phases. Do pharmaceutical co-crystals represent a new path to improved medicines? Chem. Commun. 17:1889-1896 (2004).
Berge, Stephen M. et al. Pharmaceutical Salts. Journal of Pharmaceutical Sciences 66(1):1-19 (1977).

(Continued)

*Primary Examiner* — Jennifer A Berrios
*Assistant Examiner* — Sophia Reilly
(74) *Attorney, Agent, or Firm* — Fish & Richardson P.C.

(57) ABSTRACT

Disclosed are compounds of Formula 1, and pharmaceutically acceptable salts thereof, wherein L, n, $R^1$, $R^2$, $R^6$, $R^7$, $R^8$, $R^9$, $R^{10}$, $X^3$, $X^4$ and $X^5$ are defined in the specification. This disclosure also relates to materials and methods for preparing compounds of Formula 1, to pharmaceutical compositions which contain them, and to their use for treating diseases, disorders, and conditions associated with SSTR4.

1

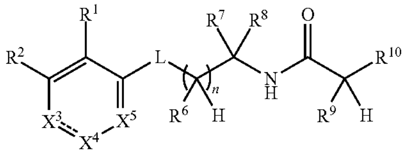

17 Claims, No Drawings

(56) References Cited

U.S. PATENT DOCUMENTS

| | | | | |
|---|---|---|---|---|
| 2025/0049772 | A1* | 2/2025 | Cheruvallath | A61K 31/438 |
| 2025/0188037 | A1* | 6/2025 | Hopkins | C07D 209/54 |

FOREIGN PATENT DOCUMENTS

| | | | | |
|---|---|---|---|---|
| CN | 110650951 | A | 1/2020 | |
| JP | 2002517500 | A | 6/2002 | |
| JP | 2007507472 | A | 3/2007 | |
| JP | 2007169270 | A | 7/2007 | |
| JP | 2017533930 | A | 11/2017 | |
| TW | I315305 | B | 10/2009 | |
| WO | WO-9111172 | A1 | 8/1991 | |
| WO | WO-9402518 | A1 | 2/1994 | |
| WO | WO-9855148 | A1 | 12/1998 | |
| WO | WO-2011053696 | A1 | 5/2011 | |
| WO | WO 2014184275 | A1 | 11/2014 | |
| WO | WO-2015037716 | A1 | 3/2015 | |
| WO | WO-2016075239 | A1 * | 5/2016 | A61P 25/04 |
| WO | 2019169153 | A1 | 9/2019 | |
| WO | WO-2021202781 | A1 | 10/2021 | |

OTHER PUBLICATIONS

Bundgaard, Hans. Design of Prodrugs. Elsevier: 7-9, 21-24 (1985).
Busche, Marc Aurel. et al. Decreased amyloid-β and increased neuronal hyperactivity by immunotherapy in Alzheimer's models. Nat Neurosci 18(12):1725-1727 (2015).
Chemical Abstracts Service. CAS Registry: 1307519-57-8. STN Entry Date Mar. 14, 2018.
Chemical Abstracts Service. CAS Registry: 1783121-31-2. STN Entry Date Mar. 14, 2018.
Chemical Abstracts Service. CAS Registry: 1795155-81-5. STN Entry Date Mar. 14, 2018.
Chemical Abstracts Service. CAS Registry: 1795375-71-1. STN Entry Date Mar. 14, 2018.
Chemical Abstracts Service. CAS Registry: 2109298-53-3. STN Entry Date Mar. 14, 2018.
Chemical Abstracts Service. CAS Registry: 2190791-42-3. STN Entry Date Mar. 14, 2018.
Chemical Abstracts Service. CAS Registry: 2191108-62-8. STN Entry Date Mar. 14, 2018.
Chemical Abstracts Service. CAS Registry: 42176-89-6. STN Entry Date Mar. 14, 2018.
Eliel, Ernest L. et al. Stereochemistry of Organic Compounds. Wiley-Interscience (1994).
Finnin, Barrie C, and Timothy M. Morgan. Transdermal Penetration Enhancers: Applications, Limitations, And Potential. Journal of Pharmaceutical Sciences 88(10):955-958 (1999).
Gastambide, Francois. et al. Hippocampal SSTR4 somatostatin receptors control the selection of memory strategies. 202(1-3):153-163 (2009).
Gennaro, Alfonso R. Remington: The Science and Practice of Pharmacy, 20th Edition. Lippincott Williams & Wilkins (2000).
Haleblian, John K. Characterization of Habits and Crystalline Modification of Solids and Their Pharmaceutical Applications. Journal of Pharmaceutical Sciences 64(8):1269-1288 (1975).
Higuchi, Takeru et al. Pro-Drugs as Novel Delivery Systems. ACS Symposium Series 14:1-129 (1975).
Larock, Richard C. et al. Comprehensive Organic Transformations: A Guide to Functional Group Preparations: Second Edition, Wiley-VCH 1-18 (1999).
Liang et al. Fast-dissolving intraoral drug delivery. Expert Opinion in Therapeutic Patents 11(6):981-986 (2001).
Lieberman, Herbert et al. Pharmaceutical Dosage Forms. Marcel Decker $2^{nd}$ edition:209-214 (1990).
Macleod, Calum. et al. N-Alkylation-Intramolecular Michael Addition: New Reaction Manifold for High Throughput Annulation of Amines. Synlett 17:2857-2861 (2009).
Meyer, Michael A. Highly Expressed Genes within Hippocampal Sector CA1: Implications for the Physiology of Memory. Neurol Int 6(2):5388, 1-4 (2014).
PCT/US2021/025231 International Search Report and Written Opinion dated Jun. 2, 2021.
Qiu, Cuie. et al. Somatostatin receptor subtype 4 couples to the M-current to regulate seizures. J Neurosci 28(14):3567-3576 (2008).
Roche, Edward B. Bioreversible Carriers In Drug Design: Theory And Application. American Pharmaceutical Association and Pergamon Press (1987).
Serrano-Pozo, Alberto et al. Neuropathological alterations in Alzheimer disease. Cold Spring Harb Perspect Med 1(1):a006189, 1-23 (2011).
Sidhu, G.S. et al. Synthese and Pharmakologie von N-Aminoacyl-benzylaminen. Archiv der Pharmazie 306(4):310-319 (1973).
Squire, Larry R, and Adam J O Dede. Conscious and unconscious memory systems. Cold Spring Harb Perspect Biol 7(3):a021667, 1-14 (2015).
Stahl, P Heinrich, and Camille G. Wermuth. Handbook of Pharmaceutical Salts: Properties, Selection, and Use. Verlag Helvetica Chimica Acta and Wiley-VCH (2002).
Verma et al. Current Status of Drug Delivery Technologies and Future Directions. Pharmaceutical Technology On-line 25(2):1-14 (2001).
Yamamoto, Kaoru et al. Chronic optogenetic activation augments aβ pathology in a mouse model of Alzheimer disease. Cell Rep 11(6):859-865 (2015).

* cited by examiner

N-HETEROARYLALKYL-2-(HETEROCYCLYL AND HETEROCYCLYLMETHYL) ACETAMIDE DERIVATIVES AS SSTR4 AGONISTS

CROSS-REFERENCE TO RELATED APPLICATIONS

This application is a 35 USC § 371 National Stage filing of International Application No. PCT/US2021/025231, filed Mar. 31, 2021, which claims the benefit of priority to U.S. Provisional Application No. 63/002,727, filed Mar. 31, 2020. The entire contents of the aforementioned applications are incorporated herein by reference in their entireties.

FIELD OF THE INVENTION

This invention relates to N-heteroarylalkyl-2-(heterocyclyl and heterocyclylmethyl)acetamide derivatives which are modulators of somatostatin receptor 4 (SSTR4), to pharmaceutical compositions which contain them, and to their use to treat diseases, disorders, and conditions associated with SSTR4, including Alzheimer's disease.

BACKGROUND OF THE INVENTION

Somatostatin receptor 4 (SSTR4) is a G-protein coupled receptor for the peptide somatostatin. SSTR4 is coupled with Gi, inhibitory G protein, which inhibits production of cyclic AMP. SSTR4 is abundantly expressed in the central nervous system (CNS) and to a lesser extent in the dorsal root ganglia and intestine. See M. A. Meyer, "Highly Expressed Genes within Hippocampal Sector CA1: Implications for the Physiology of Memory," *Neurology International* 6(2):5388 (2014). SSTR4 is highly conserved among different species. For example, human, mouse, and rat SSTR4 protein sequences share greater than 87% identity at the amino acid level. These factors—predominant expression in the brain and high degree of sequence homology across different species—suggest that SSTR4 has an important role in physiology.

Experiments using bacTRAP technology indicate SSTR4 has its strongest expression in the pyramidal neurons in the cortex and in the CA1 region of the hippocampus. This CNS expression is conserved in humans, non-human primates, and mice. The hippocampus is important for learning and memory. See L. R. Squire and A. J. Dede, "Conscious and Unconscious Memory Systems," *Cold Spring Harbor Perspectives in Biology* 7:a021667 (2015). Indeed, the CA1 region of the hippocampus is the last station in the trisynaptic circuit that governs learning. This circuit starts in the entorhinal cortex, which also contains SSTR4, extends into the dentate gyrus, then into CA3, and finally reaches the CA1 region of the hippocampus. CA1 projects out of the hippocampus through the subiculum. This circuit encodes all types of information from the external world in order to generate memories and to learn new knowledge.

Alzheimer's disease is characterized by degeneration of neurons within this circuitry, mainly in the entorhinal cortex and CA1 region of the hippocampus. See A. Serrano-Pozo et al., "Neuropathological Alterations in Alzheimer Disease," *Cold Spring Harbor Perspectives in Medicine* 1:a006189 (2011). In addition, hippocampal sst4 appears to selectively control the use of cognitive strategies by switching from hippocampus-based multiple associations to simple striatum-based behavioral responses. See F. Gastambide et al., "Hippocampal SSTR4 Somatostatin Receptors Control the Selection of Memory Strategies," *Psychopharmacology (Berl)* 202(1-3):153-63 (2009). This finding provides a strong basis for using SSTR4 agonists as a pharmacological approach to improve striatum-based learning. Id.

Moreover, recent studies also point to hyperactivity of the hippocampus as a main driver for disease progression as well as impairment of cognitive abilities in Alzheimer's patients. See M. A. Busche et al., "Decreased Amyloid-β and Increased Neuronal Hyperactivity by Immunotherapy in Alzheimer's Models," Nature Neuroscience 18(12):1725-27 (2015); see also K. Yamamoto et al., "Chronic Optogenetic Activation Augments Aβ Pathology in a Mouse Model of Alzheimer Disease," *Cell Reports* 11(6):859-65 (2015). Activation of SSTR4 receptor has been shown to play a role in controlling neuronal activity. See C. Qiu et al., "Somatostatin Receptor Subtype 4 Couples to the M-Current to Regulate Seizures," *Journal of Neuroscience* 28(14):3567-76 (2008). Thus, agonists for the receptor will likely represent good pharmacological tools to inhibit and control neuronal activity in the cortex and hippocampus.

SSTR4 agonists are expected to be useful for treating Alzheimer's disease and other CNS disorders such as epilepsy and depression.

SUMMARY OF THE INVENTION

This invention provides N-heteroarylalkyl-2-(heterocyclyl and heterocyclylmethyl)acetamide derivatives and pharmaceutically acceptable salts thereof. This invention also provides pharmaceutical compositions that contain the N-heteroarylalkyl-2-(heterocyclyl and heterocyclylmethyl) acetamide derivatives and provides for their use to treat diseases, disorders and conditions associated with SSTR4, including Alzheimer's disease and other CNS disorders.

One aspect of the invention provides compounds of Formula 1:

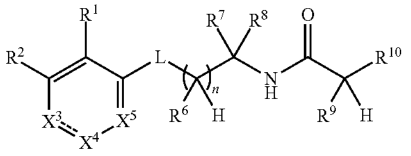

1 or a pharmaceutically acceptable salt thereof in which:

(a) $X^3$ is selected from $NR^{3N}$ and O, $X^4$ is a single bond, and $X^5$ is selected from N and $CR^5$; and
  - $R^1$ and $R^2$, together with the carbon atoms to which they are attached, form a fused ring which is benzene, wherein each non-fusion carbon atom of the fused ring is unsubstituted or is substituted with an optional substituent independently selected from:
    - (i) halo, hydroxy, and cyano; and
    - (ii) $C_{1-4}$ alkyl, $C_{3-6}$ cycloalkyl, and $C_{1-4}$ alkoxy, each substituted with 0 to 3 optional substituents independently selected from halo; or (b) $X^3$ is $CR^{3C}$, $X^4$ is selected from N and $CR^4$, and $X^5$ is selected from N and $CR^5$; and
  - $R^1$ and $R^2$ are each independently selected from:
    - (i) hydrogen, halo, hydroxy, and cyano; and
    - (ii) $C_{1-4}$ alkyl, $C_{3-6}$ cycloalkyl, and $C_{1-4}$ alkoxy, each substituted with 0 to 3 optional substituents independently selected from halo; or
  - $R^1$ and $R^2$, together with the carbon atoms to which they are attached, form a fused ring selected from furan, pyrazole, and benzene, wherein one of the nitrogen atoms of the pyrazole ring is substituted with hydrogen, $C_{1-4}$ alkyl or $C_{3-6}$ cycloalkyl, and each non-fusion carbon atom of the fused ring is unsubstituted or is substituted with an optional substituent independently selected from:

(i) halo, hydroxy, and cyano; and (ii) $C_{1-4}$ alkyl, $C_{3-6}$ cycloalkyl, and $C_{1-4}$ alkoxy, each substituted with 0 to 3 optional substituents independently selected from halo;

L is O and n is 1; or

L is a single bond and n is 0 or 1;

$R^{3N}$ is selected from hydrogen, $C_{1-4}$ alkyl and $C_{3-6}$ cycloalkyl;

$R^{3C}$ and $R^4$ are each independently selected from:

(i) hydrogen, halo, hydroxy, and cyano; and (ii) $C_{1-4}$ alkyl, $C_{3-6}$ cycloalkyl, and $C_{1-4}$ alkoxy, each substituted with 0 to 3 optional substituents independently selected from halo;

$R^5$ is selected from:

(i) hydrogen, halo, hydroxy, and cyano; and (ii) $C_{1-4}$ alkyl and $C_{1-4}$ alkoxy, each substituted with 0 to 3 optional substituents independently selected from halo; and $R^6$ is hydrogen; or $R^5$ and $R^6$ together form an ethane-1,2-diyl bridging the carbon atoms to which they are attached;

$R^7$ and $R^8$ are each independently selected from hydrogen and $C_{1-4}$ alkyl which is substituted with 0 to 3 optional substituents independently selected from halo, wherein at least one of $R^7$ and $R^8$ is not hydrogen, or $R^7$ and $R^8$, together with the carbon atom to which they are attached, form a $C_{3-6}$ cycloalkylidene;

$R^9$ is selected from hydrogen and $C_{1-4}$ alkyl which is substituted with 0 to 3 optional substituents independently selected from halo;

$R^{10}$ is selected from azetidin-1-ylmethyl, pyrrolidin-1-ylmethyl, and a heterocyclyl having the formula:

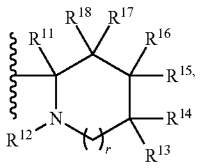

in which  indicates a point of attachment, and r is selected from 0 and 1;

$R^{11}$ is hydrogen, and $R^{12}$ is selected from hydrogen and from $C_{1-4}$ alkyl and $C_{3-6}$ cycloalkyl, each substituted with 0 to 3 optional substituents independently selected from halo, provided if $R^{12}$ is hydrogen then $R^1$ and $R^2$ form a fused ring; or $R^{11}$ and $R^{12}$ together form a propane-1,3-diyl bridging the carbon and nitrogen atoms to which they are respectively attached;

$R^{13}$, $R^{14}$, $R^{15}$, and $R^{16}$ are each independently selected from hydrogen, halo, and $C_{1-4}$ alkyl which is substituted with 0 to 3 optional substituents independently selected from halo, or $R^{13}$ and $R^{16}$ are absent and $R^{14}$ and $R^{15}$, together with the carbon atoms to which they are attached, form a fused benzene ring in which each non-fusion carbon atom is unsubstituted or is substituted with an optional substituent independently selected from:

(i) halo, hydroxy, and cyano; and (ii) $C_{1-4}$ alkyl, $C_{3-6}$ cycloalkyl, and $C_{1-4}$ alkoxy, each substituted with 0 to 3 optional substituents independently selected from halo; and $R^{17}$ and $R^{18}$ are each independently selected from hydrogen, halo and $C_{1-4}$ alkyl which is substituted with 0 to 3 optional substituents independently selected from halo;

provided the compound of Formula 1 is not:

2-(1-methylpiperidin-2-yl)-N-(1-(m-tolyl)cyclopropyl)acetamide;

N-(1-(pyridin-3-yl)pentyl)-3-(pyrrolidin-1-yl)propanamide;

N-(1-(6-methylpyridin-2-yl)propan-2-yl)-3-(pyrrolidin-1-yl)propanamide;

2-(1-methylpyrrolidin-2-yl)-N-(1-phenylethyl)acetamide;

2-(1-methylpiperidin-2-yl)-N-(1-phenylethyl)acetamide;

N-(1-phenylethyl)-3-(pyrrolidin-1-yl)propanamide;

N-(1-(3,4-dichlorophenyl)propyl)-3-(pyrrolidin-1-yl)propanamide;

N-(2-phenylpropan-2-yl)-3-(pyrrolidin-1-yl)propanamide;

N-(1-(4-methylpyridin-2-yl)propyl)-3-(pyrrolidin-1-yl)propenamide; or

N-(1-(naphthalen-1-yl)ethyl)-2-(pyrrolidin-2-yl)acetamide.

Another aspect of the invention provides a compound which is selected from the group of compounds described in the examples and their pharmaceutically acceptable salts.

A further aspect of the invention provides a pharmaceutical composition which includes a compound of Formula 1 or a pharmaceutically acceptable salt thereof, or any one of the compounds or pharmaceutically acceptable salts defined in the preceding paragraph; and a pharmaceutically acceptable excipient.

An additional aspect of the invention provides a compound of Formula 1 or a pharmaceutically acceptable salt thereof, or any one of the compounds and pharmaceutically acceptable salts defined in the preceding paragraphs, for use as a medicament.

Another aspect of the invention provides a compound of Formula 1 or a pharmaceutically acceptable salt thereof, or any one of the compounds or pharmaceutically acceptable salts defined in the preceding paragraphs, for treatment of a disease, disorder or condition associated with SSTR4.

A further aspect of the invention provides a use of a compound of Formula 1 or a pharmaceutically acceptable salt thereof, or any one of the compounds or pharmaceutically acceptable salts defined in the preceding paragraphs, for the manufacture of a medicament for the treatment of a disease, disorder or condition associated with SSTR4.

An additional aspect of the invention provides a method of treating a disease, disorder or condition associated with SSTR4, the method comprising administering to the subject an effective amount of a compound of Formula 1 or a pharmaceutically acceptable salt thereof, or any one of the compounds or pharmaceutically acceptable salts defined in the preceding paragraphs.

Another aspect of the invention provides a method of treating a disease, disorder or condition in a subject, the method comprising administering to the subject an effective amount of a compound of Formula 1 or a pharmaceutically acceptable salt thereof, or any one of the compounds or pharmaceutically acceptable salts defined in the preceding paragraphs, wherein the disease, disorder or condition is selected from Alzheimer's disease, depression, anxiety, schizophrenia, bipolar disorder, autism, epilepsy, pain, and hyperactivity disorder.

A further aspect of the invention provides an effective amount of a compound of Formula 1 or a pharmaceutically acceptable salt thereof, or any one of the compounds or pharmaceutically acceptable salts defined in the preceding paragraphs; and at least one additional pharmacologically active agent.

DETAILED DESCRIPTION OF THE INVENTION

Unless otherwise indicated, this disclosure uses definitions provided below.

"Substituted," when used in connection with a chemical substituent or moiety (e.g., a $C_{1-6}$ alkyl group), means that one or more hydrogen atoms of the substituent or moiety have been replaced with one or more non-hydrogen atoms or groups, provided valence requirements are met and a chemically stable compound results from the substitution.

"About" or "approximately," when used in connection with a measurable numerical variable, refers to the indicated value of the variable and to all values of the variable that are within the experimental error of the indicated value or within ±10 percent of the indicated value, whichever is greater.

"Alkyl" refers to straight chain and branched saturated hydrocarbon groups, generally having a specified number of carbon atoms (e.g., $C_{1-4}$ alkyl refers to an alkyl group having 1 to 4 (i.e., 1, 2, 3 or 4) carbon atoms, $C_{1-6}$ alkyl refers to an alkyl group having 1 to 6 carbon atoms, and so on). Examples of alkyl groups include methyl, ethyl, n-propyl, i-propyl, n-butyl, s-butyl, i-butyl, t-butyl, pent-1-yl, pent-2-yl, pent-3-yl, 3-methylbut-1-yl, 3-methylbut-2-yl, 2-methylbut-2-yl, 2,2,2-trimethyleth-1-yl, n-hexyl, and the like.

"Alkanediyl" refers to divalent alkyl groups, where alkyl is defined above, and generally having a specified number of carbon atoms (e.g., $C_{1-4}$ alkanediyl refers to an alkanediyl group having 1 to 4 (i.e., 1, 2, 3 or 4) carbon atoms, $C_{1-6}$ alkanediyl refers to an alkanediyl group having 1 to 6 carbon atoms, and so on). Examples of alkanediyl groups include methylene, ethane-1,1-diyl, ethane-1,2-diyl, propane-1,3-diyl, propane-1,2-diyl, propane-1,1-diyl, propane-2,2-diyl, butane-1,4-diyl, butane-1,3-diyl, butane-1,2-diyl, butane-1,1-diyl, isobutane-1,3-diyl, isobutane-1,1-diyl, isobutane-1,2-diyl, and the like.

"Alkenyl" refers to straight chain and branched hydrocarbon groups having one or more carbon-carbon double bonds, and generally having a specified number of carbon atoms.

Examples of alkenyl groups include ethenyl, 1-propen-1-yl, 1-propen-2-yl, 2-propen-1-yl, 1-buten-1-yl, 1-buten-2-yl, 3-buten-1-yl, 3-buten-2-yl, 2-buten-1-yl, 2-buten-2-yl, 2-methyl-1-propen-1-yl, 2-methyl-2-propen-1-yl, 1,3-butadien-1-yl, 1,3-butadien-2-yl, and the like.

"Alkynyl" refers to straight chain or branched hydrocarbon groups having one or more triple carbon-carbon bonds, and generally having a specified number of carbon atoms.

Examples of alkynyl groups include ethynyl, 1-propyn-1-yl, 2-propyn-1-yl, 1-butyn-1-yl, 3-butyn-1-yl, 3-butyn-2-yl, 2-butyn-1-yl, and the like.

"Halo," "halogen" and "halogeno" may be used interchangeably and refer to fluoro, chloro, bromo, and iodo.

"Haloalkyl," "haloalkenyl," and "haloalkynyl," refer, respectively, to alkyl, alkenyl, and alkynyl groups substituted with one or more halogen atoms, where alkyl, alkenyl, and alkynyl are defined above, and generally having a specified number of carbon atoms.

Examples of haloalkyl groups include fluoromethyl, difluoromethyl, trifluoromethyl, chloromethyl, dichloromethyl, trichloromethyl, 1-fluoroethyl, 1,1-difluoroethyl, 1-chloroethyl, 1,1-dichloroethyl, 1-fluoro-1-methylethyl, 1-chloro-1-methylethyl, and the like.

"Cycloalkyl" refers to saturated monocyclic and bicyclic hydrocarbon groups, generally having a specified number of carbon atoms that comprise the ring or rings (e.g., $C_{3-8}$ cycloalkyl refers to a cycloalkyl group having 3 to 8 carbon atoms as ring members). Bicyclic hydrocarbon groups may include isolated rings (two rings sharing no carbon atoms), spiro rings (two rings sharing one carbon atom), fused rings (two rings sharing two carbon atoms and the bond between the two common carbon atoms), and bridged rings (two rings sharing two carbon atoms, but not a common bond). The cycloalkyl group may be attached through any ring atom unless such attachment would violate valence requirements, and where indicated, may optionally include one or more non-hydrogen substituents unless such substitution would violate valence requirements.

Examples of monocyclic cycloalkyl groups include cyclopropyl, cyclobutyl, cyclopentyl, cyclohexyl, and the like. Examples of fused bicyclic cycloalkyl groups include bicyclo[2.1.0]pentanyl (i.e., bicyclo[2.1.0]pentan-1-yl, bicyclo[2.1.0]pentan-2-yl, and bicyclo[2.1.0]pentan-5-yl), bicyclo[3.1.0]hexanyl, bicyclo[3.2.0]heptanyl, bicyclo[4.1.0]heptanyl, bicyclo[3.3.0]octanyl, bicyclo[4.2.0]octanyl, bicyclo[4.3.0]nonanyl, bicyclo[4.4.0]decanyl, and the like. Examples of bridged cycloalkyl groups include bicyclo[2.1.1]hexanyl, bicyclo[2.2.1]heptanyl, bicyclo[3.1.1]heptanyl, bicyclo[2.2.2]octanyl, bicyclo[3.2.1]octanyl, bicyclo[4.1.1]octanyl, bicyclo[3.3.1]nonanyl, bicyclo[4.2.1]nonanyl, bicyclo[3.3.2]decanyl, bicyclo[4.2.2]decanyl, bicyclo[4.3.1]decanyl, bicyclo[3.3.3]undecanyl, bicyclo[4.3.2]undecanyl, bicyclo[4.3.3]dodecanyl, and the like.

Examples of spiro cycloalkyl groups include spiro[3.3]heptanyl, spiro[2.4]heptanyl, spiro[3.4]octanyl, spiro[2.5]octanyl, spiro[3.5]nonanyl, and the like. Examples of isolated bicyclic cycloalkyl groups include those derived from bi(cyclobutane), cyclobutanecyclopentane, bi(cyclopentane), cyclobutanecyclohexane, cyclopentanecyclohexane, bi(cyclohexane), etc.

"Cycloalkanediyl" refers to divalent cycloalkyl groups, where cycloalkyl is defined above, and generally having a specified number of carbon atoms (e.g., $C_{3-5}$ cycloalkanediyl refers to a cycloalkanediyl group having 3 to 5 (i.e., 3, 4 or 5) carbon atoms, $C_{3-6}$ cycloalkanediyl refers to a cycloalkanediyl group having 3 to 6 carbon atoms, and so on). Examples of cycloalkanediyl groups include cyclopropane-1,1-diyl, cyclopropane-1,2-diyl, cyclobutane-1,1-diyl, cyclobutane-1,2-diyl, and the like.

"Cycloalkylidene" refers to divalent monocyclic cycloalkyl groups, where cycloalkyl is defined above, which are attached through a single carbon atom of the group, and generally having a specified number of carbon atoms that comprise the ring (e.g., $C_{3-6}$ cycloalkylidene refers to a cycloalkylidene group having 3 to 6 carbon atoms as ring members). Examples include cyclopropylidene, cyclobutylidene, cyclopentylidene, and cyclohexylidene.

"Cycloalkenyl" refers to partially unsaturated monocyclic and bicyclic hydrocarbon groups, generally having a specified number of carbon atoms that comprise the ring or rings. As with cycloalkyl groups, the bicyclic cycloalkenyl groups may include isolated, spiro, fused, or bridged rings. Similarly, the cycloalkenyl group may be attached through any ring atom, and where indicated, may optionally include one or more non-hydrogen substituents unless such attachment or substitution would violate valence requirements. Examples of cycloalkenyl groups include the partially unsaturated analogs of the cycloalkyl groups described above, such as cyclobutenyl (i.e., cyclobuten-1-yl and cyclobuten-3-yl), cyclopentenyl, cyclohexenyl, bicyclo [2.2.1]hept-2-enyl, and the like.

"Aryl" refers to fully unsaturated monocyclic aromatic hydrocarbons and to polycyclic hydrocarbons having at least one aromatic ring, both monocyclic and polycyclic aryl groups generally having a specified number of carbon atoms that comprise their ring members (e.g., $C_{6-14}$ aryl refers to an aryl group having 6 to 14 carbon atoms as ring members). The group may be attached through any ring atom, and where indicated, may optionally include one or more non-hydrogen substituents unless such attachment or substitution would violate valence requirements. Examples of aryl groups include phenyl, biphenyl, cyclobutabenzenyl, indenyl, naphthalenyl, benzocycloheptanyl, biphenylenyl, fluorenyl, groups derived from cycloheptatriene cation, and the like.

"Arylene" refers to divalent aryl groups, where aryl is defined above. Examples of arylene groups include o-phenylene (i.e., benzene-1,2-diyl).

"Heterocycle" and "heterocyclyl" may be used interchangeably and refer to saturated or partially unsaturated monocyclic or bicyclic groups having ring atoms composed of carbon atoms and 1 to 4 heteroatoms independently selected from nitrogen, oxygen, and sulfur. Both the monocyclic and bicyclic groups generally have a specified number of carbon atoms in their ring or rings (e.g., $C_{2-6}$ heterocyclyl refers to a heterocyclyl group having 2 to 6 carbon atoms and 1 to 4 heteroatoms as ring members). As with bicyclic cycloalkyl groups, bicyclic heterocyclyl groups may include isolated rings, spiro rings, fused rings, and bridged rings. The heterocyclyl group may be attached through any ring atom, and where indicated, may optionally include one or more non-hydrogen substituents unless such attachment or substitution would violate valence requirements or result in a chemically unstable compound.

Examples of heterocyclyl groups include oxiranyl, thiiranyl, aziridinyl (e.g., aziridin-1-yl and aziridin-2-yl), oxetanyl, thietanyl, azetidinyl, tetrahydrofuranyl, tetrahydrothienyl, pyrrolidinyl, tetrahydropyranyl, tetrahydrothiopyranyl, piperidinyl, 1,4-dioxanyl, 1,4-oxathianyl, morpholinyl, 1,4-dithianyl, piperazinyl, 1,4-azathianyl, oxepanyl, thiepanyl, azepanyl, 1,4-dioxepanyl, 1,4-oxathiepanyl, 1,4-oxaazepanyl, 1,4-dithiepanyl, 1,4-thiazepanyl, 1,4-diazepanyl, 3,4-dihydro-2H-pyranyl, 3,6-dihydro-2H-pyranyl, 2H-pyranyl, 1,2-dihydropyridinyl, 1,2,3,4-tetrahydropyridinyl, 1,2,5,6-tetrahydropyridinyl, 1,6-dihydropyrimidinyl, 1,2,3,4-tetrahydropyrimidinyl, and 1,2-dihydropyrazolo[1,5-d][1,2,4]triazinyl.

"Heterocycle-diyl" refers to heterocyclyl groups which are attached through two ring atoms of the group, where heterocyclyl is defined above. They generally have a specified number of carbon atoms in their ring or rings (e.g., $C_{2-6}$ heterocycle-diyl refers to a heterocycle-diyl group having 2 to 6 carbon atoms and 1 to 4 heteroatoms as ring members). Examples of heterocycle-diyl groups include the multivalent analogs of the heterocycle groups described above, such as morpholine-3,4-diyl, pyrrolidine-1,2-diyl, 1-pyrrolidinyl-2-ylidene, 1-pyridinyl-2-ylidene, 1-(4H)-pyrazolyl-5-ylidene, 1-(3H)-imidazolyl-2-ylidene, 3-oxazolyl-2-ylidene, 1-piperidinyl-2-ylidene, 1-piperazinyl-6-ylidene, and the like.

"Heteroaromatic" and "heteroaryl" may be used interchangeably and refer to unsaturated monocyclic aromatic groups and to polycyclic groups having at least one aromatic ring, each of the groups having ring atoms composed of carbon atoms and 1 to 4 heteroatoms independently selected from nitrogen, oxygen, and sulfur. Both the monocyclic and polycyclic groups generally have a specified number of carbon atoms as ring members (e.g., $C_{1-9}$ heteroaryl refers to a heteroaryl group having 1 to 9 carbon atoms and 1 to 4 heteroatoms as ring members) and may include any bicyclic group in which any of the above-listed monocyclic heterocycles are fused to a benzene ring. The heteroaryl group may be attached through any ring atom (or ring atoms for fused rings), and where indicated, may optionally include one or more non-hydrogen substituents unless such attachment or substitution would violate valence requirements or result in a chemically unstable compound. Examples of heteroaryl groups include monocyclic groups such as pyrrolyl (e.g., pyrrol-1-yl, pyrrol-2-yl, and pyrrol-3-yl), furanyl, thienyl, pyrazolyl, imidazolyl, isoxazolyl, oxazolyl, isothiazolyl, thiazolyl, 1,2,3-triazolyl, 1,3,4-triazolyl, 1-oxa-2,3-diazolyl, 1-oxa-2,4-diazolyl, 1-oxa-2,5-diazolyl, 1-oxa-3,4-diazolyl, 1-thia-2,3-diazolyl, 1-thia-2,4-diazolyl, 1-thia-2,5-diazolyl, 1-thia-3,4-diazolyl, tetrazolyl, pyridinyl, pyridazinyl, pyrimidinyl, and pyrazinyl.

Examples of heteroaryl groups also include bicyclic groups such as benzofuranyl, isobenzofuranyl, benzothienyl, benzo[c]thienyl, 1H-indolyl, 3H-indolyl, isoindolyl, 1H-isoindolyl, indolinyl, isoindolinyl, benzimidazolyl, 1H-indazolyl, 2H-indazolyl, benzotriazolyl, 1H-pyrrolo[2,3-b]pyridinyl, 1H-pyrrolo[2,3-c]pyridinyl, 1H-pyrrolo[3,2-c]pyridinyl, 1H-pyrrolo[3,2-b]pyridinyl, 3H-imidazo[4,5-b]pyridinyl, 3H-imidazo[4,5-c]pyridinyl, 1H-pyrazolo[4,3-b]pyridinyl, 1H-pyrazolo[4,3-c]pyridinyl, 1H-pyrazolo[3,4-c]pyridinyl, 1H-pyrazolo[3,4-b]pyridinyl, 7H-purinyl, indolizinyl, imidazo[1,2-a]pyridinyl, imidazo[1,5-a]pyridinyl, pyrazolo[1,5-a]pyridinyl, pyrrolo[1,2-b]pyridazinyl, imidazo[1,2-c]pyrimidinyl, quinolinyl, isoquinolinyl, cinnolinyl, quinazolinyl, quinoxalinyl, phthalazinyl, 1,6-naphthyridinyl, 1,7-naphthyridinyl, 1,8-naphthyridinyl, 1,5-naphthyridinyl, 2,6-naphthyridinyl, 2,7-naphthyridinyl, pyrido[3,2-d]pyrimidinyl, pyrido[4,3-d]pyrimidinyl, pyrido[3,4-d]pyrimidinyl, pyrido[2,3-d]pyrimidinyl, pyrido[2,3-b]pyrazinyl, pyrido[3,4-b]pyrazinyl, pyrimido[5,4-d]pyrimidinyl, pyrazino[2,3-b]pyrazinyl, pyrimido[4,5-d]pyrimidinyl, 1,2,3,4-tetrahydropyrido[2,3-b]pyrazinyl, 2,3-dihydrobenzo[b][1,4]dioxinyl, 3,4-dihydro-2H-pyrido[3,2-b][1,4]oxazinyl, 2,3-dihydro-1H-benzo[d]imidazolyl, benzo[d]thiazolyl, 2,3-dihydro-1H-pyrrolo[2,3-b]pyridinyl, [1,2,4]triazolo[1,5-a]pyridinyl, 2,3-dihydro-1H-imidazo[4,5-b]pyridinyl, tetrazolo[1,5-a]pyridinyl, 7H-pyrrolo[2,3-d]pyrimidinyl, pyrazolo[1,5-a]pyrimidinyl, imidazo[1,2-a]pyrimidinyl, 4,5-dihydro-1H-pyrazolo[3,4-d]pyrimidinyl, 2,3,6,7-tetrahydro-1H-purinyl, 5H-pyrrolo[2,3-b]pyrazinyl, imidazo[1,2-a]pyrazinyl, imidazo[1,2-b]pyridazinyl, and 4,5,6,7-tetrahydropyrazolo[1,5-a]pyrazinyl.

"Heteroarylene" refers to heteroaryl groups which are attached through two ring atoms of the group, where heteroaryl is defined above. They generally have a specified number of carbon atoms in their ring or rings (e.g., $C_{3-5}$ heteroarylene refers to a heteroarylene group having 3 to 5 carbon atoms and 1 to 4 heteroatoms as ring members). Examples of heteroarylene groups include the multivalent analogs of the heteroaryl groups described above, such as pyridine-2,3-diyl, pyridine-3,4-diyl, pyrazole-4,5-diyl, pyrazole-3,4-diyl, and the like.

"Oxo" refers to a double bonded oxygen (=O).

"Leaving group" refers to any group that leaves a molecule during a fragmentation process, including substitution reactions, elimination reactions, and addition-elimination reactions. Leaving groups may be nucleofugal, in which the group leaves with a pair of electrons that formerly served as the bond between the leaving group and the molecule, or may be electrofugal, in which the group leaves without the pair of electrons. The ability of a nucleofugal leaving group to leave depends on its base strength, with the strongest bases being the poorest leaving groups. Common nucleofugal leaving groups include nitrogen (e.g., from diazonium salts); sulfonates, including alkylsulfonates (e.g., mesylate), fluoroalkylsulfonates (e.g., triflate, hexaflate, nonaflate, and tresylate), and arylsulfonates (e.g., tosylate, brosylate, closylate, and nosylate). Others include carbonates, halide ions, carboxylate anions, phenolate ions, and alkoxides. Some stronger bases, such as $NH_2^-$ and OH can be made better leaving groups by treatment with an acid. Common electrofugal leaving groups include the proton, $CO_2$, and metals.

"Opposite enantiomer" refers to a molecule that is a non-superimposable mirror image of a reference molecule, which may be obtained by inverting all the stereogenic centers of the reference molecule. For example, if the reference molecule has S absolute stereochemical configuration, then the opposite enantiomer has R absolute stereochemical configuration. Likewise, if the reference molecule has S,S absolute stereochemical configuration, then the opposite enantiomer has R,R stereochemical configuration, and so on.

"Stereoisomer" and "stereoisomers" of a compound with given stereochemical configuration refer to the opposite enantiomer of the compound and to any diastereoisomers, including geometrical isomers (Z/E) of the compound. For example, if a compound has S,R,Z stereochemical configuration, its stereoisomers would include its opposite enantiomer having R,S,Z configuration, and its diastereomers having S,S,Z configuration, R,R,Z configuration, S,R,E configuration, R,S,E configuration, S,S,E configuration, and R,R,E configuration. If the stereochemical configuration of a compound is not specified, then "stereoisomer" refers to any one of the possible stereochemical configurations of the compound.

"Substantially pure stereoisomer" and variants thereof refer to a sample containing a compound having a specific stereochemical configuration and which comprises at least about 95% of the sample.

"Pure stereoisomer" and variants thereof refer to a sample containing a compound having a specific stereochemical configuration and which comprises at least about 99.5% of the sample.

"Subject" refers to a mammal, including a human.

"Pharmaceutically acceptable" substances refer to those substances which are suitable for administration to subjects.

"Treating" refers to reversing, alleviating, inhibiting the progress of, or preventing a disease, disorder or condition to which such term applies, or to reversing, alleviating, inhibiting the progress of, or preventing one or more symptoms of such disease, disorder or condition.

"Treatment" refers to the act of "treating," as defined immediately above.

"Drug," "drug substance," "active pharmaceutical ingredient," and the like, refer to a compound (e.g., compounds of Formula 1, including subgeneric compounds and compounds specifically named in the specification) that may be used for treating a subject in need of treatment.

"Effective amount" of a drug, "therapeutically effective amount" of a drug, and the like, refer to the quantity of the drug that may be used for treating a subject and may depend on the weight and age of the subject and the route of administration, among other things.

"Excipient" refers to any diluent or vehicle for a drug.

"Pharmaceutical composition" refers to the combination of one or more drug substances and one or more excipients.

"Drug product," "pharmaceutical dosage form," "dosage form," "final dosage form" and the like, refer to a pharmaceutical composition suitable for treating a subject in need of treatment and generally may be in the form of tablets, capsules, sachets containing powder or granules, liquid solutions or suspensions, patches, films, and the like.

"Condition associated with SSTR4" and similar phrases relate to a disease, disorder or condition in a subject for which activation of SSTR4 may provide a therapeutic or prophylactic benefit.

The following abbreviations may be used in the specification: Ac (acetyl); ACN (acetonitrile); AIBN (azo-bis-isobutyronitrile); API (active pharmaceutical ingredient); aq (aqueous); BINAP (2,2'-bis(diphenylphosphino)-1,1'-binaphthyl); Boc (tert-butoxycarbonyl); Cbz (carbobenzyloxy); dba (dibenzylideneacetone); DBU (1,8-diazabicyclo [5.4.0]undec-7-ene); DCC (1,3-dicyclohexylcarbodiimide); DCE (1,1-dichloroethane); DCM (dichloromethane); DEA (diethylamine); DIAD (diisopropyl azodicarboxylate); DIPEA (N,N-diisopropylethylamine, Hünig's Base); DMA (N,N-dimethylacetamide); DMAP (4-dimethylaminopyridine); DME (1,2-dimethoxyethane); DMF (N,N-dimethylformamide); DMP (Dess-Martin periodinane); DMSO (dimethylsulfoxide); dppf (1,1'-bis(diphenylphosphino) ferrocene); DTT (dithiothreitol); $EC_{50}$ (effective concentration at half maximal response); EDA (ethoxylated dodecyl alcohol, Brj®35); EDC (N-(3-dimethylaminopropyl)-N-ethylcarbodiimide); EDTA (ethylenediaminetetraacetic acid); ee (enantiomeric excess); eq (equivalents); Et (ethyl); $Et_3N$ (triethylamine); EtOAc (ethyl acetate); EtOH (ethanol); HATU (2-(3H-[1,2,3]triazolo[4,5-b]pyridin-3-yl)-1,1,3,3-tetramethyluronium hexafluorophosphate(V)); HEPES (4-(2-hydroxyethyl)piperazine-1-ethanesulfonic acid); AcOH (acetic acid); HOBt (1H-benzo[d][1,2,3]triazol-1-ol); $IC_{50}$ (concentration at 50% inhibition); IPA (isopropanol); IPAc (isopropyl acetate); IPE (isopropylether); LDA (lithium diisopropylamide); LiHMDS (lithium bis(trimethylsilyl)amide); mCPBA (m-chloroperoxybenzoic acid); Me (methyl); MeOH (methanol); MTBE (methyl tert-butyl ether); mp (melting point); NaOt-Bu (sodium tertiary butoxide); NMM (N-methylmorpholine); NMP (N-methyl-pyrrolidone); OTf (triflate); PE (petroleum ether); Ph (phenyl); $pEC_{50}$ ($-\log_{10}(EC_{50})$, where $EC_{50}$ is given in molar (M) units); $pIC_{50}$ ($-\log_{10}(IC_{50})$, where $IC_{50}$ is given in molar (M) units); Pr (propyl); c-Pr (cyclopropyl), i-Pr (isopropyl); PTFE (polytetrafluoroethylene); PyBOP ((benzotriazol-1-yloxy)tripyrrolidinophosphonium hexafluorophosphate); PyBroP® (bromotripyrrolidinophosphonium hexafluorophosphate); RT (room temperature, approximately 20° C. to 25° C.); SFC (supercritical fluid chromatography); T3P (2,4,6-tripropyl-1,3,5,2,4,6-trioxatriphosphinane 2,4,6-trioxide); TCEP (tris(2-carboxyethyl) phosphine); TFA (trifluoroacetic acid); TFAA (2,2,2-trifluoroacetic anhydride); THE (tetrahydrofuran); TMS (trimethylsilyl); and Tris buffer (2-amino-2-hydroxymethyl-propane-1,3-diol buffer).

As described, below, this disclosure concerns compounds of Formula 1 and their pharmaceutically acceptable salts. This disclosure also concerns materials and methods for preparing compounds of Formula 1, pharmaceutical compositions which contain them, and the use of compounds of Formula 1 and their pharmaceutically acceptable salts (optionally in combination with other pharmacologically active agents) for treating diseases, disorders or conditions of the CNS, including Alzheimer's disease, and other diseases, disorders or conditions associated with SSTR4.

The compounds of Formula 1 include those in which:

(1) (a) $X^3$ is selected from $NR^{3N}$ and O, $X^4$ is a single bond, and $X^5$ is selected from N and $CR^5$; and $R^1$ and $R^2$, together with the carbon atoms to which they are attached, form a fused ring which is benzene, wherein each non-fusion carbon atom of the fused ring is unsubstituted or is substituted with an optional substituent independently selected from:

(i) halo, hydroxy, and cyano; and (ii) $C_{1-4}$ alkyl, $C_{3-6}$ cycloalkyl, and $C_{1-4}$ alkoxy, each substituted with 0 to 3 optional substituents independently selected from halo; or (b) $X^3$ is $CR^{3C}$, $X^4$ is selected from N and $CR^4$, and $X^5$ is selected from N and $CR^5$; and $R^1$ and $R^2$ are each independently selected from:

(i) hydrogen, halo, hydroxy, and cyano; and (ii) $C_{1-4}$ alkyl, $C_{3-6}$ cycloalkyl, and $C_{1-4}$ alkoxy, each substituted with 0 to 3 optional substituents independently selected from halo; or $R^1$ and $R^2$, together with the carbon atoms to which they are attached, form a fused ring selected from furan, pyrazole, and benzene, wherein one of the nitrogen atoms of the pyrazole ring is substituted with hydrogen, $C_{1-4}$ alkyl or $C_{3-6}$ cycloalkyl, and each non-fusion carbon atom of the fused ring is unsubstituted or is substituted with an optional substituent independently selected from:

(i) halo, hydroxy, and cyano; and (ii) $C_{1-4}$ alkyl, $C_{3-6}$ cycloalkyl, and $C_{1-4}$ alkoxy, each substituted with 0 to 3 optional substituents independently selected from halo;

L is O and n is 1; or

L is a single bond and n is 0 or 1;

$R^{3N}$ is selected from hydrogen, $C_{1-4}$ alkyl and $C_{3-6}$ cycloalkyl;

$R^{3C}$ and $R^4$ are each independently selected from:

(i) hydrogen, halo, hydroxy, and cyano; and (ii) $C_{1-4}$ alkyl, $C_{3-6}$ cycloalkyl, and $C_{1-4}$ alkoxy, each substituted with 0 to 3 optional substituents independently selected from halo;

$R^5$ is selected from:

(i) hydrogen, halo, hydroxy, and cyano; and (ii) $C_{1-4}$ alkyl and $C_{1-4}$ alkoxy, each substituted with 0 to 3 optional substituents independently selected from halo; and $R^6$ is hydrogen; or $R^5$ and $R^6$ together form an ethane-1,2-diyl bridging the carbon atoms to which they are attached;

$R^7$ and $R^8$ are each independently selected from hydrogen and $C_{1-4}$ alkyl which is substituted with 0 to 3 optional substituents independently selected from halo, wherein at least one of $R^7$ and $R^8$ is not hydrogen, or $R^7$ and $R^8$, together with the carbon atom to which they are attached, form a $C_{3-6}$ cycloalkylidene;

$R^9$ is selected from hydrogen and $C_{1-4}$ alkyl which is substituted with 0 to 3 optional substituents independently selected from halo;

$R^{10}$ is selected from azetidin-1-ylmethyl, pyrrolidin-1-ylmethyl, and a heterocyclyl having the formula:

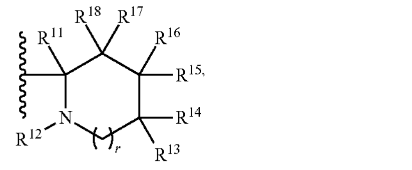

in which [wavy bond] indicates a point of attachment, and r is selected from 0 and 1;

$R^{11}$ is hydrogen, and $R^{12}$ is selected from hydrogen and from $C_{1-4}$ alkyl and $C_{3-6}$ cycloalkyl, each substituted with 0 to 3 optional substituents independently selected from halo, provided if $R^{12}$ is hydrogen then $R^1$ and $R^2$ form a fused ring; or $R^{11}$ and $R^{12}$ together form a propane-1,3-diyl bridging the carbon and nitrogen atoms to which they are respectively attached;

$R^{13}$, $R^{14}$, $R^{15}$, and $R^{16}$ are each independently selected from hydrogen, halo, and $C_{1-4}$ alkyl which is substituted with 0 to 3 optional substituents independently selected from halo, or $R^{13}$ and $R^{16}$ are absent and $R^{14}$ and $R^{15}$, together with the carbon atoms to which they are attached, form a fused benzene ring in which each non-fusion carbon atom is unsubstituted or is substituted with an optional substituent independently selected from:

(i) halo, hydroxy, and cyano; and (ii) $C_{1-4}$ alkyl, $C_{3-6}$ cycloalkyl, and $C_{1-4}$ alkoxy, each substituted with 0 to 3 optional substituents independently selected from halo; and $R^{17}$ and $R^{18}$ are each independently selected from hydrogen, halo and $C_{1-4}$ alkyl which is substituted with 0 to 3 optional substituents independently selected from halo;

provided the compound of Formula 1 is not:

2-(1-methylpiperidin-2-yl)-N-(1-(m-tolyl)cyclopropyl)acetamide;

N-(1-(pyridin-3-yl)pentyl)-3-(pyrrolidin-1-yl)propanamide;

N-(1-(6-methylpyridin-2-yl)propan-2-yl)-3-(pyrrolidin-1-yl)propanamide;

2-(1-methylpyrrolidin-2-yl)-N-(1-phenylethyl)acetamide;

2-(1-methylpiperidin-2-yl)-N-(1-phenylethyl)acetamide;

N-(1-phenylethyl)-3-(pyrrolidin-1-yl)propanamide;

N-(1-(3,4-dichlorophenyl)propyl)-3-(pyrrolidin-1-yl)propanamide;

N-(2-phenylpropan-2-yl)-3-(pyrrolidin-1-yl)propanamide;

N-(1-(4-methylpyridin-2-yl)propyl)-3-(pyrrolidin-1-yl)propenamide; or

N-(1-(naphthalen-1-yl)ethyl)-2-(pyrrolidin-2-yl)acetamide.

In addition to embodiment (1) in the preceding paragraph, the compounds of Formula 1 include those in which:

(2) $X^3$ is selected from $NR^{3N}$ and O, $X^4$ is a single bond, and $X^5$ is selected from N and $CR^5$.

In addition to embodiment (2) in the preceding paragraph, the compounds of Formula 1 include those in which each non-fusion carbon atom of the fused ring formed by $R^1$ and $R^2$ is unsubstituted or is substituted with an optional substituent independently selected from:

(3) (i) halo and hydroxy; and (ii) $C_{1-4}$ alkyl, $C_{3-6}$ cycloalkyl, and $C_{1-4}$ alkoxy, each substituted with 0 to 3 optional substituents independently selected from halo;

(4) (i) halo and hydroxy; and
(ii) $C_{1-4}$ alkyl and $C_{1-4}$ alkoxy, each substituted with 0 to 3 optional substituents independently selected from halo;
(5) halo and $C_{1-4}$ alkyl which is substituted with 0 to 3 optional substituents independently selected from halo;
(6) halo and $C_{1-3}$ alkyl which is substituted with 0 to 3 optional substituents independently selected from halo;
(7) $C_{1-3}$ alkyl which is substituted with 0 to 3 optional substituents independently selected from halo;
(8) $C_{1-3}$ alkyl; or
(9) methyl.

In in addition to embodiments (2) to (9) in the preceding paragraphs, the compounds of Formula 1 include those in which $R^{3N}$ is selected from:
(10) hydrogen and $C_{1-4}$ alkyl;
(11) hydrogen and $C_{1-3}$ alkyl;
(12) hydrogen and methyl;
(13) $C_{1-3}$ alkyl; or
(14) methyl.

In in addition to embodiments (2) to (14) in the preceding paragraphs, the compounds of Formula 1 include those in which:
(15) $X^3$ is O, $X^4$ is a single bond, and $X^5$ is N;
(16) $X^3$ is selected from $NR^{3N}$ and O, $X^4$ is a single bond, and $X^5$ is N; or
(17) $X^3$ is $NR^{3N}$, $X^4$ is a single bond, and $X^5$ is N.

In in addition to embodiments (2) to (17) in the preceding paragraphs, the compounds of Formula 1 include those in which:
(18) L is a single bond and n is 0 or 1; or
(19) L is a single bond and n is 0.

In addition to embodiment (1) above, the compounds of Formula 1 include those in which:
(20) $X^3$ is $CR^{3C}$, $X^4$ is selected from N and $CR^4$, and $X^5$ is selected from N and $CR^5$.

In addition to embodiment (20) in the preceding paragraph, the compounds of Formula 1 include those in which $R^1$ and $R^2$ are each independently selected from:
(21) (i) hydrogen, halo, hydroxy, and cyano; and
(ii) $C_{1-4}$ alkyl, $C_{3-6}$ cycloalkyl, and $C_{1-4}$ alkoxy, each substituted with 0 to 3 optional substituents independently selected from halo;
(22) (i) hydrogen and halo; and
(ii) $C_{1-4}$ alkyl, $C_{3-6}$ cycloalkyl, and $C_{1-4}$ alkoxy, each substituted with 0 to 3 optional substituents independently selected from halo;
(23) (i) hydrogen and halo; and
(ii) $C_{1-3}$ alkyl, $C_{3-6}$ cycloalkyl, and $C_{1-3}$ alkoxy, each substituted with 0 to 3 optional substituents independently selected from halo;
(24) (i) hydrogen and halo; and
(ii) methyl, ethyl, isopropyl, cyclopropyl, cyclobutyl, cyclopentyl, methoxy, ethoxy, and isopropoxy, each substituted with 0 to 3 optional substituents independently selected from halo;
(25) (i) hydrogen and halo; and
(ii) methyl, ethyl, isopropyl, cyclopropyl, methoxy, ethoxy, and isopropoxy, each substituted with 0 to 3 optional substituents independently selected from halo;
(26) (i) hydrogen and halo; and
(ii) methyl, ethyl, cyclopropyl, methoxy, and ethoxy, each substituted with 0 to 3 optional substituents independently selected from halo;
(27) (i) hydrogen, chloro, and fluoro; and
(ii) methyl, ethyl, cyclopropyl, methoxy, and ethoxy, each substituted with 0 to 3 optional substituents independently selected from halo;
(28) (i) hydrogen and halo; and
(ii) methyl, ethyl, cyclopropyl, methoxy, and ethoxy, each substituted with 0 to 3 optional substituents independently selected from chloro and fluoro;
(29) (i) hydrogen, chloro, and fluoro; and
(ii) methyl, ethyl, cyclopropyl, methoxy, and ethoxy, each substituted with 0 to 3 optional substituents independently selected from chloro and fluoro; or
(30) (i) hydrogen, chloro, and fluoro; and
(ii) methyl, ethyl, cyclopropyl, methoxy, and ethoxy, each substituted with 0 to 3 optional substituents independently selected from fluoro.

In addition to embodiment (20) above, the compounds of Formula 1 include those in which:
(31) $R^1$ and $R^2$, together with the carbon atoms to which they are attached, form a fused ring selected from furan, pyrazole, and benzene, wherein one of the nitrogen atoms of the pyrazole ring is substituted with hydrogen, $C_{1-4}$ alkyl or $C_{3-6}$ cycloalkyl, and each non-fusion carbon atom of the fused ring is unsubstituted or is substituted with an optional substituent independently selected from:
(i) halo, hydroxy, and cyano; and
(ii) $C_{1-4}$ alkyl, $C_{3-6}$ cycloalkyl, and $C_{1-4}$ alkoxy, each substituted with 0 to 3 optional substituents independently selected from halo.

In addition to embodiment (20) above, the compounds of Formula 1 include those in which:
(32) $R^1$ and $R^2$, together with the carbon atoms to which they are attached, form a fused ring which is furan, wherein each non-fusion carbon atom of the fused ring is unsubstituted or is substituted with an optional substituent independently selected from:
(i) halo, hydroxy, and cyano; and
(ii) $C_{1-4}$ alkyl, $C_{3-6}$ cycloalkyl, and $C_{1-4}$ alkoxy, each substituted with 0 to 3 optional substituents independently selected from halo.

In addition to embodiment (32) in the preceding paragraph, the compounds of Formula 1 include those in which:
(33) the fused ring formed by $R^1$, $R^2$ and the carbon atoms to which $R^1$ and $R^2$ are attached is furan having an oxygen ring atom that is bonded to the carbon atom directly attached to $R^2$.

In addition to embodiment (20) above, the compounds of Formula 1 include those in which:
(34) $R^1$ and $R^2$, together with the carbon atoms to which they are attached, form a fused ring which is pyrazole, wherein one of the nitrogen atoms of the pyrazole ring is substituted with hydrogen, $C_{1-4}$ alkyl or $C_{3-6}$ cycloalkyl, and each non-fusion carbon atom of the fused ring is unsubstituted or is substituted with an optional substituent independently selected from:
(i) halo, hydroxy, and cyano; and
(ii) $C_{1-4}$ alkyl, $C_{3-6}$ cycloalkyl, and $C_{1-4}$ alkoxy, each substituted with 0 to 3 optional substituents independently selected from halo.

In addition to embodiment (34) in the preceding paragraph, the compounds of Formula 1 include those in which the fused ring formed by $R^1$, $R^2$ and the carbon atoms to which $R^1$ and $R^2$ are attached is pyrazole:

(35) having a nitrogen ring atom that is bonded to the carbon atom directly attached to $R^2$; or

(36) having a nitrogen ring atom that is bonded to the carbon atom directly attached to $R^2$ and is substituted with hydrogen, $C_{1-4}$ alkyl or $C_{3-6}$ cycloalkyl.

In addition to embodiments (34) to (36) in the preceding paragraphs, the compounds of Formula 1 include those in which the fused ring formed by $R^1$, $R^2$ and the carbon atoms to which $R^1$ and $R^2$ are attached is pyrazole in which one of the nitrogen ring atoms is substituted with:

(37) hydrogen, $C_{1-3}$ alkyl or $C_{3-6}$ cycloalkyl;

(38) hydrogen, methyl, ethyl, isopropyl, cyclopropyl, cyclobutyl or cyclopentyl;

(39) hydrogen, methyl, ethyl, isopropyl, or cyclopropyl;

(40) hydrogen, or methyl; or

(41) methyl.

In addition to embodiment (20) above, the compounds of Formula 1 include those in which:

(42) $R^1$ and $R^2$, together with the carbon atoms to which they are attached, form a fused ring which is benzene, wherein each non-fusion carbon atom of the fused ring is unsubstituted or is substituted with an optional substituent independently selected from:
(i) halo, hydroxy, and cyano; and
(ii) $C_{1-4}$ alkyl, $C_{3-6}$ cycloalkyl, and $C_{1-4}$ alkoxy, each substituted with 0 to 3 optional substituents independently selected from halo.

In addition to embodiments (31) to (42) in the preceding paragraphs, the compounds of Formula 1 include those in which each non-fusion carbon atom of the fused ring formed by $R^1$ and $R^2$ is unsubstituted or is substituted with an optional substituent independently selected from:

(43) (i) halo and hydroxy; and
(ii) $C_{1-4}$ alkyl, $C_{3-6}$ cycloalkyl, and $C_{1-4}$ alkoxy, each substituted with 0 to 3 optional substituents independently selected from halo;

(44) (i) halo and hydroxy; and
(ii) $C_{1-4}$ alkyl and $C_{1-4}$ alkoxy, each substituted with 0 to 3 optional substituents independently selected from halo;

(45) halo and $C_{1-4}$ alkyl which is substituted with 0 to 3 optional substituents independently selected from halo;

(46) halo and $C_{1-3}$ alkyl which is substituted with 0 to 3 optional substituents independently selected from halo;

(47) $C_{1-3}$ alkyl which is substituted with 0 to 3 optional substituents independently selected from halo;

(48) $C_{1-3}$ alkyl; or

(49) methyl.

In addition to embodiments (20) to (49) in the preceding paragraphs, the compounds of Formula 1 include those in which $R^{3C}$ and $R^4$ are each independently selected from:

(50) (i) hydrogen, halo and hydroxy; and
(ii) $C_{1-4}$ alkyl, $C_{3-6}$ cycloalkyl, and $C_{1-4}$ alkoxy, each substituted with 0 to 3 optional substituents independently selected from halo;

(51) (i) hydrogen and halo; and
(ii) $C_{1-4}$ alkyl, $C_{3-6}$ cycloalkyl, and $C_{1-4}$ alkoxy, each substituted with 0 to 3 optional substituents independently selected from halo;

(52) (i) hydrogen and halo; and
(ii) $C_{1-3}$ alkyl, $C_{3-6}$ cycloalkyl, and $C_{1-3}$ alkoxy, each substituted with 0 to 3 optional substituents independently selected from halo;

(53) (i) hydrogen and halo; and
(ii) methyl, ethyl, isopropyl, cyclopropyl, cyclobutyl, cyclopentyl, methoxy, ethoxy, and isopropoxy, each substituted with 0 to 3 optional substituents independently selected from halo;

(54) (i) hydrogen and halo; and
(ii) methyl, ethyl, isopropyl, cyclopropyl, methoxy, ethoxy, and isopropoxy, each substituted with 0 to 3 optional substituents independently selected from halo;

(55) (i) hydrogen and halo; and
(ii) methyl, ethyl, cyclopropyl, methoxy, and ethoxy, each substituted with 0 to 3 optional substituents independently selected from halo;

(56) (i) hydrogen, chloro, and fluoro; and
(ii) methyl, ethyl, cyclopropyl, methoxy, and ethoxy, each substituted with 0 to 3 optional substituents independently selected from halo;

(57) (i) hydrogen and halo; and
(ii) methyl, ethyl, cyclopropyl, methoxy, and ethoxy, each substituted with 0 to 3 optional substituents independently selected from chloro and fluoro;

(58) (i) hydrogen, chloro, and fluoro; and
(ii) methyl, ethyl, cyclopropyl, methoxy, and ethoxy, each substituted with 0 to 3 optional substituents independently selected from chloro and fluoro; or

(59) (i) hydrogen, chloro, and fluoro; and
(ii) methyl, ethyl, cyclopropyl, methoxy, and ethoxy, each substituted with 0 to 3 optional substituents independently selected from fluoro.

In addition to embodiments (20) to (59) in the preceding paragraphs, the compounds of Formula 1 include those in which $R^5$ is selected from:

(60) (i) hydrogen, halo, hydroxy, and cyano; and
(ii) $C_{1-4}$ alkyl and $C_{1-4}$ alkoxy, each substituted with 0 to 3 optional substituents independently selected from halo;

(61) (i) hydrogen, halo and hydroxy; and
(ii) $C_{1-4}$ alkyl, $C_{3-6}$ cycloalkyl, and $C_{1-4}$ alkoxy, each substituted with 0 to 3 optional substituents independently selected from halo;

(62) (i) hydrogen and halo; and
(ii) $C_{1-4}$ alkyl, $C_{3-6}$ cycloalkyl, and $C_{1-4}$ alkoxy, each substituted with 0 to 3 optional substituents independently selected from halo;

(63) (i) hydrogen and halo; and
(ii) $C_{1-3}$ alkyl, $C_{3-6}$ cycloalkyl, and $C_{1-3}$ alkoxy, each substituted with 0 to 3 optional substituents independently selected from halo;

(64) (i) hydrogen and halo; and
(ii) methyl, ethyl, isopropyl, cyclopropyl, cyclobutyl, cyclopentyl, methoxy, ethoxy, and isopropoxy, each substituted with 0 to 3 optional substituents independently selected from halo;

(65) (i) hydrogen and halo; and
(ii) methyl, ethyl, isopropyl, cyclopropyl, methoxy, ethoxy, and isopropoxy, each substituted with 0 to 3 optional substituents independently selected from halo;

(66) (i) hydrogen and halo; and
(ii) methyl, ethyl, cyclopropyl, methoxy, and ethoxy, each substituted with 0 to 3 optional substituents independently selected from halo;

(67) (i) hydrogen, chloro, and fluoro; and
(ii) methyl, ethyl, cyclopropyl, methoxy, and ethoxy, each substituted with 0 to 3 optional substituents independently selected from halo;

(68) (i) hydrogen and halo; and
(ii) methyl, ethyl, cyclopropyl, methoxy, and ethoxy, each substituted with 0 to 3 optional substituents independently selected from chloro and fluoro;

(69) (i) hydrogen, chloro, and fluoro; and
(ii) methyl, ethyl, cyclopropyl, methoxy, and ethoxy, each substituted with 0 to 3 optional substituents independently selected from chloro and fluoro; or

(70) (i) hydrogen, chloro, and fluoro; and
(ii) methyl, ethyl, cyclopropyl, methoxy, and ethoxy, each substituted with 0 to 3 optional substituents independently selected from fluoro.

In addition to embodiments (20) to (59) above, the compounds of Formula 1 include those in which:

(71) $R^5$ and $R^6$ together form an ethane-1,2-diyl bridging the carbon atoms to which $R^5$ and $R^6$ are attached.

In addition to embodiments (20) to (71) in the preceding paragraphs, the compounds of Formula 1 include those in which:

(72) $X^3$ is $CR^{3C}$, $X^4$ is $CR^4$, and $X^5$ is selected from N and $CR^5$;

(73) $X^3$ is $CR^{3C}$, $X^4$ is $CR^4$, and $X^5$ is $CR^5$; or

(74) $X^3$ is $CR^{3C}$, $X^4$ is N, and $X^5$ is $CR^5$.

In addition to embodiments (20) to (59) above, the compounds of Formula 1 include those in which:

(75) $X^3$ is $CR^{3C}$, $X^4$ is $CR^4$, and $X^5$ is N.

In addition to embodiments (20) to (75) in the preceding paragraphs, the compounds of Formula 1 include those in which:

(76) L is O and n is 1.

In addition to embodiments (20) to (70) and (72) to (75) above, the compounds of Formula 1 include those in which:

(77) L is a single bond and n is 0 or 1.

In addition to embodiments (1) to (77) in the preceding paragraphs, the compounds of Formula 1 include those in which $R^7$ and $R^8$ are each independently selected from:

(78) hydrogen and $C_{1-4}$ alkyl which is substituted with 0 to 3 optional substituents independently selected from halo, wherein at least one of $R^7$ and $R^8$ is not hydrogen;

(79) hydrogen and $C_{1-3}$ alkyl which is substituted with 0 to 3 optional substituents independently selected from halo, wherein at least one of $R^7$ and $R^8$ is not hydrogen;

(80) hydrogen, methyl, ethyl, and isopropyl, wherein each methyl, ethyl, and isopropyl is substituted with 0 to 3 optional substituents independently selected from halo, wherein at least one of $R^7$ and $R^8$ is not hydrogen;

(81) hydrogen and methyl which is substituted with 0 to 3 optional substituents independently selected from halo, wherein at least one of $R^7$ and $R^8$ is not hydrogen;

(82) hydrogen, methyl, fluoromethyl, difluoromethyl, and trifluoromethyl, wherein at least one of $R^7$ and $R^8$ is not hydrogen; or

(83) hydrogen and methyl, wherein at least one of $R^7$ and $R^8$ is not hydrogen.

In addition to embodiments (78) to (83) in the preceding paragraphs, the compounds of Formula 1 include those in which:

(84) $R^8$ is hydrogen; or

(85) $R^7$ and $R^8$ are the same.

In addition to embodiments (1) to (77) above, the compounds of Formula 1 include those in which $R^7$ and $R^8$, together with the carbon atom to which they are attached, form a:

(86) $C_{3-6}$ cycloalkylidene;

(87) cyclopropylidene, cyclobutylidene, and cyclopentylidene;

(88) cyclopropylidene or cyclobutylidene; or

(89) cyclopropylidene.

In addition to embodiments (1) to (89) in the preceding paragraphs, the compounds of Formula 1 include those in which $R^9$ is selected from:

(90) hydrogen and $C_{1-3}$ alkyl which is substituted with 0 to 3 optional substituents independently selected from halo;

(91) hydrogen, methyl, ethyl, and isopropyl, wherein each methyl, ethyl, and isopropyl is substituted with 0 to 3 optional substituents independently selected from halo;

(92) hydrogen, methyl, ethyl, and isopropyl, wherein each methyl, ethyl, and isopropyl is substituted with 0 to 3 optional substituents selected from fluoro; or

(93) hydrogen, methyl, ethyl, and isopropyl.

In addition to embodiments (1) to (93) in the preceding paragraphs, the compounds of Formula 1 include those in which $R^{10}$ is:

(94) azetidin-1-ylmethyl; or

(95) pyrrolidin-1-ylmethyl.

In addition to embodiments (1) to (93) above, the compounds of Formula 1 include those in which:

(96) $R^{10}$ is a heterocyclyl having the formula:

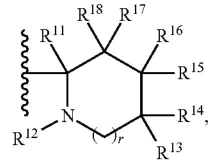

in which  indicates a point of attachment, and r is selected from 0 and 1;

$R^{11}$ is hydrogen, and $R^{12}$ is selected from hydrogen and from $C_{1-4}$ alkyl and $C_{3-6}$ cycloalkyl, each substituted with 0 to 3 optional substituents independently selected from halo, provided if $R^{12}$ is hydrogen then $R^1$ and $R^2$ form a fused ring; or $R^{11}$ and $R^{12}$ together form a propane-1,3-diyl bridging the carbon and nitrogen atoms to which they are respectively attached;

$R^{13}$, $R^{14}$, $R^{15}$, and $R^{16}$ are each independently selected from hydrogen, halo, and $C_{1-4}$ alkyl which is substituted with 0 to 3 optional substituents independently selected from halo, or $R^{13}$ and $R^{16}$ are absent and $R^{14}$ and $R^{15}$, together with the carbon atoms to which they are attached, form a fused benzene ring in which each non-fusion carbon atom is unsubstituted or is substituted with an optional substituent independently selected from:

(i) halo, hydroxy, and cyano; and (ii) $C_{1-4}$ alkyl, $C_{3-6}$ cycloalkyl, and $C_{1-4}$ alkoxy, each substituted with 0 to 3 optional substituents independently selected from halo; and $R^{17}$ and $R^{18}$ are each independently selected from hydrogen, halo and $C_{1-4}$ alkyl which is substituted with 0 to 3 optional substituents independently selected from halo.

In addition to embodiment (96) in the preceding paragraph, the compounds of Formula 1 include those in which $R^{11}$ is hydrogen and $R^{12}$ is selected from:

(97) $C_{1-4}$ alkyl and $C_{3-6}$ cycloalkyl, each substituted with 0 to 3 optional substituents independently selected from halo;

(98) $C_{1-3}$ alkyl and $C_{3-6}$ cycloalkyl, each substituted with 0 to 3 optional substituents independently selected from halo;

(99) methyl, ethyl, isopropyl, cyclopropyl, cyclobutyl, and cyclopentyl, each substituted with 0 to 3 optional substituents independently selected from halo;

(100) methyl, ethyl, isopropyl, and cyclopropyl, each substituted with 0 to 3 optional substituents independently selected from halo;

(101) methyl, ethyl, isopropyl, and cyclopropyl, each substituted with 0 to 3 optional substituents selected from fluoro;

(102) methyl, ethyl, and isopropyl, each substituted with 0 to 3 optional substituents selected from fluoro;

(103) methyl and ethyl, each substituted with 0 to 3 optional substituents selected from fluoro;

(104) methyl and ethyl; or (105) methyl.

In addition to embodiment (96) above, the compounds of Formula 1 include those in which:

(106) $R^{11}$ and $R^{12}$ together form a propane-1,3-diyl bridging the carbon and nitrogen atoms to which they are respectively attached.

In addition to embodiments (96) to (106) in the preceding paragraphs, the compounds of Formula 1 include those in which $R^{13}$, $R^{14}$, $R^{15}$, and $R^{16}$ are each independently selected from:

(107) hydrogen, halo, and $C_{1-4}$ alkyl which is substituted with 0 to 3 optional substituents independently selected from halo;

(108) hydrogen and $C_{1-4}$ alkyl which is substituted with 0 to 3 optional substituents independently selected from halo;

(109) hydrogen and $C_{1-3}$ alkyl which is substituted with 0 to 3 optional substituents independently selected from halo;

(110) hydrogen, halo, and methyl which is substituted with 0 to 3 optional substituents independently selected from halo;

(111) hydrogen, halo, and methyl which is substituted with 0 to 3 optional substituents independently selected from fluoro;

(112) hydrogen, halo, and methyl;

(113) hydrogen, fluoro, and methyl;

(114) hydrogen and methyl; or (115) hydrogen.

In addition to embodiments (107) to (114) in the preceding paragraphs, the compounds of Formula 1 include those in which:

(116) $R^{15}$ and $R^{16}$ are each hydrogen.

In addition to embodiments (96) to (106) above, the compounds of Formula 1 include those in which:

(117) $R^{13}$ and $R^{16}$ are absent and $R^{14}$ and $R^{15}$, together with the carbon atoms to which they are attached, form a fused benzene ring in which each non-fusion carbon atom is unsubstituted or is substituted with an optional substituent independently selected from:

(i) halo, hydroxy, and cyano; and (ii) $C_{1-4}$ alkyl, $C_{3-6}$ cycloalkyl, and $C_{1-4}$ alkoxy, each substituted with 0 to 3 optional substituents independently selected from halo.

In addition to embodiment (117) in the preceding paragraph, the compounds of Formula 1 include those in which each non-fusion carbon atom of the fused benzene ring formed by $R^{14}$ and $R^{15}$ is unsubstituted or is substituted with an optional substituent independently selected from:

(118) (i) halo and hydroxy; and (ii) $C_{1-4}$ alkyl, $C_{3-6}$ cycloalkyl, and $C_{1-4}$ alkoxy, each substituted with 0 to 3 optional substituents independently selected from halo;

(119) (i) halo and hydroxy; and (ii) $C_{1-4}$ alkyl and $C_{1-4}$ alkoxy, each substituted with 0 to 3 optional substituents independently selected from halo;

(120) halo and $C_{1-4}$ alkyl which is substituted with 0 to 3 optional substituents independently selected from halo;

(121) halo and $C_{1-3}$ alkyl which is substituted with 0 to 3 optional substituents independently selected from halo;

(122) $C_{1-3}$ alkyl which is substituted with 0 to 3 optional substituents independently selected from halo;

(123) $C_{1-3}$ alkyl; or (124) methyl.

In addition to embodiment (117) above, the compounds of Formula 1 include those in which:

(125) each non-fusion carbon atom of the fused benzene ring formed by $R^{14}$ and $R^{15}$ is unsubstituted.

In addition to embodiments (96) to (125) in the preceding paragraphs, the compounds of Formula 1 include those in which $R^{17}$ and $R^{18}$ are each independently selected from:

(126) hydrogen, halo and $C_{1-3}$ alkyl which is substituted with 0 to 3 optional substituents independently selected from halo;

(127) hydrogen, halo, methyl and ethyl, wherein methyl and ethyl are each substituted with 0 to 3 optional substituents independently selected from halo;

(128) hydrogen, halo and methyl;

(129) hydrogen, fluoro and methyl; or (130) hydrogen and fluoro.

In addition to embodiments (126) to (130) in the preceding paragraph, the compounds of Formula 1 include those in which:

(131) $R^{17}$ and $R^{18}$ are the same.

In addition to embodiments (96) to (131) in the preceding paragraphs, the compounds of Formula 1 include those in which:

(132) r is 0; or (133) r is 1.

Compounds of Formula 1 include embodiments (1) through (133) described in the preceding paragraphs and compounds specifically named in the examples, may exist as salts, complexes, solvates, hydrates, and liquid crystals. Likewise, compounds of Formula 1 that are salts may exist as complexes, solvates, hydrates, and liquid crystals.

Compounds of Formula 1 may form pharmaceutically acceptable complexes, salts, solvates and hydrates. These salts include acid addition salts (including di-acids) and base salts. Pharmaceutically acceptable acid addition salts include salts derived from inorganic acids such as hydrochloric acid, nitric acid, phosphoric acid, sulfuric acid, hydrobromic acid, hydroiodic acid, hydrofluoric acid, and phosphorous acids, as well nontoxic salts derived from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts include acetate, adipate, aspartate, benzoate, besylate, bicarbonate, carbonate, bisulfate, sulfate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfate, naphthylate, 2-napsylate, nicotinate, nitrate, orotate, oxalate, palmitate, pamoate, phosphate, hydrogen phosphate, dihydrogen phosphate, pyroglutamate, saccharate, stearate, succinate, tannate, tartrate, tosylate, trifluoroacetate and xinofoate salts.

Pharmaceutically acceptable base salts include salts derived from bases, including metal cations, such as an alkali or alkaline earth metal cation, as well as amines. Examples of suitable metal cations include sodium, potassium, magnesium, calcium, zinc, and aluminum. Examples of suitable amines include arginine, N,N'-dibenzylethylenediamine, chloroprocaine, choline, diethylamine, diethanolamine, dicyclohexylamine, ethylenediamine, glycine, lysine, N-methylglucamine, olamine, 2-amino-2-hydroxymethyl-propane-1,3-diol, and procaine. For a discussion of useful acid addition and base salts, see S. M. Berge et al., *J. Pharm. Sci.* (1977) 66:1-19; see also Stahl and Wermuth, *Handbook of Pharmaceutical Salts: Properties, Selection, and Use* (2002).

Pharmaceutically acceptable salts may be prepared using various methods. For example, a compound of Formula 1 may be reacted with an appropriate acid or base to give the desired salt. Alternatively, a precursor of the compound of Formula 1 may be reacted with an acid or base to remove an acid- or base-labile protecting group or to open a lactone or lactam group of the precursor. Additionally, a salt of the compound of Formula 1 may be converted to another salt (or free form) through treatment with an appropriate acid or base or through contact with an ion exchange resin. Following reaction, the salt may be isolated by filtration if it precipitates from solution, or by evaporation to recover the salt. The degree of ionization of the salt may vary from completely ionized to almost non-ionized.

Compounds of Formula 1 may exist in a continuum of solid states ranging from fully amorphous to fully crystalline. The term "amorphous" refers to a state in which the material lacks long range order at the molecular level and, depending upon temperature, may exhibit the physical properties of a solid or a liquid. Typically, such materials do not give distinctive X-ray diffraction patterns and, while exhibiting the properties of a solid, are more formally described as a liquid. Upon heating, a change from solid to liquid properties occurs which is characterized by a change of state, typically second order ("glass transition"). The term "crystalline" refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterized by a phase change, typically first order ("melting point").

Compounds of Formula 1 may also exist in unsolvated and solvated forms. The term "solvate" describes a molecular complex comprising the compound and one or more pharmaceutically acceptable solvent molecules (e.g., ethanol). The term "hydrate" is a solvate in which the solvent is water. Pharmaceutically acceptable solvates include those in which the solvent may be isotopically substituted (e.g., $D_2O$, acetone-$d_6$, DMSO-$d_6$).

A currently accepted classification system for solvates and hydrates of organic compounds is one that distinguishes between isolated site, channel, and metal-ion coordinated solvates and hydrates. See, e.g., K. R. Morris (H. G. Brittain ed.) *Polymorphism in Pharmaceutical Solids* (1995). Isolated site solvates and hydrates are ones in which the solvent (e.g., water) molecules are isolated from direct contact with each other by intervening molecules of the organic compound. In channel solvates, the solvent molecules lie in lattice channels where they are next to other solvent molecules. In metal-ion coordinated solvates, the solvent molecules are bonded to the metal ion.

When the solvent or water is tightly bound, the complex will have a well-defined stoichiometry independent of humidity. When, however, the solvent or water is weakly bound, as in channel solvates and in hygroscopic compounds, the water or solvent content will depend on humidity and drying conditions. In such cases, non-stoichiometry will typically be observed.

Compounds of Formula 1 may also exist as multi-component complexes (other than salts and solvates) in which the compound (drug) and at least one other component are present in stoichiometric or non-stoichiometric amounts. Complexes of this type include clathrates (drug-host inclusion complexes) and co-crystals. The latter are typically defined as crystalline complexes of neutral molecular constituents which are bound together through non-covalent interactions but could also be a complex of a neutral molecule with a salt. Co-crystals may be prepared by melt crystallization, by recrystallization from solvents, or by physically grinding the components together. See, e.g., O. Almarsson and M. J. Zaworotko, *Chem. Commun.* (2004) 17:1889-1896. For a general review of multi-component complexes, see J. K. Haleblian, *J. Pharm. Sci.* (1975) 64(8):1269-88.

When subjected to suitable conditions, compounds of Formula 1 may exist in a mesomorphic state (mesophase or liquid crystal). The mesomorphic state lies between the true crystalline state and the true liquid state (either melt or solution). Mesomorphism arising as the result of a change in temperature is described as "thermotropic" and mesomorphism resulting from the addition of a second component, such as water or another solvent, is described as "lyotropic." Compounds that have the potential to form lyotropic mesophases are described as "amphiphilic" and include molecules which possess a polar ionic moiety (e.g., $—COO^-Na^+$, $—COO^-K^+$, $-SO_3^-Na^+$) or polar non-ionic moiety (such as $—N^-N^+(CH_3)_3$). See, e.g., N. H. Hartshorne and A. Stuart, *Crystals and the Polarizing Microscope* (4th ed, 1970).

Each compound of Formula 1 may exist as polymorphs, stereoisomers, tautomers, or some combination thereof, may be isotopically-labeled, may result from the administration of a prodrug, or form a metabolite following administration.

"Prodrugs" refer to compounds having little or no pharmacological activity that can, when metabolized in vivo, undergo conversion to compounds having desired pharmacological activity. Prodrugs may be prepared by replacing appropriate functionalities present in pharmacologically active compounds with "pro-moieties" as described, for example, in H. Bundgaar, *Design of Prodrugs* (1985). Examples of prodrugs include ester, ether or amide derivatives of compounds of Formula 1 having carboxylic acid, hydroxy, or amino functional groups, respectively. For further discussions of prodrugs, see e.g., T. Higuchi and V. Stella "Pro-drugs as Novel Delivery Systems," *ACS Symposium Series* 14 (1975) and E. B. Roche ed., *Bioreversible Carriers in Drug Design* (1987).

"Metabolites" refer to compounds formed in vivo upon administration of pharmacologically active compounds. Examples include hydroxymethyl, hydroxy, secondary amino, primary amino, phenol, and carboxylic acid derivatives of compounds of Formula 1 having methyl, alkoxy, tertiary amino, secondary amino, phenyl, and amide groups, respectively.

Compounds of Formula 1 may exist as stereoisomers that result from the presence of one or more stereogenic centers, one or more double bonds, or both. The stereoisomers may be pure, substantially pure, or mixtures. Such stereoisomers may also result from acid addition or base salts in which the counter-ion is optically active, for example, when the counter-ion is D-lactate or L-lysine.

Compounds of Formula 1 may exist as tautomers, which are isomers resulting from tautomerization. Tautomeric isomerism includes, for example, imine-enamine, keto-enol, oxime-nitroso, and amide-imidic acid tautomerism.

Compounds of Formula 1 may exhibit more than one type of isomerism.

Geometrical (cis/trans) isomers may be separated by conventional techniques such as chromatography and fractional crystallization.

Conventional techniques for preparing or isolating a compound having a specific stereochemical configuration include chiral synthesis from a suitable optically pure precursor or resolution of the racemate (or the racemate of a salt or derivative) using, for example, chiral high-pressure liquid chromatography (HPLC). Alternatively, the racemate (or a racemic precursor) may be reacted with a suitable optically active compound, for example, an alcohol, or, in the case where the compound of Formula 1 contains an acidic or basic moiety, an acid or base such as tartaric acid or 1-phenylethylamine. The resulting diastereomeric mixture may be separated by chromatography, fractional crystallization, etc., and the appropriate diastereoisomer converted to the compound having the requisite stereochemical configuration. For a further discussion of techniques for separating stereoisomers, see E. L. Eliel and S. H. Wilen, *Stereochemistry of Organic Compounds* (1994).

Compounds of Formula 1 may possess isotopic variations, in which at least one atom is replaced by an atom having the same atomic number, but an atomic mass different from the atomic mass usually found in nature. Isotopes suitable for inclusion in compounds of Formula 1 include, for example, isotopes of hydrogen, such as $^{2}H$ and $^{3}H$; isotopes of carbon, such as $^{11}C$, $^{13}C$ and $^{14}C$; isotopes of nitrogen, such as $^{13}N$ and $^{15}N$; isotopes of oxygen, such as $^{15}O$, $^{17}O$ and $^{18}O$; isotopes of sulfur, such as $^{35}S$; isotopes of fluorine, such as 18F; isotopes of chlorine, such as $^{36}Cl$, and isotopes of iodine, such as $^{123}I$ and $^{125}I$. Use of isotopic variations (e.g., deuterium, $^{2}H$) may afford certain therapeutic advantages resulting from greater metabolic stability, for example, increased in vivo half-life or reduced dosage requirements. Additionally, certain isotopic variations of the disclosed compounds may incorporate a radioactive isotope (e.g., tritium, $^{3}H$, or $^{14}C$), which may be useful in drug and/or substrate tissue distribution studies. Substitution with positron emitting isotopes, such as $^{11}C$, $^{18}F$, $^{15}O$ and $^{13}N$, may be useful in Positron Emission Topography (PET) studies for examining substrate receptor occupancy. Isotopically-labeled compounds may be prepared by processes analogous to those described elsewhere in the disclosure using an appropriate isotopically-labeled reagent in place of a non-labeled reagent.

The compounds of Formula 1 may be prepared using the techniques described below. Some of the schemes and examples may omit details of common reactions, including oxidations, reductions, and so on, separation techniques (extraction, evaporation, precipitation, chromatography, filtration, trituration, crystallization, and the like), and analytical procedures, which are known to persons of ordinary skill in the art of organic chemistry. The details of such reactions and techniques can be found in several treatises, including Richard Larock, Comprehensive Organic Transformations (1999), and the multi-volume series edited by Michael B. Smith and others, Compendium of Organic Synthetic Methods (1974 et seq.). Starting materials and reagents may be obtained from commercial sources or may be prepared using literature methods. Some of the reaction schemes may omit minor products resulting from chemical transformations (e.g., an alcohol from the hydrolysis of an ester, $CO_2$ from the decarboxylation of a di-acid, etc.). In addition, in some instances, reaction intermediates may be used in subsequent steps without isolation or purification (i.e., in situ).

In some of the reaction schemes and examples below, certain compounds can be prepared using protecting groups, which prevent undesirable chemical reaction at otherwise reactive sites. Protecting groups may also be used to enhance solubility or otherwise modify physical properties of a compound. For a discussion of protecting group strategies, a description of materials and methods for installing and removing protecting groups, and a compilation of useful protecting groups for common functional groups, including amines, carboxylic acids, alcohols, ketones, aldehydes, and so on, see T. W. Greene and P. G. Wuts, *Protecting Groups in Organic Chemistry* (1999) and P. Kocienski, *Protective Groups* (2000).

Generally, the chemical transformations described throughout the specification may be carried out using substantially stoichiometric amounts of reactants, though certain reactions may benefit from using an excess of one or more of the reactants. Additionally, many of the reactions disclosed throughout the specification may be carried out at about room temperature (RT) and ambient pressure, but depending on reaction kinetics, yields, and so on, some reactions may be run at elevated pressures or employ higher temperatures (e.g., reflux conditions) or lower temperatures (e.g., −78° C. to 0° C.). Any reference in the disclosure and claims to a stoichiometric range, a temperature range, a pH range, etc., whether expressly using the word "range," also includes the indicated endpoints.

Many of the chemical transformations may also employ one or more compatible solvents, which may influence the reaction rate and yield. Depending on the nature of the reactants, the one or more solvents may be polar protic solvents (including water), polar aprotic solvents, non-polar solvents, or some combination. Representative solvents include saturated aliphatic hydrocarbons (e.g., n-pentane, n-hexane, n-heptane, n-octane, cyclohexane, methylcyclohexane); aromatic hydrocarbons (e.g., benzene, toluene, xylenes); halogenated hydrocarbons (e.g., methylene chloride, chloroform, carbon tetrachloride); aliphatic alcohols (e.g., methanol, ethanol, propan-1-ol, propan-2-ol, butan-1-ol, 2-methyl-propan-1-ol, butan-2-ol, 2-methyl-propan-2-ol, pentan-1-ol, 3-methyl-butan-1-ol, hexan-1-ol, 2-methoxy-ethanol, 2-ethoxy-ethanol, 2-butoxy-ethanol, 2-(2-methoxy-ethoxy)-ethanol, 2-(2-ethoxy-ethoxy)-ethanol, 2-(2-butoxy-ethoxy)-ethanol); ethers (e.g., diethyl ether, di-isopropyl ether, dibutyl ether, 1,2-dimethoxy-ethane, 1,2-diethoxy-ethane, 1-methoxy-2-(2-methoxy-ethoxy)-ethane, 1-ethoxy-2-(2-ethoxy-ethoxy)-ethane, tetrahydrofuran, 1,4-dioxane); ketones (e.g., acetone, methyl ethyl ketone); esters (methyl acetate, ethyl acetate); nitrogen-containing solvents (e.g., formamide, N,N-dimethylformamide, acetonitrile, N-methyl-pyrrolidone, pyridine, quinoline, nitrobenzene); sulfur-containing solvents (e.g., carbon disulfide, dimethyl sulfoxide, tetrahydro-thiophene-1,1,-dioxide); and phosphorus-containing solvents (e.g., hexamethylphosphoric triamide).

In the schemes, below, substituent identifiers (L, n, r, $R^1$, $R^2$, $R^6$, $R^7$, $R^8$, $R^9$, $R^{10}$, $R^{12}$, $X^3$, $X^4$ and $X^5$) are as defined above for Formula 1. As mentioned earlier, however, some of the starting materials and intermediates may include protecting groups, which are removed prior to the final product. In such cases, the substituent identifier refers to moieties defined in Formula 1 and to those moieties with appropriate protecting groups. For example, a starting material or intermediate in the schemes may include $R^{10}$ having a potentially reactive (secondary) amine. In such cases, $R^{10}$ would include the moiety with or without, say, a Boc or Cbz group attached to the amine.

Scheme A shows a general method for preparing compounds of Formula 1. In accordance with the method, an aryl or heteroaryl(alkyl or oxyalkyl)amine (A1) is reacted with a carboxylic acid (A2) or suitable base addition salt (e.g., lithium salt). The reaction is carried out using standard amide coupling agents, such as HATU, DCC, EDC hydrochloride, T3P or 2-chloro-1-methylpyridin-1-ium iodide, in the presence of a non-nucleophilic base (e.g., $Et_3N$, DIPEA) and one or more compatible solvents (e.g. ACN, DCM, DMA, DMF, NMP, pyridine, THF). The amide coupling may be carried out at temperatures which range from room temperature to about 80° C. HOBt may be used to facilitate the reaction.

Scheme A

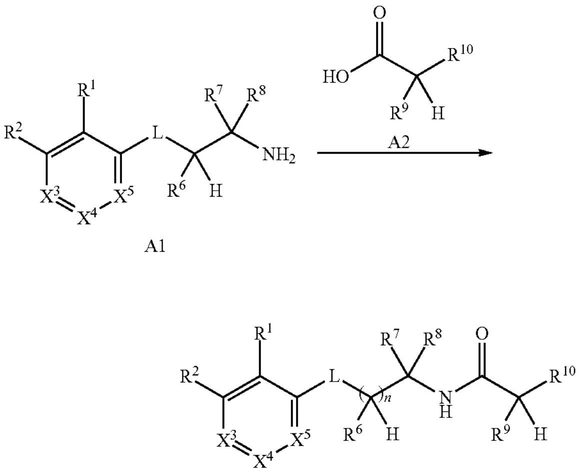

1

Though not shown in Scheme A, the carboxylic acid (A2) may include $R^{10}$ with a protected (e.g., Boc-substituted) secondary amine. In such cases, the amine is subsequently deprotected (e.g., by acid treatment) following amide coupling to reveal the secondary amine, which may be alkylated, e.g. via reaction with an alkyl halide ($R^{12}Y^1$, where $R^{12}$=$C_{1-4}$ alkyl and $C_{3-6}$ cycloalkyl, each substituted with 0 to 3 optional substituents independently selected from halo, and $Y^1$=Br, I) in the presence of a non-nucleophilic base (e.g., $K_2CO_3$) and compatible solvent (e.g., DMSO) to give $R^{10}$ with the requisite $R^{12}$. Alternatively, the secondary amine may be reacted with an appropriate alkyl aldehyde under acidic conditions in the presence of a mild reducing agent, such as sodium cyanoborohydride or sodium acetoxyborohydride, and a compatible solvent (e.g. MeOH, DCM) to give $R^{10}$ with the requisite $R^{12}$. The N-alkylation and reductive amination steps may be conducted at room temperature or above.

Scheme B shows a second general method for preparing compounds of Formula 1 (L=O, $X^5$=N). In accordance with the method, a hydroxyalkylamine (B1) is reacted with a carboxylic acid (A2) to form a hydroxyalkylamide (B2). As in Scheme A, the reaction is carried out using standard amide coupling agents in one or more compatible solvents at RT to about 80° C., optionally with HOBt. The hydroxyalkylamide (B2) is subsequently reacted with an aryl or heteroaryl reactant (B3, $Y^2$=F, Cl, Br) in the presence of a strong non-nucleophilic base (e.g. NaH) and a compatible polar aprotic solvent (e.g. DMF) to give the compound of Formula 1. The $S_NAr$ reaction may be carried out at room temperature or above.

Scheme B

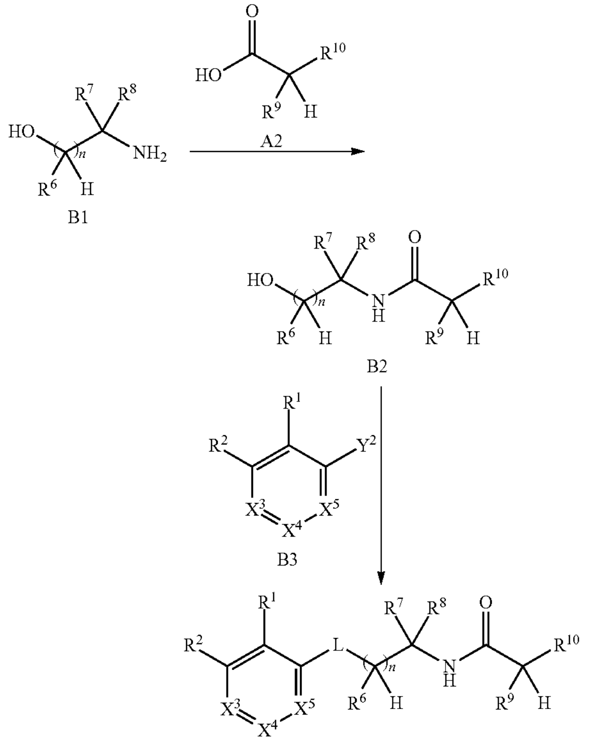

1

Scheme C shows a third general method for preparing compounds of Formula 1 when $R^{10}$ is azetidin-1-ylmethyl or pyrrolidin-1-ylmethyl (Formula 1A, s=1 or 2). In accordance with the method, an aryl or heteroaryl(alkyl or oxyalkyl)amine (A1) is reacted with an α,β-unsaturated carboxylic acid (C1). As in Scheme A, the reaction is carried out using standard amide coupling agents in one or more compatible solvents at RT to about 80° C., optionally with HOBt. The resulting amide (C2) is reacted with azetidine or pyrrolidine (C3) in a protic solvent (MeOH, water) at elevated temperature (e.g., 50-100° C.) to give the compound of Formula 1A.

The methods depicted in the schemes may be varied as desired. For example, protecting groups may be added or removed and products may be further elaborated via, for example, alkylation, acylation, hydrolysis, oxidation, reduction, amidation, sulfonation, alkynation, and the like to give the desired final product. Furthermore, any intermediate or final product which comprises mixture of stereoisomers may be optionally purified by chiral column chromatography (e.g., supercritical fluid chromatography) or by derivatization with optically-pure reagents as described above to give a desired stereoisomer.

Scheme C

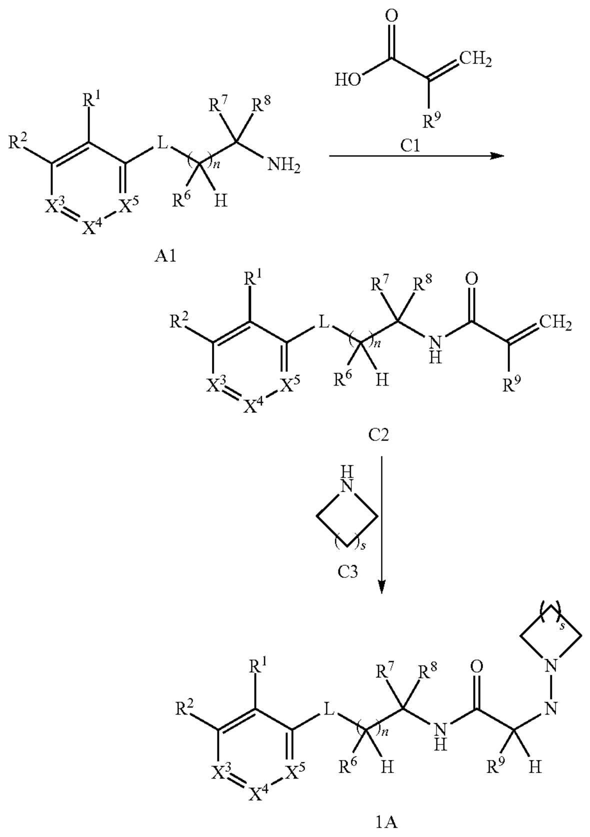

Compounds of Formula 1, which include compounds named above, and their pharmaceutically acceptable complexes, salts, solvates and hydrates, should be assessed for their biopharmaceutical properties, such as solubility and solution stability across pH, permeability, and the like, to select an appropriate dosage form and route of administration. Compounds that are intended for pharmaceutical use may be administered as crystalline or amorphous products, and may be obtained, for example, as solid plugs, powders, or films by methods such as precipitation, crystallization, freeze drying, spray drying, evaporative drying, microwave drying, or radio frequency drying.

Compounds of Formula 1 may be administered alone or in combination with one another or with one or more pharmacologically active compounds which are different than the compounds of Formula 1. Generally, one or more of these compounds are administered as a pharmaceutical composition (a formulation) in association with one or more pharmaceutically acceptable excipients. The choice of excipients depends on the mode of administration, the effect of the excipient on solubility and stability, and the nature of the dosage form, among other things. Useful pharmaceutical compositions and methods for their preparation may be found, for example, in A. R. Gennaro (ed.), *Remington: The Science and Practice of Pharmacy* (20th ed., 2000).

Compounds of Formula 1 may be administered orally. Oral administration may involve swallowing in which case the compound enters the bloodstream via the gastrointestinal tract. Alternatively, or additionally, oral administration may involve mucosal administration (e.g., buccal, sublingual, supralingual administration) such that the compound enters the bloodstream through the oral mucosa.

Formulations suitable for oral administration include solid, semi-solid and liquid systems such as tablets; soft or hard capsules containing multi- or nano-particulates, liquids, or powders; lozenges which may be liquid-filled; chews; gels; fast dispersing dosage forms; films; ovules; sprays; and buccal or mucoadhesive patches. Liquid formulations include suspensions, solutions, syrups and elixirs. Such formulations may be employed as fillers in soft or hard capsules (made, e.g., from gelatin or hydroxypropylmethylcellulose) and typically comprise a carrier (e.g., water, ethanol, polyethylene glycol, propylene glycol, methylcellulose, or a suitable oil) and one or more emulsifying agents, suspending agents or both. Liquid formulations may also be prepared by the reconstitution of a solid (e.g., from a sachet).

Compounds of Formula 1 may also be used in fast-dissolving, fast-disintegrating dosage forms such as those described in Liang and Chen, *Expert Opinion in Therapeutic Patents* (2001) 11(6):981-986.

For tablet dosage forms, depending on dose, the active pharmaceutical ingredient (API) may comprise from about 1 wt % to about 80 wt % of the dosage form or more typically from about 5 wt % to about 60 wt % of the dosage form. In addition to the API, tablets may include one or more disintegrants, binders, diluents, surfactants, glidants, lubricants, anti-oxidants, colorants, flavoring agents, preservatives, and taste-masking agents. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, $C_{1-6}$ alkyl-substituted hydroxypropylcellulose, starch, pregelatinized starch, and sodium alginate. Generally, the disintegrant will comprise from about 1 wt % to about 25 wt % or from about 5 wt % to about 20 wt % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinized starch, hydroxypropylcellulose and hydroxypropylmethylcellulose. Tablets may also contain diluents, such as lactose (monohydrate, spray-dried monohydrate, anhydrous), mannitol, xylitol, dextrose, sucrose, sorbitol, microcrystalline cellulose, starch and dibasic calcium phosphate dihydrate.

Tablets may also include surface active agents, such as sodium lauryl sulfate and polysorbate 80, and glidants such as silicon dioxide and talc. When present, surface active agents may comprise from about 0.2 wt % to about 5 wt % of the tablet, and glidants may comprise from about 0.2 wt % to about 1 wt % of the tablet.

Tablets may also contain lubricants such as magnesium stearate, calcium stearate, zinc stearate, sodium stearyl fumarate, and mixtures of magnesium stearate with sodium lauryl sulfate. Lubricants may comprise from about 0.25 wt % to about 10 wt % or from about 0.5 wt % to about 3 wt % of the tablet.

Tablet blends may be compressed directly or by roller compaction to form tablets. Tablet blends or portions of blends may alternatively be wet-, dry-, or melt-granulated, melt congealed, or extruded before tableting. If desired, prior to blending one or more of the components may be sized by screening or milling or both. The final dosage form may comprise one or more layers and may be coated, uncoated, or encapsulated. Exemplary tablets may contain up to about 80 wt % of API, from about 10 wt % to about 90 wt % of binder, from about 0 wt % to about 85 wt % of diluent, from about 2 wt % to about 10 wt % of disintegrant, and from about 0.25 wt % to about 10 wt % of lubricant. For a discussion of blending, granulation, milling, screening, tableting, coating, as well as a description of alternative techniques for preparing drug products, see A. R. Gennaro (ed.), *Remington: The Science and Practice of Pharmacy* (20th ed., 2000); H. A. Lieberman et al. (ed.), *Pharmaceutical Dosage Forms: Tablets*, Vol. 1-3 (2d ed., 1990); and D. K. Parikh & C. K. Parikh, *Handbook of Pharmaceutical Granulation Technology*, Vol. 81 (1997).

Consumable oral films for human or veterinary use are pliable water-soluble or water-swellable thin film dosage forms which may be rapidly dissolving or mucoadhesive. In addition to the API, a typical film includes one or more film-forming polymers, binders, solvents, humectants, plasticizers, stabilizers or emulsifiers, viscosity-modifying agents, and solvents. Other film ingredients may include anti-oxidants, colorants, flavorants and flavor enhancers, preservatives, salivary stimulating agents, cooling agents, co-solvents (including oils), emollients, bulking agents, anti-foaming agents, surfactants, and taste-masking agents. Some components of the formulation may perform more than one function.

In addition to dosing requirements, the amount of API in the film may depend on its solubility. If water soluble, the API would typically comprise from about 1 wt % to about 80 wt % of the non-solvent components (solutes) in the film or from about 20 wt % to about 50 wt % of the solutes in the film. A less soluble API may comprise a greater proportion of the composition, typically up to about 88 wt % of the non-solvent components in the film.

The film-forming polymer may be selected from natural polysaccharides, proteins, or synthetic hydrocolloids and typically comprises from about 0.01 wt % to about 99 wt % or from about 30 wt % to about 80 wt % of the film.

Film dosage forms are typically prepared by evaporative drying of thin aqueous films coated onto a peelable backing support or paper, which may be carried out in a drying oven or tunnel (e.g., in a combined coating-drying apparatus), in lyophilization equipment, or in a vacuum oven.

Useful solid formulations for oral administration may include immediate release formulations and modified release formulations. Modified release formulations include delayed-, sustained-, pulsed-, controlled-, targeted-, and programmed-release. For a general description of suitable modified release formulations, see U.S. Pat. No. 6,106,864. For details of other useful release technologies, such as high energy dispersions and osmotic and coated particles, see Verma et al, *Pharmaceutical Technology On-line* (2001) 25(2):1-14.

Compounds of Formula 1 may also be administered directly into the blood stream, muscle, or an internal organ of the subject. Suitable techniques for parenteral administration include intravenous, intraarterial, intraperitoneal, intrathecal, intraventricular, intraurethral, intrasternal, intracranial, intramuscular, intrasynovial, and subcutaneous administration. Suitable devices for parenteral administration include needle injectors, including microneedle injectors, needle-free injectors, and infusion devices.

Parenteral formulations are typically aqueous solutions which may contain excipients such as salts, carbohydrates and buffering agents (e.g., pH of from about 3 to about 9). For some applications, however, compounds of Formula 1 may be more suitably formulated as a sterile non-aqueous solution or as a dried form to be used in conjunction with a suitable vehicle such as sterile, pyrogen-free water. The preparation of parenteral formulations under sterile conditions (e.g., by lyophilization) may be readily accomplished using standard pharmaceutical techniques.

The solubility of compounds which are used in the preparation of parenteral solutions may be increased through appropriate formulation techniques, such as the incorporation of solubility-enhancing agents. Formulations for parenteral administration may be formulated to be immediate or modified release. Modified release formulations include delayed, sustained, pulsed, controlled, targeted, and programmed release. Thus, compounds of Formula 1 may be formulated as a suspension, a solid, a semi-solid, or a thixotropic liquid for administration as an implanted depot providing modified release of the active compound.

Examples of such formulations include drug-coated stents and semi-solids and suspensions comprising drug-loaded poly(DL-lactic-coglycolic)acid (PGLA) microspheres.

Compounds of Formula 1 may also be administered topically, intradermally, or transdermally to the skin or mucosa. Typical formulations for this purpose include gels, hydrogels, lotions, solutions, creams, ointments, dusting powders, dressings, foams, films, skin patches, wafers, implants, sponges, fibers, bandages and microemulsions. Liposomes may also be used. Typical carriers may include alcohol, water, mineral oil, liquid petrolatum, white petrolatum, glycerin, polyethylene glycol and propylene glycol. Topical formulations may also include penetration enhancers. See, e.g., Finnin and Morgan, *J. Pharm. Sci.* 88(10): 955-958 (1999).

Other means of topical administration include delivery by electroporation, iontophoresis, phonophoresis, sonophoresis and microneedle or needle-free (e.g. Powderject™ and Bioject™) injection. Formulations for topical administration may be formulated to be immediate or modified release as described above.

Compounds of Formula 1 may also be administered intranasally or by inhalation, typically in the form of a dry powder, an aerosol spray, or nasal drops. An inhaler may be used to administer the dry powder, which comprises the API alone, a powder blend of the API and a diluent, such as lactose, or a mixed component particle that includes the API and a phospholipid, such as phosphatidylcholine. For intranasal use, the powder may include a bioadhesive agent, e.g., chitosan or cyclodextrin. A pressurized container, pump, sprayer, atomizer, or nebulizer, may be used to generate the aerosol spray from a solution or suspension comprising the API, one or more agents for dispersing, solubilizing, or extending the release of the API (e.g., EtOH with or without water), one or more solvents (e.g., 1,1,1,2-tetrafluoroethane or 1,1,1,2,3,3,3-heptafluoropropane) which serve as a propellant, and an optional surfactant, such as sorbitan trioleate, oleic acid, or an oligolactic acid. An atomizer using electrohydrodynamics may be used to produce a fine mist.

Prior to use in a dry powder or suspension formulation, the drug product is usually comminuted to a particle size suitable for delivery by inhalation (typically 90% of the particles, based on volume, having a largest dimension less than 5 microns). This may be achieved by any appropriate size reduction method, such as spiral jet milling, fluid bed jet milling, supercritical fluid processing, high pressure homogenization, or spray drying.

Capsules, blisters and cartridges (made, for example, from gelatin or hydroxypropylmethyl cellulose) for use in an inhaler or insufflator may be formulated to contain a powder mixture of the active compound, a suitable powder base such as lactose or starch, and a performance modifier such as L-leucine, mannitol, or magnesium stearate. The lactose may be anhydrous or monohydrated. Other suitable excipients include dextran, glucose, maltose, sorbitol, xylitol, fructose, sucrose, and trehalose.

A suitable solution formulation for use in an atomizer using electrohydrodynamics to produce a fine mist may contain from about 1 μg to about 20 mg of the API per actuation and the actuation volume may vary from about 1 μL to about 100 μL. A typical formulation may comprise one or more compounds of Formula 1, propylene glycol, sterile water, EtOH, and NaCl. Alternative solvents, which may be used instead of propylene glycol, include glycerol and polyethylene glycol.

Formulations for inhaled administration, intranasal administration, or both, may be formulated to be immediate or modified release using, for example, PGLA. Suitable flavors, such as menthol and levomenthol, or sweeteners, such as saccharin or sodium saccharin, may be added to formulations intended for inhaled/intranasal administration.

In the case of dry powder inhalers and aerosols, the dosage unit is determined by means of a valve that delivers a metered amount. Units are typically arranged to administer a metered dose or "puff" containing from about 10 μg to about 1000 μg of the API. The overall daily dose will typically range from about 100 μg to about 10 mg which may be administered in a single dose or, more usually, as divided doses throughout the day.

The active compounds may be administered rectally or vaginally, e.g., in the form of a suppository, pessary, or enema. Cocoa butter is a traditional suppository base, but various alternatives may be used as appropriate. Formulations for rectal or vaginal administration may be formulated to be immediate or modified release as described above.

Compounds of Formula 1 may also be administered directly to the eye or ear, typically in the form of drops of a micronized suspension or solution in isotonic, pH-adjusted, sterile saline. Other formulations suitable for ocular and aural administration include ointments, gels, biodegradable implants (e.g. absorbable gel sponges, collagen), non-biodegradable implants (e.g. silicone), wafers, lenses, and particulate or vesicular systems, such as niosomes or liposomes. The formulation may include one or more polymers and a preservative, such as benzalkonium chloride. Typical polymers include crossed-linked polyacrylic acid, polyvinylalcohol, hyaluronic acid, cellulosic polymers (e.g., hydroxypropylmethylcellulose, hydroxyethylcellulose, methyl cellulose), and heteropolysaccharide polymers (e.g., gelan gum). Such formulations may also be delivered by iontophoresis. Formulations for ocular or aural administration may be formulated to be immediate or modified release as described above.

To improve their solubility, dissolution rate, taste-masking, bioavailability, or stability, compounds of Formula 1 may be combined with soluble macromolecular entities, including cyclodextrin and its derivatives and polyethylene glycol-containing polymers. For example, API-cyclodextrin complexes are generally useful for most dosage forms and routes of administration. Both inclusion and non-inclusion complexes may be used. As an alternative to direct complexation with the API, the cyclodextrin may be used as an auxiliary additive, i.e. as a carrier, diluent, or solubilizer. Alpha-, beta- and gamma-cyclodextrins are commonly used for these purposes. See, e.g., WO 91/11172, WO 94/02518, and WO 98/55148.

As noted above, one or more compounds of Formula 1, including compounds specifically named above, and their pharmaceutically active complexes, salts, solvates and hydrates, may be combined with each other or with one or more other active pharmaceutically active compounds to treat various diseases, conditions and disorders. In such cases, the active compounds may be combined in a single dosage form as described above or may be provided in the form of a kit which is suitable for coadministration of the compositions. The kit comprises (1) two or more different pharmaceutical compositions, at least one of which contains a compound of Formula 1; and (2) a device for separately retaining the two pharmaceutical compositions, such as a divided bottle or a divided foil packet. An example of such a kit is the familiar blister pack used for the packaging of tablets or capsules. The kit is suitable for administering different types of dosage forms (e.g., oral and parenteral) or for administering different pharmaceutical compositions at separate dosing intervals, or for titrating the different pharmaceutical compositions against one another. To assist with patient compliance, the kit typically comprises directions for administration and may be provided with a memory aid.

For administration to human patients, the total daily dose of the claimed and disclosed compounds is typically in the range of about 0.1 mg to about 3000 mg depending on the route of administration. For example, oral administration may require a total daily dose of from about 1 mg to about 3000 mg, while an intravenous dose may only require a total daily dose of from about 0.1 mg to about 300 mg. The total daily dose may be administered in single or divided doses and, at the physician's discretion, may fall outside of the typical ranges given above. Although these dosages are based on an average human subject having a mass of about 60 kg to about 70 kg, the physician will be able to determine the appropriate dose for a patient (e.g., an infant) whose mass falls outside of this weight range.

As noted above, the compounds of Formula 1 may be used to treat diseases, disorders, and conditions for which activation of SSTR4 is indicated. Such diseases, disorders, and conditions generally relate to any unhealthy or abnormal state in a subject for which the activation of SSTR4 provides a therapeutic benefit. More particularly, the compounds of Formula 1 may be used to treat CNS diseases, disorders or conditions, including Alzheimer's disease, and other forms of dementia (i.e., major or mild neurocognitive disorders) associated with one or more medical conditions, including frontotemporal lobar degeneration, Lewy body disease, vascular disease, traumatic brain injury, substance or medication use, HIV infection, prion disease, Parkinson's disease, and Huntington's disease. The compounds of Formula 1 may also be used to treat major or mild neurocognitive disorders associated with depression, schizophrenia, bipolar disorder, and autism. In addition, the compounds of Formula 1 may be used to treat anxiety and to treat epilepsy.

The claimed and disclosed compounds may be combined with one or more other pharmacologically active compounds or therapies to treat one or more disorders, diseases or conditions for which SSTR4 is indicated. Such combinations may offer significant therapeutic advantages, including fewer side effects, improved ability to treat underserved patient populations, or synergistic activity. For example, compounds of Formula 1, which include compounds specifically named above, and their pharmaceutically acceptable complexes, salts, solvates and hydrates, may be administered simultaneously, sequentially or separately in combination with one or more compounds or therapies for treating Alzheimer's disease, including beta-secretase inhibitors, gamma-secretase inhibitors, HMG-CoA reductase inhibitors, nonsteroidal anti-inflammatory drugs (NSAIDs, such as apazone, aspirin, celecoxib, diclofenac (with and without misoprostol), diflunisal, etodolac, fenoprofen, flurbiprofen, ibuprofen, indomethacin, ketoprofen, meclofenamate sodium, mefenamic acid, meloxicam, nabumetone, naproxen, oxaprozin, phenylbutazone, piroxicam, choline and magnesium salicylates, salsalate, and sulindac), vitamin E, and anti-amyloid antibodies. Specific examples of compounds used to treat Alzheimer's disease include donepezil, rivastigmine, memantine, and galantamine.

In addition to drugs used to improve cognition, the compounds of Formula 1 may be combined with sedatives, hypnotics, anxiolytics, antipsychotics, tranquilizers, and other medications that are used in the treatment of Alzheimer's disease. For example, the compounds of Formula 1 may be combined with one or more agents for treating depression (antidepressants) and/or schizophrenia (atypical or typical antipsychotics) including amitriptyline, amoxapine, aripiprazole, asenapine, bupropion, chlordiazepoxide, citalopram, chlorpromazine, clozapine, desipramine, desvenlafaxine, doxepin, duloxetine, escitalopram, fluoxetine, fluoxetine, fluphenazine, haloperidol, iloperidone, imipramine, isocarboxazid, lamotrigine, levomilnacipran, lurasidone, mirtazapine, nefazodone, nortriptyline, olanzapine, paliperidone, paroxetine, perphenazine, phenelzine, protriptyline, quetiapine, risperidone, selegiline, sertraline, tranylcypromine, trazodone, trimipramine, venlafaxine, vilazodone, and vortioxetine, and ziprasidone.

Likewise, the compounds of Formula 1 may be combined with one or more agents for treating anxiety (anxiolytics) including benzodiazepines (alprazolam, chlordiazepoxide, clobazepam, clonazepam, clorazepate, diazepam, estazolam, flurazepam, lorazepam, midazolam, oxazepam, prazepam, quazepam, temazepam, and triazolam), antihistamines (hydroxyzine), non-benzodiazepines (eszopiclone, zaleplon, zolpidem, and zopiclone) and buspirone.

The compounds of Formula 1 may also be combined with one or more agents for treating epilepsy (antiepileptics or anticonvulsants) including acetazolamide, carbamazepine, clobazam, clonazepam, eslicarbazepine acetate, ethosuximide, gabapentin, lacosamide, lamotrigine, levetiracetam, nitrazepam, oxcarbazepine, perampanel, piracetam, phenobarbital, phenytoin, pregabalin, primidone, retigabine, rufinamide, sodium valproate, stiripentol, tiagabine, topiramate, vigabatrin, and zonisamide.

Biological Activity

The biological activity of the compound of Formula 1 with respect to SSTR4 may be determined using the following in vitro and in vivo methods.

Inhibition of Forskolin Stimulated cAMP in Cells Overexpressing SSTR4

This cell-based assay measures the ability of compounds to inhibit forskolin stimulated cAMP in CHO-K1 cells overexpressing SSTR4. CHO-K1 cells overexpressing SSTR4 (CHO-SSTR4) are purchased from DiscoveRx (product code 95-0059C2). The CHO-SSTR4 cells are maintained in F12K media with 10% Fetal Bovine Serum (Hyclone), 1% Pen/Strep (Life Technologies), and 800 μg/mL G418 (Life Technologies). To perform the assay, 3000 cells are plated per well in white 384-well plate (Corning 3570) in 50 μL complete media and the cells are allowed to attach for 16 hours in a 37° C., 5% $CO_2$ incubator. The next day, the culture media is removed from the cells and the cells are washed (added then removed) with Krebs Ringer Buffer (ZenBio, KRB-1000 mL). Test compounds are suspended in DMSO and diluted in stimulation buffer: Krebs Ringer Buffer plus 0.5% BSA (Roche), 300 μM IBMX (Sigma), and 350 nM forskolin (Sigma). The cells are incubated in 10 μL compound/stimulation buffer for 30 minutes at room temperature. Cellular cAMP levels are detected with a HTRF LANCE Ultra cAMP kit (Perkin Elmer, catalog number TRF0264).

The assay is performed in accordance with the manufacturer's instructions. Five μL of diluted Eu-W8044 labeled streptavidin (dilution: 1:50 in cAMP Detection Buffer) is added to each well. Then 5 μL of diluted biotin cAMP (dilution: 1:150 in cAMP Detection Buffer) is added to each well. The plates are covered and allowed to incubate for 60 minutes at room temperature on a shaker. HTRF (665 nm/615 nm) is read on a Perkin Elmer ENVISION plate reader. The $pEC_{50}$ values are generated using Activity Base for Screening Data Management.

SSTR4 I-125 Somatostatin Competition Binding Assay

This membrane-based assay measures the ability of compounds to competitively inhibit binding of I-125 labeled somatostatin to SSTR4 in membranes from CHO-K1 that overexpress SSTR4. Membranes from CHO-K1 cells overexpressing SSTR4 are purchased from Perkin Elmer (catalog number ES-524-M400UA). Test compounds are suspended in DMSO and then diluted in assay buffer (25 mM HEPES pH 7.4, 10 mM $MgCl_2$, 1 mM $CaCl_2$, 0.5% BSA) plus 0.2 nM I-125 labeled somatostatin (Perkin Elmer catalog number NEX389). Fifty μL of compound/I-125 somatostatin in assay buffer are added per well to 96-well poly-propylene plate. Then 1 μg of SSTR4 membranes in 50 μL assay buffer are added per well. The Plate is incubated for 60 minutes at room temperature. FilterMat A filters (Perkin Elmer catalog number 1450-421) are pre-soaked in 0.5% PEI (Sigma catalog number P3143). The contents of the assay plate are transferred to filters with a TomTech harvester and washed 5 times with 20 mM HEPES, 100 mM NaCl. The filters are dried in a microwave oven then transferred to sample bag containing a scintillator sheet (Perkin Elmer catalog number 1450-441). The scintillator sheets are melted to filters using a heat block. The filters are then read in a MicroBeta scintillation counter. Binding Ki curves are generated using Activity Base for Screening Data Management and the results are reported as $pIC_{50}$.

SSTR1 I-125 Somatostatin Competition Binding Assay for Selectivity Versus SSTR1

This membrane-based assay measures the ability of compounds to competitively inhibit binding of I-125 labeled somatostatin to SSTR1 in membranes from CHO-K1 that overexpress SSTR1. Membranes from CHO-K1 cells overexpressing SSTR1 are purchased from Perkin Elmer (catalog number ES-520-M400UA). Test compounds are suspended in DMSO and then diluted in assay buffer (25 mM HEPES pH 7.4, 10 mM $MgCl_2$, 1 mM $CaCl_2$), 0.5% BSA) plus 0.4 nM I-125 labeled somatostatin (Perkin Elmer catalog number NEX389). Fifty μL of compound/I-125 somatostatin in assay buffer are added per well to 96-well poly-propylene plate. Then 10 μg of SSTR1 membranes in 50 μL assay buffer are added per well. The plate is incubated for 60 minutes at room temperature. FilterMat A filters (Perkin Elmer catalog number 1450-421) are pre-soaked in 0.5% PEI (Sigma catalog number P3143). The contents of the assay plate are transferred to filters with a TomTech harvester and washed 5 times with 20 mM HEPES, 100 mM NaCl. The filters are dried in a microwave oven then transferred to sample bag containing a scintillator sheet (Perkin Elmer catalog number 1450-441). The scintillator sheets are melted to the filters using a heat block. The filters are then read in a MicroBeta scintillation counter. Binding Ki curves are generated using Activity Base for Screening Data Management and the results are reported as $pIC_{50}$.

In vivo Screening Using Subcutaneous Pentylenetetrazole (PTZ)

Swiss-Webster mice, 6-8 weeks old are used in the subcutaneous PTZ model of seizures. PTZ is a GABAergic agent that blocks GABA receptors, thereby disinhibiting all CNS systems and inducing seizures in animals. Seizures can be assessed and quantified by observation of the animals in the study. Thus, this model provides a screening model to test compounds with anti-convulsant activity in mice, which is derived from the activity of the compound on the inhibitory receptor SSTR4. In accordance with the method, Swiss-Webster mice which are 6 to 8 weeks old are acclimatized to the study room prior to start the experiment (1 hour). Animals (n=6/group) are then blindly dosed with vehicle or test compound, and 15 minutes later are dosed subcutaneously with PTZ. Animals are scored based on the time it takes them to get a seizure that impairs their capacity to stand. The time is scored as latency to seizure. Number and degree of seizures are also scored, but not used in the final data.

EXAMPLES

The following examples are intended to be illustrative and non-limiting and represent specific embodiments of the present invention.

$^1H$ Nuclear magnetic resonance (NMR) spectra were obtained for many of the compounds in the following examples. Characteristic chemical shifts (6) are given in parts-per-million downfield from tetramethylsilane using conventional abbreviations for designation of major peaks, including s (singlet), d (doublet), t (triplet), q (quartet), m (multiplet), and br (broad). The following abbreviations are used for common solvents: $CDCl_3$ (deuterochloroform), DMSO-$d_6$ (deuterodimethylsulfoxide), $CD_3OD$ (deuteromethanol), $CD_3CN$ (deuteroacetonitrile), and THF-$d_8$ (deuterotetrahydrofuran). The mass spectra (m/z for $[M+H]^+$) were recorded using either electrospray ionization (ESI-MS) or atmospheric pressure chemical ionization (APCI-MS) mass spectrometry.

Where indicated, products of certain preparations and examples are purified by mass-triggered HPLC, flash chromatography, preparative TLC or SFC. Reverse phase chromatography is typically carried out on a column (e.g., Phenomenex Gemini® C18, 5 μm, ID 30 mm×150 mm) under acidic conditions ("acid mode") eluting with ACN and water mobile phases containing 0.035% and 0.05% trifluoroacetic acid (TFA), respectively, or under basic conditions ("basic mode," pH 9.5-10) eluting with water and 20/80 (v/v) water/acetonitrile mobile phases, both containing 10 mM $NH_4HCO_3$. Preparative TLC is typically carried out on silica gel 60 $F_{254}$ plates. The preparations and examples may employ SFC to separate enantiomers. After isolation by chromatography, the solvent is removed and the product is obtained by drying in a centrifugal evaporator (e.g., GeneVac™), rotary evaporator, evacuated flask, etc. Reactions in an inert (e.g., nitrogen) or reactive (e.g., $H_2$) atmosphere are typically carried out at a pressure of about 1 atmosphere (14.7 psi).

PREPARATION 1: 2-(7-methylbenzo[d]isoxazol-3-yl)propan-2-amine

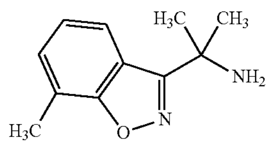

STEP A: tert-butyl (1-(3-chloro-2-fluorophenyl)-1-hydroxy-2-methylpropan-2-yl)carbamate

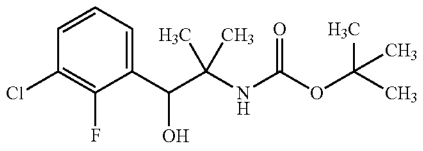 [SMILES: CC(C)(C)OC(=O)NC(C)(C)C(O)c1cccc(Cl)c1F]

To a solution of 1-chloro-2-fluorobenzene (5.3 g, 40.6 mmol) in THE (60 mL) was added n-BuLi (1.6 M in hexane, 16 mL, 25.6 mmol) dropwise at −78° C. The mixture was stirred at −78° C. for 1 hour. Next, a solution of tert-butyl N-(1,1-dimethyl-2-oxo-ethyl)carbamate (2.00 g, 10.15 mmol) in THE (10 mL) was added at −78° C. The mixture was stirred at −78° C. for another hour and then was poured into saturated aqueous $NH_4Cl$ (80 mL) and extracted with EtOAc (200 mL×2). The combined organic layers were dried over $Na_2SO_4$, filtered, and concentrated in vacuo. The residue was purified by flash silica column chromatography, using a gradient of petroleum ether/EtOAc (1:0 to 10:1), to give the title compound as a white solid (3.1 g, 86%). ESI-MS m/z $[M+H]^+$ 318.1.

STEP B: tert-butyl (1-(3-chloro-2-fluorophenyl)-2-methyl-1-oxopropan-2-yl)carbamate

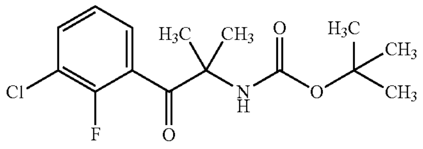 [SMILES: CC(C)(C)OC(=O)NC(C)(C)C(=O)c1cccc(Cl)c1F]

To a solution of tert-butyl (1-(3-chloro-2-fluorophenyl)-1-hydroxy-2-methylpropan-2-yl)carbamate (3.0 g, 8.50 mmol) in DCM (60 mL) was added DMP (3.93 g, 9.26 mmol) at 0° C. The mixture was stirred at 25° C. for 12 hours and then was adjusted to pH 8 by adding aqueous $NaHCO_3$. The organic layer was separated, and the aqueous layer was extracted with EtOAc (150 mL×2). The combined organic layers were dried over $Na_2SO_4$, filtered and concentrated in vacuo. The residue was purified by flash silica column chromatography, using a gradient of petroleum ether/EtOAc (1:0 to 10:1), to give the title compound as a white solid (2.3 g, 81%). ESI-MS m/z $[M+H]^+$ 316.1.

STEP C: tert-butyl (Z)-(1-(3-chloro-2-fluorophenyl)-1-(hydroxyimino)-2-methylpropan-2-yl)carbamate

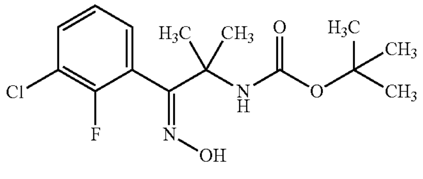 [SMILES: CC(C)(C)OC(=O)NC(C)(C)/C(=N\O)c1cccc(Cl)c1F]

To a solution of tert-butyl (1-(3-chloro-2-fluorophenyl)-2-methyl-1-oxopropan-2-yl)carbamate (2.3 g, 6.92 mmol) in EtOH (40 mL) were added NaOAc (2.84 g, 34.6 mmol) and $NH_2OH{\cdot}HCl$ (2.40 g, 34.6 mmol). The mixture was stirred at 90° C. for 12 hours and then was diluted with water (20 mL) and extracted with EtOAc (100 mL×2). The combined organic layers were dried over $Na_2SO_4$, filtered, and concentrated in vacuo. The residue was purified by flash silica column chromatography, using a gradient of petroleum ether/EtOAc (1:0 to 5:1), to give the title compound as a white solid (2.1 g, 87%). ESI-MS m/z $[M+H]^+$ 331.1.

STEP D: tert-butyl (2-(7-chlorobenzo[d]isoxazol-3-yl)propan-2-yl)carbamate

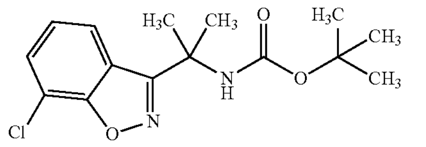 [SMILES: CC(C)(C)OC(=O)NC(C)(C)c1noc2c(Cl)cccc12]

To a solution of tert-butyl (Z)-(1-(3-chloro-2-fluorophenyl)-1-(hydroxyimino)-2-methylpropan-2-yl)carbamate (500 mg, 1.44 mmol) in THE (160 mL) was added t-BuOK (483 mg, 4.31 mmol). The mixture was stirred at 25° C. for 2 hours. The reaction was repeated using three additional batches of tert-butyl (Z)-(1-(3-chloro-2-fluorophenyl)-1-(hydroxyimino)-2-methylpropan-2-yl)carbamate (30 mg, 300 mg and 500 mg). The four batches were combined and diluted with EtOAc (300 mL). The organic layer was washed with water (300 mL×2) and then with brine (300 mL×2), dried over $Na_2SO_4$, filtered, and concentrated in vacuo. The residue was purified by flash silica column chromatography, using a gradient of petroleum ether/EtOAc (1:0 to 5:1), to give the title compound as a white solid (900 mg, 64% yield, 94% purity). ESI-MS m/z $[M+H]^+$ 311.1.

STEP E: tert-butyl (2-(7-methylbenzo[d]isoxazol-3-yl)propan-2-yl)carbamate

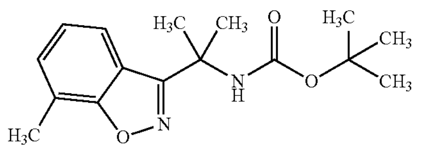 [SMILES: Cc1cccc2c(C(C)(C)NC(=O)OC(C)(C)C)noc12]

A mixture of tert-butyl (2-(7-chlorobenzo[d]isoxazol-3-yl)propan-2-yl)carbamate (900 mg, 2.72 mmol, 94% purity), methylboronic acid (818 mg, 13.7 mmol), $Pd(OAc)_2$ (122 mg, 544 μmol), $K_3PO_4$ (2.89 g, 13.6 mmol) and SPhos (224 mg, 544 μmol) in toluene (20 mL) was degassed and purged with nitrogen (3×). The mixture was stirred at 120° C. for 12 hours under nitrogen atmosphere and then was concentrated in vacuo. The residue was purified by flash silica column chromatography, using a gradient of petroleum ether/EtOAc (1:0 to 3:1), to give the title compound as a white solid (600 mg, 71%). ESI-MS m/z $[M+H]^+$ 291.1.

STEP F: 2-(7-methylbenzo[d]isoxazol-3-yl)propan-2-amine

To a solution of tert-butyl (2-(7-methylbenzo[d]isoxazol-3-yl)propan-2-yl)carbamate (550 mg, 1.78 mmol) in DCM (20 mL) was added TFA (3.76 mL, 50.8 mmol) at 0° C. The mixture was stirred at 25° C. for 0.5 hours and then was concentrated in vacuo. The residue was diluted with EtOAc (20 mL) and washed with aqueous $Na_2CO_3$ (3×20 mL). The organic layer was dried over $Na_2SO_4$, filtered and concentrated in vacuo. The product was purified by preparative TLC on silica, using DCM/MeOH (10:1) as eluent, to give the title compound as a yellow oil (203.4 mg, 58%). $^1H$ NMR (400 MHz, $CDCl_3$) δ ppm 1.69 (s, 6H), 2.57 (s, 3H), 7.18-7.24 (m, 1H), 7.29-7.33 (m, 1H), 7.69 (d, J=8.2 Hz, 1H), ESI-MS m/z $[M+H]^+$ 191.1.

PREPARATION 2: 2-(isoquinolin-1-yl)propan-2-amine

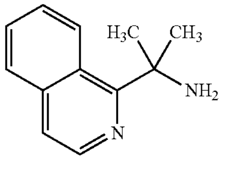

STEP A: (R,E)-N-(1-(isoquinolin-1-yl)ethylidene)-2-methylpropane-2-sulfinamide

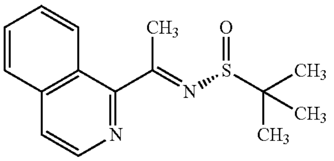 [SMILES: C/C(=N\[S@](=O)C(C)(C)C)c1nccc2ccccc12]

To a solution of 1-(1-isoquinolyl)ethanone (9.00 g, 52.6 mmol) in THE (100 mL) were added (R)-2-methylpropane-2-sulfinamide (7.65 g, 63.1 mmol) and $Ti(OEt)_4$ (17.4 mL, 84.1 mmol) at 15° C. The mixture was stirred at 70° C. for 8 hours under nitrogen and then was diluted with EtOAc (100 mL) and quenched with water (5 mL) at 0° C. The mixture was stirred for 0.5 hours and the resulting brown suspension was filtered through a pad of Celite®. The filtrate was washed with brine (10 mL 3×), dried, filtered and concentrated in vacuo. The crude product was purified by flash silica column chromatography, using a gradient of petroleum ether/EtOAc (1:0 to 3:1), to give the title compound (5.7 g, 39%). ESI-MS m/z $[M+H]^+$ 275.1.

STEP B: (R)—N-(2-(isoquinolin-1-yl)propan-2-yl)-2-methylpropane-2-sulfinamide

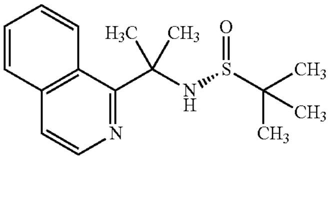 [SMILES: CC(C)(N[S@](=O)C(C)(C)C)c1nccc2ccccc12]

To a solution of (R,E)-N-(1-(isoquinolin-1-yl)ethylidene)-2-methylpropane-2-sulfinamide (13.5 g, 49.2 mmol) in toluene (260 mL) was added MeMgBr (3 M in $Et_2O$, 49.2 mL) at 0° C. The mixture was stirred at 0° C. for 2 hours under nitrogen and then was quenched with saturated aqueous $NH_4Cl$ (150 mL) at 0° C. The mixture was warmed to 15° C. and extracted with EtOAc (3×200 mL). The combined organic layers were dried, filtered and concentrated in vacuo. The crude product was purified by flash silica column chromatography, using a gradient of petroleum ether/EtOAc (1:0 to 1:1), to give the title compound (10 g, 70%). ESI-MS m/z $[M+H]^+$ 291.1.

STEP C: 2-(isoquinolin-1-yl)propan-2-amine

To a solution of (R)—N-(2-(isoquinolin-1-yl)propan-2-yl)-2-methylpropane-2-sulfinamide (5.0 g, 17.2 mmol) in MeOH (100 mL) was added HCl (4 M in dioxane, 25.8 mL) at 15° C. The mixture was stirred at 15° C. for 2 hours and then was concentrated in vacuo. The crude product was triturated with EtOAc (3×20 mL) at 15° C. for 0.5 hours. The resulting suspension was filtered, and the filter cake was dried under vacuum to give a bis-HCl salt of the title compound as a white solid (3.9 g, 87%). $^1H$ NMR (400 MHz, DMSO-$d_6$) δ ppm 1.94 (s, 6H), 7.71-7.76 (m, 1H), 7.84 (t, J=7.3 Hz, 1H), 7.92 (d, J=5.6 Hz, 1H), 8.10 (d, J=7.8 Hz, 1H), 8.45-8.52 (m, 2H), 8.66 (br s, 3H); ESI-MS m/z $[M+H]^+$ 187.2.

PREPARATION 3:
3-(azetidin-1-yl)-2-methylpropanoic acid

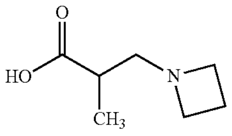

STEP A: methyl
3-(azetidin-1-yl)-2-methylpropanoate

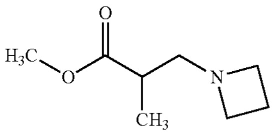

To a round-bottomed flask containing methyl 2-methylprop-2-enoate (5.91 g, 59.1 mmol) in MeOH (4 mL) was added azetidine (1.00 g, 17.5 mmol). The reaction mixture was stirred at 15° C. for 16 hours and then was quenched with water (100 mL) and extracted with DCM (80 mL). The organic layer was washed with water (2×50 mL) and with brine (2×50 mL), dried over $Na_2SO_4$, filtered and concentrated in vacuo. The residue was purified by flash silica column chromatography, using DCM as the eluent, to give the title compound as a colorless oil (0.8 g, 29%). ESI-MS m/z $[M+H]^+$ 158.1.

STEP B: 3-(azetidin-1-yl)-2-methylpropanoic acid

To a round-bottomed flask containing methyl 3-(azetidin-1-yl)-2-methylpropanoate (0.2 g, 1.27 mmol) in THE (5 mL) was added LiOH·$H_2O$ (2 M aqueous, 1.11 mL, 2.22 mmol). The reaction mixture was stirred at 15° C. for 16 hours and was then diluted with EtOAc (10 mL). The aqueous layer was adjusted to pH 5-6 with HCl (1 M), washed with DCM (2×30 mL) and lyophilized to give an HCl salt of the title compound as a white semi-solid (270 mg). $^1H$ NMR (400 MHz, $CD_3OD$) δ ppm 1.17 (d, J=7.3 Hz, 3H), 2.38-2.54 (m, 3H), 3.11-3.29 (m, 2H), 4.06-4.24 (m, 4H); ESI-MS m/z $[M+H]^+$ 144.1.

PREPARATION 4: 1-(((3-methylpyridin-2-yl)oxy)methyl)cyclopropan-1-amine

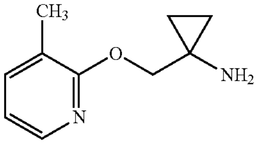

To a solution of (1-aminocyclopropyl)methanol HCl salt (3.80 g, 30.8 mmol) in dioxane (80 mL) was added NaH (60 wt % in mineral oil, 1.73 g, 43.2 mmol) portion-wise at 20° C. The mixture was stirred for 30 minutes. Next, 2-fluoro-3-methylpyridine (1.09 mL, 10.8 mmol) was added. The reaction mixture was stirred at 100° C. for 68.5 hours and then was diluted with water (50 mL) and extracted with DCM (2×300 mL). The combined organic layers were washed with brine (30 mL), dried over $Na_2SO_4$, filtered and concentrated in vacuo. The product was purified by preparative HPLC (Phenomenex Gemini® C18, 10 μm, ID 25 mm×150 mm) using a gradient of 23-53% water (with 0.04% $NH_4OH$ and 10 mM $NH_4HCO_3$) in ACN. The product-containing fraction was concentrated to give the title compound as a light-yellow oil (142 mg, 28%). $^1H$ NMR (400 MHz, DMSO-$d_6$) δ ppm 0.49-0.53 (m, 2H), 0.54-0.58 (m, 2H), 1.99 (br s, 2H), 2.17 (s, 3H), 4.15 (s, 2H), 6.85 (dd, J=7.2, 5.1 Hz, 1H), 7.51 (d, J=7.0 Hz, 1H), 7.89-7.97 (m, 1H); ESI-MS m/z $[M+H]^+$ 179.2.

PREPARATION 5: 1-(((3-methylpyridin-2-yl)oxy)methyl)cyclobutan-1-amine

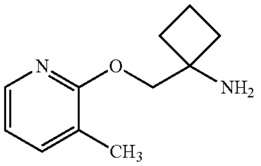

The title compound was prepared like PREPARATION 4, using (1-aminocyclobutyl)methanol (1.37 g, 13.5 mmol), and was obtained as a light-yellow oil (152.2 mg, 17.5%). $^1H$ NMR (400 MHz, DMSO-$d_6$) δ ppm 1.57-1.74 (m, 2H), 1.77-1.86 (m, 2H), 2.01 (br d, J=8.3 Hz, 2H), 2.13 (s, 3H), 4.10 (s, 2H), 6.84 (dd, J=7.0, 5.0 Hz, 1H), 7.49 (d, J=6.6 Hz, 1H), 7.93 (br d, J=2.9 Hz, 1H); ESI-MS m/z $[M+H]^+$ 193.2.

PREPARATION 6: 1-(((3-methylpyridin-2-yl)oxy)methyl)cyclopentan-1-amine

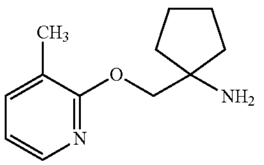

The title compound was prepared like PREPARATION 4, using (1-aminocyclopentyl)methanol (1.55 g, 13.5 mmol), and was obtained as a light-yellow oil (110 mg, 12%). $^1$H NMR (400 MHz, DMSO-$d_6$) δ ppm 1.38-1.47 (m, 2H), 1.57 (dt, J=8.5, 5.8 Hz, 2H), 1.60-1.66 (m, 2H), 1.72-1.79 (m, 2H), 2.15 (s, 3H), 4.06 (s, 2H), 6.83-6.88 (m, 1H), 7.48-7.53 (m, 1H), 7.94 (dd, J=5.0, 1.2 Hz, 1H); ESI-MS m/z $[M+H]^+$ 207.2.

PREPARATION 7: (R)-2-(1-methylpyrrolidin-2-yl)acetic acid

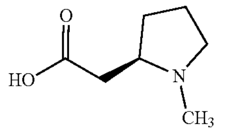

To (R)-2-(pyrrolidin-2-yl)acetic acid HCl salt (2.5 g, 15.1 mmol) and aqueous formaldehyde (37 wt %, 5.84 mL, 78.5 mmol) in MeOH (40 mL) was added Pd/C (10 wt %, 800 mg). The mixture was stirred at 30° C. for 16 hours under $H_2$ (50 psi) and then was filtered. The filtrate was concentrated in vacuo and then taken up in EtOAc (10 mL). The mixture was stirred for 20 minutes. The solids were collected by filtration and co-evaporated with toluene (2 mL) to give an HCl salt of the title compound as a white solid (2.4 g, 89%). $^1$H NMR (400 MHz, DMSO-$d_6$) δ ppm 1.59-1.71 (m, 1H), 1.84-2.00 (m, 2H), 2.20-2.30 (m, 1H), 2.67-2.78 (m, 4H), 3.05 (br dd, J=16.6, 4.5 Hz, 2H), 3.40-3.60 (m, 2H), 10.15-12.66 (m, 2H); ESI-MS m/z $[M+H]^+$ 144.2.

PREPARATION 8: (S)-2-(1-methylpyrrolidin-2-yl)acetic acid

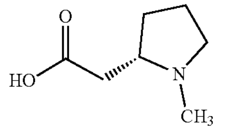

An HCl salt of the title compound was prepared like PREPARATION 7, using (S)-2-(pyrrolidin-2-yl)acetic acid HCl salt (1.68 g, 13.0 mmol), aqueous formaldehyde (37 wt %, 5.04 mL, 67.7 mmol) and Pd/C (10 wt %, 510 mg) in MeOH (30 mL), and was obtained as a white solid (1.8 g, 77%). $^1$H NMR (400 MHz, DMSO-$d_6$) δ ppm 1.59-1.73 (m, 1H), 1.82-2.03 (m, 2H), 2.20-2.35 (m, 1H), 2.64-2.82 (m, 4H), 2.94-3.09 (m, 2H), 3.41-3.66 (m, 2H), 9.97-13.14 (m, 2H); ESI-MS m/z $[M+H]^+$ 144.2.

PREPARATION 9: 2-(3-fluoro-2-methoxyphenyl)propan-2-amine

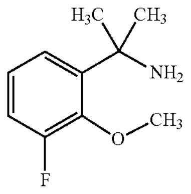

STEP A: 2-(3-fluoro-2-methoxyphenyl)propan-2-ol

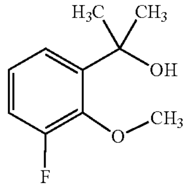

To a solution of 1-bromo-3-fluoro-2-methoxybenzene (1.00 g, 4.88 mmol) in THE (20 mL) was added i-PrMgCl (2.0 M in THF, 5.37 mL, 10.7 mmol) dropwise at 0° C. under nitrogen. The mixture was stirred at 0° C. for 2 hours. Next, acetone (340 mg, 5.85 mmol) in THE (5 mL) was added. The reaction mixture was stirred at 0° C. for another 30 minutes and then quenched with saturated aqueous $NH_4Cl$ (50 mL) at 20° C. and extracted with EtOAc (2×50 mL). The combined organic layers were dried, filtered, and concentrated under reduced pressure. The crude product was purified by flash silica column chromatography, using a gradient of petroleum ether/EtOAc (1:0 to 3:1), to give the title compound (197 mg, 20% yield, 90% purity). ESI-MS m/z $[M-OH]^+$ 167.1.

STEP B: 2-(3-fluoro-2-methoxyphenyl)propan-2-amine

To a mixture of 2-(3-fluoro-2-methoxyphenyl)propan-2-ol (1.50 g, 7.74 mmol) in toluene (20 mL) were added $TMSN_3$ (1.07 g, 9.29 mmol) and $BF_3 \cdot OEt_2$ (1.32 g, 9.28 mmol) at 20° C. under nitrogen. The reaction mixture was stirred at 20° C. for 30 minutes and then quenched with $NaHCO_3$ (20 mL) at 20° C. and extracted with EtOAc (2×20 mL). The combined organic layers were washed with brine (2×30 mL), dried, filtered and concentrated under reduced pressure to give an azide, which was subsequently dissolved in THE (10 mL) and treated with $LiAlH_4$ (1 M in THF, 7.74 mL, 7.74 mmol). The reaction mixture was stirred at 20° C. for 2 hours and then quenched with water (2 mL). The mixture was treated with aqueous NaOH (2 M, 2 mL) at 20° C., diluted with brine (50 mL) and extracted with EtOAc (2×30 mL). The combined organic layers were dried, filtered, and concentrated under reduced pressure to give crude product. A second batch was prepared from 2-(3-fluoro-2-methoxy-phenyl)propan-2-ol (196 mg, 0.958 mmol). The two batches were combined and treated with HCl (4 M in dioxane, 10 mL, 40.0 mmol), stirred at 20° C. for 2 minutes, concentrated to dryness and washed with EtOAc (2×20 mL) to give an HCl salt of the title compound (800 mg, 36%). $^1$H NMR (400 MHz, $CD_3OD$) δ ppm 1.76 (s, 6H), 4.12 (d, J=3.2 Hz, 3H), 7.08-7.18 (m, 1H), 7.18-7.30 (m, 2H); ESI-MS m/z $[M-NH2]^+$ 167.1.

PREPARATION 10: 2-(3-chloro-2-methoxyphenyl)propan-2-amine

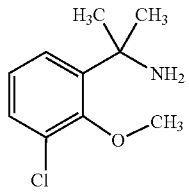

STEP A: 2-(3-chloro-2-methoxyphenyl)propan-2-ol

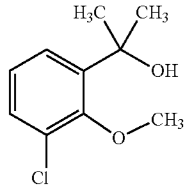

To a solution of methyl 3-chloro-2-methoxybenzoate (2.00 g, 9.97 mmol) in THE (40 mL) was added a solution of MeMgBr (3.0 M in $Et_2O$, 7.31 mL) dropwise at −78° C. under nitrogen. After 10 minutes the reaction mixture was warmed to 20° C. and stirred at 20° C. for 4 hours. The reaction mixture was then quenched with saturated aqueous $NH_4Cl$ (50 mL) at 0° C. and extracted with EtOAc (2×30 mL). The combined organic layers were dried, filtered, and concentrated under reduced pressure. The crude product was purified by flash silica column chromatography using a gradient of petroleum ether/EtOAc (1:0 to 20:1) to give the title compound as a light-yellow oil (1.75 g, 83% yield, 95% purity). ESI-MS m/z $[M-OH]^+$ 183.1.

STEP B: 2-(3-chloro-2-methoxyphenyl)propan-2-amine

The title compound was prepared like STEP B of PREPARATION 9 in which 2-(3-chloro-2-methoxyphenyl)propan-2-ol (1.84 g, 8.72 mmol), $TMSN_3$ (1.21 g, 10.5 mmol) and $BF_3 \cdot OEt_2$ (1.49 g, 10.45 mmol) in toluene (30 mL) were reacted to give an azide, which was subsequently treated with $LiAlH_4$ (1 M in THF, 8.72 mL) in THE (20 mL). Acid workup (4 M HCl in dioxane, 10 mL) gave an HCl salt of the title compound as a white solid (1.0 g, 49%). ESI-MS m/z $[M-NH_2]^+$ 183.1.

PREPARATION 11: 2-(2-methoxy-3-methylphenyl)propan-2-amine

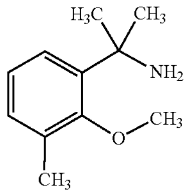

An HCl salt of the title compound was prepared like PREPARATION 10, using methyl 2-methoxy-3-methylbenzoate (1.50 g, 8.32 mmol) and MeMgBr (3.0 M in $Et_2O$, 6.10 mL, 18.3 mmol) in THE (10 mL), and was obtained as a white solid (600 mg, 33% over two steps). ESI-MS m/z $[M-NH_2]^+$ 163.1.

PREPARATION 12: 2-(3-chloro-2-methylphenyl)propan-2-amine

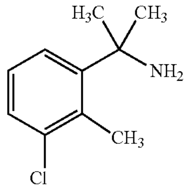

STEP A: 2-(3-chloro-2-methylphenyl)propan-2-ol

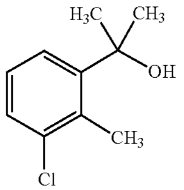

To a solution of 1-bromo-3-chloro-2-methylbenzene (5.00 g, 24.3 mmol) in THE (30 mL) was added n-BuLi (2.5 M in hexanes, 10.7 mL) dropwise at −78° C. under nitrogen. The mixture was stirred at −78° C. for 1 hour. Next, acetone (1.97 mL, 26.8 mmol) in THE (10 mL) was added and the mixture was stirred at −78° C. for another 30 minutes and then warmed to 20° C. The reaction mixture was stirred at 20° C. for 12 hours and then quenched with saturated aqueous $NH_4Cl$ (50 mL) at 20° C. and extracted with EtOAc (2×50 mL). The combined organic layers were dried, filtered and concentrated under reduced pressure. The crude product was purified by flash silica column chromatography, using a gradient of petroleum ether/EtOAc (1:0 to 5:1), to give the title compound as a light-yellow oil (3.0 g, 67% yield, 95% purity). ESI-MS m/z $[M-OH]^+$ 167.1.

STEP B: 2-(3-chloro-2-methylphenyl)propan-2-amine

The title compound was prepared like STEP B of PREPARATION 9 in which 2-(3-chloro-2-methylphenyl)propan-2- ol (1.50 g, 8.12 mmol), $TMSN_3$ (1.12 g, 9.75 mmol) and $BF_3 \cdot OEt_2$ (1.38 g, 9.75 mmol) in toluene (20 mL) were reacted to give and azide, which was subsequently treated with $LiAlH_4$ (1 M in THF, 8.12 mL, 8.12 mmol) in THE (10 mL). Acid workup (4 M HCl in dioxane, 10 mL, 40.0 mmol) gave an HCl salt of the title compound as a white solid (600 mg, 33%). ESI-MS m/z $[M-NH_2]^+$ 167.1.

PREPARATION 13: 2-(2,3-difluorophenyl)propan-2-amine

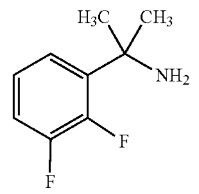

A mixture of $CeCl_3$ (4.25 g, 17.2 mmol) in THE (15 mL) was stirred under nitrogen at 20° C. for 2 hours and then cooled to −78° C. MeLi (3.1 M in diethoxymethane, 5.54 mL) was added and the mixture and stirred at −78° C. for 30 minutes. Next, 2,3-difluorobenzonitrile (800 mg, 5.75 mmol) in THE (10 mL) was added. The reaction mixture was stirred at −78° C. for 2 hours. Saturated ammonium chloride solution (2 mL) was added, followed by aqueous ammonia (28%, 4 mL). The mixture was stirred at −78° C. and then warmed to room temperature, filtered through Celite®, and washed with EtOAc (100 mL). The organic phase was washed with saturated aqueous $NaHCO_3$ (100 mL) and extracted with aqueous HCl (2 M, 50 mL). The aqueous phase was washed with EtOAc (5×50 mL), adjusted to pH 9 by treatment with $NaHCO_3$, and extracted with EtOAc (2×50 mL). The combined organic phase was dried and concentrated in vacuo. The crude product was treated with HCl in dioxane (4 M, 20 mL) and concentrated to dryness. The residue was washed with EtOAc (2×50 mL). The solid phase was collected by filtration to give an HCl salt of the title compound as a white solid (600 mg, 50%). $^1H$ NMR (400 MHz, $CD_3OD$) δ ppm 1.80 (s, 6H), 7.19-7.33 (m, 2H), 7.34-7.42 (m, 1H); ESI-MS m/z $[M+H]^+$ 172.2.

PREPARATION 14: 2-(3-fluoro-2-methylphenyl)propan-2-amine

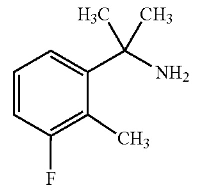

An HCl salt of the title compound was prepared like PREPARATION 13, using 3-fluoro-2-methyl benzonitrile (800 mg, 5.92 mmol), $CeCl_3$ (4.38 g, 17.8 mmol) and MeLi (3.1 M, 5.7 mL, 17.7 mmol) in THE (25 mL), and was obtained as a white solid (400 mg, 32%). ESI-MS m/z $[M-NH_2]^+$ 151.1.

PREPARATION 15: 2-(3-chloro-2-fluorophenyl)propan-2-amine

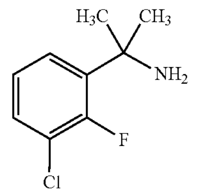

An HCl salt of the title compound was prepared like PREPARATION 13, using 3-chloro-2-fluorobenzonitrile (800 mg, 5.14 mmol), $CeCl_3$ (4.30 g, 17.4 mmol) and MeLi (3.1 M, 5.6 mL, 17.4 mmol) in THE (25 mL), and was obtained as a white solid (600 mg, 52%). ESI-MS m/z $[M+H]^+$ 188.6.

PREPARATION 16: 2-(2-chloro-3-methylphenyl)propan-2-amine

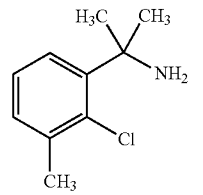

An HCl salt of the title compound was prepared like PREPARATION 13, using 2-chloro-3-methylbenzonitrile (800 mg, 5.28 mmol), $CeCl_3$ (3.90 g, 15.8 mmol) and MeLi (3.1 M, 5.08 mL, 15.7 mmol) in THE (25 mL), and was obtained as a white solid (300 mg, 25%). ESI-MS m/z $[M+H]^+$ 184.1.

PREPARATION 17: 2-(2,3-dichlorophenyl)propan-2-amine

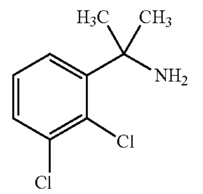

An HCl salt of the title compound was prepared like PREPARATION 13, using 2,3-dichlorobenzonitrile (1.00 g, 5.81 mmol), $CeCl_3$ (3.80 g, 15.3 mmol) and MeLi (3.1 M, 4.95 mL, 15.3 mmol) in THE (25 mL), and was obtained as a white solid (650 mg, 46%). ESI-MS m/z $[M+H]^+$ 205.1.

PREPARATION 18: 2-(1-methylpyrrolidin-2-yl)propanoic acid

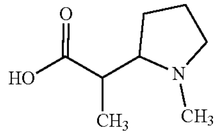

STEP A: tert-butyl 2-(2-methoxy-2-oxoethyl)pyrrolidine-1-carboxylate

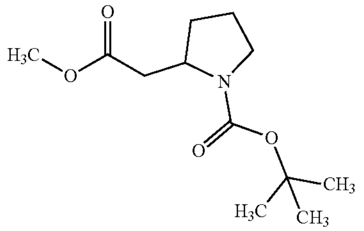 [SMILES: COC(=O)CC1CCCN1C(=O)OC(C)(C)C]

Diazomethyl(trimethyl)silane (2 M in hexane, 12 mL, 24 mmol) was added dropwise to a solution of 2-(1-tert-butoxycarbonylpyrrolidin-2-yl)acetic acid (3.00 g, 13.1 mmol) in MeOH (6 mL) and toluene (6 mL) at 0° C. The reaction mixture was stirred at 0° C. for 3 hours and then was concentrated under vacuum. The product was purified by column chromatography, eluting with petroleum ether/EtOAc (10:1). The pure fraction was concentrated to give the title compound as a light-yellow oil (3.0 g, 94%). $^{1}$H NMR (400 MHz, $CDCl_3$) δ ppm 1.47 (br s, 9H), 1.68-1.92 (m, 3H), 2.05 (br s, 1H), 2.31 (br dd, J=15.2, 9.8 Hz, 1H), 2.77-3.01 (m, 1H), 3.36 (br d, J=5.1 Hz, 2H), 3.68 (br s, 3H), 4.04-4.25 (m, 1H).

STEP B: tert-butyl 2-(1-methoxy-1-oxopropan-2-yl) pyrrolidine-1-carboxylate

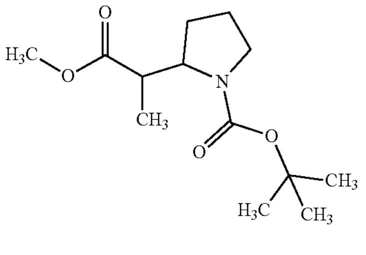 [SMILES: COC(=O)C(C)C1CCCN1C(=O)OC(C)(C)C]

To a round bottom flask containing LiHMDS (1 M in THF, 12.3 mL, 12.3 mmol) in THE (5 mL) was added tert-butyl 2-(2-methoxy-2-oxoethyl)pyrrolidine-1-carboxylate (1.00 g, 4.11 mmol) in THE (2 mL) at −78° C. The reaction mixture was stirred at −78° C. for 1 hour. Then a solution of MeI (1.23 mL, 19.7 mmol) and HMPA (1.08 mL, 6.17 mmol) in THE (3 mL) was added. The reaction mixture was stirred at −78° C. for an additional 4 hours and then was diluted with saturated aqueous $NH_4Cl$ (30 mL) and extracted with EtOAc (2×50 mL). The combined organic layers were washed with brine (20 mL), dried over $Na_2SO_4$, filtered and concentrated in vacuo. The product was purified by preparative HPLC (Phenomenex Gemini® C18, 10 μm, ID 25 mm×150 mm), using a gradient of 50-80% water (with 0.05% $NH_4OH$) in ACN, to give the title compound as a light-yellow oil (0.40 g, 35%).

STEP C: methyl 2-(pyrrolidin-2-yl)propanoate

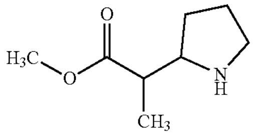

To a round bottom flask containing tert-butyl 2-(1-methoxy-1-oxopropan-2-yl)pyrrolidine-1-carboxylate (0.40 g, 1.55 mmol) in DCM (5 mL) was added TFA (1.23 g, 10.8 mmol). The reaction mixture was stirred at 15° C. for 3 hours and then was poured into ice water (5 mL) and adjusted to pH 10 by addition of saturated aqueous $Na_2CO_3$. The aqueous phase was extracted with DCM (2×50 mL), and the combined organic layers were washed with brine (20 mL), dried over $Na_2SO_4$, filtered and concentrated in vacuo to give the title compound as a light-yellow oil (330.0 mg). ESI-MS m/z $[M+H]^+$ 158.1.

STEP D: methyl 2-(1-methylpyrrolidin-2-yl)propanoate

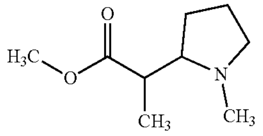

To a round bottom flask containing methyl 2-(pyrrolidin-2-yl)propanoate (0.120 g, 763 μmol) in DCE (3 mL) was added aqueous formaldehyde (37 wt %, 227 μL, 3.05 mmol) and $NaBH(OAc)_3$ (647 mg, 3.05 mmol). The reaction mixture was stirred at 15° C. for 2 hours and then was quenched with water (5 mL) and with saturated aqueous $Na_2CO_3$ (5 mL) and was extracted with DCM (2×20 mL). The combined organic layers were washed with brine (3×10 mL), dried over $Na_2SO_4$, filtered and concentrated in vacuo to give the title compound as a light-yellow oil (90.0 mg, 68%). $^{1}$H NMR (400 MHz, $CDCl_3$) δ ppm 1.11 (d, J=7.1 Hz, 1H), 1.18 (d, J=7.1 Hz, 3H), 1.58-1.78 (m, 3H), 1.84 (q, J=7.7 Hz, 2H), 2.29 (s, 1H), 2.34 (s, 3H), 2.36-2.43 (m, 1H), 2.50-2.60 (m, 1H), 2.62-2.74 (m, 1H), 3.01-3.11 (m, 1H).

STEP E: 2-(1-methylpyrrolidin-2-yl)propanoic acid

A round bottom flask was charged with methyl 2-(1-methylpyrrolidin-2-yl)propanoate (90.0 mg, 526 μmol) and aqueous HCl (3 M, 1.02 mL). The mixture was stirred at 90° C. for 16 hours and then was concentrated in vacuo to give an HCl salt of the title compound as a light-yellow gum (142 mg). $^{1}$H NMR (400 MHz, $CD_3OD$) δ ppm 1.26-1.35 (m, 3H), 1.82-1.94 (m, 1H), 2.04-2.21 (m, 3H), 2.27-2.41 (m, 1H), 2.97 (s, 3H), 3.12-3.25 (m, 2H), 3.47-3.56 (m, 1H), 3.65-3.76 (m, 1H).

PREPARATION 19: (S)-2-(azetidin-1-ylmethyl)butanoic acid

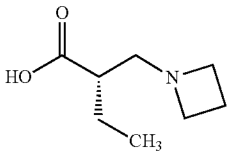

STEP A: ethyl 2-methylenebutanoate

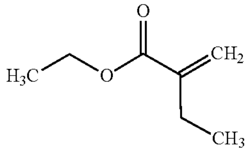

To a solution of ethyl 2-ethyl-3-oxo-butanoate (50.0 g, 316 mmol) in tetrahydrofuran (200 mL) was slowly added LiHMDS (1 M in THF, 350 mL) at −78° C. The solution was stirred for 0.5 hour. Paraformaldehyde (57.5 g, 633 mmol) was added. The mixture was stirred at 25° C. for 16.5 hours under nitrogen atmosphere and then was filtered through a pad of Celite®. The filtrate was concentrated under reduced pressure and the residue purified by flash silica column chromatography, eluting with petroleum ether/EtOAc (10:1) to give the title compound as a light-yellow liquid (35 g, 86%). $^1$HNMR (400 MHz, $CDCl_3$) δ ppm 1.08 (t, J=7.3 Hz, 3H), 1.31 (t, J=7.1 Hz, 3H), 2.33 (q, J=7.4 Hz, 2H), 4.13-4.26 (m, 2H), 5.52 (d, J=1.0 Hz, 1H), 6.13 (s, 1H).

STEP B: ethyl 2-(azetidin-1-ylmethyl)butanoate

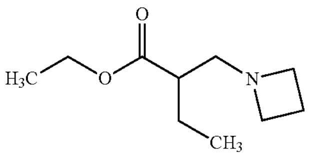

To a solution of azetidine HCl (28.1 g, 300 mmol) in ethanol (180 mL) was added $Et_3N$ (117.8 mL, 846.5 mmol) and ethyl 2-methylenebutanoate (35 g, 273 mmol). The mixture was stirred at 25° C. for 16 hours. The reaction mixture was combined with a second batch (45 g) of the reaction and was poured into water (400 mL) and extracted with DCM (2×400 mL). The combined organic layers were washed with brine (400 mL), dried over sodium sulfate, and concentrated. The crude product was purified by flash silica column chromatography, using a gradient of petroleum ether/EtOAc (10:1 to 1:1) to give the title compound as a light-yellow liquid (50 g) which was used without further purification. $^1$H NMR (400 MHz, $CDCl_3$) δ ppm 0.88 (t, J=7.5 Hz, 3H), 1.23-1.27 (m, 3H), 1.47-1.60 (m, 2H), 2.01-2.04 (m, 2H), 2.28 (tt, J=8.7, 5.6 Hz, 1H), 2.40 (dd, J=11.5, 5.6 Hz, 1H), 2.67 (dd, J=11.5, 8.8 Hz, 1H), 3.15 (sxt, J=6.8 Hz, 4H), 4.11-4.17 (m, 2H).

STEP C: lithium 2-(azetidin-1-ylmethyl)butanoate

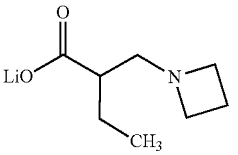

To a solution of ethyl 2-(azetidin-1-ylmethyl)butanoate (50 g, 270 mmol) in methanol (200 mL) was added $LiOH \cdot H_2O$ (11.3 g, 270 mmol) in water (50 mL). The mixture was stirred at 60° C. for 16 hours and then was concentrated to dryness to give the title compound as a light-yellow solid, which was used without purification (40 g, 91% yield). $^1$HNMR (400 MHz, DMSO-$d_6$) δ ppm 0.74-0.83 (m, 3H), 1.31-1.45 (m, 2H), 1.76-1.95 (m, 3H), 2.20 (dd, J=11.3, 6.8 Hz, 1H), 2.41-2.47 (m, 1H), 2.89-3.11 (m, 4H).

STEP D: (S)-1-phenylethyl 2-(azetidin-1-ylmethyl)butanoate

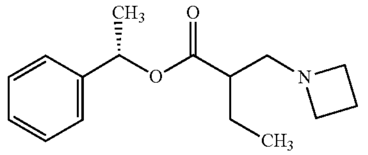 [SMILES: CCC(CN1CCC1)C(=O)O[C@@H](C)c1ccccc1]

To a mixture of lithium 2-(azetidin-1-ylmethyl)butanoate (38 g, 233 mmol) and (S)-1-phenylethan-1-ol (38.1 g, 312 mmol) in DMF (400 mL) were added EDC (89.3 g, 466 mmol) and DMAP (56.9 g, 466 mmol). The mixture was stirred at 25° C. for 16 hours and then was poured into water (250 mL) and extracted with EtOAc (2×350 mL). The combined organic layers were washed with brine (400 mL), dried over sodium sulfate, and concentrated. The reaction mixture was combined with three additional batches (24 g and 2× 1 g) of the reaction and was purified by flash silica column chromatography, using a gradient of petroleum ether/EtOAc (10:1 to 1:1) to give a colorless oil (90 g, crude). The oil was further purified by flash silica column chromatography, using a gradient of petroleum ether/EtOAc (1:0 to 5:1). The resulting colorless liquid (84 g) was purified still further by preparative HPLC (YMC Triart C18, 7 μm, ID 50 mm×250 mm) using a gradient of 45-74% ACN in water (with 0.04% $NH_4OH$+10 mM $NH_4HCO_3$) to give the title compound as a yellow liquid (38 g). $^1$HNMR (400 MHz, $CDCl_3$) δ ppm 0.75-0.94 (m, 3H), 1.46-1.65 (m, 5H), 1.92-2.03 (m, 2H), 2.27-2.51 (m, 2H), 2.61-2.77 (m, 1H), 3.01-3.28 (m, 4H), 5.86-6.01 (m, 1H), 5.93 (quin, J=6.2 Hz, 1H), 7.19-7.49 (m, 5H); ESI-MS m/z $[M+H]^+$ 262.2.

STEP E: (S)-1-phenylethyl (R)-2-(azetidin-1-ylmethyl)butanoate and (S)-1-phenylethyl (S)-2-(azetidin-1-ylmethyl)butanoate

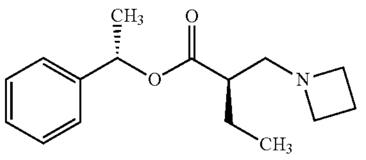

and

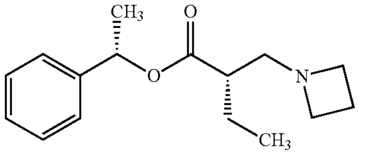

The title diastereomers of (S)-1-phenylethyl 2-(azetidin-1-ylmethyl)butanoate (35 g, 134 mmol) were separated by preparative SFC (Daicel ChiralCel OD, 10 μm, ID 50 mm×250 mm) using a mobile phase of 20% isopropanol (with 0.1% $NH_4OH$) in $CO_2$. The (S,R)-diastereomer was the first peak to elute and was obtained as a colorless oil. The (S,S)-diastereomer was the second peak to elute and was obtained as a colorless oil (17.4 g) with some (S,R) isomer remaining. Impure (S,S) diastereomer (16 g) was further separated by preparative SFC (Daicel ChiralPak IC, 10 μm, ID 50 mm×250 mm) using a mobile phase of 20% isopropanol (with 0.1% $NH_4OH$) in $CO_2$ to give the title (S,S)-diastereomer as a light-yellow oil (4.80 g, 95% purity, 99% ee). Crude (S,S)-diastereomer was also recovered as a light-yellow oil (8 g, 78% purity). ESI-MS m/z $[M+H]^+$ 262.2.

STEP F: (S)-2-(azetidin-1-ylmethyl)butanoic acid

To a suspension of $Pd(OH)_2$ on carbon (20 wt %, 1.44 g, 2.05 mmol) in methanol (100 mL) was added (S)-1-phenylethyl (S)-2-(azetidin-1-ylmethyl)butanoate (4.80 g, 17.4 mmol). The suspension was degassed under vacuum and purged with hydrogen several times. The mixture was stirred under a balloon of hydrogen (15 psi) at 25° C. for 16 hours and then was filtered through a pad of Celite®, washing the filter cake with methanol (30 mL). The combined wash and filtrate were concentrated to dryness to give the title compound as an off-white solid (2.81 g). The crude product was taken up in acetonitrile (40 mL) and concentrated to dryness to give the title compound as an off-white solid (2.7 g, 99% purity). $^1H$ NMR (400 MHz, $CD_3OD$) δ ppm 0.97 (t, J=7.5 Hz, 3H), 1.47-1.59 (m, 1H), 1.59-1.72 (m, 1H), 2.26-2.36 (m, 1H), 2.46 (quin, J=8.1 Hz, 2H), 3.13 (dd, J=12.3, 3.8 Hz, 1H), 3.26 (d, J=11.0 Hz, 1H), 4.04-4.22 (m, 4H); ESI-MS m/z $[M+H]^+$ 158.0.

PREPARATION 20: (S)-2-(azetidin-1-ylmethyl)-3-methylbutanoic acid

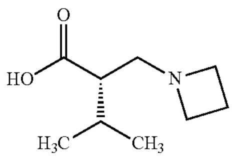

STEP A: ethyl 3-methyl-2-methylenebutanoate

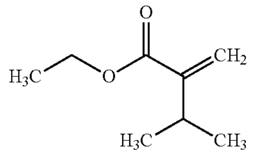

To a mixture of ethyl 2-acetyl-3-methyl-butanoate (43 g, 250 mmol) in THE (660 mL) was added LiHMDS (1 M in THF, 299.5 mL) at −78° C. The mixture was stirred at −78° C. for 0.5 hours. Paraformaldehyde (49.4 g, 549 mmol) was added. The reaction mixture was stirred at 25° C. for 16 hours and then was filtered through a pad of Celite®, washing the filter cake with petroleum ether (50 mL). The combined wash and filtrate were purified by silica column chromatography using a gradient of petroleum ether/EtOAc (1:0 to 5:1) to give title compound as a colorless liquid (140 g, 30% purity) which was used without additional purification.

STEP B: ethyl 2-(azetidin-1-ylmethyl)-3-methylbutanoate

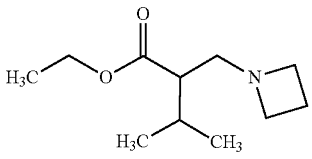

To a mixture of ethyl 3-methyl-2-methylenebutanoate (30 g, 63.3 mmol) and azetidine HCl (8.88 g, 94.9 mmol) in ethanol (50 mL) was added $Et_3N$ (44.0 mL, 316 mmol). The mixture was stirred at 25° C. for 16 hours. The reaction mixture was combined with two additional batches (8 g and 110 g) of the reaction and was diluted with water (1500 mL) and extracted with EtOAc (3×500 mL). The combined organic layers were dried over sodium sulfate and concentrated. The crude product was purified by flash silica column chromatography using a gradient of petroleum ether/EtOAc (1:0 to 2:1) to give the title compound as a colorless liquid (42 g). $^1H$ NMR (400 MHz, $CDCl_3$) δ ppm 0.91 (dd, J=15.2, 6.6 Hz, 6H), 1.22-1.29 (m, 4H), 1.80-1.89 (m, 1H), 1.97-2.06 (m, 3H), 2.14 (ddd, J=10.5, 7.3, 4.3 Hz, 1H), 2.42 (dd, J=11.5, 4.4 Hz, 1H), 2.73 (dd, J=11.4, 10.6 Hz, 1H), 3.06-3.23 (m, 4H), 4.08-4.22 (m, 2H).

STEP C: lithium 2-(azetidin-1-ylmethyl)-3-methylbutanoate

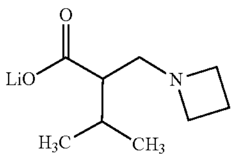

To a solution of ethyl 2-(azetidin-1-ylmethyl)-3-methylbutanoate (20 g, 100 mmol) in ethanol (200 mL) was added aqueous lithium hydroxide (2 M, 75.3 mL). The mixture was stirred at 70° C. for 36 hours. The reaction mixture was concentrated under reduced pressure and lyophilized to dryness. The title compound was obtained as a white solid (17.8 g, assumed quantitative) which was used without purification. $^1$HNMR (400 MHz, DMSO-$d_6$) δ ppm 0.83 (dd, J=12.0, 6.6 Hz, 6H), 1.67-1.92 (m, 4H), 2.18 (dd, J=11.0, 4.4 Hz, 1H), 2.52-2.60 (m, 1H), 2.52-2.60 (m, 1H), 3.00 (dt, J=10.1, 6.7 Hz, 4H).

STEP D: (S)-1-phenylethyl 2-(azetidin-1-ylmethyl)-3-methylbutanoate

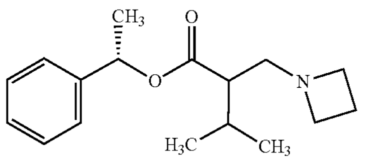 [SMILES: CC(C)C(CN1CCC1)C(=O)O[C@@H](C)c1ccccc1]

To a mixture of lithium 2-(azetidin-1-ylmethyl)-3-methylbutanoate (17.8 g, 100 mmol) and (S)-1-phenylethan-1-ol (16.4 g, 135 mmol) in DMF (180 mL) was added DMAP (14.3 g, 117 mmol) followed by EDC (22.5 g, 117 mmol). The reaction mixture was stirred at 25° C. for 12 hours and then was diluted with water (150 mL) and extracted with EtOAc (3×100 mL). The combined organic layers were dried over $Na_2SO_4$, concentrated, and purified by flash silica column chromatography using a gradient of petroleum ether/EtOAc (1:0 to 5:1) to give a colorless liquid (15 g). The colorless liquid was further purified by preparative HPLC (YMC Triart C18, 7 μm, ID 50 mm×250 mm) using a gradient of 45-77% ACN in water (0.04% $NH_4OH$+10 mM $NH_4HCO_3$) to give the title compound as a yellow oil (6.5 g, 23%). $^1$HNMR (400 MHz, $CDCl_3$) δ ppm 0.76-1.02 (m, 6H), 1.55 (dd, J=6.6, 4.6 Hz, 3H), 1.79-2.08 (m, 1H), 1.79-2.08 (m, 4H), 2.15-2.27 (m, 1H), 2.44 (ddd, J=11.5, 4.4, 1.7 Hz, 1H), 2.73 (td, J=10.9, 4.2 Hz, 1H), 2.96-3.25 (m, 4H), 5.89-6.01 (m, 1H), 7.26-7.46 (m, 5H); ESI-MS m/z $[M+H]^+$ 276.2.

STEP E: (S)-1-phenylethyl (R)-2-(azetidin-1-ylmethyl)-3-methylbutanoate and (S)-1-phenylethyl (S)-2-(azetidin-1-ylmethyl)-3-methylbutanoate

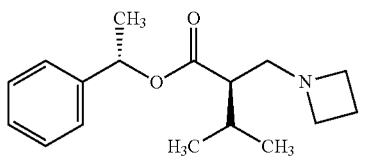

and

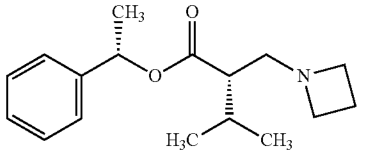

The title diastereomers of (S)-1-phenylethyl 2-(azetidin-1-ylmethyl)-3-methylbutanoate (6.5 g, 23.6 mmol) were separated by preparative SFC (Daicel ChiralPak IC, 5 μm, ID 30 mm×250 mm) using a mobile phase of 25% isopropanol (with 0.1% $NH_4OH$) in $CO_2$. The (S,R)-diastereomer was the first to elute and was obtained as a colorless oil (2.8 g, 43%). $^1$HNMR (400 MHz, $CDCl_3$) δ ppm 0.78-0.89 (m, 6H), 1.56 (d, J=6.8 Hz, 3H), 1.77-1.88 (m, 1H), 1.83 (dq, J=13.7, 6.8 Hz, 1H), 2.00 (quin, J=7.0 Hz, 2H), 2.19 (ddd, J=10.5, 7.2, 4.4 Hz, 1H), 2.43 (dd, J=11.4, 4.4 Hz, 1H), 2.66-2.79 (m, 1H), 3.05-3.26 (m, 4H), 5.94 (q, J=6.5 Hz, 1H), 7.19-7.44 (m, 6H); ESI-MS m/z $[M+H]^+$ 276.2. The (S,S)-diastereomer was the second to elute and was obtained as colorless oil (2.8 g, 43%). $^1$HNMR (400 MHz, $CDCl_3$) δ ppm 0.84-1.00 (m, 6H), 1.55 (d, J=6.5 Hz, 3H), 1.83-2.00 (m, 1H), 1.83-2.00 (m, 2H), 2.19 (ddd, J=10.3, 7.3, 4.5 Hz, 1H), 2.44 (dd, J=11.5, 4.5 Hz, 1H), 2.72 (dd, J=11.4, 10.4 Hz, 1H), 2.98-3.17 (m, 4H), 5.96 (q, J=6.7 Hz, 1H), 7.21-7.51 (m, 6H); ESI-MS m/z $[M+H]^+$ 276.2.

STEP F: (S)-2-(azetidin-1-ylmethyl)-3-methylbutanoic acid

To a solution of (S)-1-phenylethyl (S)-2-(azetidin-1-ylmethyl)-3-methylbutanoate (2.8 g, 10.2 mmol) in methanol (60 mL) was added $Pd(OH)_2$ on carbon (20 wt %, 500 mg) under nitrogen. The suspension was degassed under vacuum and purged with hydrogen several times. The mixture was stirred under hydrogen (15 psi) at 25° C. for 16 hours. The reaction mixture was filtered and concentrated under reduced pressure to give the title compound as an off-white solid (1.73 g, 94%). $^1$HNMR (400 MHz, DMSO-$d_6$) δ ppm 3.15-3.33 (m, 4H), 2.60-2.74 (m, 1H), 2.47 (br d, J=4.4 Hz, 1H), 1.91-2.06 (m, 3H), 1.75-1.87 (m, 1H), 0.86 (d, J=6.8 Hz, 6H).

PREPARATION 21: (S)-3-(azetidin-1-yl)-2-methylpropanoic acid

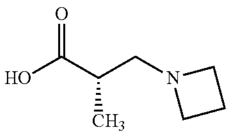

STEP A: benzyl 3-(azetidin-1-yl)-2-methylpropanoate

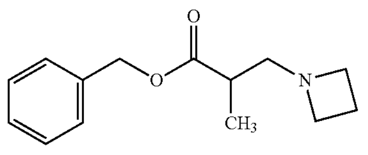 [SMILES: CC(CN1CCC1)C(=O)OCc1ccccc1]

To a round bottom flask containing azetidine hydrochloride (5.31 g, 56.8 mmol) in methanol (10 mL) were added $Et_3N$ (8.69 mL, 62.4 mmol) and benzyl methacrylate (10.0 g, 56.8 mmol). The reaction mixture was stirred at 15° C. for 16 hours and then was quenched with water (500 mL) and extracted with EtOAc (2×500 mL). The organic layers were washed with aqueous HCl (2 M, 200 mL). The aqueous layer was adjusted to pH 10 with aqueous $K_2CO_3$ and then was extracted with EtOAc (2×500 mL). The organic layers were washed with brine (2×100 mL), dried over $Na_2SO_4$, filtered and concentrated under reduced pressure to give the title compound as a light-yellow oil (6.0 g, 43%, 95% purity). $^1$H NMR (400 MHz, $CDCl_3$) δ ppm 1.16 (d, J=7.0 Hz, 3H), 1.98-2.09 (m, 2H), 2.36-2.57 (m, 2H), 2.68-2.77 (m, 1H), 3.11-3.23 (m, 5H), 5.14 (s, 2H), 7.28-7.40 (m, 5H).

STEP B: benzyl (R)-3-(azetidin-1-yl)-2-methylpropanoate and benzyl (S)-3-(azetidin-1-yl)-2-methylpropanoate

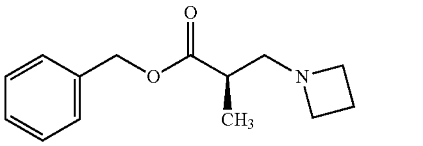

and

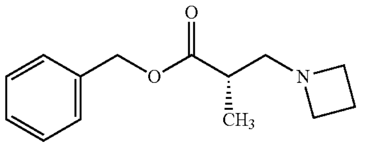

The enantiomers of benzyl 3-(azetidin-1-yl)-2-methylpropanoate (6.0 g, 24.4 mmol) were separated by preparative SFC (Daicel ChiralCel OD, 10 μm, ID 50 mm×250 mm) using a gradient of 5-15% isopropanol (with 0.1% $NH_4OH$) in $CO_2$ to give the title compounds. The stereochemistry was arbitrarily assigned. The (S)-enantiomer (1.8 g, 99% ee) and the (R)-enantiomer (2.7 g, 95% purity, 96.3% ee) were both obtained as light-yellow oils. $^1$H NMR (400 MHz, $CDCl_3$) δ ppm 1.16 (d, J=7.1 Hz, 3H), 2.01-2.09 (m, 2H), 2.43 (dd, J=11.4, 6.2 Hz, 1H), 2.53 (sxt, J=6.9 Hz, 1H), 2.75 (dd, J=11.4, 7.7 Hz, 1H), 3.19 (sxt, J=6.8 Hz, 4H), 5.14 (s, 2H), 7.29-7.40 (m, 5H); ESI-MS m/z $[M+H]^+$ 234.1.

STEP C: (S)-3-(azetidin-1-yl)-2-methylpropanoic acid

To benzyl (S)-3-(azetidin-1-yl)-2-methylpropanoate (1.05 g, 4.50 mmol) in methanol (15 mL) was added $Pd(OH)_2$ on carbon (20 wt %, 105 mg, 150 μmol) under nitrogen. The suspension was degassed under vacuum and purged with hydrogen several times. The mixture was stirred under hydrogen (15 psi) at 25° C. for 16 hours. The reaction mixture was filtered and concentrated under reduced pressure to give the title compound as a light-yellow oil (561.3 mg, 86%). $^1$H NMR (400 MHz, $CD_3OD$) δ ppm 1.16 (d, J=7.3 Hz, 3H), 2.40-2.52 (m, 3H), 3.08-3.14 (m, 1H), 3.20-3.28 (m, 1H), 4.07-4.22 (m, 4H); ESI-MS m/z $[M+H]^+$ 144.2.

PREPARATION 22: (R)-3-(azetidin-1-yl)-2-methylpropanoic acid

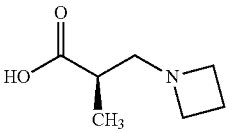

The title compound was prepared like STEP C of PREPARATION 21, using benzyl (R)-3-(azetidin-1-yl)-2-methylpropanoate. ESI-MS m/z $[M+H]^+$ 144.2.

PREPARATION 23: 2-(1,7-dimethyl-1H-indazol-3-yl)propan-2-amine

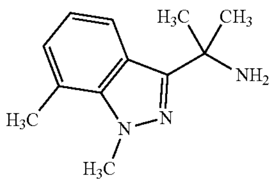

STEP A: 1,7-dimethyl-1H-indazole-3-carbonitrile

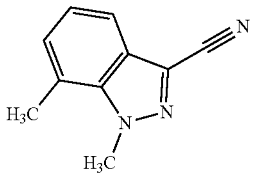

To a solution of 7-methyl-1H-indazole-3-carbonitrile (1.00 g, 6.36 mmol) in DMF (20 mL) was added NaH (60 wt %, 0.280 g, 7.00 mmol) at 0° C. The reaction mixture was stirred for 20 minutes, warming to room temperature. Methyl iodide (0.475 mL, 7.63 mmol) was added and the mixture was stirred overnight at room temperature and then was quenched with water (200 mL). The resulting precipitate was collected by filtration and dried under vacuum to give the title compound as a white solid (1.00 g, 92%). ESI-MS m/z $[M+H]^+$ 172.1.

STEP B: 2-(1,7-dimethyl-1H-indazol-3-yl)propan-2-amine

Anhydrous THE (50 mL) was added to cerium(III) chloride (4.32 g, 17.5 mmol) under $N_2$ at 0° C. and the mixture was stirred at room temperature for 2 hours. The reaction mixture was cooled to −78° C. Methyllithium-lithium bromide (1.5 M in THF, 11.68 mL, 17.5 mmol) was added dropwise and stirring was continued for 30 minutes. A solution of 1,7-dimethyl-1H-indazole-3-carbonitrile (1.00 g, 5.84 mmol) in anhydrous THE (20 mL) was added dropwise. The mixture was stirred for 30 minutes at −78° C. and then at room temperature overnight. The reaction was quenched with saturated aqueous $NH_4Cl$ (20 mL). Next, aqueous NaOH (50%) was added until a precipitate formed. The mixture was filtered through Celite® and the filtrate was extracted with EtOAc. The combined organic layers were dried over $MgSO_4$ and concentrated. The crude residue was purified by flash silica column chromatography to give the title compound as an off-white solid (0.420 g, 35%). ESI-MS m/z $[M-NH_2]^+$ 187.2.

PREPARATION 24: 2-methyl-1-((3-methylpyridin-2-yl)oxy)propan-2-amine

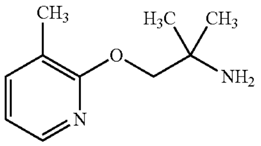

In a 125 mL round-bottomed flask, 2-amino-2-methylpropan-1-ol (3.45 mL, 36.0 mmol) was dissolved in dioxane (16 mL) to give a colorless solution. The reaction mixture was cooled to 0° C. and sodium hydride (60 wt %, 1.51 g, 37.8 mmol) was added portion-wise. After stirring for 20 minutes, 2-fluoro-3-methylpyridine (1.00 g, 9.00 mmol) was added. The mixture was heated at 100° C. for 1 hour. The reaction mixture was then cooled to room temperature, diluted with DCM, washed with water, dried over $MgSO_4$, filtered, and concentrated to give the title compound as a yellow oil (2.06 g, 78% purity) which was used without further purification. ESI-MS m/z $[M+H]^+$ 181.1.

PREPARATION 25: 1-((3-(difluoromethyl)pyridin-2-yl)oxy)-2-methylpropan-2-amine

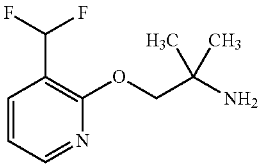

In a 250 mL round-bottomed flask, 2-amino-2-methylpropan-1-ol (2.42 g, 27.2 mmol) was dissolved in dioxane (13.6 mL) to give a colorless solution. The solution was cooled to 0° C. and sodium hydride (60 wt %, 1.14 g, 28.6 mmol) was added. After 20 minutes, a solution of 3-(difluoromethyl)-2-fluoropyridine (1.00 g, 6.80 mmol) in dioxane (2 mL) was added dropwise. The mixture was heated at 100° C. for 1 hour. After cooling to room temperature, the mixture was diluted with DCM, washed with water, dried over $MgSO_4$, filtered, and concentrated. The residue was purified via flash silica column chromatography (120 g NH silica) using a gradient of 0-10% MeOH in DCM. The pure fractions were evaporated to afford the title compound as a colorless oil (1.41 g, 96%).

PREPARATION 26: 2-(furo[3,2-c]pyridin-4-yl)propan-2-amine

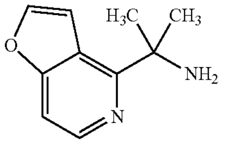

Cerium (III) chloride (5.13 g, 20.8 mmol) was added to THE (63.1 mL) at 0° C. under nitrogen. The mixture was stirred for 30 minutes at 0° C., allowed to warm to room temperature, and then was stirred for 160 minutes. Next, the reaction mixture was cooled to −78° C. MeLi-LiBr (13.9 mL, 20.8 mmol) was added and the mixture was stirred at −78° C. for 30 minutes. A solution of furo[3,2-c]pyridine-4-carbonitrile (1.00 g, 6.94 mmol) in THE (6.31 mL) was added dropwise. The reaction mixture was kept at −78° C. for 30 minutes and then was stirred at room temperature overnight. The reaction mixture was quenched with saturated aqueous $NH_4Cl$, diluted with 1 M aqueous NaOH, extracted with EtOAc, dried over $Na_2SO_4$, filtered, and concentrated in vacuo. The crude product was taken up in DCM and purified by flash column chromatography (NH silica), eluting with a gradient of 20-40% EtOAc in heptanes to give the title compound as a yellow oil (0.459 g, 38%). $^1H$ NMR (400 MHz, DMSO-$d_6$) δ ppm 1.44-1.57 (m, 6H), 7.47 (dd, J=2.3, 1.1 Hz, 1H), 7.49-7.61 (m, 1H), 8.03 (d, J=2.3 Hz, 1H), 8.26-8.42 (m, 1H).

PREPARATION 27: 1-((3-cyclopropylpyridin-2-yl)oxy)-2-methylpropan-2-amine

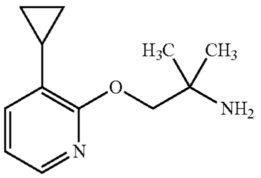

To a stirred suspension of NaH (0.444 g, 11.1 mmol) in THE (30 mL) was added 2-amino-2-methylpropan-1-ol (0.976 mL, 10.2 mmol). The mixture was stirred at room temperature for 1 hour. A solution of 3-cyclopropyl-2-fluoropyridine (1.27 g, 9.26 mmol) in THE (10 mL) was added and the mixture was stirred at room temperature overnight. Water (50 mL) was added, followed by EtOAc (20 mL), and the layers were separated. The aqueous layer was extracted with EtOAc and the combined organic layers were dried over anhydrous $MgSO_4$, filtered, and concentrated under reduced pressure. The crude residue was purified by flash silica column chromatography to give the title compound as a clear oil (1.06 g, 55.5%). ESI-MS m/z $[M+H]^+$ 207.2.

PREPARATION 28: 1-((3-ethoxypyridin-2-yl)oxy)-2-methylpropan-2-amine

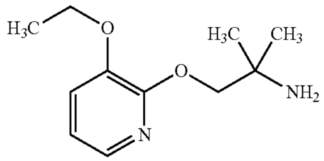

To a stirred suspension of NaH (60 wt %, 0.170 g, 4.25 mmol) in THE (20 mL) was added 2-amino-2-methylpropan-1-ol (0.373 mL, 3.90 mmol). The mixture was stirred at room temperature for 10 minutes. A solution of 3-ethoxy-2-fluoropyridine (0.500 g, 3.54 mmol) in THE (10 mL) was added and the mixture was stirred at room temperature overnight. Water (50 mL) was added, followed by EtOAc (20 mL), and the layers were separated. The aqueous layer was extracted with EtOAc and the combined organic layers were dried over $MgSO_4$, filtered, and concentrated under reduced pressure. The crude residue was purified by flash silica column chromatography to give the title compound as a clear oil (0.440 g, 59%). ESI-MS m/z $[M+H]^+$ 211.2.

PREPARATION 29: 2-methyl-1-((3-(trifluoromethoxy)pyridin-2-yl)oxy)propan-2-amine

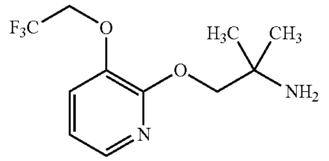 [SMILES: CC(C)(N)COc1ncccc1OCC(F)(F)F]

To a stirred suspension of NaH (60 wt %, 0.243 g, 6.07 mmol) in THE (30 mL) was added 2-amino-2-methylpropan-1-ol (0.534 mL, 5.57 mmol). The mixture was stirred at room temperature for 20 minutes. A solution of 2-chloro-3-(trifluoromethoxy)pyridine (1.00 g, 5.06 mmol) in THE (10 mL) was added and the mixture was stirred at room temperature overnight. Water (100 mL) was added and then the mixture was diluted with EtOAc. The aqueous layer was extracted with EtOAc and the combined organic layers were dried over anhydrous $MgSO_4$, filtered, and concentrated under reduced pressure. The crude residue was purified by flash silica column chromatography to give the title compound as a clear oil (0.550 g, 43%). ESI-MS m/z $[M+H]^+$ 251.2.

PREPARATION 30: (S)—N-(1-hydroxy-2-methylpropan-2-yl)-2-(1-methylpyrrolidin-2-yl)acetamide

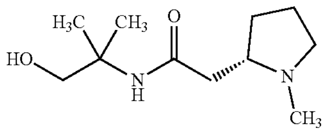

To a solution of (S)-2-(1-methylpyrrolidin-2-yl)acetic acid (500 mg, 3.49 mmol) in DMF (17.5 mL) was added HATU (1328 mg, 3.49 mmol), followed by DIPEA (1.83 mL, 10.5 mmol). The reaction mixture was stirred at room temperature for 5 minutes. Next, 2-amino-2-methylpropan-1-ol (342 mg, 3.84 mmol) was added. The solution was stirred at room temperature overnight and then was evacuated to remove solvent. The residue was purified by automated flash column chromatography (NH silica gel) using a gradient of 0-10% MeOH in DCM to give the title compound as a light-yellow oil (350 mg, 47%). ESI-MS m/z $[M+H]^+$ 215.2.

PREPARATION 31: 2-(chroman-2-yl)propan-2-amine

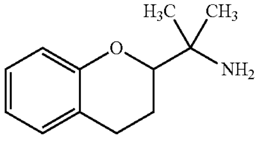

STEP A: 2-(chroman-2-yl)propan-2-ol

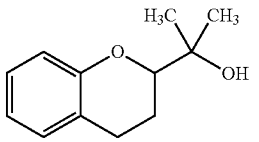

Methylmagnesium bromide (1.0 M, 4.0 mL, 4.04 mmol) in THE (9.6 mL) was added dropwise to a stirred solution of methyl chromane-2-carboxylate (370 mg, 1.92 mmol) in dry THE (9.6 mL) at 0° C. under nitrogen. Stirring was continued at 0° C. for 5 minutes and then at room temperature for 2 hours. The reaction mixture was cooled to 0° C. Saturated aqueous $NH_4Cl$ was added dropwise, followed by EtOAc. The organic layer was separated, washed with brine, dried over $Na_2SO_4$ and concentrated under reduced pressure to give the title compound (350 mg, 95%) which was used without further purification. $^1H$ NMR (400 MHz, $CD_3OD$) δ ppm 1.28 (s, 3H), 1.32 (s, 3H), 1.71-1.86 (m, 1H), 2.05 (ddt, J=13.4, 5.8, 2.0 Hz, 1H), 2.73-2.95 (m, 2H), 3.79 (dd, J=11.5, 2.0 Hz, 1H), 6.80-6.89 (m, 2H), 7.00-7.13 (m, 2H).

STEP B: N-(2-(chroman-2-yl)propan-2-yl)acetamide $H_3C$ $CH_3$

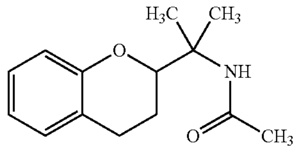 [SMILES: CC(=O)NC(C)(C)C1CCc2ccccc2O1]

To a stirred solution of 2-(chroman-2-yl)propan-2-ol (190 mg, 0.988 mmol) in dry ACN (9.9 mL) and acetic acid (0.1 mL, 1.76 mmol) at 0° C. was added sulfuric acid (50.0 µL, 0.939 mmol) dropwise. Stirring was continued at 0° C. for 5 minutes and then at room temperature overnight. The reaction mixture was treated with 5M ammonium hydroxide (38.5 µL, 0.988 mmol) followed by EtOAc. The organic layer was washed with brine and concentrated under reduced pressure. The residue was purified by flash silica column chromatography using a gradient of 30-60% EtOAc in heptanes to furnish the title compound as a white solid (26 mg, 11%). ESI-MS m/z $[M+H]^+$ 234.2.

STEP C: 2-(chroman-2-yl)propan-2-amine

To a solution of N-(2-(chroman-2-yl)propan-2-yl)acetamide (26 mg, 0.11 mmol) in DME (0.2 mL) and ethylene glycol (0.2 mL) was added potassium hydroxide (50.0 mg, 0.892 mmol). The reaction mixture was heated at 150° C. for 36 hours. Water (1.0 mL) and EtOAc (10 mL) were added. The organic layer was washed with brine (2×3 mL) and dried over anhydrous $Na_2SO_4$. The solvent was removed to give the title compound as a brown sticky oil (20 mg, 94%) which was used without further purification. ESI-MS m/z $[M+H]^+$ 192.2.

PREPARATION 32: 2-(5-methylisoquinolin-1-yl)propan-2-amine

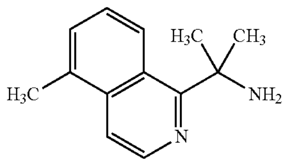

Anhydrous THE (30.7 mL) was added to anhydrous cerium(III) chloride (3.97 g, 16.1 mmol) at 0° C. under $N_2$ atmosphere. The reaction mixture was stirred for 2 hours, gradually warming to room temperature. The stirred mixture was then cooled to −78° C. and a 1.5 M solution of MeLi-LiBr (10.75 mL, 16.12 mmol) in diethyl ether was added. Stirring was continued for 30 minutes at −78° C. at which time a solution of 5-methylisoquinoline-1-carbonitrile (0.904 g, 5.37 mmol) in anhydrous THE (5.12 mL) was added. The reaction mixture was stirred for 30 minutes at −78° C. and then overnight at room temperature. Saturated aqueous $NH_4Cl$ was added to the mixture. A precipitate formed, and the mixture was made basic with aqueous $NH_4OH$. The reaction mixture was filtered through a pad of Celite®, rinsing with diethyl ether. The organic and aqueous layers were separated, and the organic layer was set aside. The aqueous layer was washed twice with diethyl ether. The organic layers were combined and washed with saturated aqueous NaCl, dried over $Na_2SO_4$, filtered, and concentrated under reduced pressure. The residue was taken up in methanol and filtered through a hydrophilic PTFE 0.45 m Millipore® filter, rinsing with methanol. The filtrate was purified by preparative HPLC (Phenomenex Gemini® C18, 5 μm, ID 30 mm×150 mm) using a gradient of 15-65% water/ACN in water (basic mode). The pure fractions were evaporated to afford the title compound as a reddish-brown oil (260.3 mg, 24%) which was used without additional purification. ESI-MS m/z $[M+H]^+$ 201.1.

PREPARATION 33: 1-((2-methoxypyridin-3-yl)methyl)cyclopropan-1-amine

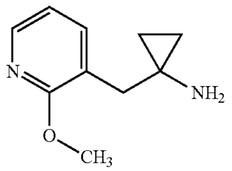

To a solution of 2-(2-methoxypyridin-3-yl)acetonitrile (0.325 g, 2.19 mmol) and titanium(IV) isopropoxide (0.707 mL, 2.41 mmol) in THE (11.0 mL) was added a solution of 3 M ethylmagnesium bromide in diethyl ether (1.46 mL, 4.39 mmol) dropwise at room temperature. The reaction mixture was stirred at room temperature for 1 hour. Next, $BF_3{\cdot}OEt_2$ (0.556 ml, 4.39 mmol) was added. The reaction mixture was stirred at room temperature for an additional 30 minutes and then was quenched with water (2 mL), followed by aqueous HCl (1 M, 20 mL) and DCM (50 mL). Aqueous 1 M NaOH was added until the pH of the mixture was basic. The organic layer was separated, and the aqueous phase was extracted with DCM. The combined organic layers were dried over $Na_2SO_4$, filtered, and concentrated.

The residue was purified by automated flash silica column chromatography using a gradient of 0-20% methanol in DCM. The pure fractions were evaporated to afford the title compound as a pale-yellow oil (0.187 g, 48%). ESI-MS m/z $[M+H]^+$ 179.1.

PREPARATION 34: 2-(1-methyl-1H-pyrazolo[4,3-c]pyridin-4-yl)propan-2-amine

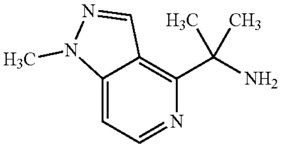

Anhydrous THE (100 mL) was added to cerium(III) chloride (5.00 g, 20.3 mmol) under nitrogen at 0° C. The reaction mixture was stirred at room temperature for 2 hours and then cooled to −78° C. Next, MeLi·LiBr (1.5 M, 13.53 mL, 20.3 mmol) was added dropwise and reaction mixture was stirred for 30 minutes. A solution of 1-methyl-1H-pyrazolo[4,3-c]pyridine-4-carbonitrile (1.07 g, 6.77 mmol) in anhydrous THE (33 mL) was added dropwise. The mixture was stirred for 30 minutes at −78° C. and then at room temperature overnight. The reaction was quenched with saturated aqueous $NH_4Cl$ and 1 M aqueous NaOH was added until a precipitate was formed. The mixture was filtered through Celite® and the filtrate was extracted with EtOAc. The combined organic layers were dried over $MgSO_4$ and concentrated. The residue was purified by flash silica column chromatography using a gradient 0-10% MeOH in DCM to give the title compound. ESI-MS m/z $[M+H]^+$ 191.2.

PREPARATION 35: 2-(4-methylisoquinolin-1-yl)propan-2-amine

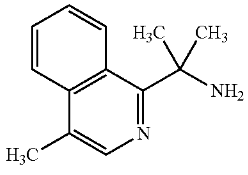

STEP A: 4-methylisoquinoline-1-carbonitrile

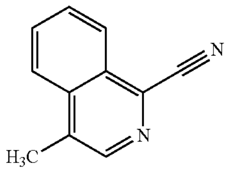

To a round-bottomed flask equipped with a stir bar were added 1-chloro-4-methylisoquinoline (1.85 g, 10.4 mmol) and zinc(II) cyanide (1.834 g, 15.62 mmol) in DMA, followed by $Pd_2(dba)_3$ (0.572 g, 0.625 mmol) and dppf (0.693 g, 1.25 mmol) under nitrogen atmosphere. The reaction mixture was stirred at 115° C. for 4 hours and then was cooled to room temperature, diluted with water and extracted with EtOAc. The organic layers were collected, filtered through $MgSO_4$, and concentrated in vacuo. The residue was purified by automated flash silica column chromatography (220 g column) using a gradient of 10-70% EtOAc in heptanes. The product-containing fractions were evaporated to afford the title compound as an off-white/yellow solid (1.554 g, 89%). ESI-MS m/z $[M+H]^+$ 169.1.

STEP B: 2-(4-methylisoquinolin-1-yl)propan-2-amine

The title compound was prepared like PREPARATION 34, using cerium(III) chloride (6.83 g, 27.7 mmol) and MeLi·LiBr (1.5 M, 18.5 mL, 27.7 mmol) in THE (100 mL), followed by 4-methylisoquinoline-1-carbonitrile (1.554 g, 9.24 mmol) in THE (33 mL). The product was purified by flash silica column chromatography using a gradient of 0-30% MeOH in DCM to give the title compound as a yellow oil (60 mg, 3.2%). ESI-MS m/z $[M+H]^+$ 201.2.

PREPARATION 36: 2-(1-(tert-butoxycarbonyl)-3,3-difluoropyrrolidin-2-yl)acetic acid

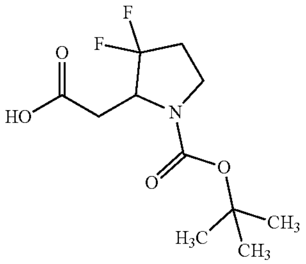 [SMILES: CC(C)(C)OC(=O)N1CCC(F)(F)C1CC(=O)O]

STEP A: tert-butyl 3,3-difluoro-2-(2-methoxy-2-oxoethyl)pyrrolidine-1-carboxylate

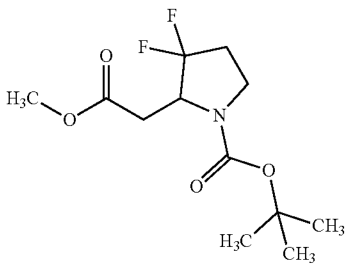 [SMILES: COC(=O)CC1N(C(=O)OC(C)(C)C)CCC1(F)F]

To a stirred solution of tert-butyl 2-(2-methoxy-2-oxoethyl)-3-oxopyrrolidine-1-carboxylate (2.91 mL, 13.6 mmol) in DCM (30.1 mL) at 0° C. was added Deoxo-Fluor® (1.00 g, 4.52 mmol). The solution was stirred at room temperature overnight and then the reaction was quenched with EtOAc. The combined organic layers were washed with brine, dried over $Na_2SO_4$, and concentrated under reduced pressure to give the title compound (500 mg, 40%) which was used without further purification.

STEP B: 2-(1-(tert-butoxycarbonyl)-3,3-difluoropyrrolidin-2-yl)acetic acid

To a 100 mL round bottom flask containing a solution of tert-butyl 3,3-difluoro-2-(2-methoxy-2-oxoethyl)pyrrolidine-1-carboxylate (500 mg, 1.79 mmol) in dioxane (4.97 mL) was added 1 M aqueous LiOH (7.16 mL, 7.16 mmol). The reaction mixture was stirred at room temperature overnight and then was diluted with water, acidified, and extracted with EtOAc. The organic layers were combined, dried over $Na_2SO_4$, and concentrated in vacuo to give the title compound as an orange oil. ESI-MS m/z $[M+H]^+$ 266.1.

PREPARATION 37: N-(2-(2-chlorophenyl)propan-2-yl)methacrylamide

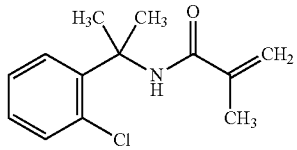 [SMILES: C=C(C)C(=O)NC(C)(C)c1ccccc1Cl]

A mixture of 2-(2-chlorophenyl)propan-2-amine hydrochloride (0.863 g, 4.19 mmol) and methacrylic acid (0.360 g, 4.19 mmol) in DMA (14 mL) was treated with DIPEA (2.19 mL, 12.6 mmol) and HATU (2.39 g, 6.28 mmol) and was stirred at room temperature overnight. The reaction mixture was diluted with water and extracted with EtOAc (3×). The organic phase was washed with water and saturated aqueous NaCl, dried over $Na_2SO_4$, filtered, and concentrated under reduced pressure. The residue was purified by automated flash silica column chromatography using a gradient of 0-60% EtOAc in heptanes. The product-containing fractions were evaporated to afford the title compound as a white solid (875.9 mg, 88%). ESI-MS $[M+H]^+$ 238.1.

PREPARATION 38: (R)-2,2-difluoro-1-(2-methoxyphenyl)ethan-1-amine

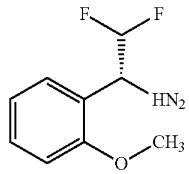

STEP A: (S,E)-N-(2-methoxybenzylidene)-2-methylpropane-2-sulfinamide

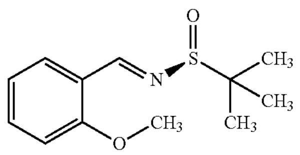 [SMILES: COc1ccccc1/C=N/[S@@](=O)C(C)(C)C]

To a 20 mL microwave vial equipped with stir bar were 2-methoxybenzaldehyde (1.634 g, 12.00 mmol), (S)-2- methylpropane-2-sulfinamide (1.454 g, 12.00 mmol) and tetraethoxytitanium (5.03 mL, 24.0 mmol). The vial was sealed and heated in a Biotage® microwave reactor at 70° C. for 15 minutes. After cooling to room temperature, the reaction mixture was diluted with EtOAc (60 mL) and treated with brine (3.0 mL) with rapid stirring. The resulting suspension was filtered through a pad of Celite® and rinsed with EtOAc. The organic filtrate was dried over $Na_2SO_4$, filtered again, and evaporated to give the title compound as a yellow oil (2.42 g, 84%). ESI-MS m/z $[M+H]^+$ 240.3.

STEP B: (S)—N—((R)-2,2-difluoro-1-(2-methoxyphenyl)-2-(phenylsulfonyl)ethyl)-2-methylpropane-2-sulfinamide

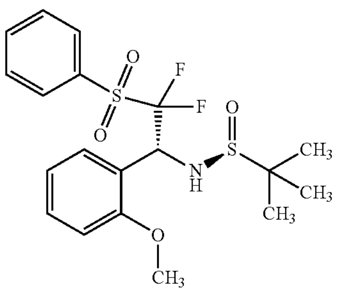 [SMILES: COc1ccccc1[C@@H](N[S@@](=O)C(C)(C)C)C(F)(F)S(=O)(=O)c1ccccc1]

An oven-dried 500 mL round-bottomed flask equipped with a stir bar was charged with (S,E)-N-(2-methoxybenzylidene)-2-methylpropane-2-sulfinamide (2.42 g, 10.1 mmol) and ((difluoromethyl)sulfonyl)benzene (1.767 g, 9.19 mmol) under nitrogen atmosphere. Tetrahydrofuran (115 mL) was added and the reaction mixture was cooled to −78° C. in a dry ice/acetone bath. A 1 M LiHMDS in THE solution (11.03 mL, 11.03 mmol) at −78° C. was added and the reaction mixture was stirred for 90 minutes at −78° C. The reaction mixture was removed from the dry ice bath, diluted with isopropyl acetate, and quenched with aqueous $NH_4Cl$. The reaction mixture was transferred to a separatory funnel, diluted with water, partitioned, and extracted with isopropyl acetate. The combined organic layers were washed with saturated aqueous NaCl, dried over $Na_2SO_4$, filtered, and concentrated under reduced pressure. The residue was dry loaded onto silica using DCM and purified by automated flash silica column chromatography using a gradient of 0-70% EtOAc in heptanes. The product-containing fractions were evaporated to afford the title compound as a light-yellow oil/foam (1.65 g, 42%). ESI-MS m/z $[M+H]^+$ 432.3.

STEP C: (S)—N—((R)-2,2-difluoro-1-(2-methoxyphenyl)ethyl)-2-methylpropane-2-sulfinamide

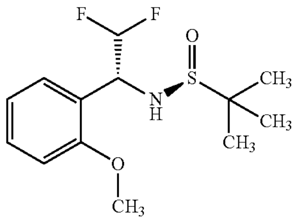 [SMILES: COc1ccccc1[C@@H](N[S@@](=O)C(C)(C)C)C(F)F]

To a stirred solution of (S)—N—((R)-2,2-difluoro-1-(2-methoxyphenyl)-2-(phenylsulfonyl)ethyl)-2-methylpropane-2-sulfinamide (1.65 g, 3.81 mmol) in DMF (31.8 mL) was added a prepared solution of sodium acetate (3.13 g, 38.1 mmol) in acetic acid (2.18 mL, 38.1 mmol) and water (6.36 mL). The clear solution became slightly cloudy. To the reaction mixture was added magnesium (1.39 g, 57.2 mmol) powder in portions over a 20-minute period. A warming of the reaction flask and gas evolution were observed. The reaction mixture was stirred for 2 hours at room temperature and then was diluted with isopropyl acetate and extracted with water, followed by saturated aqueous NaCl. The organic phase was dried over $Na_2SO_4$, filtered, and concentrated under reduced pressure. The resulting yellow oil was purified by automated flash silica column chromatography using a gradient of 20-100% EtOAc in heptanes and then a gradient of 20-80% EtOAc in heptanes.

The product-containing fractions were evaporated to afford the title compound as a white solid (0.553 g, 50%). ESI-MS m/z $[M+H]^+$ 292.3.

STEP D: (R)-2,2-difluoro-1-(2-methoxyphenyl)ethan-1-amine

To a solution of (S)—N—((R)-2,2-difluoro-1-(2-methoxyphenyl)ethyl)-2-methylpropane-2-sulfinamide (0.553 g, 1.90 mmol) in DCM (1.90 mL) was added 4 M HCl in dioxane (1.90 mL, 7.59 mmol). The reaction mixture was stirred at room temperature for 3 hours and then was concentrated under reduced pressure. The solids were dispersed in diethyl ether and collected by vacuum filtration to give an HCl salt of the title compound as a white powder (0.337 g, 79%). ESI-MS m/z $[M+H]^+$ 188.2.

PREPARATION 39: (R)-2,2-difluoro-1-(3-fluorophenyl)ethan-1-amine

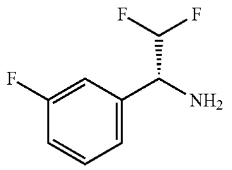 [SMILES: N[C@H](c1cccc(F)c1)C(F)F]

An HCl salt of the title compound was prepared like PREPARATION 38, using 3-fluorobenzaldehyde (1.489 g, 12.00 mmol), (S)-2-methylpropane-2-sulfinamide (1.454 g, 12.00 mmol) and tetraethoxytitanium (5.03 mL, 24.0 mmol), and was obtained as a white solid (0.913 g, ~70% purity, 25% yield over 4 steps). ESI-MS m/z $[M+H]^+$ 176.2.

PREPARATION 40: (R)-2,2-difluoro-1-(4-fluorophenyl)ethan-1-amine

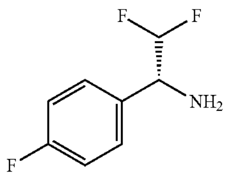 [SMILES: N[C@H](c1ccc(F)cc1)C(F)F]

An HCl salt of the title compound was prepared like PREPARATION 38, using 4-fluorobenzaldehyde (1.862 g, 15.00 mmol), (S)-2-methylpropane-2-sulfinamide (1.818 g, 15.00 mmol) and tetraethoxytitanium (6.29 mL, 30.0 mmol), and was obtained as a white solid (0.743 g, 23% over 4 steps). ESI-MS m/z $[M+H]^+$ 176.2.

PREPARATION 41: (R)-2,2-difluoro-1-phenylethan-1-amine

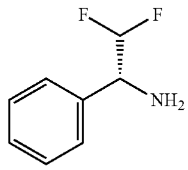 [SMILES: N[C@H](c1ccccc1)C(F)F]

STEP A: (S)—N—((R)-2,2-difluoro-1-phenyl-2-(phenylsulfonyl)ethyl)-2-methylpropane-2-sulfinamide

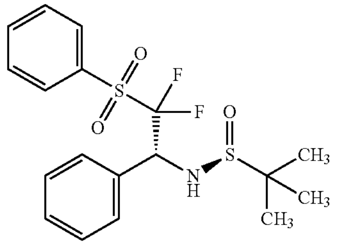 [SMILES: CC(C)(C)[S@](=O)N[C@H](c1ccccc1)C(F)(F)S(=O)(=O)c1ccccc1]

A heat-dried 1000 mL three-necked flask equipped with a thermocouple and stir bar was evacuated and backfilled with nitrogen. Next, the flask was charged with ((difluoromethyl) sulfonyl)benzene (4.00 g, 20.8 mmol), (S,E)-N-benzylidene-2-methylpropane-2-sulfinamide (4.79 g, 22.9 mmol) and THF (260 mL). The reaction mixture was cooled in a dry ice/acetone bath to −78° C. and 1 M lithium bis(trimethylsilyl)amide in THE (25.0 mL, 25.0 mmol) was added over a 10-minute period. The reaction mixture was stirred at −78° C. for 90 minutes and then was removed from the dry ice bath, diluted with isopropyl acetate (200 mL) and quenched with saturated aqueous $NH_4Cl$ (100 mL). The reaction mixture was transferred to a separatory funnel, diluted with water (200 mL) and extracted with isopropyl acetate (3×400 mL). The organic layers were combined, washed with brine (300 mL), dried with sodium sulfate and concentrated to an oil which solidified overnight. The product was purified by flash silica column chromatography (220 g silica) using a gradient of 20-85% EtOAc in heptanes to give the title compound as a white solid (6.1 g, 73%). ESI-MS m/z $[M+H]^+$ 402.4.

STEP B: (S)—N—((R)-2,2-difluoro-1-phenylethyl)-2-methylpropane-2-sulfinamide

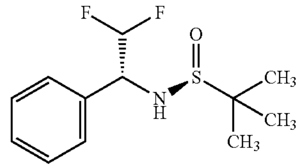 [SMILES: CC(C)(C)[S@](=O)N[C@H](c1ccccc1)C(F)F]

To a stirred solution of (S)—N—((R)-2,2-difluoro-1-phenyl-2-(phenylsulfonyl)ethyl)-2-methylpropane-2-sulfinamide (6.1 g, 15.2 mmol) in DMF (141 mL) was added a prepared solution of sodium acetate (12.46 g, 152 mmol), acetic acid (8.70 mL, 152 mmol) and water (28.1 mL). The reaction temperature warmed slightly from 21° C. to 27° C. and the clear solution became cloudy. To the stirred reaction mixture was added magnesium powder (5.54 g, 228 mmol) in portions over a 30-minute period. The temperature of the mixture rose from 26° C. to 45° C. with gas evolution and foaming during the addition. The reaction mixture was stirred at room temperature for 1 hour and then was diluted with isopropyl acetate (500 mL) and washed with water (2×300 mL) followed by brine (300 mL). The organic layer was collected, dried over sodium sulfate and concentrated to an oil. The product was purified by flash silica column chromatography (120 g silica) using a gradient of 20-100% EtOAc in heptanes to give the title compound as a semi-solid (2.93 g, 74%). ESI-MS m/z $[M+H]^+$ 262.3.

STEP C: (R)-2,2-difluoro-1-phenylethan-1-amine

To a solution of (S)—N—((R)-2,2-difluoro-1-phenylethyl)-2-methylpropane-2-sulfinamide (2.9 g, 11.1 mmol) in DCM (10 mL) was added 4 M HCl in dioxane (11.1 mL, 44.4 mmol). The reaction mixture was stirred at room temperature for 2 hours and then was concentrated in vacuo. The solids were dispersed in diethyl ether (30 mL) and collected by filtering under nitrogen to give an HCl salt of the title compound as a white powder (1.93 g, 90%). ESI-MS m/z $[M+H]^+$ 158.1.

PREPARATION 42: (S)-2,2-difluoro-1-phenylethan-1-amine

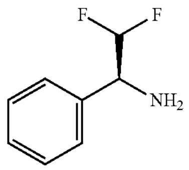 [SMILES: N[C@@H](c1ccccc1)C(F)F]

An HCl salt of the title compound was prepared like PREPARATION 41, using ((difluoromethyl)sulfonyl)benzene (1.60 g, 8.33 mmol), (R,E)-N-benzylidene-2-methylpropane-2-sulfinamide (1.92 g, 9.16 mmol) and lithium bis(trimethylsilyl)amide solution (1 M in THF, 9.99 mL, 9.99 mmol) in THF (83 mL), and was obtained as a white powder (0.60 g, 37% over three steps). ESI-MS m/z $[M+H]^+$ 158.1.

PREPARATION 43: (R)-2-fluoro-1-phenylethan-1-amine

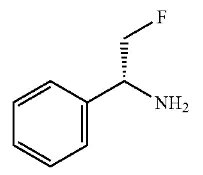

An HCl salt of the title compound was prepared like PREPARATION 41, using ((fluoromethyl)sulfonyl)benzene (1.73 g, 9.95 mmol), (S,E)-N-benzylidene-2-methylpropane-2-sulfinamide (2.29 g, 10.9 mmol) and lithium bis(trimethylsilyl)amide (1 M in THF, 11.9 mL, 11.9 mmol) in THF (124 mL), and was obtained as a white solid (0.418 g, 24% over 3 steps). ESI-MS m/z $[M+H]^+$ 140.1.

PREPARATION 44: lithium 3-(azetidin-1-yl)propanoate

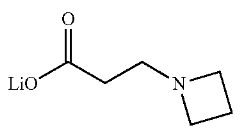

To a solution of methyl 3-(azetidin-1-yl)propanoate (0.900 g, 6.29 mmol) in MeOH (20 mL) was added 2 M LiOH (3.46 mL, 6.91 mmol). The mixture was stirred at 60° C. overnight and then was concentrated to give an oily white solid. Acetonitrile (30 mL) was added and the resulting precipitate was collected and dried at 40° C. under vacuum overnight to give the title compound as a white solid (0.844 g, 99%).

PREPARATION 45: (R)—N-(2-(2-fluorophenyl)propan-2-yl)-2-(pyrrolidin-2-yl)acetamide

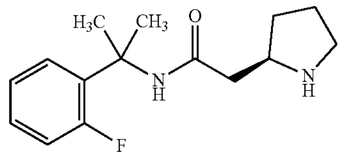 [SMILES: CC(C)(NC(=O)C[C@H]1CCCN1)c1ccccc1F]

STEP A: tert-butyl (R)-2-(2-((2-(2-fluorophenyl)propan-2-yl)amino)-2-oxoethyl)pyrrolidine-1-carboxylate

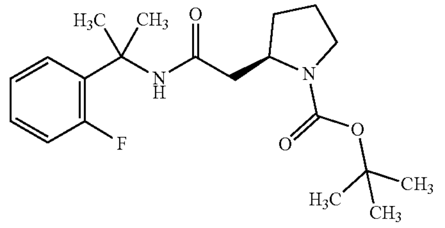 [SMILES: CC(C)(C)OC(=O)N1CCC[C@@H]1CC(=O)NC(C)(C)c1ccccc1F]

A solution of 2-(2-fluorophenyl)propan-2-amine (120 mg, 0.783 mmol), (R)-2-(1-(tert-butoxycarbonyl)pyrrolidin-2-yl)acetic acid (216 mg, 0.940 mmol), HATU (365 mg, 0.940 mmol) and $Et_3N$ (437 μL, 3.13 mmol) in THE (3.92 mL) was stirred at room temperature overnight. The reaction mixture was diluted with MeOH and filtered through a hydrophilic PTFE 0.45 m Millipore® filter. The filtrate was purified by preparative HPLC (Phenomenex Gemini® C18, 5 μm, ID 30 mm×150 mm) using a gradient of 10-100% ACN in water (acid mode). The product-containing fractions were evaporated to give the title compound as a white solid (177 mg, 62%). ESI-MS m/z $[M+H]^+$ 365.4.

STEP B: (R)—N-(2-(2-fluorophenyl)propan-2-yl)-2-(pyrrolidin-2-yl)acetamide

To a solution of tert-butyl (R)-2-(2-((2-(2-fluorophenyl)propan-2-yl)amino)-2-oxoethyl)pyrrolidine-1-carboxylate (177 mg, 0.486 mmol) in DCM (1.94 mL) and MeOH (0.5 mL) was added 4 M HCl in dioxane (728 μL, 2.91 mmol). The reaction mixture was stirred at room temperature overnight and then was diluted with MeOH and filtered through a hydrophilic PTFE 0.45 m Millipore® filter. The filtrate was purified by preparative HPLC (Phenomenex Gemini® C18, 5 μm, ID 30 mm×150 mm) using a gradient of 10-100% ACN in water (acid mode). The product-containing fractions were evaporated to give a TFA salt of the title compound as a colorless oil (140 mg, 76%). $^1H$ NMR (400 MHz, $CDCl_3$) δ ppm 1.70 (d, J=5.0 Hz, 6H), 1.85-2.04 (m, 2H), 2.07-2.17 (m, 1H), 2.64-2.83 (m, 2H), 3.09-3.26 (m, 2H), 3.82 (br d, J=6.0 Hz, 1H), 4.33-4.62 (m, 1H), 6.99 (ddd, J=12.7, 8.2, 1.2 Hz, 1H), 7.03 (br s, 1H), 7.10 (td, J=7.5, 1.2 Hz, 1H), 7.23 (tdd, J=7.6, 5.1, 1.8 Hz, 1H), 7.33 (td, J=8.2, 1.8 Hz, 1H), 9.26 (br s, 1H), 9.65-9.77 (m, 1H); ESI-MS m/z $[M+H]^+$ 265.4.

PREPARATION 46: (S)—N-(2-(2-fluorophenyl)propan-2-yl)-2-(pyrrolidin-2-yl)acetamide

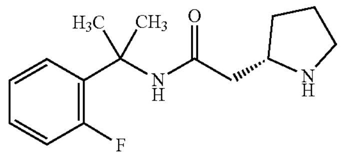 [SMILES: CC(C)(NC(=O)C[C@@H]1CCCN1)c1ccccc1F]

A TFA salt of the title compound was prepared like PREPARATION 45, using 2-(2-fluorophenyl)propan-2-amine (125 mg, 0.816 mmol), (S)-2-(1-(tert-butoxycarbonyl)pyrrolidin-2-yl)acetic acid (224 mg, 0.979 mmol), $Et_3N$ (455 μL, 3.26 mmol) and HATU (380 mg, 0.979 mmol) in THE (4.08 mL), and was obtained as a colorless semisolid (174 mg, 56% over two steps). $^1H$ NMR (400 MHz, $CDCl_3$) δ ppm 1.70 (app d, J=2.3 Hz, 6H), 1.84-2.03 (m, 2H), 2.07-2.16 (m, 1H), 2.63-2.74 (m, 1H), 2.77-2.85 (m, 1H), 3.08-3.23 (m, 2H), 3.80 (br d, J=6.5 Hz, 1H), 6.24-6.42 (m, 1H), 6.99 (ddd, J=12.7, 8.2, 1.0 Hz, 1H), 7.06-7.12 (m, 1H), 7.18-7.25 (m, 2H), 7.32 (td, J=8.2, 1.8 Hz, 1H), 9.22 (br s, 1H), 9.46-9.60 (m, 1H); ESI-MS m/z $[M+H]^+$ 265.4.

PREPARATION 47: 2-((S)-pyrrolidin-2-yl)-N-(2,2,2-trifluoro-1-(p-tolyl)ethyl)acetamide

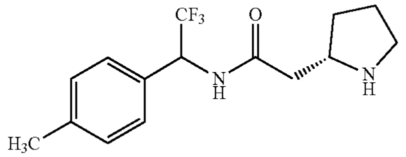 [SMILES: Cc1ccc(C(NC(=O)C[C@@H]2CCCN2)C(F)(F)F)cc1]

To a vial containing (S)-2-(1-(tert-butoxycarbonyl)pyrrolidin-2-yl)acetic acid (48 mg, 0.20 mmol) in DMF (3 mL) was added 2,2,2-trifluoro-1-(p-tolyl)ethan-1-amine (40 mg, 0.21 mmol), HATU (105 mg, 0.275 mmol) and DIPEA (55 mg, 0.42 mmol). The solution was stirred at room temperature overnight. Next, TFA (2 mL) was added. The reaction mixture was stirred at room temperature for 3 hours and then was concentrated under reduced pressure, filtered and purified by preparative HPLC (Phenomenex Gemini® C18, 5 μm, ID 30 mm×150 mm) eluting with a gradient of 20-30% ACN in water (acid mode). The pure fractions were combined and evaporated to obtain a TFA salt of the title compound as a clear oil (17 mg, 27%). $^{1}$H NMR (400 MHz, $CD_3OD$) δ ppm 1.61-1.75 (m, 1H), 1.88-2.12 (m, 2H), 2.14-2.28 (m, 1H), 2.32-2.36 (m, 3H), 2.69-2.95 (m, 2H), 3.23-3.30 (m, 2H), 3.74-3.91 (m, 1H), 5.63-5.73 (m, 1H), 7.18-7.25 (m, 2H), 7.32-7.38 (m, 2H); ESI-MS m/z $[M+H]^+$ 301.2.

EXAMPLE 1: N-(2-(1,7-dimethyl-1H-indazol-3-yl)propan-2-yl)-2-(1-methylpyrrolidin-2-yl)acetamide

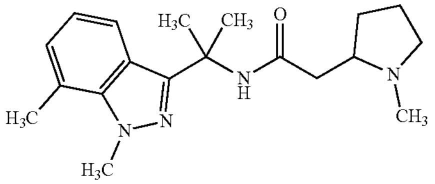 [SMILES: Cc1cccc2c(C(C)(C)NC(=O)CC3CCCN3C)nn(C)c12]

STEP A: N-(2-(1,7-dimethyl-1H-indazol-3-yl)propan-2-yl)-2-(pyrrolidin-2-yl)acetamide

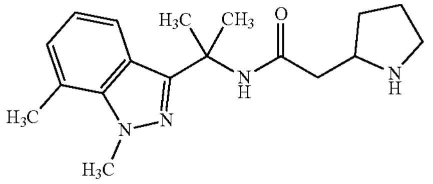 [SMILES: Cc1cccc2c(C(C)(C)NC(=O)CC3CCCN3)nn(C)c12]

To a solution of $Et_3N$ (0.351 mL, 2.52 mmol), 2-(1,7-dimethyl-1H-indazol-3-yl)propan-2-amine (0.171 g, 0.841 mmol), and 2-(1-(tert-butoxycarbonyl)pyrrolidin-2-yl)acetic acid (0.212 g, 0.925 mmol) in DMF (4.20 mL) was added HATU (0.352 g, 0.925 mmol). The reaction mixture was stirred at room temperature overnight and then was diluted with EtOAc, washed repeatedly with water, dried over $Na_2SO_4$, filtered, and concentrated in vacuo. The concentrate was taken up into dioxane (4.20 mL) and acidified with 4 M HCl in dioxane (4.20 mL, 16.8 mmol). The mixture was stirred at room temperature overnight and then was concentrated in vacuo. The product was taken up into DMF and MeOH, filtered, and purified by preparative HPLC (Phenomenex Gemini® C18, 5 μm, ID 30 mm×150 mm) using a gradient of 10-100% water/ACN in water (basic mode). The product-containing fractions were evaporated to afford the title compound (0.160 g, 60%).

STEP B: N-(2-(1,7-dimethyl-1H-indazol-3-yl)propan-2-yl)-2-(1-methylpyrrolidin-2-yl)acetamide To a solution of aqueous formaldehyde (37 wt %, 0.413 g, 5.09 mmol), acetic acid (0.146 mL, 2.54 mmol) and N-(2-(1,7-dimethyl-1H-indazol-3-yl)propan-2-yl)-2-(pyrrolidin-2-yl)acetamide (0.160 g, 0.509 mmol) in MeOH (8.48 mL) was added sodium cyanoborohydride (0.320 g, 5.09 mmol). The mixture was stirred at room temperature for 2 hours and then was diluted with MeOH and DMF, filtered and purified by preparative HPLC (Phenomenex Gemini® C18, 5 μm, ID 30 mm×150 mm) using a gradient of 10-100% water/ACN in water (basic mode). The product-containing fractions were evaporated to afford the title compound as a white solid (0.113 g, 68%). $^{1}$H NMR (400 MHz, $CD_3OD$) δ ppm 1.42-1.57 (m, 1H), 1.64-1.82 (m, 9H), 1.82-1.96 (m, 1H), 2.12-2.26 (m, 2H), 2.26-2.35 (m, 3H), 2.41-2.52 (m, 2H), 2.73 (s, 3H), 2.97-3.06 (m, 1H), 4.24 (s, 3H), 6.83-6.99 (m, 1H), 7.00-7.12 (m, 1H), 7.57-7.71 (m, 1H); ESI-MS m/z $[M+H]^+$ 329.1.

EXAMPLE 2: N-(2-(1-methyl-1H-indazol-3-yl)propan-2-yl)-2-(1-methylpiperidin-2-yl)acetamide

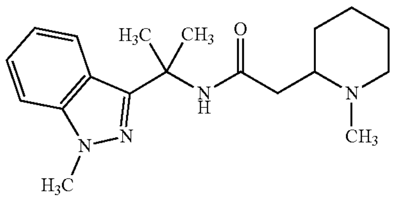 [SMILES: CN1CCCCC1CC(=O)NC(C)(C)c1nn(C)c2ccccc12]

To a solution of pyridine (0.131 mL, 1.62 mmol), 2-(1-methyl-1H-indazol-3-yl)propan-2-amine (0.061 g, 0.324 mmol) and 2-(1-methylpiperidin-2-yl)acetic acid (0.051 g, 0.324 mmol) in ACN (0.433 mL) was added T3P (50 wt % in EtOAc, 0.965 mL, 1.62 mmol). The reaction mixture was stirred at room temperature for 24 hours and then was diluted with MeOH, filtered and purified by preparative HPLC (Phenomenex Gemini® C18, 5 μm, ID 30 mm×150 mm) using a gradient of 10-100% water/ACN in water (basic mode) to give the title compound as a clear semisolid (27 mg, 25%). $^{1}$H NMR (400 MHz, $CD_3OD$) δ ppm 1.14-1.38 (m, 2H), 1.48-1.69 (m, 4H), 1.71-1.86 (m, 6H), 2.07-2.26 (m, 5H), 2.29-2.44 (m, 1H), 2.49-2.63 (m, 1H), 2.73-2.88 (m, 1H), 3.29-3.32 (m, 5H), 3.35 (s, 1H), 3.94-4.05 (m, 3H), 7.04-7.11 (m, 1H), 7.31-7.39 (m, 1H), 7.42-7.49 (m, 1H), 7.79-7.85 (m, 1H); ESI-MS m/z $[M+H]^+$ 329.1.

EXAMPLE 3: (R)—N-(2-(1-methyl-1H-indazol-3-yl)propan-2-yl)-2-(1-methylpyrrolidin-2-yl)acetamide

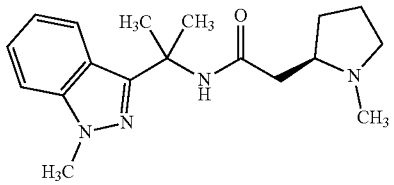 [SMILES: CN1CCC[C@@H]1CC(=O)NC(C)(C)c1nn(C)c2ccccc12]

STEP A: (R)—N-(2-(1-methyl-1H-indazol-3-yl) propan-2-yl)-2-(pyrrolidin-2-yl)acetamide

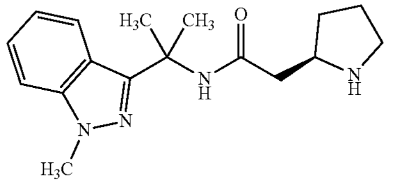 [SMILES: Cn1nc(C(C)(C)NC(=O)C[C@H]2CCCN2)c2ccccc21]

To a solution of $Et_3N$ (0.228 mL, 1.63 mmol), 2-(1-methyl-1H-indazol-3-yl)propan-2-amine (0.103 g, 0.544 mmol), and (R)-2-(1-(tert-butoxycarbonyl)pyrrolidin-2-yl) acetic acid (0.137 g, 0.599 mmol) in DMF (2.72 mL) was added HATU (0.228 g, 0.599 mmol). The reaction mixture was stirred at room temperature for 12 minutes and then was diluted with EtOAc, washed repeatedly with water, dried over $Na_2SO_4$, filtered and concentrated in vacuo. The concentrate was taken up in dioxane (2.72 mL) and acidified with 4 M HCl in dioxane (2.72 mL, 10.9 mmol). The mixture was stirred at room temperature for two hours. Next, MeOH (2 mL) was added and the residual solid was dissolved. The mixture was stirred at room temperature overnight and was concentrated in vacuo. The product was taken up in MeOH and DMF, filtered and purified by preparative HPLC (Phenomenex Gemini® C18, 5 μm, ID 30 mm×150 mm) using a gradient of 10-100% water/ACN in water (basic mode) to give the title compound (86 mg, 53%).

STEP B: (R)—N-(2-(1-methyl-1H-indazol-3-yl) propan-2-yl)-2-(1-methylpyrrolidin-2-yl)acetamide To a solution of aqueous formaldehyde (37 wt %, 0.116 g, 1.43 mmol) and (R)—N-(2-(1-methyl-1H-indazol-3-yl)propan-2-yl)-2-(pyrrolidin-2-yl)acetamide (0.086 g, 0.286 mmol) in MeOH (4.77 mL) was added sodium cyanoborohydride (0.090 g, 1.43 mmol). The reaction mixture was stirred at room temperature for 24 hours and then was diluted with MeOH and DMF, filtered and purified by preparative HPLC (Phenomenex Gemini® C18, 5 μm, ID 30 mm×150 mm) using a gradient of 10-100% water/ACN in water (basic mode). The product-containing fractions were evaporated to afford the title compound as a white solid (50 mg, 56%). $^1H$ NMR (400 MHz, $CD_3OD$) δ ppm 1.44-1.62 (m, 1H), 1.66-1.79 (m, 2H), 1.78-1.84 (m, 6H), 1.85-2.01 (m, 1H), 2.16-2.30 (m, 2H), 2.32 (s, 2H), 2.29-2.38 (m, 1H), 2.43-2.60 (m, 2H), 3.01-3.10 (m, 1H), 4.01 (s, 3H), 7.10 (ddd, J=8.1, 6.9, 0.9 Hz, 1H), 7.31-7.41 (m, 1H), 7.41-7.51 (m, 1H), 7.45-7.54 (m, 1H), 7.76-7.94 (m, 1H); ESI-MS m/z $[M+H]^+$ 315.1.

EXAMPLE 4: (S)—N-(2-(1-methyl-1H-indazol-3-yl)propan-2-yl)-2-(1-methylpyrrolidin-2-yl)acetamide

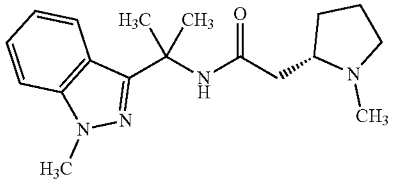 [SMILES: CN1CCC[C@H]1CC(=O)NC(C)(C)c1nn(C)c2ccccc12]

STEP A: (S)—N-(2-(1-methyl-1H-indazol-3-yl) propan-2-yl)-2-(pyrrolidin-2-yl)acetamide

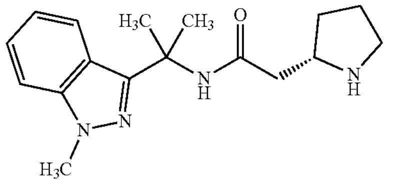 [SMILES: Cn1nc(C(C)(C)NC(=O)C[C@@H]2CCCN2)c2ccccc21]

To a solution of $Et_3N$ (0.236 mL, 1.70 mmol), 2-(1-methyl-1H-indazol-3-yl)propan-2-amine (0.107 g, 0.565 mmol) and (S)-2-(1-(tert-butoxycarbonyl)pyrrolidin-2-yl) acetic acid (0.143 g, 0.622 mmol) in DMF (2.83 mL) was added HATU (0.236 g, 0.622 mmol). The reaction mixture was stirred at room temperature for 12 minutes and then was diluted with EtOAc, washed repeatedly with water, dried over $Na_2SO_4$, filtered, and concentrated in vacuo. The concentrate was taken up in dioxane (2.72 mL) and acidified with 4 M HCl in dioxane (2.72 mL, 10.9 mmol). The mixture was stirred at room temperature for two hours.

Next, MeOH (2 mL) was added and the residual solid was dissolved. The mixture was stirred at room temperature overnight and then was concentrated in vacuo. The product was taken up in MeOH and DMF, filtered and purified by preparative HPLC (Phenomenex Gemini® C18, 5 μm, ID 30 mm×150 mm) using a gradient of 10-100% water/ACN in water (basic mode) to give the title compound (80 mg, 47%).

STEP B: (S)—N-(2-(1-methyl-1H-indazol-3-yl) propan-2-yl)-2-(1-methylpyrrolidin-2-yl)acetamide To a solution of aqueous formaldehyde (37 wt %, 0.108 g, 1.33 mmol) and (S)—N-(2-(1-methyl-1H-indazol-3-yl) propan-2-yl)-2-(pyrrolidin-2-yl)acetamide (0.080 g, 0.266 mmol) in MeOH (4.44 mL) was added sodium cyanoborohydride (0.167 g, 2.66 mmol). The mixture was stirred at room temperature for two hours and then was diluted with MeOH and DMF, filtered and purified by preparative HPLC (Phenomenex Gemini® C18, 5 μm, ID 30 mm×150 mm) using a gradient of 10-100% water/ACN in water (basic mode) to give the title compound as a white solid (44 mg, 52%). $^1H$ NMR (400 MHz, $CD_3OD$) δ ppm 1.43-1.60 (m, 1H), 1.65-1.77 (m, 2H), 1.81 (d, J=4.1 Hz, 6H), 1.86-2.03

(m, 1H), 2.15-2.28 (m, 2H), 2.32 (s, 3H), 2.40-2.56 (m, 2H), 3.04 (ddd, J=9.7, 7.3, 2.8 Hz, 1H), 3.96-4.06 (m, 3H), 7.02-7.18 (m, 1H), 7.30-7.43 (m, 1H), 7.44-7.52 (m, 1H), 7.78-7.90 (m, 1H); ESI-MS m/z $[M+H]^+$ 315.1.

EXAMPLE 5: N-(2-(isoquinolin-1-yl)propan-2-yl)-3-(pyrrolidin-1-yl)propanamide

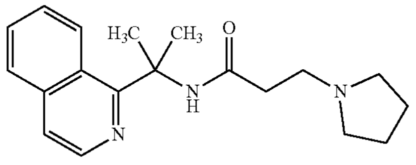 [SMILES: CC(C)(NC(=O)CCN1CCCC1)c1nccc2ccccc12]

To a mixture of 2-(isoquinolin-1-yl)propan-2-amine (37.5 mg, 0.201 mmol) and 3-(pyrrolidin-1-yl)propanoic acid (31.7 mg, 0.221 mmol) in DMA (1.0 mL) were added DIPEA (105 μL, 0.604 mmol) and HATU (115 mg, 0.302 mmol). The reaction mixture was stirred at room temperature overnight and then was filtered through a hydrophilic PTFE 0.45 m Millipore® filter, rinsing with methanol. The filtrate was purified by preparative HPLC (Phenomenex Gemini® C18, 5 μm, ID 30 mm×150 mm) using a gradient of 10-65% water/ACN in water (basic mode). Product-containing fractions were evaporated and lyophilized to afford the title compound as a white solid (17.2 mg, 27%). $^1H$ NMR (400 MHz, $CD_3OD$) δ ppm 1.74-1.79 (m, 4H), 1.87 (s, 6H), 2.34-2.41 (m, 2H), 2.47-2.55 (m, 4H), 2.57-2.64 (m, 2H), 7.57 (ddd, J=8.6, 7.0, 1.5 Hz, 1H), 7.61-7.72 (m, 2H), 7.90 (d, J=8.0 Hz, 1H), 8.35 (d, J=5.5 Hz, 1H), 8.66 (dd, J=8.8, 0.8 Hz, 1H); ESI-MS m/z $[M+H]^+$ 312.20.

EXAMPLE 6: N-(2-(isoquinolin-1-yl)propan-2-yl)-2-(1-methylpiperidin-2-yl)acetamide

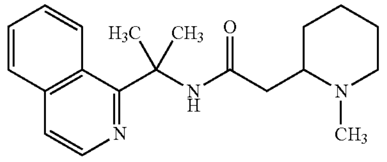 [SMILES: CN1CCCCC1CC(=O)NC(C)(C)c1nccc2ccccc12]

The title compound was prepared like EXAMPLE 5, using 2-(isoquinolin-1-yl)propan-2-amine (36.5 mg, 0.196 mmol), 2-(1-methylpiperidine-2-yl)acetic acid (33.9 mg, 0.216 mmol), DIPEA (103 μL, 0.588 mmol) and HATU (112 mg, 0.294 mmol) in DMA (1.3 mL), and was obtained as an off-white solid (41.2 mg, 65%). $^1H$ NMR (400 MHz, $CD_3OD$) δ ppm 1.16-1.30 (m, 2H), 1.42-1.65 (m, 4H), 1.88 (s, 6H), 2.09-2.18 (m, 2H), 2.21 (s, 3H), 2.25-2.34 (m, 1H), 2.55 (dd, J=14.3, 4.5 Hz, 1H), 2.76-2.85 (m, 1H), 7.58 (ddd, J=8.6, 7.0, 1.2 Hz, 1H), 7.63-7.72 (m, 2H), 7.89-7.95 (m, 1H), 8.37 (d, J=5.8 Hz, 1H), 8.64-8.71 (m, 1H); ESI-MS m/z $[M+H]^+$ 326.15.

EXAMPLE 7: N-(2-(5-methylisoquinolin-1-yl)propan-2-yl)-2-(1-methylpiperidin-2-yl)acetamide

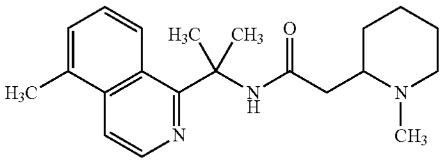 [SMILES: Cc1cccc2c(C(C)(C)NC(=O)CC3CCCCN3C)nccc12]

To a mixture of 2-(5-methylisoquinolin-1-yl)propan-2-amine (32.2 mg, 0.161 mmol) and 2-(1-methylpiperidin-2-yl)acetic acid (27.8 mg, 0.177 mmol) in DMA (1.07 mL) were added DIPEA (84 μL, 0.48 mmol) and HATU (92 mg, 0.24 mmol). The reaction mixture was stirred at room temperature for 5 hours and then was filtered through a hydrophilic PTFE 0.45 m Millipore® filter, rinsing with methanol. The filtrate was purified by preparative HPLC (Phenomenex Gemini® C18, 5 μm, ID 30 mm×150 mm) using a gradient of 10-70% water/ACN in water (basic mode). Product-containing fractions were evaporated and lyophilized to afford the title compound as a white solid (19.9 mg, 36%). $^1H$ NMR (400 MHz, $CD_3OD$) δ ppm 1.16-1.30 (m, 2H), 1.39-1.68 (m, 4H), 1.88 (s, 6H), 2.14 (br dd, J=14.2, 8.4 Hz, 2H), 2.21 (s, 3H), 2.26-2.37 (m, 1H), 2.54 (dd, J=14.3, 4.5 Hz, 1H), 2.69 (s, 3H), 2.76-2.86 (m, 1H), 7.46 (dd, J=8.8, 7.0 Hz, 1H), 7.54 (d, J=7.0 Hz, 1H), 7.81 (dd, J=5.9, 0.9 Hz, 1H), 8.42 (d, J=6.0 Hz, 1H), 8.54 (d, J=8.8 Hz, 1H); ESI-MS m/z $[M+H]^+$ 340.20.

EXAMPLE 8: (R)—N-(2-(5-methylisoquinolin-1-yl)propan-2-yl)-2-(1-methylpiperidin-2-yl)acetamide

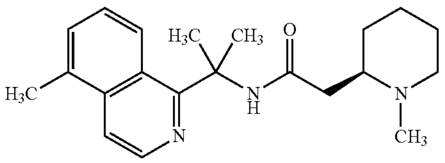 [SMILES: Cc1cccc2c(C(C)(C)NC(=O)C[C@H]3CCCCN3C)nccc12]

EXAMPLE 9: (S)—N-(2-(5-methylisoquinolin-1-yl)propan-2-yl)-2-(1-methylpiperidin-2-yl)acetamide

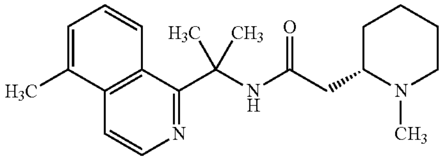 [SMILES: Cc1cccc2c(C(C)(C)NC(=O)C[C@@H]3CCCCN3C)nccc12]

The title enantiomers of racemic N-(2-(5-methylisoquinolin-1-yl)propan-2-yl)-2-(1-methylpiperidin-2-yl)acetamide (505 mg, 1.49 mmol) were separated by preparative SFC (Celluose 2, 5 μm, ID 30 mm×250 mm) using a mobile phase of 40% EtOH (with 0.1% $NH_4OH$) in $CO_2$. The first eluting compound was arbitrarily assigned as the (R)-enantiomer (173.6 mg, 34%) and the second eluting compound was arbitrarily assigned as the (S)-enantiomer (166.2 mg, 33%). $^1H$ NMR (500 MHz, $CD_3OD$) δ ppm 1.31-1.63 (m, 4H), 1.65-1.80 (m, 3H), 1.90 (s, 6H), 2.56-2.85 (m, 8H), 3.10 (br d, J=3.6 Hz, 1H), 3.13-3.23 (m, 1H), 7.45-7.52 (m, 1H), 7.53-7.59 (m, 1H), 7.82 (dd, J=6.0, 1.0 Hz, 1H), 8.43 (d, J=6.0 Hz, 1H), 8.52 (d, J=8.7 Hz, 1H); ESI-MS m/z $[M+H]^+$ 340.20.

EXAMPLE 10: N-(2-(1-methyl-1H-indazol-3-yl)propan-2-yl)-2-(tetrahydro-1H-pyrrolizin-7a(5H)-yl)acetamide

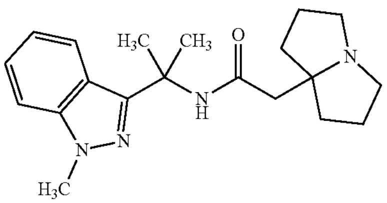 [SMILES: Cn1nc(C(C)(C)NC(=O)CC23CCCN2CCC3)c2ccccc21]

To a solution of pyridine (0.094 mL, 1.16 mmol), 2-(1-methyl-1H-indazol-3-yl)propan-2-amine (0.044 g, 0.232 mmol) and 2-(tetrahydro-1H-pyrrolizin-7a(5H)-yl)acetic acid (0.039 g, 0.232 mmol) in ACN (0.310 mL) was added T3P (50 wt % in EtOAc, 0.691 mL, 1.16 mmol). The reaction mixture was stirred for 24 hours and then was diluted with MeOH, filtered and purified by preparative HPLC (Phenomenex Gemini® C18, 5 μm, ID 30 mm×150 mm) using a gradient of 10-100% water/ACN in water (basic mode). The product was further purified by preparative HPLC (Xbridge) using a gradient of ACN in water (acid mode) to give a TFA salt of the title compound (8.0 mg, 10%). $^1H$ NMR (400 MHz, $CD_3OD$) δ ppm 1.78-1.92 (m, 8H), 1.94-2.13 (m, 6H), 2.72-2.79 (m, 2H), 3.00-3.11 (m, 2H), 3.38-3.52 (m, 2H), 4.01 (s, 3H), 7.07-7.17 (m, 1H), 7.35-7.44 (m, 1H), 7.46-7.53 (m, 1H), 7.82-7.90 (m, 1H), 8.71-8.88 (m, 1H); ESI-MS m/z $[M+H]^+$ 341.1.

EXAMPLE 11: N-(2-(3-chlorophenyl)propan-2-yl)-2-(1-methylpiperidin-2-yl)acetamide

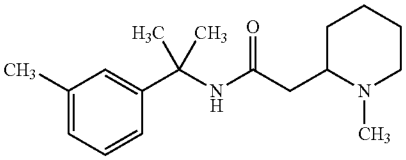 [SMILES: Cc1cccc(C(C)(C)NC(=O)CC2CCCCN2C)c1]

To a solution of pyridine (0.069 mL, 0.859 mmol), 2-(3-chlorophenyl)propan-2-amine (0.049 g, 0.286 mmol) and 2-(1-methylpiperidin-2-yl)acetic acid (0.045 g, 0.286 mmol) in ACN (0.382 mL) was added T3P (50 wt % in EtOAc, 0.511 mL, 0.859 mmol). The reaction mixture was stirred at room temperature overnight and then was diluted with MeOH, filtered and purified by preparative HPLC (Phenomenex Gemini® C18, 5 μm, ID 30 mm×150 mm) using a gradient of 10-100% water/ACN in water (basic mode) to give the title compound (25 mg, 28%). $^1H$ NMR (400 MHz, $CD_3OD$) δ ppm 1.27-1.45 (m, 2H), 1.51-1.81 (m, 10H), 2.14-2.26 (m, 2H), 2.27-2.34 (m, 3H), 2.37-2.50 (m, 1H), 2.52-2.67 (m, 1H), 2.79-2.93 (m, 1H), 7.16-7.23 (m, 1H), 7.25-7.35 (m, 2H), 7.35-7.41 (m, 1H); ESI-MS m/z $[M+H]^+$ 309.1.

EXAMPLE 12: N-(2-(3-chlorophenyl)propan-2-yl)-2-(1-methylpyrrolidin-2-yl)acetamide

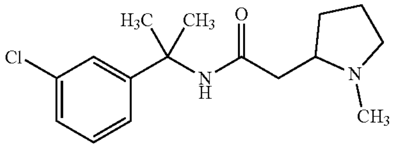 [SMILES: CN1CCCC1CC(=O)NC(C)(C)c1cccc(Cl)c1]

STEP A: N-(2-(3-chlorophenyl)propan-2-yl)-2-(pyrrolidin-2-yl)acetamide

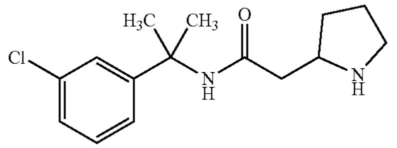 [SMILES: CC(C)(NC(=O)CC1CCCN1)c1cccc(Cl)c1]

To a solution of pyridine (0.152 mL, 1.88 mmol), 2-(3-chlorophenyl)propan-2-amine (0.107 g, 0.628 mmol) and 2-(1-(tert-butoxycarbonyl)pyrrolidin-2-yl)acetic acid (0.144 g, 0.628 mmol) in ACN (0.837 mL) was added T3P (50 wt % in EtOAc, 1.12 mL, 1.88 mmol). The reaction mixture was stirred at room temperature for 18 hours and then was diluted with saturated aqueous $NH_4Cl$, extracted with EtOAc, dried over $Na_2SO_4$, filtered and concentrated in vacuo. The concentrate was taken up into dioxane (6 mL) and acidified with 4 M HCl in dioxane (2.98 mL, 11.9 mmol). The mixture was stirred at room temperature for 6 hours and then was concentrated in vacuo, diluted with MeOH, filtered and purified by preparative HPLC (Phenomenex Gemini® C18, 5 μm, ID 30 mm×150 mm) using a gradient of 10-100% water/ACN in water (basic mode) to give the title compound (0.176 g, assumed quantitative).

STEP B: N-(2-(3-chlorophenyl)propan-2-yl)-2-(1-methylpyrrolidin-2-yl)acetamide

To a solution of N-(2-(3-chlorophenyl)propan-2-yl)-2-(pyrrolidin-2-yl)acetamide (0.176 g, 0.628 mmol) and aqueous formaldehyde (37 wt %, 0.225 g, 2.77 mmol) in MeOH (2.77 mL) was added sodium cyanoborohydride (0.174 g, 2.77 mmol). The reaction mixture was stirred at room temperature overnight and then was sonicated, filtered and purified by preparative HPLC (Phenomenex Gemini® C18, 5 μm, ID 30 mm×150 mm) using a gradient of 10-100% water/ACN in water (basic mode) to give the title compound as a crystalline white solid (41 mg, 22% over two steps). $^1H$ NMR (400 MHz, $CD_3OD$) δ ppm 1.53-1.70 (m, 7H), 1.73-1.88 (m, 2H), 1.96-2.09 (m, 2H), 2.19-2.31 (m, 2H), 2.33-2.41 (m, 3H), 2.45-2.61 (m, 2H), 3.08 (ddd, J=9.7, 6.8, 3.3 Hz, 1H), 7.18-7.23 (m, 1H), 7.26-7.34 (m, 2H), 7.35-7.39 (m, 1H), 7.36-7.44 (m, 1H); ESI-MS m/z $[M+H]^+$ 295.1.

EXAMPLE 13: N-(2-(furo[3,2-c]pyridin-4-yl)propan-2-yl)-2-(1-methylpiperidin-2-yl)acetamide

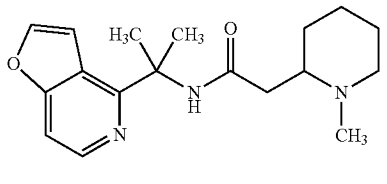 [SMILES: CN1CCCCC1CC(=O)NC(C)(C)c1nccc2occc12]

To a solution of pyridine (0.039 mL, 0.477 mmol), 2-(furo[3,2-c]pyridin-4-yl)propan-2-amine (0.028 g, 0.159 mmol) and 2-(1-methylpiperidin-2-yl)acetic acid (0.025 g, 0.159 mmol) in ACN was added T3P (50 wt % in EtOAc, 0.284 mL, 0.477 mmol). The reaction mixture was stirred at room temperature overnight and then was diluted with MeOH, filtered and purified by preparative HPLC (Phenomenex Gemini® C18, 5 μm, ID 30 mm×150 mm) using a gradient of 10-100% water/ACN in water (basic mode) to give the title compound (17 mg, 34%). $^1$H NMR (400 MHz, $CD_3OD$) δ ppm 0.98-1.18 (m, 1H), 1.20-1.45 (m, 3H), 1.51-1.72 (m, 5H), 1.72-1.80 (m, 7H), 2.15-2.27 (m, 3H), 2.26-2.30 (m, 3H), 2.34-2.50 (m, 1H), 2.55-2.68 (m, 1H), 2.77-2.93 (m, 1H), 7.09-7.22 (m, 1H), 7.37-7.57 (m, 1H), 7.78-7.92 (m, 1H), 8.25-8.43 (m, 1H); ESI-MS m/z $[M+H]^+$ 316.1.

EXAMPLE 14: (R)—N-(2-(furo[3,2-c]pyridin-4-yl)propan-2-yl)-2-(1-methylpiperidin-2-yl)acetamide

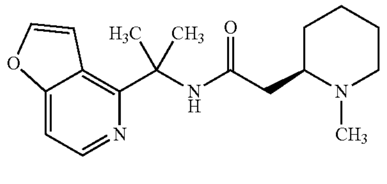 [SMILES: CN1CCCC[C@@H]1CC(=O)NC(C)(C)c1nccc2occc12]

and

EXAMPLE 15: (S)—N-(2-(furo[3,2-c]pyridin-4-yl)propan-2-yl)-2-(1-methylpiperidin-2-yl)acetamide

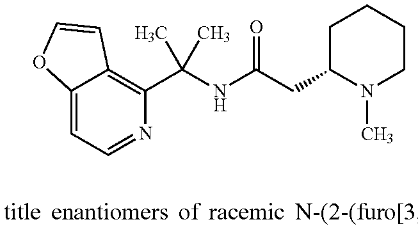

The title enantiomers of racemic N-(2-(furo[3,2-c]pyridin-4-yl)propan-2-yl)-2-(1-methylpiperidin-2-yl)acetamide (0.582 g, 1.84 mmol) were separated by preparative SFC. The first eluting compound was arbitrarily assigned as the (R)-enantiomer and was obtained as an off-white solid (265.5 mg, 46%) and the second eluting compound was arbitrarily assigned as the (S)-enantiomer (251.9 mg, 43%). $^1$H NMR (400 MHz, $CD_3OD$) δ ppm 1.21-1.34 (m, 2H), 1.47-1.68 (m, 4H), 1.70-1.80 (m, 6H), 2.07-2.30 (m, 5H), 2.31-2.45 (m, 1H), 2.59 (dd, J=14.4, 4.8 Hz, 1H), 2.75-2.91 (m, 1H), 7.12 (dd, J=2.3, 1.0 Hz, 1H), 7.44 (dd, J=5.8, 0.9 Hz, 1H), 7.83 (d, J=2.3 Hz, 1H), 8.21-8.39 (m, 1H); ESI-MS m/z $[M+H]^+$ 316.1.

EXAMPLE 16: (R)—N-(2-(isoquinolin-1-yl)propan-2-yl)-2-(1-methylpyrrolidin-2-yl)acetamide

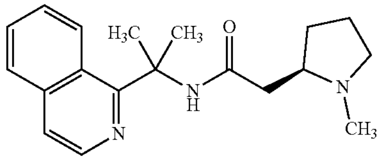 [SMILES: CN1CCC[C@@H]1CC(=O)NC(C)(C)c1nccc2ccccc12]

STEP A: tert-butyl (R)-2-(2-((2-(isoquinolin-1-yl)propan-2-yl)amino)-2-oxoethyl)pyrrolidine-1-carboxylate

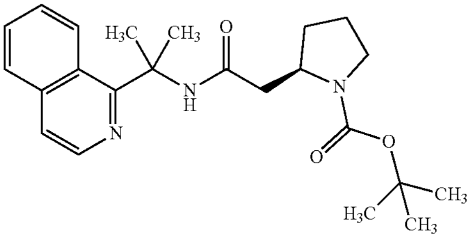 [SMILES: CC(C)(C)OC(=O)N1CCC[C@@H]1CC(=O)NC(C)(C)c1nccc2ccccc12]

To a solution of 2-(isoquinolin-1-yl)propan-2-amine (60 mg, 0.32 mmol) and (R)-2-(1-(tert-butoxycarbonyl)pyrrolidin-2-yl)acetic acid (81 mg, 0.35 mmol) in DMA (2.15 mL) were added DIPEA (169 μL, 0.966 mmol) and HATU (184 mg, 0.483 mmol). The reaction mixture was stirred at room temperature overnight and then was quenched with water and saturated aqueous $NH_4Cl$ and extracted with EtOAc. The organic phase was washed with saturated aqueous NaCl, dried over $Na_2SO_4$, filtered, and concentrated under reduced pressure. The residue was purified by automated flash silica column chromatography using a gradient of 20-80% EtOAc in heptanes. Product-containing fractions were evaporated to afford the title compound as a colorless oil (128 mg, assumed quantitative). ESI-MS m/z $[M+H]^+$ 398.4.

STEP B: (R)—N-(2-(isoquinolin-1-yl)propan-2-yl)-2-(pyrrolidin-2-yl)acetamide

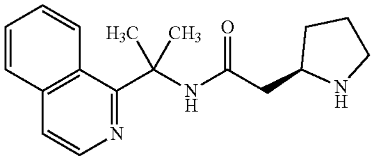 [SMILES: CC(C)(NC(=O)C[C@H]1CCCN1)c1nccc2ccccc12]

To a solution of tert-butyl (R)-2-(2-((2-(isoquinolin-1-yl)propan-2-yl)amino)-2-oxoethyl)pyrrolidine-1-carboxylate (128 mg, 0.322 mmol) in dioxane (1.61 mL) was added with 4 M HCl in dioxane (1.61 mL, 6.44 mmol). The reaction mixture was stirred at room temperature for 1.75 hours and then was concentrated under reduced pressure and evaporated again with diethyl ether to give the bis-HCl salt of the title compound (119 mg, assumed quantitative). ESI-MS m/z $[M+H]^+$ 298.3.

STEP C: (R)—N-(2-(isoquinolin-1-yl)propan-2-yl)-2-(1-methylpyrrolidin-2-yl)acetamide To a solution of (R)—N-(2-(isoquinolin-1-yl)propan-2-yl)-2-(pyrrolidin-2-yl)acetamide dihydrochloride (119 mg, 0.322 mmol) in methanol (3.22 mL) were added aqueous formaldehyde (37 wt %, 131 mg, 1.61 mmol) and sodium cyanoborohydride (1M in THF, 1.61 mL, 1.61 mmol). The reaction mixture was stirred at room temperature overnight. Following reaction, the mixture was concentrated under reduced pressure and then taken up in methanol. The resulting solution was filtered through a hydrophilic PTFE 0.45 m Millipore® filter, rinsing with methanol. The filtrate was purified by preparative HPLC (Phenomenex Gemini® C18, 5 μm, ID 30 mm×150 mm) using a gradient of water/ACN in water (basic mode). Product-containing fractions were evaporated and lyophilized to afford the title compound as a white solid (43.8 mg, 44% over three steps). $^1$H NMR (400 MHz, $CD_3OD$) δ ppm 1.27-1.40 (m, 1H), 1.52-1.72 (m, 3H), 1.77 (2 s, 6H), 1.99-2.13 (m, 2H), 2.17 (s, 3H), 2.24-2.34 (m, 1H), 2.34-2.42 (m, 1H), 2.92 (ddd, J=9.7, 7.2, 2.6 Hz, 1H), 7.47 (ddd, J=8.6, 7.0, 1.4 Hz, 1H), 7.53 (d, J=5.6 Hz, 1H), 7.58 (ddd, J=8.1, 6.9, 1.1 Hz, 1H), 7.80 (d, J=8.2 Hz, 1H), 8.25 (d, J=5.6 Hz, 1H), 8.56 (dd, J=8.8, 0.9 Hz, 1H); ESI-MS m/z $[M+H]^+$ 312.10.

EXAMPLE 17: (R)—N-(2-(5-methylisoquinolin-1-yl)propan-2-yl)-2-(1-methylpyrrolidin-2-yl)acetamide

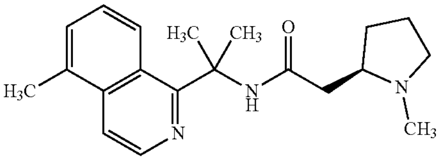 [SMILES: Cc1cccc2c(C(C)(C)NC(=O)C[C@H]3CCCN3C)nccc12]

The title compound was prepared like EXAMPLE 16, using 2-(5-methylisoquinolin-1-yl)propan-2-amine (71.3 mg, 0.356 mmol), (R)-2-(1-(tert-butoxycarbonyl)pyrrolidin-2-yl)acetic acid (90 mg, 0.39 mmol), DIPEA (187 μL, 1.07 mmol) and HATU (203 mg, 0.534 mmol) in DMA (2.37 mL), and was obtained as a white solid (31.4 mg, 27% over three steps). $^1$H NMR (400 MHz, $CD_3OD$) δ ppm 1.34-1.51 (m, 1H), 1.63-1.82 (m, 3H), 1.87 (s, 6H), 2.08-2.25 (m, 2H), 2.28 (s, 3H), 2.37-2.53 (m, 2H), 2.68 (s, 3H), 3.03 (ddd, J=9.7, 7.2, 3.0 Hz, 1H), 7.44 (dd, J=8.8, 7.0 Hz, 1H), 7.50-7.55 (m, 1H), 7.79 (dd, J=6.0, 0.9 Hz, 1H), 8.40 (d, J=5.9 Hz, 1H), 8.53 (d, J=8.8 Hz, 1H); ESI-MS m/z $[M+H]^+$ 326.15.

EXAMPLE 18: (S)—N-(2-(5-methylisoquinolin-1-yl)propan-2-yl)-2-(1-methylpyrrolidin-2-yl)acetamide

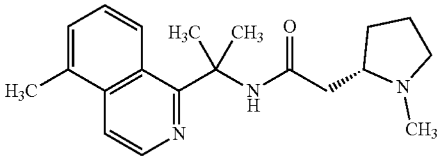 [SMILES: Cc1cccc2c(C(C)(C)NC(=O)C[C@@H]3CCCN3C)nccc12]

The title compound was prepared like EXAMPLE 16, using 2-(5-methylisoquinolin-1-yl)propan-2-amine (71.3 mg, 0.356 mmol), (S)-2-(1-(tert-butoxycarbonyl)pyrrolidin-2-yl)acetic acid (90 mg, 0.39 mmol), DIPEA (187 μL, 1.07 mmol) and HATU (203 mg, 0.534 mmol) in DMA (2.37 mL), and was obtained as a white solid (26.7 mg, 23% over three steps). $^1$H NMR (400 MHz, $CD_3OD$) δ ppm 1.34-1.51 (m, 1H), 1.63-1.82 (m, 3H), 1.87 (s, 6H), 2.08-2.25 (m, 2H), 2.28 (s, 3H), 2.37-2.53 (m, 2H), 2.68 (s, 3H), 3.03 (ddd, J=9.7, 7.2, 3.0 Hz, 1H), 7.44 (dd, J=8.8, 7.0 Hz, 1H), 7.50-7.55 (m, 1H), 7.79 (dd, J=6.0, 0.9 Hz, 1H), 8.40 (d, J=5.9 Hz, 1H), 8.53 (d, J=8.8 Hz, 1H); ESI-MS m/z $[M+H]^+$ 326.20.

EXAMPLE 19: (R)—N-(2-(7-methylbenzo[d]isoxazol-3-yl)propan-2-yl)-2-(1-methylpyrrolidin-2-yl)acetamide

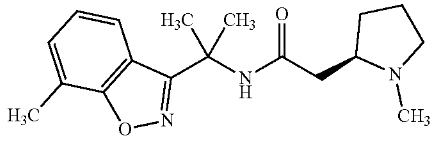 [SMILES: Cc1cccc2c(C(C)(C)NC(=O)C[C@H]3CCCN3C)noc12]

The title compound was prepared like EXAMPLE 16, using 2-(7-methylbenzo[d]isoxazol-3-yl)propan-2-amine (350 mg, 1.84 mmol), (R)-2-(1-(tert-butoxycarbonyl)pyrrolidin-2-yl)acetic acid (422 mg, 1.84 mmol), DIPEA (964 μL, 5.52 mmol) and HATU (1.049 g, 2.76 mmol) in DMA (10 mL), and was obtained as a white solid (290 mg, 50% over three steps). $^1$H NMR (400 MHz, d4-methanol) δ ppm 1.50 (dddd, J=12.6, 10.1, 8.5, 5.9 Hz, 1H), 1.69-1.78 (m, 2H), 1.80 (app d, J=2.8 Hz, 6H), 1.84-1.97 (m, 1H), 2.19-2.31 (m, 2H), 2.33 (s, 3H), 2.45-2.60 (m, 5H), 3.07 (ddd, J=9.8, 7.2, 3.1 Hz, 1H), 7.19-7.27 (m, 1H), 7.37 (dt, J=7.3, 1.0 Hz, 1H), 7.63-7.70 (m, 1H); ESI-MS m/z $[M+H]^+$ 316.20.

EXAMPLE 20: (S)—N-(2-(isoquinolin-1-yl)propan-2-yl)-2-(2-methyl-1,2,3,4-tetrahydroisoquinolin-3-yl)acetamide

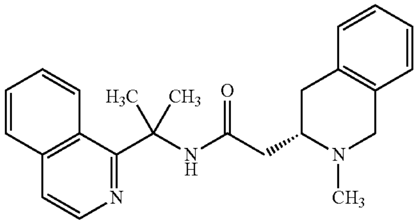 [SMILES: CN1Cc2ccccc2C[C@H]1CC(=O)NC(C)(C)c1nccc2ccccc12]

The title compound was prepared like EXAMPLE 16, using 2-(isoquinolin-1-yl)propan-2-amine (93 mg, 0.50 mmol), (S)-2-(2-(tert-butoxycarbonyl)-1,2,3,4-tetrahydroquinolin-3-yl)acetic acid (146 mg, 0.500 mmol), DIPEA (262 μL, 1.50 mmol) and HATU (285 mg, 0.750 mmol) in DMA (2 mL), and was obtained as a white solid (29.5 mg, 16% over three steps). $^1$H NMR (400 MHz, $CD_3OD$) δ ppm 1.89 (app d, J=3.6 Hz, 6H), 2.19 (dd, J=14.3, 9.2 Hz, 1H), 2.38 (s, 3H), 2.46-2.62 (m, 2H), 2.65-2.74 (m, 1H), 3.08 (ddt, J=9.2, 6.7, 4.8 Hz, 1H), 3.63-3.79 (m, 2H), 6.93-6.99 (m, 1H), 7.02-7.08 (m, 1H), 7.10-7.18 (m, 2H), 7.59 (ddd, J=8.6, 7.0, 1.4 Hz, 1H), 7.66 (d, J=5.3 Hz, 1H), 7.72 (ddd, J=8.1, 6.9, 1.1 Hz, 1H), 7.94 (d, J=8.2 Hz, 1H), 8.38 (d, J=5.6 Hz, 1H), 8.67 (dd, J=8.7, 0.8 Hz, 1H); ESI-MS m/z $[M+H]^+$ 374.20.

EXAMPLE 21: (S)—N-(2-(7-methylbenzo[d]isoxazol-3-yl)propan-2-yl)-2-(1-methylpyrrolidin-2-yl) acetamide

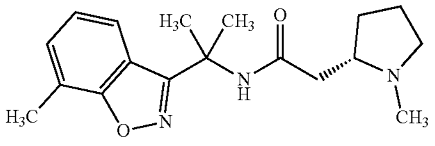 [SMILES: Cc1cccc2c(C(C)(C)NC(=O)C[C@@H]3CCCN3C)noc12]

The title compound was prepared like EXAMPLE 16, using 2-(7-methylbenzo[d]isoxazol-3-yl)propan-2-amine (0.350 g, 1.84 mmol), (S)-2-(1-(tert-butoxycarbonyl)pyrrolidin-2-yl)acetic acid (422 mg, 1.84 mmol), DIPEA (964 μL, 5.52 mmol) and HATU (1.049 g, 2.76 mmol) in DMA (10 mL), and was obtained as a white solid (235.7 mg, 41% over three steps). $^1$H NMR (400 MHz, $CD_3OD$) δ ppm 1.50 (dddd, J=12.6, 10.0, 8.4, 6.0 Hz, 1H), 1.80 (app d, J=2.8 Hz, 6H), 1.84-1.97 (m, 1H), 2.19-2.30 (m, 2H), 2.33 (s, 3H), 2.45-2.61 (m, 5H), 3.07 (ddd, J=9.8, 7.1, 3.2 Hz, 1H), 7.20-7.27 (m, 1H), 7.37 (dt, J=7.2, 1.0 Hz, 1H), 7.67 (dt, J=8.0, 0.8 Hz, 1H); ESI-MS m/z $[M+H]^+$ 316.20.

EXAMPLE 22: (S)—N-(2-(3-methylisoquinolin-1-yl)propan-2-yl)-2-(1-methylpyrrolidin-2-yl)acetamide

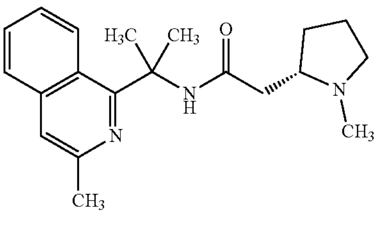 [SMILES: Cc1cc2ccccc2c(C(C)(C)NC(=O)C[C@@H]2CCCN2C)n1]

The title compound was prepared like EXAMPLE 16, using 2-(3-methylisoquinolin-1-yl)propan-2-amine (0.300 g, 1.50 mmol), (S)-2-(1-(tert-butoxycarbonyl)pyrrolidin-2-yl)acetic acid (0.344 g, 1.50 mmol), DIPEA (1.05 mL, 6.00 mmol) and HATU (0.856 g, 2.25 mmol) in DMA (7.5 mL), and was obtained as a white solid (201.4 mg, 41% over three steps). $^1$H NMR (400 MHz, $CD_3OD$) δ ppm 1.41-1.56 (m, 1H), 1.64-1.86 (m, 3H), 1.89 (app d, J=2.3 Hz, 6H), 2.12-2.27 (m, 2H), 2.31 (s, 3H), 2.41-2.55 (m, 2H), 2.64 (d, J=0.6 Hz, 3H), 3.05 (ddd, J=9.8, 7.2, 2.8 Hz, 1H), 7.40-7.51 (m, 2H), 7.60 (ddd, J=8.2, 6.9, 1.0 Hz, 1H), 7.79 (d, J=8.2 Hz, 1H), 8.57 (dd, J=8.7, 0.8 Hz, 1H); ESI-MS m/z $[M+H]^+$ 326.10.

EXAMPLE 23: (S)—N-(2-(isoquinolin-1-yl)propan-2-yl)-2-(pyrrolidin-2-yl)acetamide

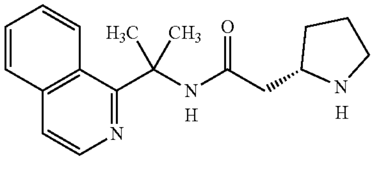

STEP A: tert-butyl (S)-2-(2-((2-(isoquinolin-1-yl)propan-2-yl)amino)-2-oxoethyl)pyrrolidine-1-carboxylate

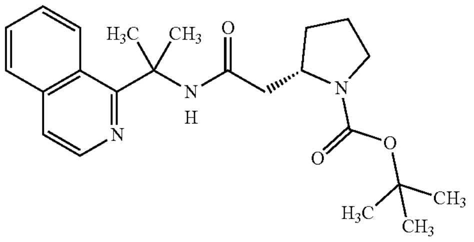

To a three-neck flask equipped with mechanical stirrer, thermometer and $N_2$ inlet were added the dihydrochloride salt of 2-(isoquinolin-1-yl)propan-2-amine (292.3 g, 1.13 mol), (S)-2-(1-(tert-butoxycarbonyl)pyrrolidin-2-yl)acetic acid (284 g, 1.24 mol) and DMF (5500 mL). The resulting suspension was stirred for 15 minutes at 14° C. and then $Et_3N$ (550 mL, 3.95 mol) was added over a 1-minute period, followed by solid HATU (462 g, 1.22 mol) at room temperature over a 2-minute period. The reaction mixture was stirred at room temperature for 15 hours and then was diluted with iPrOAc (6000 mL) and partitioned with water (3000 mL). The aqueous and organic layers were separated. The aqueous phase was washed with iPrOAc (1500 mL). The organic layers were combined, washed with brine (1500 mL), dried over $Na_2SO_4$, filtered, rinsed with iPrOAc and concentrated in a rotary evaporator. Some product was detected in the aqueous layers, so each was basified with $Et_3N$ (5 mL) and washed with iPrOAc (500 mL). The organic phase was washed with brine (250 mL), dried over $Na_2SO_4$, filtered, rinsed with iPrOAc and concentrated via rotary evaporation. The organic extracts were combined, concentrated and dried in vacuo to provide the crude product as a brown oil. A portion of the brown oil solidified to furnish an oily solid after standing overnight. The oily solid was dispersed in EtOAc, filtered, with cold EtOAc (2×) and cold heptane. The resulting solid was dried in vacuo to provide the pure product (35 g). The filtrate was concentrated via rotary evaporation, diluted with heptane and EtOAc, and purified by silica column chromatography using a gradient of 15-70% EtOAc in heptanes (2310 g silica gel, RediSep® Rf Gold). The product-containing fractions were combined, concentrated in a rotary evaporator, and dried in vacuo to provide the pure product as an off-white solid. The pure fractions were combined with the filtered solid to provide the title compound as a white solid (305.8 g, 68.2%). $^1$H NMR (400 MHz, $CD_3OD$) δ ppm 1.37-1.54 (m, 10H), 1.63-1.93 (m, 9H), 2.04-2.31 (m, 1H), 2.62-2.77 (m, 1H), 3.22-3.30 (m, 2H), 3.86-4.02 (m, 1H), 7.58 (ddd, J=8.6, 7.0, 1.2 Hz, 1H), 7.64 (d, J=5.8 Hz, 1H), 7.68 (ddd, J=8.0, 6.9, 0.9 Hz, 1H), 7.90 (d, J=8.0 Hz, 1H), 8.35 (d, J=5.8 Hz, 1H), 8.68 (br d, J=8.3 Hz, 1H); ESI-MS m/z $[M+H]^+$ 398.2.

STEP B: (S)—N-(2-(isoquinolin-1-yl)propan-2-yl)-2-(pyrrolidin-2-yl)acetamide

To a three-neck flask equipped with overhead stirrer, thermometer, addition funnel and $N_2$ inlet were added tert-butyl (S)-2-(2-((2-(isoquinolin-1-yl)propan-2-yl)amino)-2-oxoethyl)pyrrolidine-1-carboxylate (305.7 g, 769 mmol) and DCM (2570 mL) at room temperature. The resulting yellow solution was cooled to 0-5° C. and 4 M HCl in dioxane (1538 mL, 6.15 mol) was added dropwise at 0-5° C. over a 2.25-hour period. The reaction mixture was stirred at 0-5° C. for 8 hours to give a yellow suspension which was warmed to 15° C. over a 1-hour period. The resulting solid was pressure-filtered using nitrogen, rinsed with $Et_{20}$ (4×300 mL) and dried in vacuo to provide the dihydrochloride salt of the title compound as a hygroscopic, off-white solid (282.7 g, 99.2% yield, 96-97% ee). $^1$H NMR (400 MHz, DMSO-$d_6$) δ ppm 1.28-1.43 (m, 1H), 1.61-1.86 (m, 3H), 1.93 (d, J=7.5 Hz, 6H), 2.64-2.72 (m, 3H), 2.91-3.13 (m, 2H), 3.30-3.46 (m, 1H), 7.88 (br t, J=7.8 Hz, 1H), 8.05 (br t, J=7.5 Hz, 1H), 8.25 (br d, J=7.8 Hz, 2H), 8.53 (d, J=6.3 Hz, 1H), 8.96 (d, J=9.0 Hz, 1H), 9.02-9.28 (m, 2H), 9.76 (br s, 1H); ESI-MS m/z $[M+H]^+$ 298.2.

EXAMPLE 24: (S)—N-(2-(isoquinolin-1-yl)propan-2-yl)-2-(1-methylpyrrolidin-2-yl)acetamide

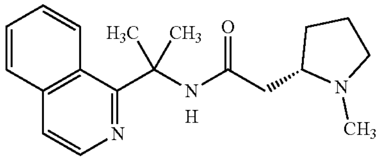

STEP A: (S)—N-(2-(isoquinolin-1-yl)propan-2-yl)-2-(1-methylpyrrolidin-2-yl)acetamide

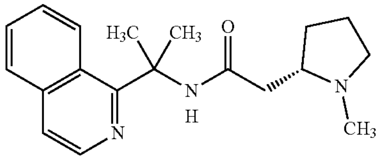

To a three-neck flask equipped with overhead stirrer, thermometer, addition funnel and $N_2$ inlet were added (S)—N-(2-(isoquinolin-1-yl)propan-2-yl)-2-(pyrrolidin-2-yl)acetamide dihydrochloride (282.7 g, 763 mmol) and MeOH (7650 mL). The resulting orange solution was cooled to 6° C. and aqueous formaldehyde (37 wt %, 170.5 mL, 2.29 mol) was added over a 3-minute period. The mixture was stirred at 6° C. for 5 minutes. Next, sodium triacetoxyborohydride (485 g, 2.29 mol) was added in portions over a 25-minute period. The reaction mixture was stirred at 3-7° C. for 2.5 hours. Extra aqueous formaldehyde (37 wt %, 28.4 mL, 382 mmol) was added to the flask and the reaction mixture was stirred for 1 minute at room temperature. Additional sodium triacetoxyborohydride (80.9 g, 382 mmol) was also added to the flask in portions over a 5-minute period, and the reaction mixture was stirred at room temperature for 2 hours and then was concentrated in vacuo at 35° C. in a rotary evaporator. The resulting yellow suspension was reconstituted in MeOH (1500 mL), concentrated again via rotary evaporation, and then dried for 30 minutes at 35° C. in the rotary evaporator. The yellow suspension was suspended in EtOAc (1500 mL), stirred in the rotary evaporator at 35° C. for 15 minutes and then at room temperature for 15 minutes. The solids were filtered, rinsed with EtOAc (3×300 mL), and the filtrate was dried in vacuo to provide a clear, yellow oil. The oil was dissolved in DCM and purified by silica column chromatography using a gradient of 0-5% MeOH in DCM (2240 g NH 60 μM spherical silica gel, Shoko Scientific Purif-Pack®). The pure fractions were combined, concentrated via rotary evaporation, and dried in vacuo to provide the crude product, which was dissolved in EtOAc (1000 mL) and partitioned with 2 M aqueous $Na_2CO_3$ (500 mL). The aqueous phase was washed with EtOAc (3×1000 mL). The organic layers were combined, dried over $Na_2SO_4$, filtered, rinsed with EtOAc, concentrated via rotary evaporation, and dried in vacuo to provide the title compound as a light-yellow solid (193.8 g, 81.5% yield, 95.6% ee). $^1$H NMR (400 MHz, DMSO-$d_6$) δ ppm 1.26-1.38 (m, 1H), 1.48-1.64 (m, 3H), 1.73 (s, 6H), 1.93-2.05 (m, 2H), 2.14 (s, 3H), 2.16-2.24 (m, 1H), 2.30 (dd, J=13.7, 4.4 Hz, 1H), 2.83-2.92 (m, 1H), 7.55 (ddd, J=8.6, 7.0, 1.5 Hz, 1H), 7.64 (d, J=5.3 Hz, 1H), 7.68 (ddd, J=8.2, 6.9, 1.0 Hz, 1H), 7.92 (d, J=7.5 Hz, 1H), 8.37 (d, J=5.8 Hz, 1H), 8.69 (dd, J=8.8, 0.8 Hz, 1H), 8.74 (s, 1H); ESI-MS m/z $[M+H]^+$ 312.1.

STEP B: (S)—N-(2-(isoquinolin-1-yl)propan-2-yl)-2-(1-methylpyrrolidin-2-yl)acetamide (1R,3S)-1,2,2-trimethylcyclopentane-1,3-dicarboxylate

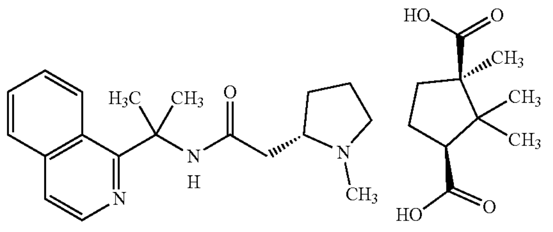

To a three-neck reaction flask equipped with overhead stirrer, thermometer and $N_2$ inlet were added D-(+)-camphoric acid (170 g, 849 mmol) and iPrOAc (3526 mL) at 40° C. to furnish a colorless solution. A small portion of the title compound (2532 mg) was added as a seed crystal. Next, (S)—N-(2-(isoquinolin-1-yl)propan-2-yl)-2-(1-methylpyrrolidin-2-yl)acetamide (176.3 g, 566 mmol) was added in portions over a 2-minute period to furnish a yellow suspension. The mixture was heated at 40° C. for 5 minutes with stirring, then cooled slowly to room temperature without stirring over a 2-hour period. The resulting solid was filtered, rinsed with iPrOAc (3×584 mL), and dried in vacuo to provide the title compound as a white solid (313.6 g, 91%)

with a molar ratio of (S)—N-(2-(isoquinolin-1-yl)propan-2-yl)-2-(1-methylpyrrolidin-2-yl)acetamide:D-(+)-camphoric acid of 2:3. $^1$H NMR (400 MHz, DMSO-$d_6$) δ ppm 0.77 (s, 4H), 1.13 (s, 4H), 1.19 (s, 4H), 1.25-1.43 (m, 3H), 1.48-1.65 (m, 3H), 1.66-1.78 (m, 8H), 1.97-2.10 (m, 3H), 2.16 (s, 3H), 2.25 (br d, J=7.8 Hz, 1H), 2.28-2.42 (m, 3H), 2.73 (dd, J=9.8, 9.0 Hz, 2H), 2.85-2.94 (m, 1H), 7.55 (ddd, J=8.6, 7.0, 1.5 Hz, 1H), 7.64 (d, J=5.3 Hz, 1H), 7.68 (ddd, J=8.1, 6.8, 1.1 Hz, 1H), 7.89-7.98 (m, 1H), 8.36 (d, J=5.5 Hz, 1H), 8.68 (dd, J=8.5, 0.8 Hz, 1H), 8.75 (s, 1H), 12.17 (br s, 3H); ESI-MS m/z $[M+H]^+$ 312.2 (early peak), $[M+Na]^+$ 223.1 (late peak).

STEP C: (S)—N-(2-(isoquinolin-1-yl)propan-2-yl)-2-(1-methylpyrrolidin-2-yl)acetamide (S)—N-(2-(isoquinolin-1-yl)propan-2-yl)-2-(1-methylpyrrolidin-2-yl)acetamide (1R,3S)-1,2,2-trimethylcyclopentane-1,3-dicarboxylate (314 g, 513 mmol) was suspended in iPrOAc (3500 mL) and 2 M aqueous $Na_2CO_3$ (898 mL) to furnish a two-phase suspension. Water (175 mL) was added to aid dissolution. The layers were separated. The organic phase was washed with water (3×600 mL), concentrated via rotary evaporation and dried in vacuo at 40° C. The resulting solid was suspended in iPrOAc (500 mL), mixed in the rotary evaporator at 40° C. for 5 minutes, and then was concentrated via rotary evaporation to azeotrope off residual water. This process was repeated two more times with iPrOAc (2×500 mL). The solid was dried in vacuo at 40° C. in the rotary evaporator and then at 70° C. in a high vacuum oven for 6 hours to provide the title compound as an off-white solid (134.41 g, 84% yield, 99% ee). $^1$H NMR (400 MHz, DMSO-$d_6$) δ ppm 1.25-1.38 (m, 1H), 1.45-1.64 (m, 3H), 1.73 (s, 6H), 1.93-2.05 (m, 2H), 2.14 (s, 3H), 2.16-2.24 (m, 1H), 2.30 (dd, J=13.7, 4.4 Hz, 1H), 2.84-2.91 (m, 1H), 7.55 (ddd, J=8.6, 7.0, 1.2 Hz, 1H), 7.64 (d, J=5.3 Hz, 1H), 7.68 (ddd, J=8.2, 6.9, 1.0 Hz, 1H), 7.90-7.95 (m, 1H), 8.36 (d, J=5.8 Hz, 1H), 8.69 (dd, J=8.8, 0.8 Hz, 1H), 8.74 (s, 1H); ESI-MS m/z $[M+H]^+$ 312.2.

EXAMPLE 25: N-(2-(furo[3,2-c]pyridin-4-yl)propan-2-yl)-2-(1-methylpyrrolidin-2-yl)acetamide

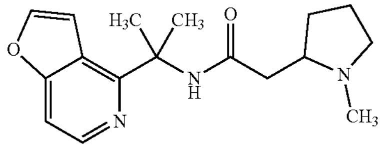

To a solution of pyridine (0.413 mL, 5.11 mmol), 2-(furo[3,2-c]pyridin-4-yl)propan-2-amine (0.150 g, 0.851 mmol) and 2-(1-(tert-butoxycarbonyl)pyrrolidin-2-yl)acetic acid (0.195 g, 0.851 mmol) in ACN (3.87 mL) was added T3P (50 wt % in EtOAc, 3.04 mL, 5.11 mmol). The reaction mixture was stirred at room temperature for 2 days and then was diluted with saturated aqueous $NH_4Cl$, extracted with EtOAc, dried over $Na_2SO_4$, filtered and concentrated in vacuo. The concentrate was taken up in dioxane (6 mL) and treated with 4 M HCl in dioxane (4.26 mL, 17.0 mmol). The mixture was heated to reflux with a heat gun and then was allowed to cool to room temperature. The solution was concentrated in vacuo to afford an HCl salt of the title compound, which was taken up in MeOH (3 mL). Next, aqueous formaldehyde (37 wt %, 0.691 g, 8.51 mmol) and sodium cyanoborohydride (0.535 g, 8.51 mmol) were added. The reaction mixture was stirred for 24 hours and then was sonicated, filtered and purified by preparative HPLC (Phenomenex Gemini® C18, 5 μm, ID 30 mm×150 mm) using a gradient of 10-100% water/ACN in water (basic mode) to give the title compound as a white solid (22 mg, 8.6%). $^1$H NMR (400 MHz, $CD_3OD$) δ ppm 1.44-1.63 (m, 1H), 1.66-1.88 (m, 8H), 1.90-2.02 (m, 1H), 2.02-2.10 (m, 1H), 2.18-2.31 (m, 2H), 2.32-2.38 (m, 3H), 2.44-2.62 (m, 2H), 3.02-3.14 (m, 1H), 6.98-7.28 (m, 1H), 7.34-7.60 (m, 1H), 7.71-7.96 (m, 1H), 8.34 (d, J=5.9 Hz, 1H); ESI-MS m/z $[M+H]^+$ 302.1.

EXAMPLE 26: N-(2-(1-methyl-1H-pyrazolo[4,3-c]pyridin-4-yl)propan-2-yl)-2-(1-methylpiperidin-2-yl)acetamide

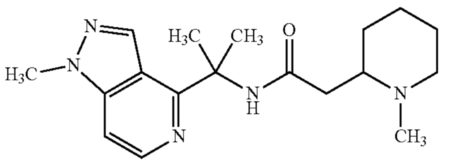 [SMILES: CN1CCCCC1CC(=O)NC(C)(C)c1nccc2c1cnn2C]

To a vial were added 2-(1-methylpiperidin-2-yl)acetic acid (42.1 mg, 0.268 mmol), 2-(1-methyl-1H-pyrazolo[4,3-c]pyridin-4-yl)propan-2-amine (51 mg, 0.268 mmol), $Et_3N$ (37.4 μL, 0.268 mmol), HATU (102 mg, 0.268 mmol) and DMF (3 mL). The reaction mixture was stirred at room temperature overnight and then was purified by preparative HPLC (Phenomenex Gemini® C18, 5 μm, ID 30 mm×150 mm) using a gradient of 10-100% water/ACN in water (basic mode) to give the title compound as a white solid (15 mg, 17%). $^1$H NMR (400 MHz, $CD_3OD$) δ ppm 1.21-1.37 (m, 2H), 1.53-1.73 (m, 5H), 1.78 (d, J=5.6 Hz, 6H), 2.14-2.40 (m, 7H), 2.61 (dd, J=14.4, 4.7 Hz, 1H), 2.80-2.87 (m, 1H), 4.07 (s, 3H), 7.45 (dd, J=6.2, 1.0 Hz, 1H), 8.26 (d, J=6.0 Hz, 1H), 8.32 (s, 1H); ESI-MS m/z $[M+H]^+$ 330.3.

EXAMPLE 27: 2-(1-ethylpyrrolidin-2-yl)-N-(2-(furo[3,2-c]pyridin-4-yl)propan-2-yl)acetamide

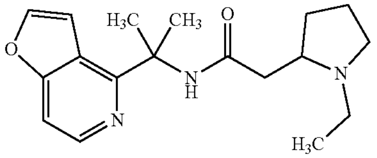 [SMILES: CCN1CCCC1CC(=O)NC(C)(C)c1nccc2occc12]

To a solution of $Et_3N$ (0.137 mL, 0.984 mmol), 2-(furo[3,2-c]pyridin-4-yl)propan-2-amine (0.065 g, 0.369 mmol) and 2-(1-ethylpyrrolidin-2-yl)acetic acid hydrochloride (0.048 g, 0.246 mmol) in DMF (2.46 mL) was added HATU (0.140 g, 0.369 mmol). The reaction mixture was stirred at room temperature for 2 days and then was diluted with MeOH, filtered and purified by preparative HPLC (Phenomenex Gemini® C18, 5 μm, ID 30 mm×150 mm) using a gradient of 10-100% water/ACN in water (basic mode) to give the title compound as a light-yellow crystalline solid (48 mg, 62%). $^1$H NMR (400 MHz, $CD_3OD$) δ ppm 1.06-1.19 (m, 3H), 1.41-1.61 (m, 1H), 1.77 (d, J=14.9 Hz, 6H), 1.84-2.01 (m, 1H), 2.12-2.32 (m, 3H), 2.44-2.56 (m, 1H), 2.60-2.73 (m, 1H), 2.85-2.97 (m, 1H), 3.12-3.22 (m, 1H), 7.07-7.24 (m, 1H), 7.37-7.53 (m, 1H), 7.78-7.92 (m, 1H), 8.27-8.42 (m, 1H); ESI-MS m/z $[M+H]^+$ 316.1.

EXAMPLE 28: N-(2-methyl-1-((3-(trifluoromethyl)pyridin-2-yl)oxy)propan-2-yl)-2-(1-methylpyrrolidin-2-yl)acetamide

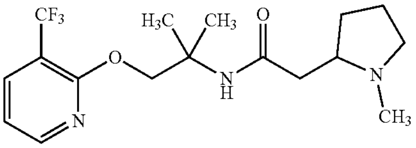 [SMILES: CN1CCCC1CC(=O)NC(C)(C)COc1ncccc1C(F)(F)F]

STEP A: N-(2-methyl-1-((3-(trifluoromethyl)pyridin-2-yl)oxy)propan-2-yl)-2-(pyrrolidin-2-yl)acetamide

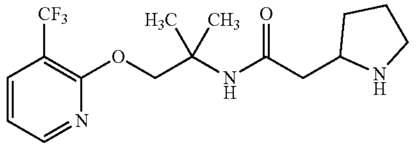 [SMILES: CC(C)(COc1ncccc1C(F)(F)F)NC(=O)CC1CCCN1]

A solution of 2-(1-(tert-butoxycarbonyl)pyrrolidin-2-yl)acetic acid (23.4 mg, 0.102 mmol), DIPEA (0.060 ml, 0.342 mmol), 2-chloro-1-methylpyridinium iodide (26.2 mg, 0.102 mmol) and NMP (0.5 mL) was stirred for 15 minutes. Next, 2-methyl-1-((3-(trifluoromethyl)pyridin-2-yl)oxy)propan-2-amine (20 mg, 0.085 mmol) was added and the solution was stirred at 45° C. for 3 days and then concentrated in vacuo. The mixture was treated with 4 M HCl in dioxane (1 mL), shaken for 30 minutes and then purified by preparative HPLC (Phenomenex Gemini® C18, 5 μm, ID 30 mm×150 mm) using a gradient of 10-90% ACN in water (acid mode). The product-containing fractions were combined and dried in a GeneVac™ evaporator to afford a TFA salt of the title compound as a film (4.9 mg, 16.6%). ESI-MS m/z $[M+H]^+$ 346.1.

STEP B: N-(2-methyl-1-((3-(trifluoromethyl)pyridin-2-yl)oxy)propan-2-yl)-2-(1-methylpyrrolidin-2-yl)acetamide To a vial charged with N-(2-methyl-1-((3-(trifluoromethyl)pyridin-2-yl)oxy)propan-2-yl)-2-(pyrrolidin-2-yl)acetamide (4.9 mg, 0.014 mmol) and formaldehyde (2.1 μL, 0.028 mmol) in MeOH (0.6 mL) was added sodium cyanoborohydride (1M, 28 μL, 0.028 mmol) at room temperature. The mixture was stirred at room temperature for 1 hour and then MeOH (0.5 mL) was added. The reaction mixture was purified by preparative HPLC (Phenomenex Gemini® C18, 5 μm, ID 30 mm×150 mm) using a gradient of 10-90% ACN in water (acid mode). The pure fractions were combined and dried in a GeneVac™ evaporator to afford a TFA salt of the title compound as a colorless film (4.1 mg, 80%). ESI-MS m/z $[M+H]^+$ 360.2.

EXAMPLE 29: N-(2-methyl-1-((3-(trifluoromethyl)pyridin-2-yl)oxy)propan-2-yl)-2-(1-methylpiperidin-2-yl)acetamide

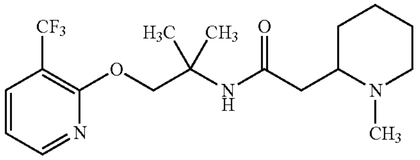

A solution of 2-(1-methylpiperidin-2-yl)acetic acid (16.1 mg, 0.102 mmol), DIPEA (44.1 mg, 0.342 mmol), 2-chloro-1-methylpyridin-1-ium iodide (26.2 mg, 0.102 mmol) and NMP (0.5 mL) was stirred at 45° C. for 30 minutes. Next, 2-methyl-1-((3-(trifluoromethyl)pyridin-2-yl)oxy)propan-2-amine (20 mg, 0.085 mmol) was added. The solution was stirred at 45° C. for 4 hours and then was purified by preparative HPLC (Phenomenex Gemini® C18, 5 μm, ID 30 mm×150 mm) using a gradient of 10-90% ACN in water (acid mode). The product was subsequently re-purified by preparative HPLC (Phenomenex Gemini® C18, 5 μm, ID 30 mm×150 mm) using a gradient of 20-100% water/ACN in water (basic mode). The product-containing fractions were combined and dried in a GeneVac™ evaporator to afford the title compound as a yellow solid (5.4 mg, 17%). $^1H$ NMR (400 MHz, $CD_3OD$) δ ppm 1.28-1.39 (m, 2H), 1.44 (s, 6H), 1.50-1.71 (m, 4H), 2.19-2.28 (m, 2H), 2.31 (s, 3H), 2.45-2.55 (m, 2H), 2.88 (br d, J=12.0 Hz, 1H), 4.60 (s, 2H), 7.10 (t, J=6.2 Hz, 1H), 8.00 (d, J=7.4 Hz, 1H), 8.35 (dt, J=5.0, 0.9 Hz, 1H); ESI-MS m/z $[M+H]^+$ 374.2.

EXAMPLE 30: N-(2-(4-chlorophenyl)propan-2-yl)-2-(1-methylpiperidin-2-yl)acetamide

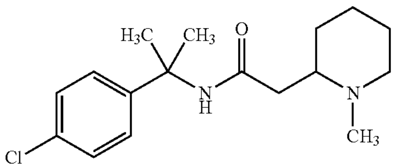 [SMILES: CN1CCCCC1CC(=O)NC(C)(C)c1ccc(Cl)cc1]

To a solution of $Et_3N$ (0.113 mL, 0.809 mmol), 2-(4-chlorophenyl)propan-2-amine hydrochloride (0.050 g, 0.243 mmol) and 2-(1-methylpiperidin-2-yl)acetic acid (0.025 g, 0.162 mmol) in DMF (1.62 mL) was added HATU (0.092 g, 0.243 mmol). The reaction mixture stirred at room temperature overnight and then was diluted with MeOH, filtered and purified by preparative HPLC (Phenomenex Gemini® C18, 5 μm, ID 30 mm×150 mm) using a gradient of 10-100% water/ACN in water (basic mode) to give the title compound as a yellowish orange semisolid (28 mg, 56%). $^1H$ NMR (400 MHz, $CD_3OD$) δ ppm 1.22-1.41 (m, 2H), 1.47-1.76 (m, 11H), 2.11-2.23 (m, 2H), 2.23-2.29 (m, 3H), 2.32-2.45 (m, 1H), 2.48-2.59 (m, 1H), 2.76-2.87 (m, 1H), 4.83 (s, 2H), 7.23-7.29 (m, 2H), 7.32-7.36 (m, 1H), 7.34-7.34 (m, 1H); ESI-MS m/z $[M+H]^+$ 309.1.

EXAMPLE 31: N—((S)-1-(4-chlorophenyl)ethyl)-2-((S)-1-methylpyrrolidin-2-yl)acetamide

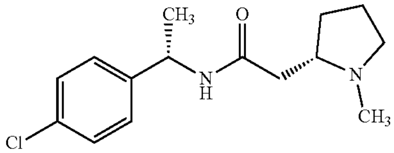 [SMILES: C[C@H](NC(=O)C[C@@H]1CCCN1C)c1ccc(Cl)cc1]

To a solution of $Et_3N$ (0.258 mL, 1.849 mmol), (S)-1-(4-chlorophenyl)ethan-1-amine (0.086 g, 0.555 mmol) and (S)-2-(1-(tert-butoxycarbonyl)pyrrolidin-2-yl)acetic acid (0.106 g, 0.462 mmol) in DMF (4.62 mL) was added HATU (0.211 g, 0.555 mmol). The reaction mixture was stirred at room temperature overnight and then was diluted with MeOH, filtered and purified by preparative HPLC (Phenomenex Gemini® C18, 5 μm, ID 30 mm×150 mm) using a gradient of 10-100% water/ACN in water (basic mode). The product-containing fractions were combined, taken up in a 4 M HCl/dioxane solution (2.31 mL, 9.25 mmol) and stirred at room temperature overnight. The reaction mixture was concentrated in vacuo give a an HCl salt of the title compound, which was taken up in MeOH (5 mL). Next, aqueous formaldehyde (37 wt %, 0.231 g, 2.31 mmol) and sodium cyanoborohydride (0.145 g, 2.31 mmol) were added and the mixture was stirred overnight. The solution was then sonicated, filtered and purified by preparative HPLC (Phenomenex Gemini® C18, 5 μm, ID 30 mm×150 mm) using a gradient of 10-100% water/ACN in water (basic mode) to give the title compound as a white solid (53 mg, 41%). $^1H$ NMR (400 MHz, $CD_3OD$) δ ppm 1.37-1.47 (m, 3H), 1.48-1.65 (m, 1H), 1.68-1.85 (m, 2H), 1.94-2.07 (m, 1H), 2.12-2.27 (m, 2H), 2.28 (s, 3H), 2.47-2.63 (m, 2H), 2.98-3.12 (m, 1H), 4.92-5.06 (m, 1H), 7.24-7.37 (m, 4H); ESI-MS m/z $[M+H]^+$ 281.1.

EXAMPLE 32: N—((S)-1-(4-fluorophenyl)ethyl)-2-((S)-1-methylpyrrolidin-2-yl)acetamide

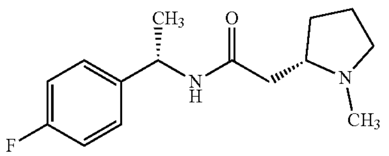 [SMILES: C[C@H](NC(=O)C[C@@H]1CCCN1C)c1ccc(F)cc1]

The title compound was prepared like EXAMPLE 31, using HATU (0.193 g, 0.508 mmol), $Et_3N$, (0.236 mL, 1.69 mmol), (S)-1-(4-fluorophenyl)ethan-1-amine (0.071 g, 0.508 mmol) and (S)-2-(1-(tert-butoxycarbonyl)pyrrolidin-2-yl)acetic acid (0.097 g, 0.423 mmol) in DMF (4.23 mL), and was obtained as a white solid (39 mg, 35%). $^1H$ NMR (400 MHz, $CD_3OD$) δ ppm 1.37-1.47 (m, 3H), 1.48-1.65 (m, 1H), 1.70-1.85 (m, 2H), 1.92-2.07 (m, 1H), 2.13-2.27 (m, 2H), 2.27-2.33 (m, 3H), 2.41-2.68 (m, 2H), 3.05 (ddd, J=9.8, 6.2, 4.0 Hz, 1H), 3.31 (dt, J=3.3, 1.6 Hz, 1H), 4.92-5.13 (m, 1H), 6.84-7.14 (m, 2H), 7.19-7.40 (m, 2H); ESI-MS m/z $[M+H]^+$ 265.1.

EXAMPLE 33: (S)—N-(2-(2,5-dichlorophenyl)propan-2-yl)-2-(1-methylpyrrolidin-2-yl)acetamide

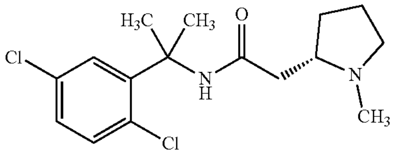 [SMILES: CN1CCC[C@H]1CC(=O)NC(C)(C)c1cc(Cl)ccc1Cl]

The title compound was prepared like EXAMPLE 31, using HATU (0.205 g, 0.539 mmol), $Et_3N$ (0.250 mL, 1.80 mmol), 2-(2,5-dichlorophenyl)propan-2-amine (0.110 g, 0.539 mmol) and (S)-2-(1-(tert-butoxycarbonyl)pyrrolidin-2-yl)acetic acid (0.103 g, 0.449 mmol) in DMF (4.49 mL), and was obtained as a white solid (35 mg, 24%). $^1H$ NMR (400 MHz, $CD_3OD$) δ ppm 1.46-1.62 (m, 1H), 1.66-1.83 (m, 8H), 1.90-2.07 (m, 1H), 2.10-2.26 (m, 2H), 2.26-2.39 (m, 3H), 2.42-2.58 (m, 2H), 2.95-3.13 (m, 1H), 7.14-7.25 (m, 1H), 7.26-7.36 (m, 1H), 7.44-7.56 (m, 1H); ESI-MS m/z $[M+H]^+$ 331.0.

EXAMPLE 34: (S)—N-(2-(furo[3,2-c]pyridin-4-yl)propan-2-yl)-2-(1-methylpyrrolidin-2-yl)acetamide

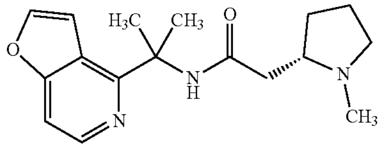 [SMILES: CN1CCC[C@H]1CC(=O)NC(C)(C)c1nccc2occc12]

The title compound was prepared like EXAMPLE 31, using HATU (0.233 g, 0.612 mmol), $Et_3N$ (0.285 mL, 2.041 mmol), 2-(furo[3,2-c]pyridin-4-yl)propan-2-amine (0.108 g, 0.612 mmol) and (S)-2-(1-(tert-butoxycarbonyl)pyrrolidin-2-yl)acetic acid (0.117 g, 0.510 mmol) in DMF (5.10 mL), and was obtained as a white solid (64 mg, 42%). $^1H$ NMR (400 MHz, $CD_3OD$) δ ppm 1.41-1.56 (m, 1H), 1.62-1.82 (m, 8H), 1.85-2.01 (m, 1H), 2.13-2.27 (m, 2H), 2.27-2.36 (m, 3H), 2.38-2.60 (m, 2H), 2.96-3.09 (m, 1H), 7.06-7.23 (m, 1H), 7.37-7.53 (m, 1H), 7.77-7.93 (m, 1H), 8.23-8.39 (m, 1H); ESI-MS m/z $[M+H]^+$ 302.1.

EXAMPLE 35: (S)—N-(2-(4-chlorophenyl)propan-2-yl)-2-(1-methylpyrrolidin-2-yl)acetamide

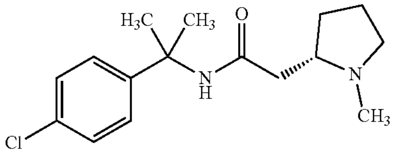 [SMILES: CN1CCC[C@H]1CC(=O)NC(C)(C)c1ccc(Cl)cc1]

The title compound was prepared like EXAMPLE 31, using HATU (0.271 g, 0.712 mmol), $Et_3N$ (0.413 mL, 2.97 mmol), 2-(4-chlorophenyl)propan-2-amine hydrochloride (0.108 g, 0.612 mmol) and (S)-2-(1-(tert-butoxycarbonyl)pyrrolidin-2-yl)acetic acid (0.147 g, 0.712 mmol) in DMF (5.93 mL), and was obtained as a clear semisolid (63 mg, 36%). $^1H$ NMR (400 MHz, $CD_3OD$) δ ppm 1.50-1.67 (m, 7H), 1.71-1.84 (m, 2H), 1.91-2.07 (m, 1H), 2.11-2.30 (m, 2H), 2.33 (s, 3H), 2.41-2.61 (m, 2H), 2.98-3.10 (m, 1H), 7.21-7.31 (m, 2H), 7.32-7.42 (m, 2H); ESI-MS m/z $[M+H]^+$ 295.1.

EXAMPLE 36: N—((S)-1-(4-chlorophenyl)ethyl)-2-((R)-1-methylpyrrolidin-2-yl)acetamide

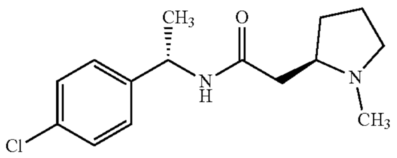 [SMILES: C[C@H](NC(=O)C[C@H]1CCCN1C)c1ccc(Cl)cc1]

To a solution of $Et_3N$ (0.292 mL, 2.09 mmol), (S)-1-(4-chlorophenyl)ethan-1-amine (0.098 g, 0.628 mmol) and (R)-2-(1-(tert-butoxycarbonyl)pyrrolidin-2-yl)acetic acid (0.120 g, 0.523 mmol) in DMF (5.23 mL) was added HATU (0.239 g, 0.628 mmol). The reaction mixture was stirred at room temperature overnight and then was diluted with MeOH, filtered and purified by preparative HPLC (Phenomenex Gemini® C18, 5 μm, ID 30 mm×150 mm) using a gradient of 10-100% water/ACN in water (basic mode). The pure fractions were combined and taken up in a solution of 4 M HCl in dioxane (2.62 mL, 10.47 mmol). The reaction mixture was stirred at room temperature overnight and then was concentrated in vacuo to give an HCl salt of the title compound, which was taken up in MeOH (5 mL). Next, formaldehyde (0.212 g, 2.62 mmol) and sodium cyanoborohydride (1 M in THF, 2.62 mL, 2.62 mmol) were added. The reaction mixture was stirred for 2 hours and then was sonicated, filtered and purified by preparative HPLC (Phenomenex Gemini® C18, 5 μm, ID 30 mm×150 mm) using a gradient of 10-100% water/ACN in water (basic mode) to give the title compound as a white solid (83 mg, 56%). $^1H$ NMR (400 MHz, $CD_3OD$) δ ppm 1.37-1.46 (m, 3H), 1.47-1.58 (m, 1H), 1.65-1.79 (m, 2H), 1.84-1.99 (m, 1H), 2.13-2.29 (m, 2H), 2.29-2.37 (m, 3H), 2.47-2.58 (m, 2H), 2.96-3.11 (m, 1H), 4.91-5.04 (m, 1H), 7.20-7.40 (m, 4H); ESI-MS m/z $[M+H]^+$ 281.0.

EXAMPLE 37: N—((S)-1-(4-fluorophenyl)ethyl)-2-((R)-1-methylpyrrolidin-2-yl)acetamide

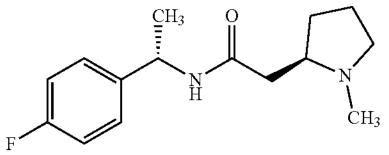 [SMILES: C[C@H](NC(=O)C[C@H]1CCCN1C)c1ccc(F)cc1]

The title compound was prepared like EXAMPLE 36, using HATU (0.239 g, 0.628 mmol), $Et_3N$ (0.292 mL, 2.09 mmol), (S)-1-(4-fluorophenyl)ethan-1-amine (0.087 g, 0.628 mmol) and (R)-2-(1-(tert-butoxycarbonyl)pyrrolidin-2-yl)acetic acid (0.120 g, 0.523 mmol) in DMF (5.23 mL), and was obtained as a white solid (92 mg, 66%). $^1H$ NMR (400 MHz, $CD_3OD$) δ ppm 1.38-1.44 (m, 3H), 1.45-1.57 (m, 1H), 1.65-1.81 (m, 2H), 1.84-1.99 (m, 1H), 2.11-2.29 (m, 2H), 2.29-2.36 (m, 3H), 2.46-2.59 (m, 2H), 2.94-3.08 (m, 1H), 3.27-3.33 (m, 1H), 4.92-5.07 (m, 1H), 6.90-7.09 (m, 2H), 7.24-7.42 (m, 2H); ESI-MS m/z $[M+H]^+$ 265.1.

EXAMPLE 38: (R)—N-(2-(2,5-dichlorophenyl)propan-2-yl)-2-(1-methylpyrrolidin-2-yl)acetamide

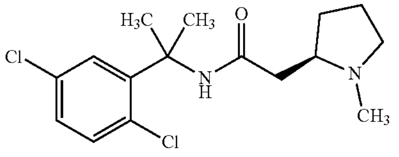 [SMILES: CN1CCC[C@@H]1CC(=O)NC(C)(C)c1cc(Cl)ccc1Cl]

The title compound was prepared like EXAMPLE 36, using HATU (0.239 g, 0.628 mmol), $Et_3N$ (0.292 mL, 2.09 mmol), 2-(2,5-dichlorophenyl)propan-2-amine (0.128 g, 0.628 mmol) and (R)-2-(1-(tert-butoxycarbonyl)pyrrolidin-2-yl)acetic acid (0.120 g, 0.523 mmol) in DMF (5.23 mL), and was obtained as a white solid (93 mg, 54%). $^1H$ NMR (400 MHz, $CD_3OD$) δ ppm 1.47-1.63 (m, 1H), 1.73 (m, 8H), 1.91-2.06 (m, 1H), 2.12-2.29 (m, 2H), 2.32 (s, 3H), 2.49 (s, 2H), 2.97-3.10 (m, 1H), 7.12-7.24 (m, 1H), 7.25-7.36 (m, 1H), 7.41-7.56 (m, 1H); ESI-MS m/z $[M+H]^+$ 331.0.

EXAMPLE 39: (R)—N-(2-(furo[3,2-c]pyridin-4-yl)propan-2-yl)-2-(1-methylpyrrolidin-2-yl)acetamide

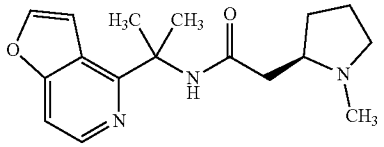 [SMILES: CN1CCC[C@@H]1CC(=O)NC(C)(C)c1nccc2occc12]

The title compound was prepared like EXAMPLE 36, using HATU (0.239 g, 0.628 mmol), $Et_3N$ (0.292 mL, 2.09 mmol), 2-(furo[3,2-c]pyridin-4-yl)propan-2-amine (0.111 g, 0.628 mmol) and (R)-2-(1-(tert-butoxycarbonyl)pyrrolidin-2-yl)acetic acid (0.120 g, 0.523 mmol) in DMF (5.23 mL), and was obtained as a clear solid (45 mg, 28%). $^1H$ NMR (400 MHz, $CD_3OD$) δ ppm 1.40-1.60 (m, 1H), 1.75 (m, 7H), 1.85-2.01 (m, 1H), 2.12-2.26 (m, 2H), 2.31 (s, 3H), 2.40-2.60 (m, 2H), 3.04 (ddd, J=9.7, 7.2, 2.9 Hz, 1H), 3.26-3.32 (m, 2H), 7.04-7.22 (m, 1H), 7.34-7.53 (m, 1H), 7.76-7.88 (m, 1H), 8.24-8.41 (m, 1H); ESI-MS m/z $[M+H]^+$ 302.1.

EXAMPLE 40: (R)—N-(2-(4-chlorophenyl)propan-2-yl)-2-(1-methylpyrrolidin-2-yl)acetamide

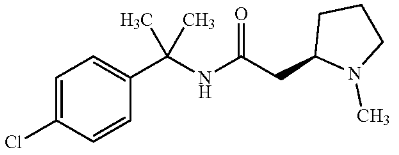 [SMILES: CN1CCC[C@@H]1CC(=O)NC(C)(C)c1ccc(Cl)cc1]

The title compound was prepared like EXAMPLE 36, using HATU (0.239 g, 0.628 mmol), $Et_3N$ (0.365 mL, 2.62 mmol), 2-(4-chlorophenyl)propan-2-amine hydrochloride (0.129 g, 0.628 mmol) and (R)-2-(1-(tert-butoxycarbonyl)pyrrolidin-2-yl)acetic acid (0.120 g, 0.523 mmol) in DMF (5.23 mL), and was obtained as a clear semisolid (80 mg, 52%). $^1H$ NMR (400 MHz, $CD_3OD$) δ ppm 1.50-1.66 (m, 7H), 1.70-1.85 (m, 2H), 1.92-2.10 (m, 1H), 2.15-2.31 (m, 2H), 2.31-2.37 (m, 3H), 2.43-2.63 (m, 2H), 3.06 (ddd, J=9.8, 6.2, 3.9 Hz, 1H), 3.31 (dt, J=3.3, 1.6 Hz, 2H), 7.22-7.30 (m, 2H), 7.32-7.38 (m, 2H); ESI-MS m/z $[M+H]^+$ 295.1.

EXAMPLE 41: N-(2-(7-methylbenzo[d]isoxazol-3-yl)propan-2-yl)-2-(1-methylpiperidin-2-yl)acetamide

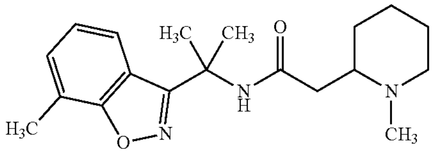 [SMILES: Cc1cccc2c(C(C)(C)NC(=O)CC3CCCCN3C)noc12]

To a vial were added 2-(1-methylpiperidin-2-yl)acetic acid (30.0 mg, 0.191 mmol), HATU (72.6 mg, 0.191 mmol), 2-(7-methylbenzo[d]isoxazol-3-yl)propan-2-amine (36.3 mg, 0.191 mmol), $Et_3N$ (26.6 μL, 0.191 mmol) and DMF (1 mL). The reaction mixture was stirred at room temperature overnight and then was purified by preparative HPLC (Phenomenex Gemini® C18, 5 μm, ID 30 mm×150 mm) using a gradient of 10-100% water/ACN in water (basic mode) to give the title compound as a light brown solid (27 mg, 43%). $^1H$ NMR (400 MHz, $CD_3OD$) δ ppm 1.18-1.35 (m, 2H), 1.50-1.70 (m, 4H), 1.80 (d, J=1.5 Hz, 6H), 2.12-2.25 (m, 5H), 2.28-2.42 (m, 1H), 2.52-2.62 (m, 4H), 2.77-2.86 (m, 1H), 7.22 (t, J=7.6 Hz, 1H), 7.35 (dt, J=7.2, 0.9 Hz, 1H), 7.66 (d, J=7.7 Hz, 1H); ESI-MS m/z $[M+H]^+$ 330.3.

EXAMPLE 42: N-(2-(4-methylisoquinolin-1-yl)propan-2-yl)-2-(1-methylpiperidin-2-yl)acetamide

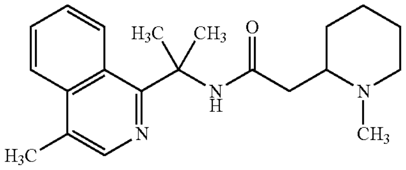 [SMILES: Cc1cnc(C(C)(C)NC(=O)CC2CCCCN2C)c2ccccc12]

The title compound was prepared like EXAMPLE 41, using 2-(4-methylisoquinolin-1-yl)propan-2-amine (30.0 mg, 0.150 mmol), 2-(1-methylpiperidin-2-yl)acetic acid (23.6 mg, 0.150 mmol), $Et_3N$ (20.9 μL, 0.150 mmol), and HATU (57.0 mg, 0.150 mmol) in DMF to give a colorless oil (23 mg, 45%). $^1H$ NMR (400 MHz, $CD_3OD$) δ ppm 1.28-1.35 (m, 1H), 1.37-1.61 (m, 2H), 1.68 (br d, J=10.9 Hz, 2H), 1.73-1.90 (m, 1H), 2.04-2.08 (m, 6H), 2.62-2.71 (m, 3H), 2.76-2.92 (m, 5H), 3.10-3.17 (m, 1H), 3.13-3.20 (m, 1H), 3.29-3.36 (m, 2H), 8.02 (t, J=7.8 Hz, 1H), 8.22 (ddd, J=8.4, 7.2, 1.0 Hz, 1H), 8.31 (s, 1H), 8.43 (d, J=8.5 Hz, 1H), 9.06 (d, J=8.8 Hz, 1H); ESI-MS m/z $[M+H]^+$ 340.4.

EXAMPLE 43: (R)—N-(2-(7-methylbenzo[d]isoxazol-3-yl)propan-2-yl)-2-(1-methylpiperidin-2-yl)acetamide

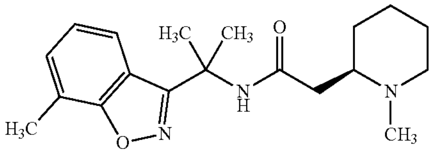 [SMILES: Cc1cccc2c(C(C)(C)NC(=O)C[C@H]3CCCCN3C)noc12]

EXAMPLE 44: (S)—N-(2-(7-methylbenzo[d]isoxazol-3-yl)propan-2-yl)-2-(1-methylpiperidin-2-yl)acetamide

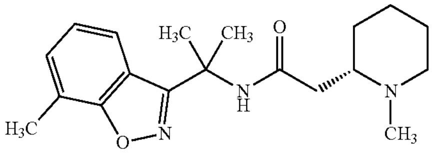 [SMILES: Cc1cccc2c(C(C)(C)NC(=O)C[C@@H]3CCCCN3C)noc12]

The title enantiomers of racemic N-(2-(7-methylbenzo[d]isoxazol-3-yl)propan-2-yl)-2-(1-methylpiperidin-2-yl)acetamide (728 mg, 2.37 mmol) were separated by preparative SFC (Daicel Chiralpak AD, 5 μm, ID 30 mm×250 mm). The first eluting compound was arbitrarily assigned as the (R)-enantiomer and was obtained as a white solid (324 mg, 45%) and the second eluting compound was arbitrarily assigned as the (S)-enantiomer and was obtained as a white solid (329 mg, 45%). $^1H$ NMR (400 MHz, $CD_3OD$) δ ppm 1.23-1.35 (m, 2H), 1.52-1.69 (m, 4H), 1.80 (app d, J=1.9 Hz, 6H), 2.17-2.28 (m, 5H), 2.35-2.45 (m, 1H), 2.53-2.62 (m, 4H), 2.80-2.88 (m, 1H), 7.20-7.25 (m, 1H), 7.36 (d, J=7.0 Hz, 1H), 7.66 (d, J=7.7 Hz, 1H); ESI-MS m/z $[M+H]^+$ 330.1.

EXAMPLE 45: N-(2-(2,5-dichlorophenyl)propan-2-yl)-2-(1-methylpiperidin-2-yl)acetamide

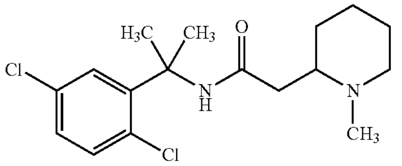 [SMILES: CN1CCCCC1CC(=O)NC(C)(C)c1cc(Cl)ccc1Cl]

To a solution of $Et_3N$ (0.177 mL, 1.27 mmol), 2-(2,5-dichlorophenyl)propan-2-amine (0.097 g, 0.477 mmol) and 2-(1-methylpiperidin-2-yl)acetic acid (0.050 g, 0.318 mmol) in DMF (3.18 mL) was added HATU (0.181 g, 0.477 mmol). The reaction mixture was stirred at room temperature overnight and then was diluted with MeOH, filtered and purified by preparative HPLC (Phenomenex Gemini® C18, 5 μm, ID 30 mm×150 mm) using a gradient of 10-100% water/ACN in water (basic mode) to give the title compound as a white solid (23 mg, 21%). $^1H$ NMR (400 MHz, $CD_3OD$) δ ppm 1.22-1.40 (m, 2H), 1.48-1.77 (m, 10H), 2.09-2.22 (m, 2H), 2.22-2.33 (m, 3H), 2.33-2.47 (m, 1H), 2.48-2.63 (m, 1H), 2.76-2.91 (m, 1H), 3.31-3.38 (m, 4H), 7.14-7.25 (m, 1H), 7.25-7.36 (m, 1H), 7.45-7.60 (m, 1H); ESI-MS m/z $[M+H]^+$ 345.0.

EXAMPLE 46: (R)—N-(2-methyl-1-((3-methylpyridin-2-yl)oxy)propan-2-yl)-2-(1-methylpyrrolidin-2-yl)acetamide

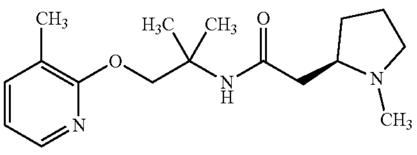 [SMILES: Cc1cccnc1OCC(C)(C)NC(=O)C[C@H]1CCCN1C]

STEP A: tert-butyl (R)-2-(2-((2-methyl-1-((3-methylpyridin-2-yl)oxy)propan-2-yl)amino)-2-oxoethyl)pyrrolidine-1-carboxylate

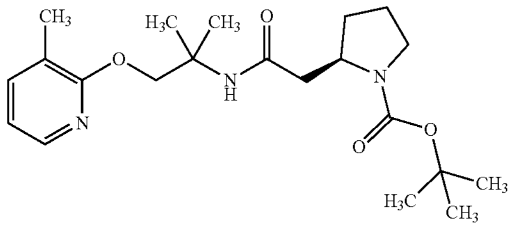 [SMILES: Cc1cccnc1OCC(C)(C)NC(=O)C[C@H]1CCCN1C(=O)OC(C)(C)C]

To a 20 mL vial were added 2-methyl-1-((3-methylpyridin-2-yl)oxy)propan-2-amine (78% purity, 0.080 g, 0.346 mmol), (R)-2-(1-(tert-butoxycarbonyl)pyrrolidin-2-yl)acetic acid (0.079 g, 0.346 mmol), HATU (0.132 g, 0.346 mmol), DIPEA (0.181 mL, 1.039 mmol) and DMF (3 mL). The resulting yellow solution was stirred at room temperature overnight and then was treated with water and extracted with EtOAc. The organic phase was washed with brine, dried over $MgSO_4$, filtered and concentrated to give the title compound as a light brown film (136 mg, assumed quantitative).

STEP B: (R)—N-(2-methyl-1-((3-methylpyridin-2-yl)oxy)propan-2-yl)-2-(pyrrolidin-2-yl)acetamide

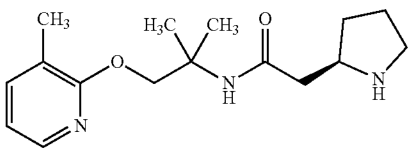 [SMILES: Cc1cccnc1OCC(C)(C)NC(=O)C[C@H]1CCCN1]

To a 125 mL flask were added tert-butyl (R)-2-(2-((2-methyl-1-((3-methylpyridin-2-yl)oxy)propan-2-yl)amino)-2-oxoethyl)pyrrolidine-1-carboxylate (0.136 g, 0.346 mmol) in dioxane (3 mL) and 4 M HCl in dioxane (0.346 mL, 1.38 mmol). The resulting brown solution was stirred at room temperature overnight and then was concentrated to dryness to give an HCl salt of the title compound as a light brown film (113 mg, assumed quantitative).

STEP C: (R)—N-(2-methyl-1-((3-methylpyridin-2-yl)oxy)propan-2-yl)-2-(1-methylpyrrolidin-2-yl)acetamide To a 125 mL flask were added (R)—N-(2-methyl-1-((3-methylpyridin-2-yl)oxy)propan-2-yl)-2-(pyrrolidin-2-yl)acetamide HCl salt (113 mg, 0.346 mmol) and aqueous formaldehyde (37 wt %, 0.053 mL, 0.685 mmol) in methanol (3 mL) followed by sodium cyanoborohydride (43.1 mg, 0.685 mmol). The mixture was stirred at room temperature overnight and then was purified by preparative HPLC (Phenomenex Gemini® C18, 5 μm, ID 30 mm×150 mm) using a gradient of 10-100% ACN in water (acid mode) to give a TFA salt of the title compound (51.1 mg, 35% over three steps). $^1H$ NMR (500 MHz, $CD_3OD$) δ ppm 1.45 (d, J=2.7 Hz, 6H), 1.67-1.77 (m, 1H), 1.82-1.94 (m, 1H), 1.98-2.08 (m, 1H), 2.21 (s, 4H), 2.70 (br d, J=5.4 Hz, 2H), 2.83-2.93 (m, 3H), 3.03-3.14 (m, 1H), 3.51-3.69 (m, 2H), 4.30-4.39 (m, 1H), 4.45-4.56 (m, 1H), 6.79-6.89 (m, 1H), 7.42-7.55 (m, 1H), 7.82-7.95 (m, 1H); ESI-MS m/z $[M+H]^+$ 306.4.

EXAMPLE 47: (S)—N-(2-methyl-1-((3-methylpyridin-2-yl)oxy)propan-2-yl)-2-(1-methylpyrrolidin-2-yl)acetamide

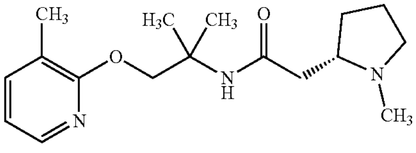 [SMILES: CN1CCC[C@H]1CC(=O)NC(C)(C)COc1ncccc1C(F)(F)F]

STEP A: tert-butyl (S)-2-(2-((2-methyl-1-((3-methylpyridin-2-yl)oxy)propan-2-yl)amino)-2-oxoethyl)pyrrolidine-1-carboxylate

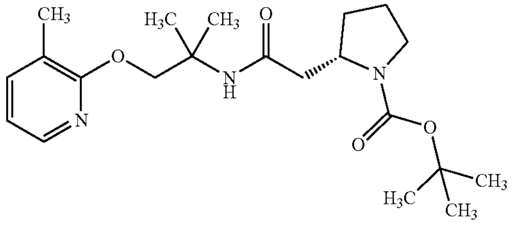 [SMILES: CC(C)(COc1ncccc1C(F)(F)F)NC(=O)C[C@@H]1CCCN1C(=O)OC(C)(C)C]

To a vial were added 2-methyl-1-((3-methylpyridin-2-yl)oxy)propan-2-amine (78% purity, 0.070 g, 0.303 mmol), (S)-2-(1-(tert-butoxycarbonyl)pyrrolidin-2-yl)acetic acid (0.069 g, 0.303 mmol), HATU (0.115 g, 0.303 mmol), DIPEA (0.158 mL, 1.039 mmol) and DMF (3 mL). The resulting yellow solution was stirred at room temperature overnight and then was treated with water and extracted with EtOAc. The organic phase was washed with brine, dried over $MgSO_4$, filtered and concentrated to give the title compound as a light brown film (119 mg, assumed quantitative).

STEP B: (S)—N-(2-methyl-1-((3-methylpyridin-2-yl)oxy)propan-2-yl)-2-(pyrrolidin-2-yl)acetamide

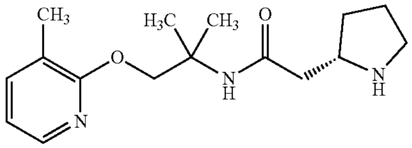 [SMILES: CC(C)(COc1ncccc1C(F)(F)F)NC(=O)C[C@@H]1CCCN1]

To a 125 mL flask were added tert-butyl (S)-2-(2-((2-methyl-1-((3-methylpyridin-2-yl)oxy)propan-2-yl)amino)-2-oxoethyl)pyrrolidine-1-carboxylate (0.119 g, 0.303 mmol) in dioxane (3 mL) and 4 M HCl in dioxane (0.346 mL, 1.38 mmol). The resulting brown solution was stirred at room temperature overnight. Extra HCl (4 M in dioxane, 0.346 mL, 1.38 mmol) was added and the mixture was again stirred at room temperature overnight. The mixture was concentrated to dryness to give an HCl salt of the title compound as a light brown film (99 mg, assumed quantitative).

STEP C: (S)—N-(2-methyl-1-((3-methylpyridin-2-yl)oxy)propan-2-yl)-2-(1-methylpyrrolidin-2-yl)acetamide To a 125 mL flask were added (S)—N-(2-methyl-1-((3-methylpyridin-2-yl)oxy)propan-2-yl)-2-(pyrrolidin-2-yl)acetamide HCl salt (99 mg, 0.303 mmol) and aqueous formaldehyde (37 wt %, 0.053 mL, 0.685 mmol) in methanol (3 mL) followed by sodium cyanoborohydride (43.1 mg, 0.685 mmol). The mixture was stirred at room temperature overnight and then was purified by preparative HPLC (Phenomenex Gemini® C18, 5 μm, ID 30 mm×150 mm) using a gradient of 10-100% ACN in water (acid mode) to give a TFA salt of the title compound (56.2 mg, 44% over three steps). $^1$H NMR (500 MHz, $CD_3OD$) δ ppm 1.44-1.48 (m, 6H), 1.67-1.79 (m, 1H), 1.85-1.97 (m, 1H), 1.98-2.09 (m, 1H), 2.21 (s, 3H), 2.24-2.33 (m, 1H), 2.71 (s, 2H), 2.86-2.93 (m, 3H), 3.04-3.13 (m, 1H), 3.53-3.70 (m, 2H), 4.32-4.41 (m, 1H), 4.47-4.56 (m, 1H), 6.81-6.89 (m, 1H), 7.47-7.54 (m, 1H), 7.83-7.95 (m, 1H); ESI-MS m/z $[M+H]^+$ 306.4.

EXAMPLE 48: (S)—N-(2-methyl-1-((3-(trifluoromethyl)pyridin-2-yl)oxy)propan-2-yl)-2-(1-methylpyrrolidin-2-yl)acetamide

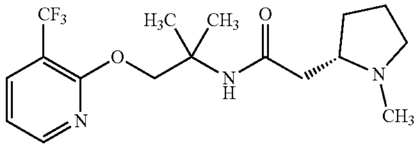

STEP A: tert-butyl (S)-2-(2-((2-methyl-1-((3-(trifluoromethyl)pyridin-2-yl)oxy)propan-2-yl)amino)-2-oxoethyl)pyrrolidine-1-carboxylate

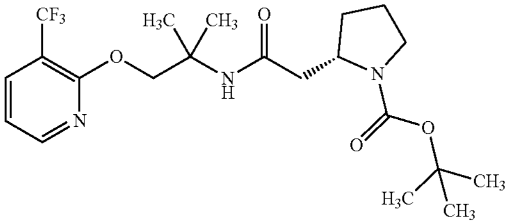

To a solution of (S)-2-(1-(tert-butoxycarbonyl)pyrrolidin-2-yl)acetic acid HCl (50.0 mg, 0.218 mmol) and HATU (71.5 mg, 0.188 mmol) in DMF (0.9 mL) was added DIPEA (0.115 mL, 0.659 mmol) at room temperature. The reaction mixture was stirred for 5-10 minutes. Next, 2-methyl-1-((3-(trifluoromethyl)pyridin-2-yl)oxy)propan-2-amine (52.9 mg, 0.226 mmol) was added and the mixture was stirred at room temperature overnight. The residue was taken up in methanol and filtered through a hydrophilic PTFE 0.45 m Millipore® filter, rinsing with methanol. The filtrate was purified by preparative HPLC (Phenomenex Gemini® C18, 5 μm, ID 30 mm×150 mm) using a gradient of 10-50% ACN in water (acid mode) to give a TFA salt of the title compound as a colorless oil (96 mg, 91%).

STEP B: (S)—N-(2-methyl-1-((3-(trifluoromethyl)pyridin-2-yl)oxy)propan-2-yl)-2-(pyrrolidin-2-yl)acetamide

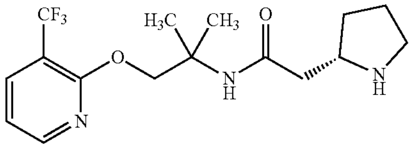

To a solution of tert-butyl (S)-2-(2-((2-methyl-1-((3-(trifluoromethyl)pyridin-2-yl)oxy)propan-2-yl)amino)-2-oxoethyl)pyrrolidine-1-carboxylate TFA salt (96 mg, 0.172 mmol) in DCM (5.0 mL) was added TFA (2.5 mL). The resulting solution was stirred at room temperature for 1 hour. The solvent was removed under vacuum to give a TFA salt of the title compound as a colorless oil, which was used without further purification (79 mg, 100%).

STEP C: (S)—N-(2-methyl-1-((3-(trifluoromethyl)pyridin-2-yl)oxy)propan-2-yl)-2-(1-methylpyrrolidin-2-yl)acetamide A mixture of (S)—N-(2-methyl-1-((3-(trifluoromethyl)pyridin-2-yl)oxy)propan-2-yl)-2-(pyrrolidin-2-yl)acetamide TFA salt (79 mg, 0.172 mmol), paraformaldehyde (12.7 mg, 0.422 mmol), sodium triacetoxyborohydride (179 mg, 0.845 mmol) and DIPEA (148 μL, 0.845 mmol) in DCM (2.1 mL) was stirred at room temperature for 2 days. Next, EtOAc (10 mL) and saturated aqueous $NaHCO_3$ (10 mL) were added, and the reaction mixture was stirred vigorously for 1 hour. The organic layer was washed with brine (2×3 mL) and concentrated under vacuum. The concentrate was taken up in methanol and filtered through a hydrophilic PTFE 0.45 m Millipore® filter, rinsing with methanol. The filtrate was purified by preparative HPLC (Phenomenex Gemini® C18, 5 μm, ID 30 mm×150 mm) using a gradient of 10-50% ACN in water (acid mode) to give a colorless oil, which was dissolved in MeOH and filtered through Agilent Strato-spheres SPE (PL-$HCO_3$ MP) resin to provide the title compound as a colorless oil (23 mg, 37%). $^1H$ NMR (400 MHz, $CD_3OD$) δ ppm 1.46 (d, J=2.4 Hz, 6H), 1.73-1.85 (m, 1H), 1.89-2.02 (m, 1H), 2.04-2.17 (m, 1H), 2.31 (dtd, J=13.5, 8.2, 5.5 Hz, 1H), 2.72 (dd, J=5.3, 1.2 Hz, 2H), 2.93 (s, 3H), 3.13 (dt, J=11.5, 8.3 Hz, 1H), 3.53-3.63 (m, 1H), 3.65-3.75 (m, 1H), 4.52-4.71 (m, 2H), 7.08-7.15 (m, 1H), 7.97-8.06 (m, 1H), 8.32-8.40 (m, 1H); ESI-MS m/z $[M+H]^+$ 360.1.

EXAMPLE 49: (R)—N-(2-methyl-1-((3-(trifluoromethyl)pyridin-2-yl)oxy)propan-2-yl)-2-(1-methylpyrrolidin-2-yl)acetamide

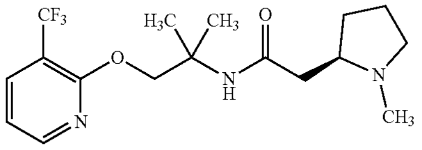 [SMILES: CN1CCC[C@@H]1CC(=O)NC(C)(C)COc1ncccc1C(F)(F)F]

The title compound was prepared like EXAMPLE 48, using (R)-2-(1-(tert-butoxycarbonyl)pyrrolidin-2-yl)acetic acid (50.0 mg, 0.218 mmol) and 2-methyl-1-((3-(trifluoromethyl)pyridin-2-yl)oxy)propan-2-amine (52.9 mg, 0.226 mmol) in STEP A, tert-butyl (R)-2-(2-((2-methyl-1-((3-(trifluoromethyl)pyridin-2-yl)oxy)propan-2-yl)amino)-2-oxoethyl)pyrrolidine-1-carboxylate (95 mg, 0.170 mmol) TFA salt in STEP B, and (R)—N-(2-methyl-1-((3-(trifluoromethyl)pyridin-2-yl)oxy)propan-2-yl)-2-(pyrrolidin-2-yl)acetamide TFA salt (97 mg, 0.211 mmol) and formaldehyde (12.68 mg, 0.422 mmol) in STEP C. The title compound was obtained as a colorless oil (19 mg, 25%). $^1H$ NMR (400 MHz, $CD_3OD$) δ ppm 1.46 (d, J=2.6 Hz, 6H), 1.72-1.85 (m, 1H), 1.89-2.01 (m, 1H), 2.04-2.17 (m, 1H), 2.25-2.38 (m, 1H), 2.71 (d, J=5.0 Hz, 2H), 2.93 (s, 3H), 3.08-3.19 (m, 1H), 3.54-3.75 (m, 2H), 4.52-4.72 (m, 2H), 7.07-7.15 (m, 1H), 7.99-8.09 (m, 1H), 8.31-8.40 (m, 1H); ESI-MS m/z $[M+H]^+$ 360.1.

EXAMPLE 50: 2-(1-ethylpyrrolidin-2-yl)-N-(2-methyl-1-((3-(trifluoromethyl)pyridin-2-yl)oxy)propan-2-yl)acetamide

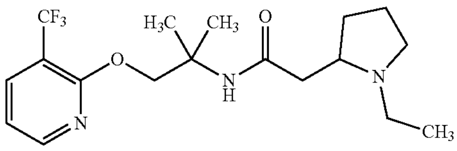 [SMILES: CCN1CCCC1CC(=O)NC(C)(C)COc1ncccc1C(F)(F)F]

A TFA salt of the title compound was prepared like EXAMPLE 48 (STEP A), using 2-(1-ethylpyrrolidin-2-yl) acetic acid hydrochloride (15 mg, 0.077 mmol) and 2-methyl-1-((3-(trifluoromethyl)pyridin-2-yl)oxy)propan-2-amine (20 mg, 0.085 mmol), and was obtained as a colorless oil (23 mg, 61%). $^1H$ NMR (400 MHz, $CD_3OD$) S ppm 1.34 (t, J=7.3 Hz, 3H), 1.46 (d, J=1.1 Hz, 6H), 1.72-1.85 (m, 1H), 1.93-2.16 (m, 2H), 2.23-2.37 (m, 1H), 2.70 (d, J=5.4 Hz, 2H), 3.04-3.22 (m, 2H), 3.41-3.56 (m, 1H), 3.62-3.74 (m, 2H), 4.53-4.68 (m, 2H), 7.06-7.16 (m, 1H), 7.95-8.05 (m, 1H), 8.32-8.40 (m, 1H); ESI-MS m/z $[M+H]^+$ 374.20.

EXAMPLE 51: (S)-2-(1-ethylpyrrolidin-2-yl)-N-(2-methyl-1-((3-(trifluoromethyl)pyridin-2-yl)oxy)propan-2-yl)acetamide

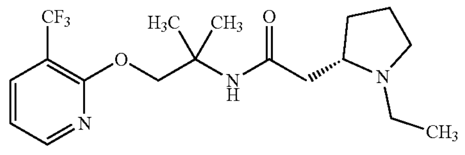 [SMILES: CCN1CCC[C@H]1CC(=O)NC(C)(C)COc1ncccc1C(F)(F)F]

A mixture of (S)—N-(2-methyl-1-((3-(trifluoromethyl) pyridin-2-yl)oxy)propan-2-yl)-2-(pyrrolidin-2-yl)acetamide TFA salt (40 mg, 0.087 mmol), iodoethane (16.3 mg, 0.104 mmol) and potassium carbonate (60 mg, 0.435 mmol) in DMSO (0.87 mL) was stirred at room temperature overnight. The reaction mixture was purified by preparative HPLC (Phenomenex Gemini® C18, 5 μm, ID 30 mm×150 mm) using a gradient of 10-70% water/ACN in water (basic mode) to give the title compound as a light-yellow oil (3.3 mg, 10%). $^1H$ NMR (400 MHz, $CD_3OD$) δ ppm 1.11 (t, J=7.2 Hz, 3H), 1.44 (d, J=2.0 Hz, 6H), 1.51-1.61 (m, 1H), 1.71-1.82 (m, 2H), 1.86-2.00 (m, 1H), 2.15-2.26 (m, 3H), 2.40 (dd, J=14.3, 4.3 Hz, 1H), 2.68 (qd, J=7.9, 4.3 Hz, 1H), 2.90 (dq, J=12.1, 7.4 Hz, 1H), 3.11-3.20 (m, 1H), 4.50-4.65 (m, 2H), 7.06-7.14 (m, 1H), 7.97-8.04 (m, 1H), 8.30-8.39 (m, 1H); ESI-MS m/z $[M+H]^+$ 374.1.

EXAMPLE 52: (S)-2-(1-(2-fluoroethyl)pyrrolidin-2-yl)-N-(2-methyl-1-((3-(trifluoromethyl)pyridin-2-yl) oxy)propan-2-yl)acetamide

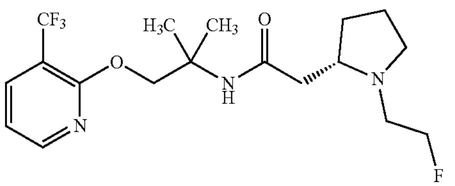 [SMILES: CC(C)(COc1ncccc1C(F)(F)F)NC(=O)C[C@@H]1CCCN1CCF]

The title compound was prepared like EXAMPLE 51, using (S)—N-(2-methyl-1-((3-(trifluoromethyl)pyridin-2-yl)oxy)propan-2-yl)-2-(pyrrolidin-2-yl)acetamide TFA salt (40 mg, 0.087 mmol), 1-bromo-2-fluoroethane (13.3 mg, 0.104 mmol) and potassium carbonate (48 mg, 0.348 mmol) in DMSO (0.87 mL), and was obtained as a colorless oil (4.5 mg, 13.2%). $^1H$ NMR (400 MHz, $CD_3OD$) δ ppm 1.43 (s, 6H), 1.52-1.64 (m, 1H), 1.71-1.86 (m, 2H), 1.89-2.01 (m, 1H), 2.20-2.41 (m, 3H), 2.42-2.59 (m, 1H), 2.76 (qd, J=7.6, 4.3 Hz, 1H), 3.05-3.18 (m, 1H), 3.20-3.27 (m, 1H), 4.40-4.53 (m, 1H), 4.56-4.68 (m, 3H), 7.05-7.14 (m, 1H), 7.96-8.04 (m, 1H), 8.29-8.38 (m, 1H); ESI-MS m/z $[M+H]^+$ 392.1.

EXAMPLE 53: (S)-2-(1-cyclopropylpyrrolidin-2-yl)-N-(2-methyl-1-((3-(trifluoromethyl)pyridin-2-yl)oxy)propan-2-yl)acetamide

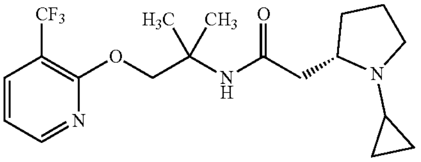 [SMILES: CC(C)(COc1ncccc1C(F)(F)F)NC(=O)C[C@@H]1CCCN1C1CC1]

A mixture of (S)—N-(2-methyl-1-((3-(trifluoromethyl)pyridin-2-yl)oxy)propan-2-yl)-2-(pyrrolidin-2-yl)acetamide TFA salt (40 mg, 0.084 mmol), (1-ethoxycyclopropoxy)trimethylsilane (18.2 mg, 0.104 mmol), sodium triacetoxyhydroborate (74 mg, 0.348 mmol) and DIPEA (0.061 mL, 0.348 mmol, 4.0 eq) in DCM (0.87 mL) was stirred at room temperature overnight. The reaction mixture was quenched with saturated aqueous $NaHCO_3$ and then was extracted with EtOAc (3×4.0 mL). The organic phase was concentrated and purified by preparative HPLC (Phenomenex Gemini® C18, 5 µm, ID 30 mm×150 mm) using a gradient of 10-50% ACN in water (acid mode) to give a TFA salt of the title compound as a colorless oil (3.0 mg, 6.9%). $^1$H NMR (400 MHz, $CD_3OD$) δ ppm 0.83-1.07 (m, 4H), 1.23-1.39 (m, 1H), 1.44 (s, 6H), 1.71-1.85 (m, 1H), 1.89-2.02 (m, 1H), 2.03-2.16 (m, 1H), 2.22-2.38 (m, 1H), 2.64-2.86 (m, 3H), 3.69 (ddd, J=12.0, 7.9, 4.6 Hz, 1H), 3.81-3.92 (m, 1H), 4.59 (s, 2H), 7.06-7.14 (m, 1H), 7.96-8.02 (m, 1H), 8.30-8.36 (m, 1H); ESI-MS m/z $[M+H]^+$ 386.10.

EXAMPLE 54: (S)—N-(1-(((3-methylpyridin-2-yl)oxy)methyl)cyclopropyl)-2-(1-methylpyrrolidin-2-yl)acetamide

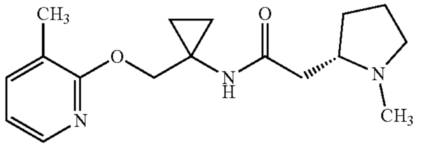 [SMILES: Cc1cccnc1OCC1(NC(=O)C[C@@H]2CCCN2C)CC1]

STEP A: (S)—N-(1-(((3-methylpyridin-2-yl)oxy)methyl)cyclopropyl)-2-(pyrrolidin-2-yl)acetamide

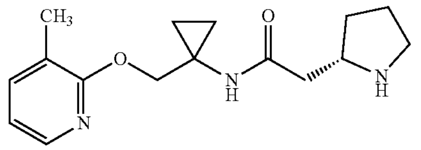 [SMILES: Cc1cccnc1OCC1(NC(=O)C[C@@H]2CCCN2)CC1]

The title compound was prepared like STEP A and STEP B of EXAMPLE 48, starting from (S)-2-(1-(tert-butoxycarbonyl)pyrrolidin-2-yl)acetic acid (30 mg, 0.131 mmol) and 1-(((3-methylpyridin-2-yl)oxy)methyl)cyclopropan-1-amine (28 mg, 0.157 mmol). The resulting intermediate tert-butyl (S)-2-(2-((1-(((3-methylpyridin-2-yl)oxy)methyl)cyclopropyl)amino)-2-oxoethyl)pyrrolidine-1-carboxylate TFA salt (50 mg, 0.099 mmol) was treated with TFA (1 mL) and concentrated. The colorless residue was dissolved in MeOH and filtered through Agilent Stratospheres SPE (PL-$HCO_3$ MP) resin to afford the title compound as a white solid (33 mg).

STEP B: (S)—N-(1-(((3-methylpyridin-2-yl)oxy)methyl)cyclopropyl)-2-(1-methylpyrrolidin-2-yl)acetamide A mixture of (S)—N-(1-(((3-methylpyridin-2-yl)oxy)methyl)cyclopropyl)-2-(pyrrolidin-2-yl)acetamide (16 mg, 0.055 mmol), paraformaldehyde (3.3 mg, 0.11 mmol) and sodium triacetoxyborohydride (46.9 mg, 0.221 mmol) in DCM (553 µL) was stirred at room temperature for 16 hours and then was purified by preparative HPLC (Phenomenex Gemini® C18, 5 µm, ID 30 mm×150 mm) using a gradient of 10-50% ACN in water (acid mode) to give a TFA salt of the title compound as a white oil (4.2 mg, 18%). $^1$H NMR (400 MHz, $CD_3OD$) δ ppm 0.84-0.92 (m, 2H), 0.97-1.04 (m, 2H), 1.71-1.87 (m, 1H), 1.96-2.17 (m, 2H), 2.23 (s, 3H), 2.27-2.40 (m, 1H), 2.69 (d, J=5.6 Hz, 2H), 2.95 (br s, 3H), 3.11-3.23 (m, 1H), 3.60-3.77 (m, 2H), 4.34-4.54 (m, 2H), 6.85 (dd, J=7.1, 5.1 Hz, 1H), 7.44-7.54 (m, 1H), 7.86-7.96 (m, 1H); ESI-MS m/z $[M+H]^+$ 304.2.

EXAMPLE 55: (S)—N-(1-(((3-methylpyridin-2-yl)oxy)methyl)cyclobutyl)-2-(1-methylpyrrolidin-2-yl)acetamide

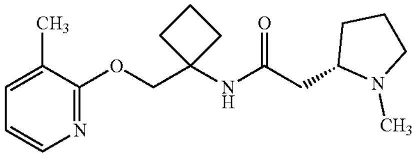 [SMILES: Cc1cccnc1OCC1(NC(=O)C[C@@H]2CCCN2C)CCC1]

A TFA salt of the title compound was prepared like EXAMPLE 54, using 1-(((3-methylpyridin-2-yl)oxy)methyl)cyclobutan-1-amine (30 mg, 0.157 mmol) and (S)-2-(1-(tert-butoxycarbonyl)pyrrolidin-2-yl)acetic acid (30 mg, 0.131 mmol), and was obtained as a colorless oil (16 mg, 28% over three steps). $^1$H NMR (400 MHz, $CD_3OD$) δ ppm 1.69-1.84 (m, 1H), 1.94-2.17 (m, 4H), 2.23 (s, 3H), 2.27-2.42 (m, 5H), 2.71 (dd, J=5.3, 2.7 Hz, 2H), 2.94 (s, 3H), 3.09-3.20 (m, 1H), 3.54-3.64 (m, 1H), 3.66-3.76 (m, 1H), 4.52-4.66 (m, 2H), 6.88 (dd, J=7.0, 5.1 Hz, 1H), 7.48-7.55 (m, 1H), 7.94 (ddt, J=5.1, 1.2, 0.6 Hz, 1H); ESI-MS m/z $[M+H]^+$ 318.1.

EXAMPLE 56: (S)—N-(1-(((3-methylpyridin-2-yl)oxy)methyl)cyclopentyl)-2-(1-methylpyrrolidin-2-yl)acetamide

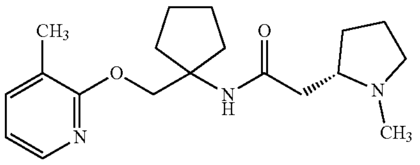 [SMILES: Cc1cccnc1OCC1(NC(=O)C[C@@H]2CCCN2C)CCCC1]

A TFA salt of the title compound was prepared like EXAMPLE 54, using 1-(((3-methylpyridin-2-yl)oxy)

methyl)cyclopentan-1-amine (32 mg, 0.157 mmol) and (S)-2-(1-(tert-butoxycarbonyl)pyrrolidin-2-yl)acetic acid (30 mg, 0.131 mmol), and was obtained as a colorless oil (14 mg, 24% over three steps). $^1$H NMR (400 MHz, $CD_3OD$) δ ppm 1.65-1.85 (m, 5H), 1.87-2.00 (m, 3H), 2.03-2.16 (m, 3H), 2.23 (s, 3H), 2.24-2.34 (m, 1H), 2.65-2.78 (m, 2H), 2.92 (s, 3H), 3.07-3.16 (m, 1H), 3.52-3.62 (m, 1H), 3.64-3.73 (m, 1H), 4.41-4.65 (m, 2H), 6.87 (dd, J=7.2, 5.1 Hz, 1H), 7.49-7.54 (m, 1H), 7.87-7.95 (m, 1H); ESI-MS m/z [M+H]$^+$ 332.1.

EXAMPLE 57: (R)-2-(1-ethylpyrrolidin-2-yl)-N-(2-methyl-1-((3-(trifluoromethyl)pyridin-2-yl)oxy)propan-2-yl)acetamide

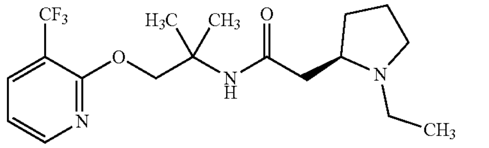 [SMILES: CCN1CCC[C@@H]1CC(=O)NC(C)(C)COc1ncccc1C(F)(F)F]

A mixture of (R)—N-(2-methyl-1-((3-(trifluoromethyl)pyridin-2-yl)oxy)propan-2-yl)-2-(pyrrolidin-2-yl)acetamide TFA salt (40.0 mg, 0.087 mmol), iodoethane (16.3 mg, 0.104 mmol) and potassium carbonate (60 mg, 0.435 mmol) in DMF (0.87 mL) was stirred at room temperature for 1 day. The reaction mixture was taken up in methanol and filtered through a hydrophilic PTFE 0.45 m Millipore® filter, rinsing with methanol. The reaction mixture was purified by preparative HPLC (Phenomenex Gemini® C18, 5 μm, ID 30 mm×150 mm) using a gradient of 10-50% ACN in water (acid mode) to give a TFA salt of the title compound as a colorless oil (13 mg, 31%). $^1$H NMR (400 MHz, $CD_3OD$) δ ppm 1.25 (t, J=7.3 Hz, 3H), 1.38 (s, 6H), 1.64-1.75 (m, 1H), 1.85-2.04 (m, 2H), 2.21 (dtd, J=13.4, 7.9, 6.0 Hz, 1H), 2.55-2.69 (m, 2H), 2.94-3.13 (m, 2H), 3.38 (dq, J=12.8, 7.3 Hz, 1H), 3.55-3.67 (m, 2H), 4.46-4.59 (m, 2H), 6.98-7.07 (m, 1H), 7.89-7.94 (m, 1H), 7.98 (br s, 1H), 8.25-8.30 (m, 1H); ESI-MS m/z [M+H]$^+$ 374.10.

EXAMPLE 58: (R)-2-(1-(2-fluoroethyl)pyrrolidin-2-yl)-N-(2-methyl-1-((3-(trifluoromethyl)pyridin-2-yl)oxy)propan-2-yl)acetamide

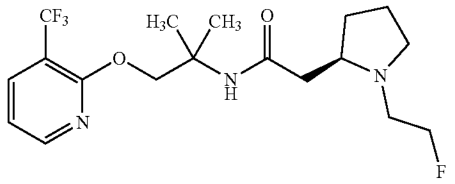 [SMILES: CC(C)(COc1ncccc1C(F)(F)F)NC(=O)C[C@H]1CCCN1CCF]

A TFA salt of the title compound was prepared like EXAMPLE 57, using (R)—N-(2-methyl-1-((3-(trifluoromethyl)pyridin-2-yl)oxy)propan-2-yl)-2-(pyrrolidin-2-yl)acetamide TFA salt (40.0 mg, 0.087 mmol), 1-bromo-2-fluoroethane (13.3 mg, 0.104 mmol) and potassium carbonate (48 mg, 0.348 mmol) in DMF (0.87 mL), and was obtained as a colorless oil (6 mg, 14%). $^1$H NMR (400 MHz, $CD_3OD$) δ ppm 1.46 (d, J=0.9 Hz, 6H), 1.74-1.85 (m, 1H), 1.93-2.18 (m, 2H), 2.25-2.41 (m, 1H), 2.75 (d, J=5.4 Hz, 2H), 3.20-3.30 (m, 1H), 3.38-3.54 (m, 1H), 3.70-3.90 (m, 3H), 4.53-4.59 (m, 1H), 4.62-4.68 (m, 1H), 4.71-4.77 (m, 1H), 4.87 (t, J=4.5 Hz, 1H), 7.07-7.16 (m, 1H), 7.99-8.05 (m, 1H), 8.10 (br s, 1H), 8.33-8.39 (m, 1H); ESI-MS m/z [M+H]$^+$ 392.1.

EXAMPLE 59: (R)-2-(1-cyclopropylpyrrolidin-2-yl)-N-(2-methyl-1-((3-(trifluoromethyl)pyridin-2-yl)oxy)propan-2-yl)acetamide

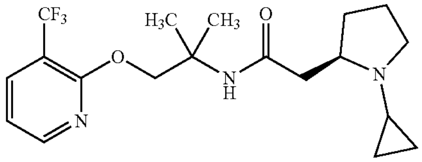 [SMILES: CC(C)(COc1ncccc1C(F)(F)F)NC(=O)C[C@H]1CCCN1C1CC1]

A mixture of (R)—N-(2-methyl-1-((3-(trifluoromethyl)pyridin-2-yl)oxy)propan-2-yl)-2-(pyrrolidin-2-yl)acetamide TFA salt (40.0 mg, 0.087 mmol), (1-ethoxycyclopropoxy)trimethylsilane (18.2 mg, 0.104 mmol), sodium triacetoxyhydroborate (74 mg, 0.348 mmol) and DIPEA (0.061 mL, 0.348 mmol) in DCM (0.87 mL) was stirred at room temperature overnight. The reaction mixture was quenched with saturated aqueous $NaHCO_3$ and extracted with EtOAc (3×4.0 mL). The organic phase was concentrated purified by preparative HPLC on (Phenomenex Gemini® C18, 5 μm, ID 30 mm×150 mm) using a gradient of 10-70% water/ACN in water (basic mode) to give the title compound as a colorless oil (3.6 mg, 11%). $^1$H NMR (400 MHz, $CD_3OD$) δ ppm 0.37-0.86 (m, 4H), 1.44 (s, 6H), 1.54-1.68 (m, 1H), 1.71-1.92 (m, 2H), 1.96-2.18 (m, 1H), 2.29-2.53 (m, 1H), 2.58-2.80 (m, 2H), 2.97-3.29 (m, 2H), 4.59 (s, 2H), 7.03-7.16 (m, 1H), 8.01 (dt, J=7.5, 1.2 Hz, 1H), 8.36 (dt, J=5.0, 1.2 Hz, 1H); ESI-MS m/z [M+H]$^+$ 386.1.

EXAMPLE 60: N—((S)-1-(4-chlorophenyl)ethyl)-2-(1-methylpiperidin-2-yl)acetamide

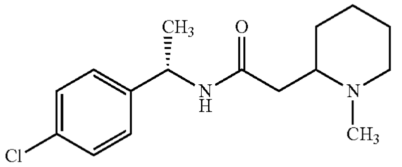 [SMILES: C[C@H](NC(=O)CC1CCCCN1C)c1ccc(Cl)cc1]

To a solution of $Et_3N$ (0.177 mL, 1.27 mmol), (S)-1-(4-chlorophenyl)ethan-1-amine (0.074 g, 0.477 mmol) and 2-(1-methylpiperidin-2-yl)acetic acid (0.050 g, 0.318 mmol) in DMF (3.18 mL) was added HATU (0.181 g, 0.477 mmol). The mixture was stirred at room temperature overnight and then was diluted with MeOH, filtered and purified by preparative HPLC (Phenomenex Gemini® C18, 5 μm, ID 30 mm×150 mm) using a gradient of 10-100% water/ACN in water (basic mode) to give the title compound (74 mg, 79%). $^1$H NMR (400 MHz, $CDCl_3$) δ ppm 1.19-1.42 (m, 2H), 1.42-1.49 (m, 3H), 1.49-1.75 (m, 4H), 1.75-1.86 (m, 2H), 2.12 (tdd, J=11.8, 11.8, 7.7, 2.8 Hz, 1H), 2.17-2.26 (m, 2H), 2.28 (s, 2H), 2.33 (s, 2H), 2.59-2.80 (m, 1H), 2.88-3.02 (m, 1H), 5.03-5.20 (m, 1H), 7.15-7.38 (m, 4H), 8.80-9.40 (m, 1H).

EXAMPLE 61: N—((S)-1-(4-fluorophenyl)ethyl)-2-(1-methylpiperidin-2-yl)acetamide

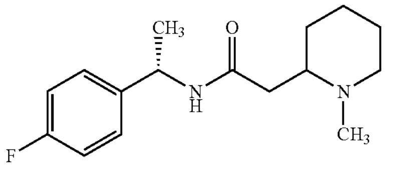 [SMILES: C[C@H](NC(=O)CC1CCCCN1C)c1ccc(F)cc1]

To a solution of $Et_3N$ (0.177 mL, 1.27 mmol), (S)-1-(4-fluorophenyl)ethan-1-amine (0.066 g, 0.477 mmol) and 2-(1-methylpiperidin-2-yl)acetic acid (0.050 g, 0.318 mmol) in DMF (3.18 mL) was added HATU (0.181 g, 0.477 mmol). The mixture was stirred at room temperature overnight and then was diluted with MeOH, filtered and purified by preparative HPLC (Phenomenex Gemini® C18, 5 μm, ID 30 mm×150 mm) using a gradient of 10-100% water/ACN in water (basic mode) to give the title compound (58 mg, 66%). $^1H$ NMR (400 MHz, $CDCl_3$) δ ppm 1.18-1.43 (m, 2H), 1.43-1.50 (m, 3H), 1.50-1.74 (m, 4H), 1.74-1.84 (m, 2H), 2.06-2.17 (m, 1H), 2.17-2.26 (m, 2H), 2.26-2.30 (m, 2H), 2.31-2.37 (m, 1H), 2.60-2.79 (m, 1H), 2.82-3.04 (m, 1H), 5.13 (quin, J=7.2 Hz, 1H), 6.91-7.14 (m, 2H), 7.16-7.34 (m, 2H), 8.80-9.20 (m, 1H).

EXAMPLE 62: 2-(1-ethylpyrrolidin-2-yl)-N-(2-methyl-1-((3-methylpyridin-2-yl)oxy)propan-2-yl)acetamide

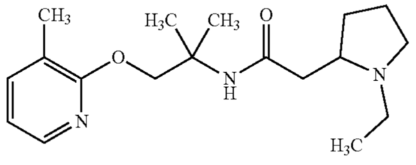 [SMILES: CCN1CCCC1CC(=O)NC(C)(C)COc1ncccc1C]

To a vial were added 2-methyl-1-((3-methylpyridin-2-yl)oxy)propan-2-amine (0.030 g, 0.166 mmol), 2-(1-ethylpyrrolidin-2-yl)acetic acid HCl (0.032 g, 0.166 mmol), HATU (0.063 g, 0.166 mmol) and DIPEA (0.087 mL, 0.499 mmol) in DMF (2 mL). The resulting yellow solution was stirred at room temperature overnight and then was purified by preparative HPLC (Phenomenex Gemini® C18, 5 μm, ID 30 mm×150 mm) using a gradient of 10-100% ACN in water (acid mode) to give a TFA salt of the title compound as a colorless film (37.2 mg, 52%). $^1H$ NMR (400 MHz, $CD_3OD$) δ ppm 1.31 (s, 3H), 1.46 (s, 6H), 1.66-1.80 (m, 1H), 1.91-2.12 (m, 2H), 2.22 (s, 4H), 2.62-2.77 (m, 2H), 2.99-3.16 (m, 2H), 3.38-3.49 (m, 1H), 3.60-3.70 (m, 2H), 4.35-4.53 (m, 2H), 6.81-6.88 (m, 1H), 7.46-7.53 (m, 1H), 7.86-7.95 (m, 1H); ESI-MS m/z $[M+H]^+$ 320.3.

EXAMPLE 63: 2-(1-ethylpyrrolidin-2-yl)-N-(1-(((3-methylpyridin-2-yl)oxy)methyl)cyclopropyl)acetamide

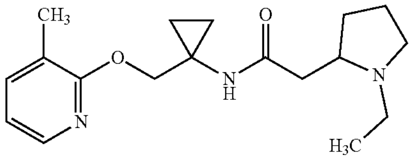 [SMILES: CCN1CCCC1CC(=O)NC1(COc2ncccc2C)CC1]

To a solution of 2-(1-ethylpyrrolidin-2-yl)acetic acid (15 mg, 0.095 mmol) and HATU (36.3 mg, 0.095 mmol) in DMF (636 μL) was added DIPEA (66.7 μl, 0.382 mmol). The reaction mixture was stirred at room temperature for 5 minutes and then 1-(((3-methylpyridin-2-yl)oxy)methyl)cyclopropan-1-amine (20.4 mg, 0.114 mmol) was added. The solution was stirred at room temperature for 8 hours and then purified by preparative HPLC (Phenomenex Gemini® C18, 5 μm, ID 30 mm×150 mm) using a gradient of 10-50% ACN in water (acid mode) to give a TFA salt of the title compound as a colorless oil (20 mg, 49%). $^1H$ NMR (400 MHz, $CD_3OD$) δ ppm 0.82-0.90 (m, 2H), 0.95-1.03 (m, 2H), 1.34 (t, J=7.3 Hz, 3H), 1.67-1.82 (m, 1H), 1.93-2.14 (m, 2H), 2.22 (s, 3H), 2.24-2.35 (m, 1H), 2.58-2.72 (m, 2H), 3.01-3.22 (m, 2H), 3.43-3.57 (m, 1H), 3.62-3.76 (m, 2H), 4.33-4.50 (m, 2H), 6.84 (dd, J=7.2, 5.0 Hz, 1H), 7.45-7.51 (m, 1H), 7.82-7.92 (m, 1H); ESI-MS m/z $[M+H]^+$ 318.0.

EXAMPLE 64: 2-(1-ethylpyrrolidin-2-yl)-N-(1-(((3-methylpyridin-2-yl)oxy)methyl)cyclobutyl)acetamide

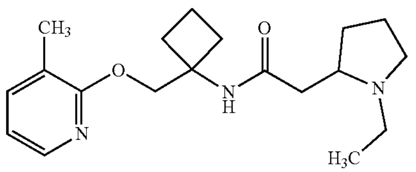 [SMILES: CCN1CCCC1CC(=O)NC1(COc2ncccc2C)CCC1]

A TFA salt of the title compound was prepared like EXAMPLE 63, using 1-(((3-methylpyridin-2-yl)oxy)methyl)cyclobutan-1-amine (22 mg, 0.114 mmol) and 2-(1-ethylpyrrolidin-2-yl)acetic acid (15 mg, 0.095 mmol), and was obtained as a colorless oil (25 mg, 59%). $^1H$ NMR (400 MHz, $CD_3OD$) δ ppm 1.32 (t, J=7.2 Hz, 3H), 1.68-1.81 (m, 1H), 1.90-2.10 (m, 4H), 2.21 (s, 3H), 2.27 (br dd, J=13.3, 5.6 Hz, 1H), 2.34 (t, J=7.9 Hz, 4H), 2.68 (d, J=5.6 Hz, 2H), 3.01-3.20 (m, 2H), 3.42-3.53 (m, 1H), 3.61-3.73 (m, 2 H), 4.49-4.64 (m, 2H), 6.86 (dd, J=7.0, 5.1 Hz, 1H), 7.50 (dd, J=7.1, 0.9 Hz, 1H), 7.87-7.96 (m, 1H); ESI-MS m/z $[M+H]^+$ 332.1.

EXAMPLE 65: 2-(1-ethylpyrrolidin-2-yl)-N-(1-(((3-methylpyridin-2-yl)oxy)methyl)cyclopentyl)acetamide

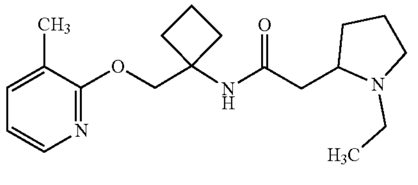 [SMILES: CCN1CCCC1CC(=O)NC1(COc2ncccc2C)CCC1]

A TFA salt of the title compound was prepared like EXAMPLE 63, using 1-(((3-methylpyridin-2-yl)oxy)methyl)cyclopentan-1-amine (23.6 mg, 0.114 mmol) and 2-(1-ethylpyrrolidin-2-yl)acetic acid (15 mg, 0.095 mmol), and was obtained as a colorless oil (18 mg, 41%). $^1$H NMR (400 MHz, $CD_3OD$) δ ppm 1.31 (t, J=7.3 Hz, 3H), 1.62-1.82 (m, 5H), 1.89-2.14 (m, 6H), 2.21 (s, 3H), 2.23-2.30 (m, 1H), 2.68 (d, J=5.5 Hz, 2H), 2.99-3.17 (m, 2H), 3.38-3.54 (m, 2H), 3.60-3.71 (m, 2H), 4.37-4.64 (m, 2H), 6.85 (dd, J=7.2, 5.1 Hz, 1H), 7.43-7.53 (m, 1H), 7.85-7.97 (m, 1H); ESI-MS m/z $[M+H]^+$ 346.1.

EXAMPLE 66: (R)—N-(2-methyl-1-((3-methylpyridin-2-yl)oxy)propan-2-yl)-2-((S)-1-methylpyrrolidin-2-yl)propanamide and (S)—N-(2-methyl-1-((3-methylpyridin-2-yl)oxy)propan-2-yl)-2-((R)-1-methylpyrrolidin-2-yl)propanamide

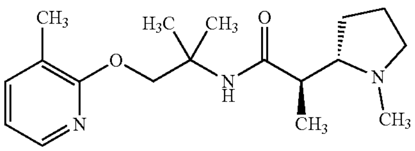

and

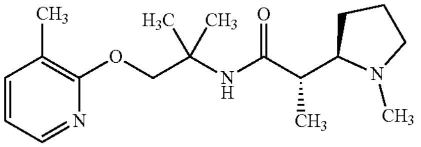

EXAMPLE 67: (S)—N-(2-methyl-1-((3-methylpyridin-2-yl)oxy)propan-2-yl)-2-((S)-1-methylpyrrolidin-2-yl)propanamide and (R)—N-(2-methyl-1-((3-methylpyridin-2-yl)oxy)propan-2-yl)-2-((R)-1-methylpyrrolidin-2-yl)propanamide

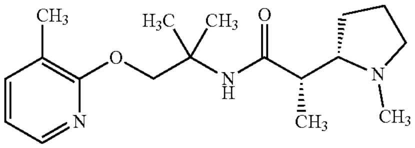

and

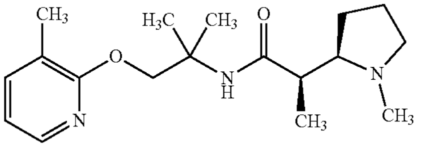

To a vial were added 2-methyl-1-((3-methylpyridin-2-yl)oxy)propan-2-amine (0.050 g, 0.277 mmol), 2-(1-methylpyrrolidin-2-yl)propanoic acid (0.141 g, 0.277 mmol), HATU (0.105 g, 0.277 mmol) and DIPEA (0.145 mL, 0.832 mmol) in DMF (2 mL). The resulting yellow solution was stirred at room temperature overnight and then was purified by preparative HPLC (Phenomenex Gemini® C18, 5 μm, ID 30 mm×150 mm) using a gradient of 10-100% ACN in water (acid mode) to give TFA salts of the title compounds. The early eluting compound was arbitrarily assigned as the mixture of (S,R)- and (R,S)-enantiomers and was obtained as a colorless film (1.8 mg, 1.5%). $^1$H NMR (400 MHz, $CD_3OD$) δ ppm 1.28-1.35 (m, 3H), 1.46 (s, 6H), 1.68-1.88 (m, 2H), 1.94-2.04 (m, 1H), 2.22 (s, 3H), 2.24-2.36 (m, 1H), 2.67-2.78 (m, 1H), 2.91 (s, 3H), 3.06-3.17 (m, 1H), 3.49-3.59 (m, 2H), 4.33-4.44 (m, 1H), 4.52-4.58 (m, 1H), 6.86 (dd, J=7.1, 5.1 Hz, 1H), 7.40-7.55 (m, 1H), 7.78-7.96 (m, 1H); ESI-MS m/z $[M+H]^+$ 320.3. The late eluting compound was arbitrarily assigned as the mixture of the (S,S)- and (R,R)-enantiomers and was obtained as a colorless film (12.9 mg, 11%). $^1$H NMR (400 MHz, $CD_3OD$) δ ppm 1.28 (dd, J=12.0, 7.2 Hz, 3H), 1.43-1.50 (m, 6H), 1.71-2.08 (m, 3H), 2.22 (s, 4H), 2.90 (d, J=9.5 Hz, 4H), 3.07-3.16 (m, 1H), 3.40-3.66 (m, 2H), 4.40 (s, 1H), 4.47-4.61 (m, 1H), 6.81-6.90 (m, 1H), 7.47-7.55 (m, 1H), 7.82-7.95 (m, 1H); ESI-MS m/z $[M+H]^+$ 320.3.

EXAMPLE 68: 2-(1,5-dimethylpyrrolidin-2-yl)-N-(2-methyl-1-((3-methylpyridin-2-yl)oxy)propan-2-yl)acetamide

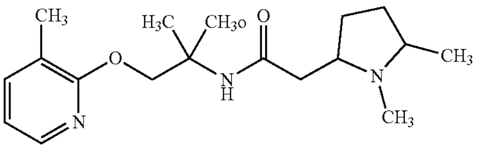

STEP A: methyl 2-(1,5-dimethylpyrrolidin-2-yl)acetate

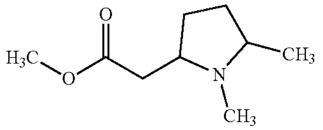

To a 100 mL round-bottomed flask were added methyl 2-(5-methylpyrrolidin-2-yl)acetate HCl (0.250 g, 1.03 mmol) and aqueous formaldehyde (37 wt %, 0.160 mL, 2.06 mmol) in MeOH (6 mL) followed by sodium cyanoborohydride (0.130 g, 2.06 mmol). The mixture was stirred at room temperature overnight and then was concentrated to dryness to give the title compound as a white solid (0.177 g, assumed quantitative), which was used without further purification. ESI-MS m/z $[M+H]^+$ 172.2.

STEP B: 2-(1,5-dimethylpyrrolidin-2-yl)acetic acid

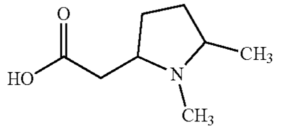

To a 100 mL round-bottomed flask were added methyl 2-(1,5-dimethylpyrrolidin-2-yl)acetate (0.177 g, 1.03 mmol) and lithium hydroxide (2 M, 2.07 mL, 4.13 mmol). The resulting brown solution was stirred at room temperature for 5 hours and then was filtered. The filtrate was concentrated to dryness to give the title compound as an off-white solid (0.488 g, 33% purity). ESI-MS m/z $[M+H]^+$ 158.2.

STEP C: 2-(1,5-dimethylpyrrolidin-2-yl)-N-(2-methyl-1-((3-methylpyridin-2-yl)oxy)propan-2-yl)acetamide To a vial were added 2-methyl-1-((3-methylpyridin-2-yl)oxy)propan-2-amine (0.100 g, 0.555 mmol), 2-(1,5-dimethylpyrrolidin-2-yl)acetic acid (33%, 0.264 g, 0.183 mmol), HATU (0.211 g, 0.555 mmol) and DIPEA (0.290 mL, 1.66 mmol) in DMF (2 mL).

The resulting yellow solution was stirred at room temperature overnight and then was purified by preparative HPLC (Phenomenex Gemini® C18, 5 μm, ID 30 mm×150 mm) using a gradient of 10-100% ACN in water (acid mode) to give a TFA salt of the title compound (9.3 mg, 11%). $^1H$ NMR (400 MHz, $CD_3OD$) δ ppm 1.28-1.43 (m, 4H), 1.46 (d, J=2.0 Hz, 6H), 1.64-1.88 (m, 2H), 2.10 (s, 1H), 2.22 (s, 4H), 2.63-2.74 (m, 2H), 2.79 (s, 3H), 3.65-3.93 (m, 1H), 4.33-4.56 (m, 2H), 6.82-6.90 (m, 1H), 7.46-7.53 (m, 1H), 7.85-7.96 (m, 1H); ESI-MS m/z $[M+H]^+$ 320.5.

EXAMPLE 69: N-(2-methyl-1-((3-methylpyridin-2-yl)oxy)propan-2-yl)-2-(1-methylpiperidin-2-yl)acetamide

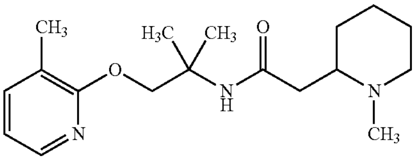 [SMILES: Cc1cccnc1OCC(C)(C)NC(=O)CC1CCCCN1C]

To a vial were added 2-methyl-1-((3-methylpyridin-2-yl)oxy)propan-2-amine (68.0 mg, 0.377 mmol), 2-(1-methylpiperidin-2-yl)acetic acid (59.3 mg, 0.377 mmol), HATU (143 mg, 0.377 mmol) and DIPEA (0.197 mL, 1.13 mmol) in DMF (2 mL). The resulting yellow solution was stirred at room temperature overnight and then was purified by preparative HPLC (Phenomenex Gemini® C18, 5 μm, ID 30 mm×150 mm) using a gradient of 10-100% ACN in water (acid mode) to give a TFA salt of the title compound (31.2 mg, 19%). $^1H$ NMR (400 MHz, $CD_3OD$) δ ppm 1.46 (d, J=2.9 Hz, 6H), 1.51-1.64 (m, 2H), 1.66-1.77 (m, 2H), 1.82-1.92 (m, 2H), 2.22 (s, 3H), 2.54-2.65 (m, 1H), 2.73-2.80 (m, 1H), 2.85 (s, 3H), 2.88-3.04 (m, 1H), 3.22-3.28 (m, 1H), 3.38-3.49 (m, 1H), 4.39 (s, 1H), 4.55 (s, 1H), 6.80-6.95 (m, 1H), 7.47-7.56 (m, 1H), 7.86-7.95 (m, 1H); ESI-MS m/z $[M+H]^+$ 320.3.

EXAMPLE 70: (R)—N-(2-(3-methylisoquinolin-1-yl)propan-2-yl)-2-(1-methylpyrrolidin-2-yl)acetamide

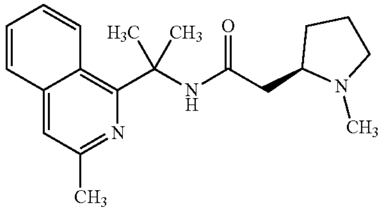 [SMILES: Cc1cc2ccccc2c(C(C)(C)NC(=O)C[C@H]2CCCN2C)n1]

STEP A: tert-butyl (R)-2-(2-((2-(3-methylisoquinolin-1-yl)propan-2-yl)amino)-2-oxoethyl)pyrrolidine-1-carboxylate

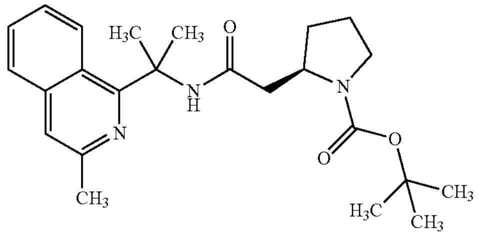 [SMILES: Cc1cc2ccccc2c(C(C)(C)NC(=O)C[C@H]2CCCN2C(=O)OC(C)(C)C)n1]

A mixture of 2-(3-methylisoquinolin-1-yl)propan-2-amine (0.300 g, 1.50 mmol) and (R)-2-(1-(tert-butoxycarbonyl)pyrrolidin-2-yl)acetic acid (0.344 g, 1.50 mmol) in DMA (7.50 mL) was treated with DIPEA (1.05 mL, 6.00 mmol) and HATU (0.856 g, 2.25 mmol). The reaction mixture was stirred overnight at room temperature. The reaction was quenched with saturated aqueous $NH_4Cl$ and extracted twice with EtOAc. The organics were washed with saturated aqueous NaCl, dried over $Na_2SO_4$, filtered, and concentrated under reduced pressure. The residue was purified by flash silica column chromatography using a gradient of 10% to 70% EtOAc in heptanes. Fractions were evaporated to afford the title compound (600 mg, 97%). ESI-MS $[M+H]^+$ m/z 412.

STEP B: (R)—N-(2-(3-methylisoquinolin-1-yl)propan-2-yl)-2-(pyrrolidin-2-yl)acetamide

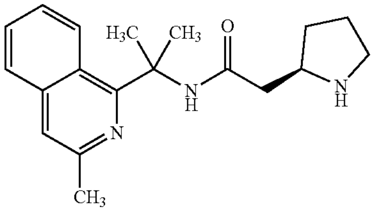 [SMILES: Cc1cc2ccccc2c(C(C)(C)NC(=O)C[C@H]2CCCN2)n1]

To a round bottom flask were added 4 M HCl in dioxane (3.64 mL, 14.6 mmol) and a solution of tert-butyl (R)-2-(2-((2-(3-methylisoquinolin-1-yl)propan-2-yl)amino)-2-oxoethyl)pyrrolidine-1-carboxylate (0.600 g, 1.46 mmol) in dioxane (3.6 mL). The reaction mixture was concentrated and the resulting solid was washed with MeOH to give an HCl salt of the title compound (0.452 g), which was used without further purification. ESI-MS m/z $[M+H]^+$ 312.3.

STEP C: (R)—N-(2-(3-methylisoquinolin-1-yl)propan-2-yl)-2-(1-methylpyrrolidin-2-yl)acetamide To a solution of (R)—N-(2-(3-methylisoquinolin-1-yl)propan-2-yl)-2-(pyrrolidin-2-yl)acetamide (0.452 g, 1.45 mmol) and aqueous formaldehyde (37 wt %, 0.108 mL, 1.45 mmol) in MeOH was added acetic acid (0.33 mL, 5.8 mmol). The mixture was stirred at room temperature for 1 hour and then sodium triacetoxyborohydride (0.923 g, 4.35 mmol) was added. The reaction mixture was stirred at room temperature overnight and then was concentrated in vacuo and extracted with EtOAc. The organic layers were combined, dried over $MgSO_4$, filtered and concentrated in vacuo. The resulting residue was suspended in MeOH and purified by preparative HPLC (Phenomenex Gemini® C18, 5 μm, ID 30 mm×150 mm) using a gradient of 10-100% water/ACN in water (basic mode) to give the title compound as a white solid (32 mg, 6.8% over 2 steps). $^1H$ NMR (400 MHz, $CD_3OD$) δ ppm 1.38-1.57 (m, 1H), 1.65-1.90 (m, 9H), 2.12-2.24 (m, 2H), 2.29 (s, 3H), 2.39-2.54 (m, 2H), 2.63 (s, 3H), 3.00-3.07 (m, 1H), 7.42-7.50 (m, 2H), 7.60 (t, J=7.5 Hz, 1H), 7.78 (d, J=8.2 Hz, 1H), 8.58 (d, J=8.6 Hz, 1H); ESI-MS m/z $[M+H]^+$ 326.3.

EXAMPLE 71: N-(1-(((3-methylpyridin-2-yl)oxy)methyl)cyclopropyl)-2-(1-methylpyrrolidin-2-yl)propanamide

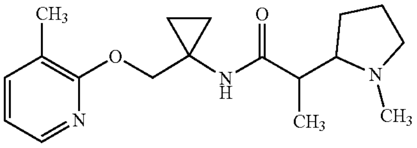 [SMILES: Cc1cccnc1OCC1(NC(=O)C(C)C2CCCN2C)CC1]

To a solution of 2-(1-methylpyrrolidin-2-yl)propanoic acid (44.1 mg, 0.084 mmol) and HATU (35.2 mg, 0.093 mmol) in DMF (0.84 mL) was added DIPEA (44.1 μL, 0.252 mmol). The reaction mixture was stirred at room temperature for 5 minutes and then 1-(((3-methylpyridin-2-yl)oxy)methyl)cyclopropan-1-amine (15 mg, 0.084 mmol) was added. The resulting solution was stirred at room temperature for 16 hours and then was purified by preparative HPLC (Phenomenex Gemini® C18, 5 μm, ID 30 mm×150 mm) using a gradient of 10-50% ACN in water (acid mode) to give a TFA salt of the title compound as a colorless oil (4 mg, 11%). $^1H$ NMR (400 MHz, $CD_3OD$) δ ppm 0.83-0.94 (m, 2H), 0.96-1.07 (m, 2H), 1.28 (dd, J=14.2, 7.2 Hz, 3H), 1.70-1.86 (m, 1H), 1.89-2.00 (m, 1H), 2.02-2.15 (m, 1H), 2.24 (s, 3H), 2.27-2.41 (m, 1H), 2.63-2.91 (m, 1H), 2.95 (d, J=5.9 Hz, 3H), 3.10-3.23 (m, 1H), 3.44-3.72 (m, 2H), 4.33-4.55 (m, 2H), 6.86 (dd, J=7.1, 5.1 Hz, 1H), 7.46-7.54 (m, 1H), 7.91 (dd, J=5.1, 1.2 Hz, 1H); ESI-MS m/z $[M+H]^+$ 318.1.

EXAMPLE 72: (S)—N-(2-methyl-1-((3-(trifluoromethoxy)pyridin-2-yl)oxy)propan-2-yl)-2-(1-methylpyrrolidin-2-yl)acetamide

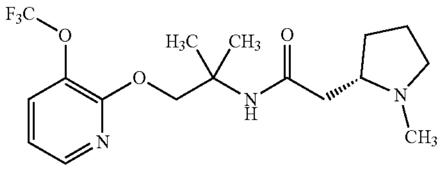 [SMILES: CN1CCC[C@H]1CC(=O)NC(C)(C)COc1ncccc1OC(F)(F)F]

A TFA salt of the title compound was prepared like EXAMPLE 71, using 2-methyl-1-((3-(trifluoromethoxy)pyridin-2-yl)oxy)propan-2-amine (52 mg, 0.210 mmol) and (S)-2-(1-methylpyrrolidin-2-yl)acetic acid (25 mg, 0.175 mmol), and was obtained as a white solid (36 mg, 42%). $^1H$ NMR (400 MHz, $CD_3OD$) δ ppm 1.46 (d, J=2.6 Hz, 6H), 1.76-1.87 (m, 1H), 1.89-2.00 (m, 1H), 2.03-2.20 (m, 1H), 2.32 (dtd, J=13.4, 8.2, 5.5 Hz, 1H), 2.69-2.76 (m, 2H), 2.94 (s, 3H), 3.07-3.19 (m, 1H), 3.60 (tt, J=8.5, 5.2 Hz, 1H), 3.65-3.77 (m, 1H), 4.42-4.68 (m, 2H), 7.05 (dd, J=7.8, 5.0 Hz, 1H), 7.66-7.75 (m, 1H), 8.12 (dd, J=5.0, 1.6 Hz, 1H); ESI-MS m/z $[M+H]^+$ 376.2.

EXAMPLE 73: (S)—N-(1-((3-cyclopropylpyridin-2-yl)oxy)-2-methylpropan-2-yl)-2-(1-methylpyrrolidin-2-yl)acetamide

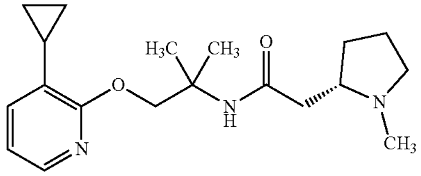 [SMILES: CN1CCC[C@H]1CC(=O)NC(C)(C)COc1ncccc1C1CC1]

A TFA salt of the title compound was prepared like EXAMPLE 71, using 1-((3-cyclopropylpyridin-2-yl)oxy)-2-methylpropan-2-amine (40 mg, 0.192 mmol) and (S)-2-(1-methylpyrrolidin-2-yl)acetic acid (25 mg, 0.175 mmol), and was obtained as a colorless oil (24 mg, 31%). $^1H$ NMR (400 MHz, $CD_3OD$) δ ppm 0.65-0.76 (m, 2H), 0.93-1.02 (m, 2H), 1.50 (d, J=2.3 Hz, 6H), 1.71-1.83 (m, 1H), 1.92 (ddd, J=13.5, 8.5, 5.2 Hz, 1H), 2.03-2.15 (m, 2H), 2.25-2.36 (m, 1H), 2.72 (dd, J=8.7, 5.2 Hz, 2H), 2.93 (s, 3H), 3.06-3.19 (m, 1H), 3.55-3.74 (m, 2H), 4.37-4.63 (m, 2H), 6.87 (dd, J=7.4, 5.0 Hz, 1H), 7.25-7.32 (m, 1H), 7.89 (dd, J=5.0, 1.8 Hz, 1H); ESI-MS m/z $[M+H]^+$ 332.3.

EXAMPLE 74: N-(1-(2-methoxybenzyl)cyclopropyl)-2-(1-methylpiperidin-2-yl)acetamide

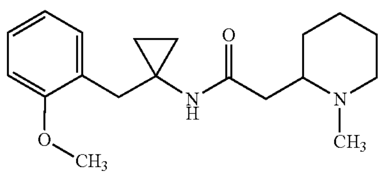 [SMILES: COc1ccccc1CC1(NC(=O)CC2CCCCN2C)CC1]

To a mixture of 1-(2-methoxybenzyl)cyclopropan-1-amine hydrochloride (42.7 mg, 0.200 mmol) and 2-(1-methylpiperidin-2-yl)acetic acid (31.4 mg, 0.200 mmol) in DMA (1 mL) was added DIPEA (105 μL, 0.600 mmol) and HATU (114 mg, 0.300 mmol). The reaction mixture was stirred at room temperature for 2 hours and then was filtered through a hydrophilic PTFE 0.45 m Millipore® filter, rinsing with methanol. The filtrate was purified by preparative HPLC (Phenomenex Gemini® C18, 5 μm, ID 30 mm×150 mm) using a gradient of 20-80% water/ACN in water (basic mode). The product-containing fractions were evaporated and lyophilized to give the title compound as an off-white solid (11.0 mg, 17%). $^1$H NMR (400 MHz, $CD_3OD$) δ ppm 0.63-0.74 (m, 2H), 0.76-0.90 (m, 2H), 1.13-1.41 (m, 2H), 1.43-1.77 (m, 4H), 1.99-2.09 (m, 1H), 2.11-2.27 (m, 4H), 2.35-2.48 (m, 2H), 2.76-2.86 (m, 1H), 2.96 (d, J=2.3 Hz, 2H), 3.81 (s, 3H), 6.88 (td, J=7.4, 1.1 Hz, 1H), 6.94 (d, J=7.9 Hz, 1H), 7.15-7.25 (m, 2H); ESI-MS m/z [M+H]$^+$ 317.10.

EXAMPLE 75: (R)—N-(2-(2-methoxyphenyl)propan-2-yl)-2-methyl-3-(pyrrolidin-1-yl)propanamide

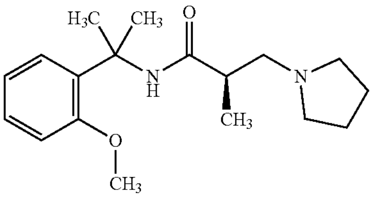 [SMILES: COc1ccccc1C(C)(C)NC(=O)[C@H](C)CN1CCCC1]

and

EXAMPLE 76: (S)—N-(2-(2-methoxyphenyl)propan-2-yl)-2-methyl-3-(pyrrolidin-1-yl)propanamide

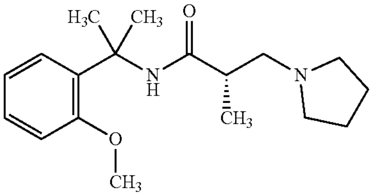 [SMILES: COc1ccccc1C(C)(C)NC(=O)[C@@H](C)CN1CCCC1]

To a mixture of 2-methyl-3-(pyrrolidin-1-yl)propanoic acid hydrochloride (0.800 g, 4.13 mmol), 2-(2-methoxyphenyl)propan-2-amine (0.683 g, 4.13 mmol) and DIPEA (2.89 mL, 16.5 mmol) in DMF (30 mL) was added HATU (3.14 g, 8.26 mmol). The reaction mixture was stirred at room temperature overnight and then was diluted with water (100 mL) and extracted with EtOAc (3×20 mL). The combined organic layers were washed with brine, dried over $MgSO_4$, filtered and concentrated under reduced pressure. The resulting residue was purified by preparative SFC (ChiralPak IC, 5 μm, ID 30 mm×250 mm) using a mobile phase of iPrOH (with 0.1% $NH_4OH$) in $CO_2$ the title enantiomers. The first eluting compound was arbitrarily assigned as the (R)-enantiomer and was obtained as a yellow solid (0.202 g, 16.1%) and the second eluting compound was arbitrarily assigned as the (S)-enantiomer and was obtained as a yellow solid (0.219 g, 17.4%). $^1$H NMR (400 MHz, DMSO-$d_6$) δ ppm 0.98 (d, J=6.9 Hz, 3H), 1.61 (s, 3H), 1.65 (s, 3H), 1.73 (br s, 4H), 2.30-2.42 (m, 1H), 2.50-2.78 (m, 6H), 6.83 (t, J=7.2 Hz, 1H), 6.95 (d, J=7.8 Hz, 1H), 7.17 (t, J=7.6 Hz, 1H), 7.32 (dd, J=7.8, 1.6 Hz, 1H), 8.10 (s, 1H); ESI-MS m/z [M+H]$^+$ 305.3.

EXAMPLE 77: N-(2-methyl-1-((3-methylpyridin-2-yl)oxy)propan-2-yl)-2-(tetrahydro-1H-pyrrolizin-7a(5H)-yl)acetamide

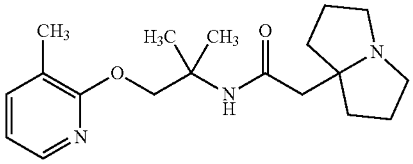 [SMILES: Cc1cccnc1OCC(C)(C)NC(=O)CC12CCCN1CCC2]

To a vial were added 2-methyl-1-((3-methylpyridin-2-yl)oxy)propan-2-amine (0.060 g, 0.333 mmol), 2-(tetrahydro-1H-pyrrolizin-7a(5H)-yl)acetic acid HCl (0.068 g, 0.333 mmol), HATU (0.127 g, 0.333 mmol) and DIPEA (0.174 mL, 0.999 mmol) in DMF (2 mL). The resulting yellow solution was stirred at room temperature overnight and then was purified by preparative HPLC (Phenomenex Gemini® C18, 5 μm, ID 30 mm×150 mm) using a gradient of 10-100% water/ACN in water (basic mode). $^1$H NMR (400 MHz, $CD_3OD$) δ ppm 1.45 (s, 6H), 1.60-1.92 (m, 8H), 2.22 (d, J=7.1 Hz, 5H), 2.53-2.65 (m, 2H), 2.97 (br d, J=10.7 Hz, 2H), 4.40 (s, 2H), 6.77-6.89 (m, 1H), 7.42-7.52 (m, 1H), 7.85-7.96 (m, 1H); ESI-MS m/z [M+H]$^+$ 332.5.

EXAMPLE 78: N-(1-((3-(difluoromethyl)pyridin-2-yl)oxy)-2-methylpropan-2-yl)-2-(tetrahydro-1H-pyrrolizin-7a(5H)-yl)acetamide

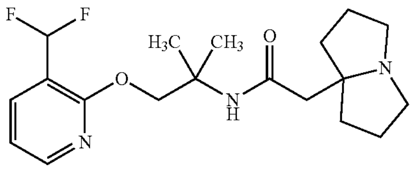 [SMILES: CC(C)(COc1ncccc1C(F)F)NC(=O)CC12CCCN1CCC2]

A TFA salt of the title compound was prepared like EXAMPLE 77, using 1-((3-(difluoromethyl)pyridin-2-yl)oxy)-2-methylpropan-2-amine (0.060 g, 0.277 mmol), 2-(tetrahydro-1H-pyrrolizin-7a(5H)-yl)acetic acid HCl (0.057 g, 0.277 mmol), HATU (0.106 g, 0.277 mmol) and DIPEA (0.145 mL, 0.832 mmol), and was obtained as a colorless semisolid (68.8 mg, 52%). $^1$H NMR (400 MHz, $CD_3OD$) δ ppm 1.45 (s, 6H), 1.85-2.02 (m, 6H), 2.03-2.15 (m, 2H), 2.68 (s, 2H), 3.08-3.19 (m, 2H), 3.56-3.67 (m, 2H), 4.57 (s, 2H), 6.73-6.96 (m, 1H), 7.01-7.12 (m, 1H), 7.81-7.97 (m, 1H), 8.17-8.29 (m, 1H); ESI-MS m/z [M+H]$^+$ 368.3.

EXAMPLE 79: N-(1-((2-methoxypyridin-3-yl)methyl)cyclopropyl)-2-(1-methylpiperidin-2-yl)acetamide

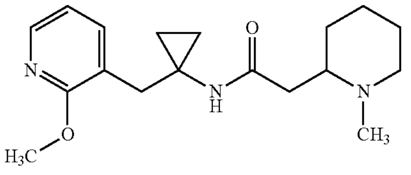 [SMILES: COc1ncccc1CC1(NC(=O)CC2CCCCN2C)CC1]

To a mixture of 1-((2-methoxypyridin-3-yl)methyl)cyclopropan-1-amine hydrochloride (91.0 mg, 0.511 mmol) and 2-(1-methylpiperidin-2-yl)acetic acid (80.0 mg, 0.511 mmol) in DMA (2.55 mL) were added DIPEA (268 μL, 1.53 mmol) and HATU (291 mg, 0.766 mmol). The reaction mixture was stirred at room temperature for 2 hours and then was filtered through a hydrophilic PTFE 0.45 m Millipore® filter, rinsing with methanol. The filtrate was purified by preparative HPLC (Phenomenex Gemini® C18, 5 μm, ID 30 mm×150 mm) using a gradient of 10-60% water/ACN in water (basic mode). The product-containing fractions were evaporated and lyophilized to give the title compound as a pale yellow solid (58.8 mg, 36%). $^1H$ NMR (400 MHz, $CD_3OD$) δ ppm 0.69-0.77 (m, 2H), 0.82-0.90 (m, 2H), 1.13-1.39 (m, 2H), 1.46-1.74 (m, 4H), 1.99-2.10 (m, 1H), 2.21 (s, 4H), 2.37-2.49 (m, 2H), 2.81 (br d, J=10.8 Hz, 1H), 2.92 (s, 2H), 3.93 (s, 3H), 6.91 (dd, J=7.2, 5.1 Hz, 1H), 7.57 (dd, J=7.2, 1.9 Hz, 1H), 8.01 (dd, J=5.1, 1.9 Hz, 1H); ESI-MS m/z $[M+H]^+$ 318.30.

EXAMPLE 80: (S)—N-(2-(2,3-dichlorophenyl)propan-2-yl)-2-(1-methylpyrrolidin-2-yl)acetamide

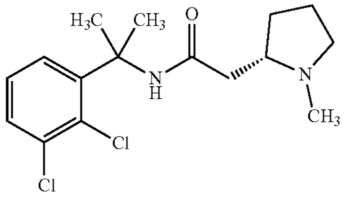 [SMILES: CN1CCC[C@H]1CC(=O)NC(C)(C)c1cccc(Cl)c1Cl]

STEP A: tert-butyl (S)-2-(2-((2-(2,3-dichlorophenyl)propan-2-yl)amino)-2-oxoethyl)pyrrolidine-1-carboxylate

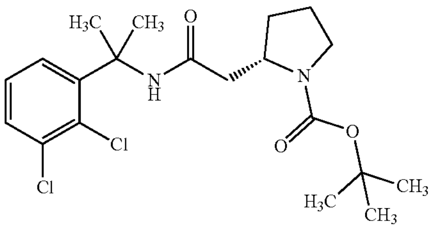 [SMILES: CC(C)(C)OC(=O)N1CCC[C@H]1CC(=O)NC(C)(C)c1cccc(Cl)c1Cl]

To a vial were added (S)-2-(1-(tert-butoxycarbonyl)pyrrolidin-2-yl)acetic acid (0.150 g, 0.654 mmol), 2-(2,3-dichlorophenyl)propan-2-amine (0.134 g, 0.654 mmol), HATU (249 mg, 0.654 mmol) and $Et_3N$ (91 μL, 0.654 mmol) in DMF (2 mL). The reaction mixture was stirred at room temperature for 5 hours and then was diluted with water (20 mL) and extracted with EtOAc. The organic layers were combined, dried over $Na_2SO_4$ and concentrated in vacuo to give the title compound (272 mg, assumed quantitative), which was used without further purification. ESI-MS m/z $[M+H]^+$ 415.3.

STEP B: (S)—N-(2-(2,3-dichlorophenyl)propan-2-yl)-2-(pyrrolidin-2-yl)acetamide

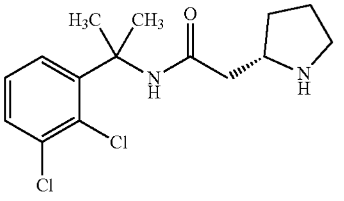 [SMILES: CC(C)(NC(=O)C[C@@H]1CCCN1)c1cccc(Cl)c1Cl]

To a vial containing a solution of tert-butyl (S)-2-(2-((2-(2,3-dichlorophenyl)propan-2-yl)amino)-2-oxoethyl)pyrrolidine-1-carboxylate (272 mg, 0.655 mmol) in dioxane (1.64 mL) was added 4 M HCl in dioxane (1.64 mL, 6.55 mmol). The reaction mixture was stirred at room temperature overnight and then was concentrated in vacuo. The solids were washed with MeOH to give an HCl salt of the title compound (230 mg, assumed quantitative), which was used without further purification. ESI-MS m/z $[M+H]^+$ 315.2.

STEP C: (S)—N-(2-(2,3-dichlorophenyl)propan-2-yl)-2-(1-methylpyrrolidin-2-yl)acetamide To a solution of (S)—N-(2-(2,3-dichlorophenyl)propan-2-yl)-2-(pyrrolidin-2-yl)acetamide HCl (230 mg, 0.655 mmol) and formaldehyde (73.0 μL, 0.980 mmol) in MeOH (4 mL) was added acetic acid (150 μL, 2.61 mmol). The reaction mixture was stirred at room temperature for 1 hour. Next, sodium triacetoxyborohydride (415 mg, 1.96 mmol) was added. The reaction mixture was stirred at room temperature overnight and then was filtered and purified by preparative HPLC (Phenomenex Gemini® C18, 5 μm, ID 30 mm×150 mm) using a gradient of 10-100% ACN in water (acid mode) to give a TFA salt of the title compound as a clear oil (4.0 mg, 1.4% over three steps). $^1H$ NMR (400 MHz, $CD_3OD$) δ ppm 1.79 (d, J=3.8 Hz, 6H), 1.89-2.01 (m, 1H), 2.03-2.19 (m, 1H), 2.27-2.38 (m, 1H), 2.77 (d, J=5.4 Hz, 2H), 2.87 (s, 3H), 3.09 (dt, J=11.5, 8.3 Hz, 1H), 3.50-3.68 (m, 2H), 7.28 (t, J=8.0 Hz, 1H), 7.45 (dd, J=8.0, 1.5 Hz, 1H), 7.54 (dd, J=8.0, 1.5 Hz, 1H); ESI-MS m/z $[M+H]^+$ 329.2.

EXAMPLE 81: (S)—N-(1-(3-methylbenzyl)cyclopropyl)-2-(1-methylpyrrolidin-2-yl)acetamide

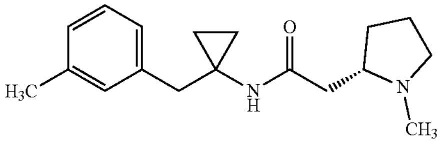 [SMILES: Cc1cccc(CC2(NC(=O)C[C@@H]3CCCN3C)CC2)c1]

The title compound was prepared like EXAMPLE 80, using 1-(3-methylbenzyl)cyclopropan-1-amine (141 mg, 0.872 mmol), (S)-2-(1-(tert-butoxycarbonyl)pyrrolidin-2-yl) acetic acid (200 mg, 0.872 mmol), $Et_3N$ (243 μL, 1.74 mmol) and HATU (332 mg, 0.872 mmol) in DMF. In STEP C, the reaction did not proceed to completion at room temperature, so the reaction mixture was heated at 45° C. for 1 hour prior to purification. The title compound was obtained as a white solid (11 mg, 4.4% over three steps). $^1H$ NMR (400 MHz, $CD_3OD$) δ ppm 0.69-0.86 (m, 3H), 1.37-1.49 (m, 1H), 1.62-1.77 (m, 2H), 1.90-2.10 (m, 2H), 2.18-2.29 (m, 4H), 2.33 (s, 3H), 2.36-2.52 (m, 2H), 2.82-2.93 (m, 2H), 3.00 (br t, J=8.4 Hz, 1H), 7.00-7.07 (m, 3H), 7.16 (t, J=7.0 Hz, 1H); ESI-MS m/z $[M+H]^+$ 287.3.

EXAMPLE 82: (S)—N-(2-(2,3-difluorophenyl)propan-2-yl)-2-(1-methylpyrrolidin-2-yl)acetamide

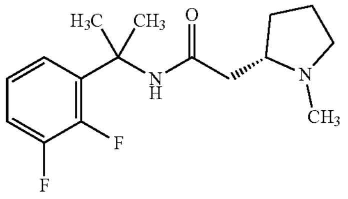 [SMILES: CN1CCC[C@H]1CC(=O)NC(C)(C)c1cccc(F)c1F]

A TFA salt of the title compound was prepared like EXAMPLE 80, using 2-(2,3-difluorophenyl)propan-2-amine (112 mg, 0.654 mmol), and was obtained as a clear oil (16 mg, 6.2% over three steps). $^1H$ NMR (400 MHz, $CD_3OD$) δ ppm 1.72-1.85 (m, 7H), 1.89-2.03 (m, 1H), 2.04-2.20 (m, 1H), 2.23-2.39 (m, 1H), 2.68-2.85 (m, 2H), 2.90 (s, 3H), 3.11 (dt, J=11.5, 8.3 Hz, 1H), 3.54-3.71 (m, 2H), 7.07-7.23 (m, 3H); ESI-MS m/z $[M+H]^+$ 297.3.

EXAMPLE 83: (S)—N-(2-(3-chloro-2-fluorophenyl)propan-2-yl)-2-(1-methylpyrrolidin-2-yl)acetamide

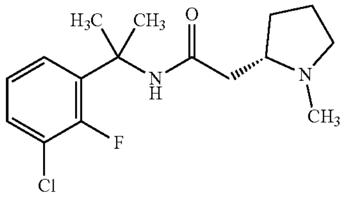 [SMILES: CN1CCC[C@H]1CC(=O)NC(C)(C)c1cccc(Cl)c1F]

A TFA salt of the title compound was prepared like EXAMPLE 80, using 2-(3-chloro-2-fluorophenyl)propan-2-amine (123 mg, 0.654 mmol), and was obtained as a clear oil (48 mg, 17% over three steps). $^1H$ NMR (400 MHz, $CD_3OD$) δ ppm 1.71-1.86 (m, 7H), 1.89-2.15 (m, 2H), 2.33 (dtd, J=13.3, 8.2, 8.2, 5.6 Hz, 1H), 2.67-2.86 (m, 2H), 2.89 (s, 3H), 3.10 (dt, J=11.5, 8.3 Hz, 1H), 3.54-3.71 (m, 2H), 7.12 (td, J=8.0, 1.1 Hz, 1H), 7.32-7.40 (m, 2H); ESI-MS m/z $[M+H]^+$ 313.2.

EXAMPLE 84: (R)—N-(1-((3-(difluoromethyl)pyridin-2-yl)oxy)-2-methylpropan-2-yl)-2-(1-methylpyrrolidin-2-yl)acetamide

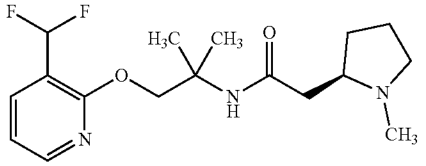 [SMILES: CN1CCC[C@@H]1CC(=O)NC(C)(C)COc1ncccc1C(F)F]

To a vial were added 1-((3-(difluoromethyl)pyridin-2-yl)oxy)-2-methylpropan-2-amine (0.070 g, 0.324 mmol), (R)-2-(1-methylpyrrolidin-2-yl)acetic acid (0.046 g, 0.324 mmol), HATU (0.123 g, 0.324 mmol) and DIPEA (0.169 mL, 0.971 mmol) in DMF (3 mL). The resulting yellow solution was stirred at room temperature overnight and then was purified by preparative HPLC (Phenomenex Gemini® C18, 5 μm, ID 30 mm×150 mm) using a gradient of 10-100% water/ACN in water (basic mode) to give the title compound as a colorless film (35.4 mg, 32%). $^1H$ NMR (400 MHz, $CD_3OD$) δ ppm 1.42 (s, 6H), 1.47-1.58 (m, 1H), 1.64-1.77 (m, 2H), 1.83-2.00 (m, 1H), 2.09-2.25 (m, 2H), 2.28 (s, 3H), 2.39-2.54 (m, 2H), 2.95-3.07 (m, 1H), 4.52 (d, J=0.8 Hz, 2H), 6.75-6.94 (m, 1H), 7.02-7.10 (m, 1H), 7.85-7.94 (m, 1H), 8.18-8.28 (m, 1H); ESI-MS m/z $[M+H]^+$ 342.2.

EXAMPLE 85: (S)—N-(1-((3-(difluoromethyl)pyridin-2-yl)oxy)-2-methylpropan-2-yl)-2-(1-methylpyrrolidin-2-yl acetamide

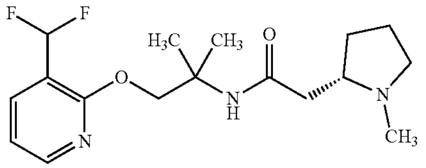 [SMILES: CN1CCC[C@H]1CC(=O)NC(C)(C)COc1ncccc1C(F)F]

To a vial were added 1-((3-(difluoromethyl)pyridin-2-yl)oxy)-2-methylpropan-2-amine (0.070 g, 0.324 mmol), (S)-2-(1-methylpyrrolidin-2-yl)acetic acid (0.046 g, 0.324 mmol), HATU (0.123 g, 0.324 mmol) and DIPEA (0.169 mL, 0.971 mmol) in DMF (3 mL). The resulting yellow solution was stirred at room temperature overnight and then was purified by preparative HPLC (Phenomenex Gemini® C18, 5 μm, ID 30 mm×150 mm) using a gradient of 10-50% ACN in water (acid mode) to give a TFA salt of the title compound as a colorless film (29.5 mg, 20%). $^1H$ NMR (400 MHz, $CD_3OD$) δ ppm 1.44 (d, J=0.6 Hz, 6H), 1.69-1.82 (m, 1H), 1.89-2.10 (m, 2H), 2.21-2.34 (m, 1H), 2.67-2.74 (m, 2H), 2.90 (s, 3H), 3.04-3.16 (m, 1H), 3.52-3.61 (m, 1H), 3.62-3.75 (m, 1H), 4.51 (s, 1H), 4.56-4.63 (m, 1H), 6.75-6.97 (m, 1H), 7.02-7.11 (m, 1H), 7.85-7.94 (m, 1H), 8.20-8.28 (m, 1H); ESI-MS m/z $[M+H]^+$ 342.2.

EXAMPLE 86: (S)—N-(2-(2-fluoro-3-methylphenyl)propan-2-yl)-2-(1-methylpyrrolidin-2-yl)acetamide

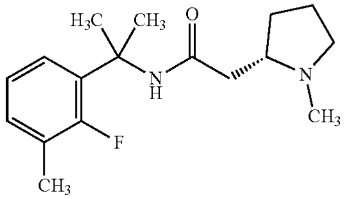 [SMILES: Cc1cccc(C(C)(C)NC(=O)C[C@@H]2CCCN2C)c1F]

To a vial were added (S)-2-(1-methylpyrrolidin-2-yl)acetic acid (30 mg, 0.21 mmol), 2-(2-fluoro-3-methylphenyl) propan-2-amine (35 mg, 0.21 mmol), HATU (80 mg, 0.21 mmol) and $Et_3N$ (29 μL, 0.21 mmol) in DMF (2 mL). The reaction mixture was stirred at room temperature for several hours and then was diluted with water and extracted with EtOAc. The organic layers were combined, dried over $Na_2SO_4$ and concentrated in vacuo. The residue was purified by preparative HPLC (Phenomenex Gemini® C18, 5 μm, ID 30 mm×150 mm) using a gradient of 10-100% ACN in water (acid mode) to give a TFA salt of the title compound as a clear oil (26 mg, 30%). $^1H$ NMR (400 MHz, $CD_3OD$) δ ppm 1.72 (d, J=2.5 Hz, 6H), 1.88-2.00 (m, 1H), 2.02-2.18 (m, 1H), 2.24 (d, J=2.5 Hz, 3H), 2.69-2.82 (m, 2H), 2.89 (s, 3H), 3.10 (dt, J=11.4, 8.4 Hz, 1H), 3.54-3.70 (m, 2H), 7.00 (t, J=7.6 Hz, 1H), 7.12 (t, J=6.9 Hz, 1H), 7.22 (td, J=7.9, 1.4 Hz, 1H); ESI-MS m/z $[M+H]^+$ 293.2.

EXAMPLE 87: (R)—N-(2-(2-fluoro-3-methylphenyl)propan-2-yl)-2-(1-methylpyrrolidin-2-yl)acetamide

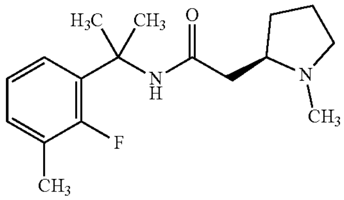 [SMILES: Cc1cccc(C(C)(C)NC(=O)C[C@H]2CCCN2C)c1F]

A TFA salt of the title compound was prepared like EXAMPLE 86, using (R)-2-(1-methylpyrrolidin-2-yl)acetic acid (30 mg, 0.21 mmol), and was obtained as a clear oil (26 mg, 30%). $^1H$ NMR (400 MHz, $CD_3OD$) δ ppm 1.72 (d, J=2.5 Hz, 6H), 2.03-2.18 (m, 1H), 2.24 (d, J=2.5 Hz, 3H), 2.67-2.83 (m, 2H), 2.89 (s, 3H), 3.10 (dt, J=11.5, 8.3 Hz, 1H), 3.53-3.70 (m, 2H), 6.97-7.03 (m, 1H), 7.11 (t, J=6.9 Hz, 1H), 7.22 (td, J=7.9, 1.3 Hz, 1H); ESI-MS m/z $[M+H]^+$ 293.2.

EXAMPLE 88: (S)—N-(2-(2-chloro-3-methylphenyl)propan-2-yl)-2-(1-methylpyrrolidin-2-yl)acetamide

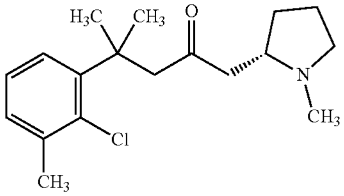 [SMILES: Cc1cccc(C(C)(C)CC(=O)C[C@@H]2CCCN2C)c1Cl]

A TFA salt of the title compound was prepared like EXAMPLE 86, using 2-(2-chloro-3-methylphenyl)propan-2-amine (38.5 mg, 0.21 mmol), and was obtained as a clear oil (23 mg, 26%). $^1H$ NMR (400 MHz, $CD_3OD$) δ ppm 1.26 (d, J=7.0 Hz, 3H), 1.81 (s, 6H), 1.91-2.17 (m, 4H), 2.38 (s, 3H), 2.88-3.15 (m, 4H), 3.34-3.41 (m, 1H), 3.57 (br s, 2H), 7.16-7.24 (m, 2H), 7.43 (dd, J=7.5, 2.1 Hz, 1H); ESI-MS m/z $[M+H]^+$ 309.2.

EXAMPLE 89: (S)—N-(2-(3-fluoro-2-methylphenyl)propan-2-yl)-2-(1-methylpyrrolidin-2-yl)acetamide

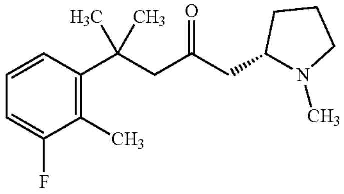 [SMILES: Cc1c(F)cccc1C(C)(C)CC(=O)C[C@@H]1CCCN1C]

A TFA salt of the title compound was prepared like EXAMPLE 86, using 2-(3-fluoro-2-methylphenyl)propan-2-amine (35 mg, 0.21 mmol), and was obtained as a clear oil (30 mg, 35%). $^1H$ NMR (400 MHz, $CD_3OD$) δ ppm 1.71-1.84 (m, 6H), 1.94-2.20 (m, 2H), 2.29-2.44 (m, 4H), 2.69-2.85 (m, 2H), 2.89 (s, 3H), 3.10 (dt, J=11.5, 8.2 Hz, 1H), 3.53-3.72 (m, 2H), 6.93 (t, J=8.7 Hz, 1H), 7.15 (td, J=7.9, 6.3 Hz, 1H), 7.21-7.26 (m, 1H); ESI-MS m/z $[M+H]^+$ 293.2.

EXAMPLE 90: (R)—N-(2-(3-fluoro-2-methylphenyl)propan-2-yl)-2-(1-methylpyrrolidin-2-yl)acetamide

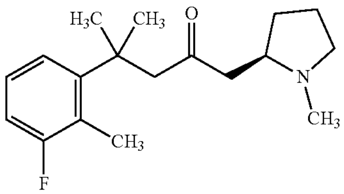 [SMILES: Cc1c(F)cccc1C(C)(C)CC(=O)C[C@H]1CCCN1C]

A TFA salt of the title compound was prepared like EXAMPLE 86, using (R)-2-(1-methylpyrrolidin-2-yl)acetic acid (30 mg, 0.21 mmol) and 2-(3-fluoro-2-methylphenyl) propan-2-amine (35 mg, 0.21 mmol), and was obtained as a clear oil (31 mg, 36%). $^1$H NMR (400 MHz, $CD_3OD$) δ ppm 1.71-1.84 (m, 6H), 1.94-2.20 (m, 2H), 2.29-2.44 (m, 4H), 2.69-2.86 (m, 2H), 2.89 (s, 3H), 3.10 (dt, J=11.4, 8.3 Hz, 1H), 3.53-3.71 (m, 2H), 6.93 (t, J=9.0 Hz, 1H), 7.15 (td, J=8.1, 6.1 Hz, 1H), 7.21-7.26 (m, 1H), ESI-MS m/z $[M+H]^+$ 293.2.

EXAMPLE 91: (R)—N-(2-(2-chloro-3-methylphenyl)propan-2-yl)-2-(1-methylpyrrolidin-2-yl)acetamide

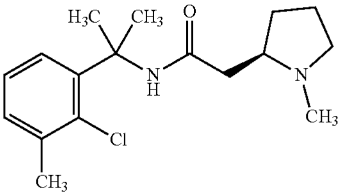 [SMILES: Cc1cccc(C(C)(C)NC(=O)C[C@H]2CCCN2C)c1Cl]

A TFA salt of the title compound was prepared like EXAMPLE 86, using (R)-2-(1-methylpyrrolidin-2-yl)acetic acid (150 mg, 1.05 mmol), 2-(2-chloro-3-methylphenyl) propan-2-amine (192 mg, 1.05 mmol), HATU (398 mg, 1.05 mmol) and $Et_3N$ (146 μL, 1.05 mmol) in DMF (2 mL), and was obtained as a clear oil (19 mg, 4.3%). $^1$H NMR (400 MHz, $CD_3OD$) δ ppm 1.79 (d, J=2.9 Hz, 6H), 2.03-2.14 (m, 1H), 2.28-2.39 (m, 4H), 2.68-2.83 (m, 2H), 2.86 (s, 3H), 3.09 (dt, J=11.5, 8.3 Hz, 1H), 3.52-3.69 (m, 2H), 7.15-7.23 (m, 2H), 7.41 (dd, J=7.4, 2.1 Hz, 1H); ESI-MS m/z $[M+H]^+$ 309.2.

EXAMPLE 92: (S)—N-(2-(2,3-dimethylphenyl)propan-2-yl)-2-(1-methylpyrrolidin-2-yl)acetamide

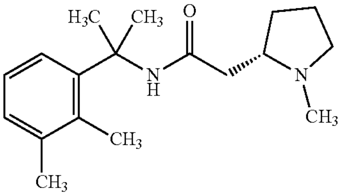 [SMILES: Cc1cccc(C(C)(C)NC(=O)C[C@@H]2CCCN2C)c1C]

A TFA salt of the title compound was prepared like EXAMPLE 86, using (S)-2-(1-methylpyrrolidin-2-yl)acetic acid (30 mg, 0.21 mmol), 2-(2,3-dimethylphenyl)propan-2-amine (34.2 mg, 0.21 mmol), HATU (80 mg, 0.21 mmol) and $Et_3N$ (58 μL, 0.42 mmol) in DMF (2 mL), and was obtained as a clear oil (40 mg, 47%). $^1$H NMR (400 MHz, $CD_3OD$) δ ppm 1.75 (d, J=7.2 Hz, 6H), 1.91-2.16 (m, 2H), 2.25-2.40 (m, 6H), 2.67-2.82 (m, 2H), 2.88 (s, 3H), 3.09 (dt, J=11.5, 8.3 Hz, 1H), 3.52-3.70 (m, 2H), 7.01-7.08 (m, 2H), 7.28 (d, J=6.5 Hz, 1H); ESI-MS m/z $[M+H]^+$ 289.4.

EXAMPLE 93: (S)—N-(2-(2-chloro-3-fluorophenyl)propan-2-yl)-2-(1-methylpyrrolidin-2-yl)acetamide

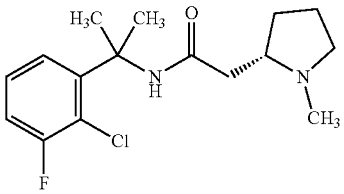 [SMILES: CN1CCC[C@H]1CC(=O)NC(C)(C)c1cccc(F)c1Cl]

A TFA salt of the title compound was prepared like EXAMPLE 86, using 2-(2-chloro-3-fluorophenyl)propan-2-amine (39.3 mg, 0.21 mmol), and was obtained as a clear oil (33 mg, 37%). $^1$H NMR (400 MHz, $CD_3OD$) δ ppm 1.78 (d, J=4.8 Hz, 6H), 1.90-2.15 (m, 2H), 2.27-2.38 (m, 1H), 2.72-2.90 (m, 5H), 3.10 (dt, J=11.5, 8.3 Hz, 1H), 3.52-3.70 (m, 2H), 7.13 (t, J=8.3 Hz, 1H), 7.27-7.41 (m, 2H), 8.73 (br s, 1H); ESI-MS m/z $[M+H]^+$ 313.3.

EXAMPLE 94: (R)—N-(2-(2-chloro-3-fluorophenyl)propan-2-yl)-2-(1-methylpyrrolidin-2-yl)acetamide

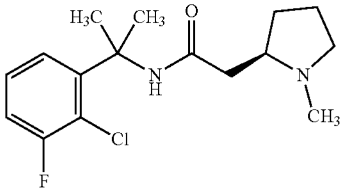 [SMILES: CN1CCC[C@@H]1CC(=O)NC(C)(C)c1cccc(F)c1Cl]

A TFA salt of the title compound was prepared like EXAMPLE 86, using (R)-2-(1-methylpyrrolidin-2-yl)acetic acid (30 mg, 0.21 mmol) and 2-(2-chloro-3-fluorophenyl) propan-2-amine (39.3 mg, 0.21 mmol), and was obtained as a clear oil (31 mg, 35%). $^1$H NMR (400 MHz, $CD_3OD$) δ ppm 1.78 (d, J=4.8 Hz, 6H), 1.91-2.15 (m, 2H), 2.27-2.38 (m, 1H), 2.72-2.90 (m, 5H), 3.10 (dt, J=11.5, 8.3 Hz, 1H), 3.52-3.70 (m, 2H), 7.13 (t, J=8.4 Hz, 1H), 7.27-7.40 (m, 2H), 8.73 (br s, 1H); ESI-MS m/z $[M+H]^+$ 313.3.

EXAMPLE 95: N—((S)-1-(4-fluoro-2-methoxyphenyl)ethyl)-2-((S)-1-methylpyrrolidin-2-yl)acetamide

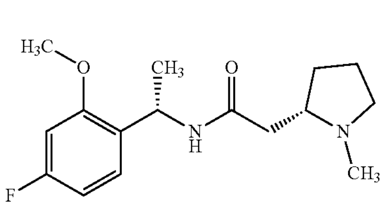 [SMILES: COc1cc(F)ccc1[C@H](C)NC(=O)C[C@@H]1CCCN1C]

A TFA salt of the title compound was prepared like EXAMPLE 86, using (S)-2-(1-methylpyrrolidin-2-yl)acetic acid (35 mg, 0.244 mmol), (S)-1-(4-fluoro-2-methoxyphenyl)ethan-1-amine (41.4 mg, 0.244 mmol), HATU (93 mg, 0.244 mmol) and $Et_3N$ (34.1 μL, 0.244 mmol) in DMF (2 mL), and was obtained as a clear oil (15 mg, 15%). $^1$H NMR (400 MHz, $CD_3OD$) δ ppm 1.45 (d, J=7.0 Hz, 3H), 1.71-1.88 (m, 1H), 1.91-2.05 (m, 1H), 2.05-2.19 (m, 1H), 2.28-2.41 (m, 1H), 2.69-2.87 (m, 2H), 2.94 (s, 3H), 3.14 (dt, J=11.5, 8.2 Hz, 1H), 3.59-3.76 (m, 2H), 3.86 (s, 3H), 4.98 (q, J=7.0 Hz, 1H), 7.03-7.12 (m, 3H); ESI-MS m/z $[M+H]^+$ 295.3.

EXAMPLE 96: (R)—N-(2-(2,3-dichlorophenyl)propan-2-yl)-2-(1-methylpyrrolidin-2-yl)acetamide

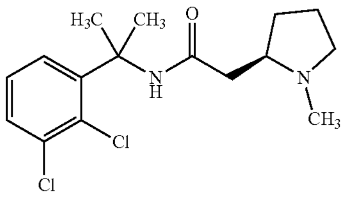 [SMILES: CN1CCC[C@@H]1CC(=O)NC(C)(C)c1cccc(Cl)c1Cl]

A TFA salt of the title compound was prepared like EXAMPLE 86, using (R)-2-(1-methylpyrrolidin-2-yl)acetic acid (35 mg, 0.244 mmol), 2-(2,3-dichlorophenyl)propan-2-amine (49.9 mg, 0.244 mmol), HATU (93 mg, 0.244 mmol) and $Et_3N$ (34.1 μL, 0.244 mmol) in DMF (2 mL), and was obtained as a clear oil (17 mg, 16%). $^1H$ NMR (400 MHz, $CD_3OD$) δ ppm 1.79 (d, J=3.9 Hz, 6H), 1.90-2.15 (m, 2H), 2.33 (dtd, J=13.3, 8.2, 5.4 Hz, 1H), 2.71-2.89 (m, 5H), 3.09 (dt, J=11.5, 8.3 Hz, 1H), 3.52-3.69 (m, 2H), 7.28 (t, J=8.0 Hz, 1H), 7.45 (dd, J=8.0, 1.5 Hz, 1H), 7.53 (dd, J=8.0, 1.5 Hz, 1H); ESI-MS m/z $[M+H]^+$ 329.3.

EXAMPLE 97: 2-(3,3-difluoro-1-methylpyrrolidin-2-yl)-N-(2-(isoquinolin-1-yl)propan-2-yl)acetamide

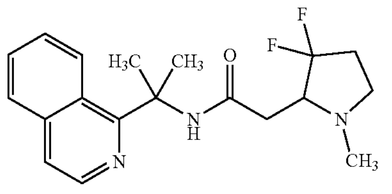 [SMILES: CN1CCC(F)(F)C1CC(=O)NC(C)(C)c1nccc2ccccc12]

STEP A: tert-butyl 3,3-difluoro-2-(2-((2-(isoquinolin-1-yl)propan-2-yl)amino)-2-oxoethyl)pyrrolidine-1-carboxylate

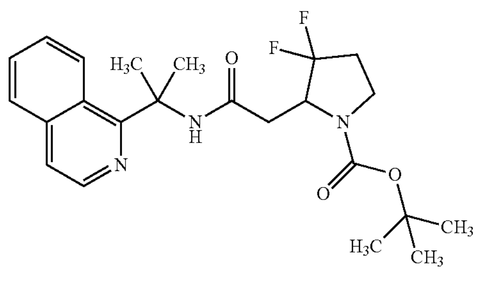 [SMILES: CC(C)(C)OC(=O)N1CCC(F)(F)C1CC(=O)NC(C)(C)c1nccc2ccccc12]

To a vial were added 2-(1-(tert-butoxycarbonyl)-3,3-difluoropyrrolidin-2-yl)acetic acid (150 mg, 0.565 mmol), 2-(isoquinolin-1-yl)propan-2-amine (105 mg, 0.565 mmol), HATU (215 mg, 0.565 mmol) and $Et_3N$ (158 μL, 1.131 mmol) in DMF (2 mL). The reaction mixture was stirred at room temperature for several hours and then was extracted with EtOAc. The organic layers were combined, dried over $Na_2SO_4$, filtered, and concentrated in vacuo to give the title compound (245 mg, assumed quantitative), which was used without further purification.

STEP B: 2-(3,3-difluoropyrrolidin-2-yl)-N-(2-(isoquinolin-1-yl)propan-2-yl)acetamide

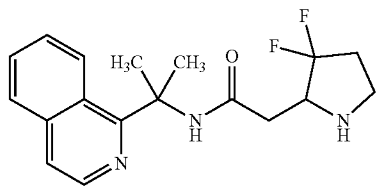 [SMILES: CC(C)(NC(=O)CC1NCCC1(F)F)c1nccc2ccccc12]

To a vial containing tert-butyl 3,3-difluoro-2-(2-((2-(isoquinolin-1-yl)propan-2-yl)amino)-2-oxoethyl)pyrrolidine-1-carboxylate (245 mg, 0.565 mmol) in dioxane (1.41 mL) was added 4 M HCl in dioxane (1.41 mL, 5.65 mmol). The reaction mixture was stirred at room temperature overnight and then was concentrated in vacuo to give an HCl salt of the title compound (209 mg, assumed quantitative), which was used without further purification.

STEP C: 2-(3,3-difluoro-1-methylpyrrolidin-2-yl)-N-(2-(isoquinolin-1-yl)propan-2-yl)acetamide To a solution of 2-(3,3-difluoropyrrolidin-2-yl)-N-(2-(isoquinolin-1-yl)propan-2-yl)acetamide (209 mg, 0.565 mmol) and formaldehyde (63.0 μL, 0.846 mmol) in MeOH (3.76 mL) was added acetic acid (129 μL, 2.256 mmol). The reaction mixture was stirred at room temperature for 1 hour and then sodium triacetoxyborohydride (359 mg, 1.69 mmol) was added. The reaction mixture was stirred at room temperature overnight and then was filtered and purified by preparative HPLC (Phenomenex Gemini® C18, 5 μm, ID 30 mm×150 mm) using a gradient of 10-100% water/ACN in water (basic mode) to give the title compound as a clear oil (5 mg, 2.5% over three steps). $^1H$ NMR (400 MHz, $CD_3OD$) δ ppm 2.04 (d, J=1.5 Hz, 6H), 2.31-2.50 (m, 1H), 2.51-2.67 (m, 1H), 2.75-2.83 (m, 3H), 2.88-3.03 (m, 2H), 3.35-3.50 (m, 1H), 3.73 (ddd, J=11.8, 8.5, 3.5 Hz, 1H), 3.91 (tt, J=12.3, 6.0 Hz, 1H), 7.91-7.97 (m, 1H), 8.06-8.12 (m, 1H), 8.21-8.27 (m, 2H), 8.42 (d, J=6.40 Hz, 1H), 8.91-8.97 (m, 1H); ESI-MS m/z $[M+H]^+$ 348.4.

EXAMPLE 98: 2-(3,3-difluoro-1-methylpyrrolidin-2-yl)-N-(2-(5-methylisoquinolin-1-yl)propan-2-yl)acetamide

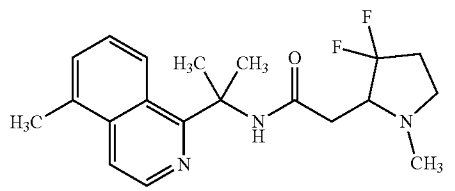 [SMILES: Cc1cccc2c(C(C)(C)NC(=O)CC3N(C)CCC3(F)F)nccc12]

The title compound was prepared like EXAMPLE 97, using 2-(5-methylisoquinolin-1-yl)propan-2-amine (113 mg, 0.565 mmol), and was obtained as a pale beige solid (14 mg, 6.9% over three steps). $^1$H NMR (400 MHz, $CD_3OD$) δ ppm 1.89 (d, J=3.1 Hz, 6H), 2.14-2.37 (m, 7H), 2.45-2.59 (m, 1H), 2.66-2.79 (m, 4H), 3.00-3.10 (m, 1H), 7.44-7.56 (m, 2H), 7.81 (dd, J=5.9, 0.9 Hz, 1H), 8.41 (d, J=6.0 Hz, 1H), 8.54 (d, J=8.7 Hz, 1H); ESI-MS m/z $[M+H]^+$ 362.4.

EXAMPLE 99: 2-(3,3-difluoro-1-methylpyrrolidin-2-yl)-N-(2-(furo[3,2-c]pyridin-4-yl)propan-2-yl)acetamide

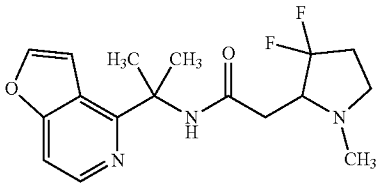 [SMILES: CN1CCC(F)(F)C1CC(=O)NC(C)(C)c1nccc2occc12]

The title compound was prepared like EXAMPLE 97, using 2-(furo[3,2-c]pyridin-4-yl)propan-2-amine (100 mg, 0.565 mmol), and was obtained as an orange solid (8 mg, 4.2% over three steps). $^1$H NMR (400 MHz, $CD_3OD$) δ ppm 1.78 (d, J=3.9 Hz, 6H), 2.19-2.44 (m, 7H), 2.54-2.66 (m, 1H), 2.83 (td, J=11.5, 5.6 Hz, 1H), 3.03-3.16 (m, 1H), 7.16 (dd, J=2.4, 1.0 Hz, 1H), 7.46 (dd, J=5.8, 1.0 Hz, 1H), 7.84 (d, J=2.3 Hz, 1H), 8.34 (d, J=5.8 Hz, 1H); ESI-MS m/z $[M+H]^+$ 338.3.

EXAMPLE 100: 2-(3,3-difluoropyrrolidin-2-yl)-N-(2-(isoquinolin-1-yl)propan-2-yl)acetamide

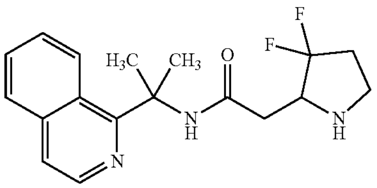 [SMILES: CC(C)(NC(=O)CC1NCCC1(F)F)c1nccc2ccccc12]

STEP A: tert-butyl 3,3-difluoro-2-(2-((2-(isoquinolin-1-yl)propan-2-yl)amino)-2-oxoethyl)pyrrolidine-1-carboxylate

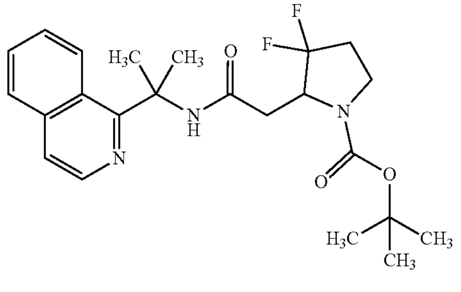 [SMILES: CC(C)(C)OC(=O)N1CCC(F)(F)C1CC(=O)NC(C)(C)c1nccc2ccccc12]

To a 20 mL vial were added 2-(1-(tert-butoxycarbonyl)-3,3-difluoropyrrolidin-2-yl)acetic acid (75 mg, 0.283 mmol), 2-(isoquinolin-1-yl)propan-2-amine (52.7 mg, 0.283 mmol), HATU (108 mg, 0.283 mmol) and $Et_3N$ (79 μL, 0.565 mmol) in DMF (2 mL). The reaction mixture was stirred at room temperature for several hours and then was extracted with EtOAc. The organic layers were combined, dried over $NaSO_4$ and concentrated in vacuo to give the title compound (123 mg, 0.284 mmol) which was used without further purification. ESI-MS m/z $[M+H]^+$ 434.5.

STEP B: 2-(3,3-difluoropyrrolidin-2-yl)-N-(2-(isoquinolin-1-yl)propan-2-yl)acetamide To a 20 mL vial charged with tert-butyl 3,3-difluoro-2-(2-((2-(isoquinolin-1-yl)propan-2-yl)amino)-2-oxoethyl) pyrrolidine-1-carboxylate (123 mg, 0.284 mmol) in dioxane (709 μL) was added 4 M HCl in dioxane (709 μL, 2.84 mmol). The reaction mixture was stirred at room temperature overnight and then was washed with MeOH and purified by preparative HPLC (Phenomenex Gemini® C18, 5 μm, ID 30 mm×150 mm) using a gradient of 10-100% water/ACN in water (basic mode) to give the title compound as an orange oil (3 mg, 3.2% over two steps). $^1$H NMR (400 MHz, $CD_3OD$) δ ppm 1.87-1.95 (m, 6H), 2.04-2.28 (m, 2H), 2.36 (ddd, J=15.4, 8.8, 1.1 Hz, 1H), 2.54 (dd, J=15.4, 4.6 Hz, 1H), 2.89-2.97 (m, 1H), 3.01-3.18 (m, 1H), 3.26-3.32 (m, 1H), 7.57-7.71 (m, 3H), 7.91 (d, J=8.2 Hz, 1H), 8.37 (d, J=5.6 Hz, 1H), 8.68 (dd, J=8.7, 0.8 Hz, 1H); ESI-MS m/z $[M+H]^+$ 334.3.

EXAMPLE 101: 2-(3,3-difluoropyrrolidin-2-yl)-N-(2-(5-methylisoquinolin-1-yl)propan-2-yl)acetamide

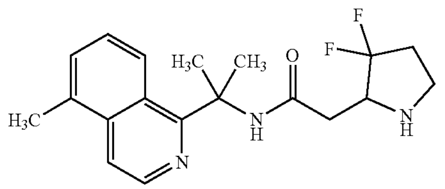 [SMILES: Cc1cccc2c(C(C)(C)NC(=O)CC3NCCC3(F)F)nccc12]

The title compound was prepared like EXAMPLE 100, using 2-(5-methylisoquinolin-1-yl)propan-2-amine (56.6 mg, 0.283 mmol), and was obtained as a white film (4 mg, 4.2% over two steps). $^1$H NMR (400 MHz, $CD_3OD$) δ ppm 2.03-2.09 (m, 6H), 2.41-2.62 (m, 2H), 2.77-2.87 (m, 4H), 2.98 (dd, J=17.1, 4.3 Hz, 1H), 3.35-3.49 (m, 2H), 3.92-4.02 (m, 1H), 7.88 (dd, J=8.9, 7.2 Hz, 1H), 8.01 (d, J=7.2 Hz, 1H), 8.46-8.51 (m, 2H), 8.86 (d, J=8.7 Hz, 1H); ESI-MS m/z $[M+H]^+$ 348.4.

EXAMPLE 102: (S)—N-(2-methyl-1-((4-methylpyridin-2-yl)oxy)propan-2-yl)-2-(1-methylpyrrolidin-2-yl)acetamide

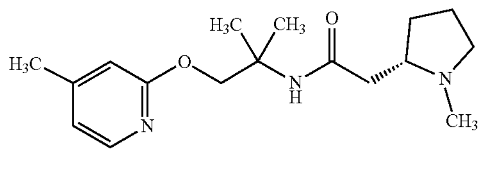 [SMILES: Cc1ccnc(OCC(C)(C)NC(=O)C[C@@H]2CCCN2C)c1]

To a solution of (S)—N-(1-hydroxy-2-methylpropan-2-yl)-2-(1-methylpyrrolidin-2-yl)acetamide (25 mg, 0.117 mmol) in DMF (1.17 mL) was added NaH (60 wt %, 7.0 mg, 0.175 mmol). The reaction mixture was stirred at room temperature for 5 minutes. Next, 2-fluoro-4-methylpyridine (14.3 mg, 0.128 mmol) was added. The reaction mixture was stirred at room temperature for 16 hours and then was quenched with aqueous 1 N HCl (0.15 mL) and purified by preparative HPLC (Phenomenex Gemini® C18, 5 μm, ID 30 mm×150 mm) using a gradient of 10-70% water/ACN in water (basic mode). The title compound was obtained as a colorless oil (5.8 mg, 16%). $^1$H NMR (400 MHz, $CD_3OD$) δ ppm 1.43 (d, J=3.0 Hz, 6H), 1.50-1.65 (m, 1H), 1.70-1.87 (m, 2H), 1.91-2.01 (m, 1H), 2.11-2.28 (m, 2H), 2.31 (s, 3H), 2.33 (s, 3H), 2.38-2.45 (m, 1H), 2.51 (qd, J=8.0, 4.5 Hz, 1H), 3.02 (ddd, J=9.6, 7.3, 2.8 Hz, 1H), 4.27-4.42 (m, 2H), 6.66 (dt, J=1.4, 0.7 Hz, 1H), 6.77-6.87 (m, 1H), 7.96 (d, J=5.3 Hz, 1H); ESI-MS m/z $[M+H]^+$ 306.2.

EXAMPLE 103: (S)—N-(2-methyl-1-((5-methylpyridin-2-yl)oxy)propan-2-yl)-2-(1-methylpyrrolidin-2-yl)acetamide

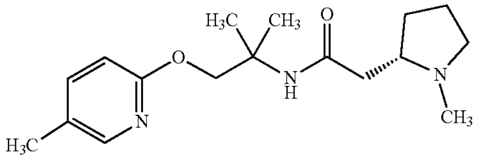 [SMILES: Cc1ccc(OCC(C)(C)NC(=O)C[C@@H]2CCCN2C)nc1]

The title compound was prepared like EXAMPLE 102, using (S)—N-(1-hydroxy-2-methylpropan-2-yl)-2-(1-methylpyrrolidin-2-yl)acetamide (25 mg, 0.117 mmol) and 2-fluoro-5-methylpyridine (14 mg, 0.128 mmol), and was obtained as a give a colorless oil (6.7 mg, 19%). $^1$H NMR (400 MHz, $CD_3OD$) δ ppm 1.32 (d, J=3.01 Hz, 6H), 1.39-1.52 (m, 1H), 1.60-1.73 (m, 2H), 1.80-1.93 (m, 1H), 2.07-2.14 (m, 2H), 2.15 (s, 3H), 2.22 (s, 3H), 2.27-2.35 (m, 1H), 2.43 (br dd, J=6.3, 1.9 Hz, 1H), 2.88-2.98 (m, 1H), 4.17-4.29 (m, 2H), 6.61 (d, J=8.3 Hz, 1H), 7.38-7.47 (m, 1H), 7.81 (dt, J=2.5, 0.8 Hz, 1H); ESI-MS m/z $[M+H]^+$ 306.2.

EXAMPLE 104: (S)—N-(2-methyl-1-((6-methylpyridin-2-yl)oxy)propan-2-yl)-2-(1-methylpyrrolidin-2-yl)acetamide

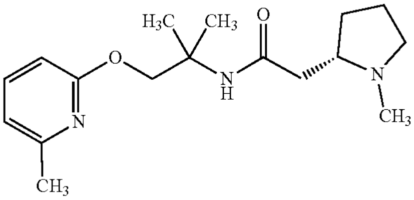 [SMILES: Cc1cccc(OCC(C)(C)NC(=O)C[C@@H]2CCCN2C)n1]

The title compound was prepared like EXAMPLE 102, using (S)—N-(1-hydroxy-2-methylpropan-2-yl)-2-(1-methylpyrrolidin-2-yl)acetamide (25 mg, 0.117 mmol) and 2-fluoro-6-methylpyridine (14 mg, 0.128 mmol), and was obtained as a colorless oil (10 mg, 28%). $^1$H NMR (400 MHz, $CD_3OD$) δ ppm 1.32 (d, J=2.1 Hz, 6H), 1.41-1.51 (m, 1H), 1.56-1.72 (m, 2H), 1.81-1.95 (m, 1H), 2.06-2.21 (m, 2H), 2.24 (s, 3H), 2.29-2.35 (m, 4H), 2.47 (br dd, J=10.5, 5.1 Hz, 1H), 2.90-3.00 (m, 1H), 4.25 (d, J=1.4 Hz, 2H), 6.43-6.53 (m, 1H), 6.70 (d, J=7.1 Hz, 1H), 7.45 (dd, J=8.2, 7.3 Hz, 1H); ESI-MS m/z $[M+H]^+$ 306.2.

EXAMPLE 105: (S)—N-(1-((4-chloro-5-fluoropyridin-2-yl)oxy)-2-methylpropan-2-yl)-2-(1-methylpyrrolidin-2-yl)acetamide

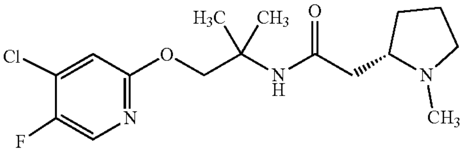 [SMILES: CN1CCC[C@H]1CC(=O)NC(C)(C)COc1cc(Cl)c(F)cn1]

The title compound was prepared like EXAMPLE 102, using (S)—N-(1-hydroxy-2-methylpropan-2-yl)-2-(1-methylpyrrolidin-2-yl)acetamide (25 mg, 0.117 mmol) and 4-chloro-2,5-difluoropyridine (19 mg, 0.128 mmol), and was obtained as a white solid (8 mg, 20%). $^1$H NMR (400 MHz, $CD_3OD$) δ ppm 1.42 (d, J=2.4 Hz, 6H), 1.52-1.65 (m, 1H), 1.72-1.87 (m, 2H), 1.92-2.05 (m, 1H), 2.18-2.33 (m, 2H), 2.36 (s, 3H), 2.41-2.49 (m, 1H), 2.58 (br d, J=2.4 Hz, 1H), 3.08 (br t, J=6.2 Hz, 1H), 4.35-4.47 (m, 2H), 6.98 (d, J=4.9 Hz, 1H), 8.10 (d, J=1.1 Hz, 1H); ESI-MS m/z $[M+H]^+$ 345.10.

EXAMPLE 106: (R)—N-(2-methyl-1-((3-(trifluoromethoxy)pyridin-2-yl)oxy)propan-2-yl)-2-(1-methylpyrrolidin-2-yl)acetamide

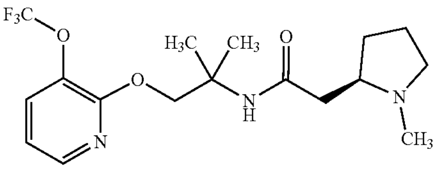 [SMILES: CN1CCC[C@@H]1CC(=O)NC(C)(C)COc1ncccc1OC(F)(F)F]

To a solution of (R)-2-(1-methylpyrrolidin-2-yl)acetic acid (25 mg, 0.175 mmol) and HATU (66.4 mg, 0.175 mmol) in DMF (1.16 mL) was added DIPEA (122 μL, 0.698 mmol). The reaction mixture was stirred at room temperature for 5 minutes. Next, 2-methyl-1-((3-(trifluoromethoxy)pyridin-2-yl)oxy)propan-2-amine (48.1 mg, 0.192 mmol) was added. The reaction mixture was stirred at room temperature for 16 h and then was purified by preparative HPLC (Phenomenex Gemini® C18, 5 μm, ID 30 mm×150 mm) using a gradient of 10-100% water/ACN in water (basic mode) to give the title compound as a colorless oil (18 mg, 28%). $^1$H NMR (400 MHz, $CD_3OD$) δ ppm 1.44 (d, J=1.2 Hz, 6H), 1.52-1.62 (m, 1H), 1.68-1.85 (m, 2H), 1.91-2.03 (m, 1H), 2.14-2.28 (m, 2H), 2.32 (s, 3H), 2.40-2.46 (m, 1H), 2.47-2.56 (m, 1H), 3.04 (ddd, J=9.7, 7.2, 2.9 Hz, 1H), 4.54 (s, 2H), 7.04 (dd, J=7.9, 5.0 Hz, 1H), 7.65-7.70 (m, 1H), 8.11 (dd, J=5.0, 1.6 Hz, 1H); ESI-MS m/z $[M+H]^+$ 376.20.

EXAMPLE 107: (R)—N-(1-((3-ethoxypyridin-2-yl)oxy)-2-methylpropan-2-yl)-2-(1-methylpyrrolidin-2-yl)acetamide

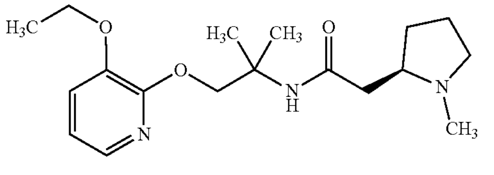 [SMILES: CCOc1cccnc1OCC(C)(C)NC(=O)C[C@H]1CCCN1C]

The title compound was prepared like EXAMPLE 106, using (R)-2-(1-methylpyrrolidin-2-yl)acetic acid (25 mg, 0.175 mmol) and 2-methyl-1-((3-(trifluoromethoxy)pyridin-2-yl)oxy)propan-2-amine (40 mg, 0.192 mmol), and was obtained as a colorless oil (24 mg, 41%). $^1$H NMR (400 MHz, $CD_3OD$) δ ppm 1.42 (t, J=7.0 Hz, 3H), 1.45 (d, J=3.6 Hz, 6H), 1.51-1.63 (m, 1H), 1.66-1.84 (m, 2H), 1.89-2.04 (m, 1H), 2.14-2.27 (m, 2H), 2.31 (s, 3H), 2.38-2.45 (m, 1H), 2.47-2.55 (m, 1H), 3.01 (ddd, J=9.6, 7.5, 2.6 Hz, 1H), 4.09 (q, J=7.0 Hz, 2H), 4.36-4.50 (m, 2H), 6.89 (dd, J=7.8, 5.0 Hz, 1H), 7.23 (dd, J=7.8, 1.6 Hz, 1H), 7.65 (dd, J=5.1, 1.6 Hz, 1H); ESI-MS m/z [M+H]$^+$ 336.2.

EXAMPLE 108: (R)—N-(1-((3-cyclopropylpyridin-2-yl)oxy)-2-methylpropan-2-yl)-2-(1-methylpyrrolidin-2-yl)acetamide

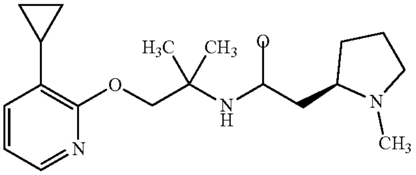 [SMILES: CN1CCC[C@@H]1CC(C)(O)NC(C)(C)COc1ncccc1C1CC1]

The title compound was prepared like EXAMPLE 106, using (R)-2-(1-methylpyrrolidin-2-yl)acetic acid (25 mg, 0.175 mmol) and 1-((3-cyclopropylpyridin-2-yl)oxy)-2-methylpropan-2-amine (39.6 mg, 0.192 mmol), and was obtained as a colorless oil (21 mg, 36%). $^1$H NMR (400 MHz, $CD_3OD$) δ ppm 0.63-0.74 (m, 2H), 0.90-1.06 (m, 2H), 1.48 (d, J=1.6 Hz, 6H), 1.52-1.61 (m, 1H), 1.69-1.80 (m, 2H), 1.90-2.01 (m, 1H), 2.07-2.25 (m, 3H), 2.31 (s, 3H), 2.41-2.48 (m, 1H), 2.51 (dd, J=8.0, 4.5 Hz, 1H), 3.01 (ddd, J=9.7, 7.1, 3.1 Hz, 1H), 4.44 (d, J=0.9 Hz, 2H), 6.86 (dd, J=7.4, 5.0 Hz, 1H), 7.26 (dd, J=7.3, 1.8 Hz, 1H), 7.89 (dd, J=5.0, 1.8 Hz, 1H); ESI-MS m/z [M+H]$^+$ 332.2.

EXAMPLE 109: (S)—N-(1-((3-ethoxypyridin-2-yl)oxy)-2-methylpropan-2-yl)-2-(1-methylpyrrolidin-2-yl)acetamide

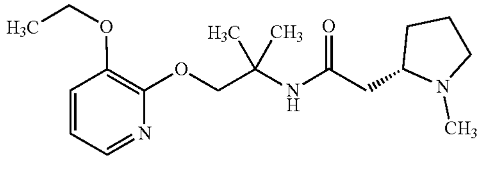 [SMILES: CCOc1cccnc1OCC(C)(C)NC(=O)C[C@@H]1CCCN1C]

The title compound was prepared like EXAMPLE 106, using (S)-2-(1-methylpyrrolidin-2-yl)acetic acid (25 mg, 0.175 mmol) and (1-((3-ethoxypyridin-2-yl)oxy)-2-methylpropan-2-amine (40.4 mg, 0.192 mmol), and was obtained as a colorless oil (9 mg, 15%). $^1$H NMR (400 MHz, $CD_3OD$) δ ppm 1.31 (t, J=7.0 Hz, 3H), 1.34 (d, J=3.5 Hz, 6H), 1.41-1.52 (m, 1H), 1.56-1.72 (m, 2H), 1.77-1.90 (m, 1H), 2.01-2.16 (m, 2H), 2.20 (s, 3H), 2.27-2.34 (m, 1H), 2.37-2.45 (m, 1H), 2.90 (ddd, J=9.6, 7.5, 2.6 Hz, 1H), 3.97 (q, J=7.0 Hz, 2H), 4.25-4.38 (m, 2H), 6.77 (dd, J=7.8, 5.1 Hz, 1H), 7.12 (dd, J=7.8, 1.5 Hz, 1H), 7.54 (dd, J=5.2, 1.5 Hz, 1H); ESI-MS m/z [M+H]$^+$ 336.3.

EXAMPLE 110: (R)—N-(2-(isoquinolin-1-yl)propan-2-yl)-2-((S)-1-methylpyrrolidin-2-yl)propanamide and (S)—N-(2-(isoquinolin-1-yl)propan-2-yl)-2-((R)-1-methylpyrrolidin-2-yl)propanamide

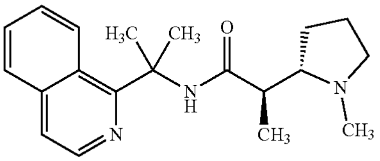

and

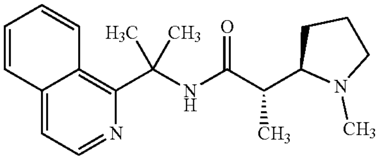

EXAMPLE 111: (R)—N-(2-(isoquinolin-1-yl)propan-2-yl)-2-((R)-1-methylpyrrolidin-2-yl)propanamide and (S)—N-(2-(isoquinolin-1-yl)propan-2-yl)-2-((S)-1-methylpyrrolidin-2-yl)propanamide

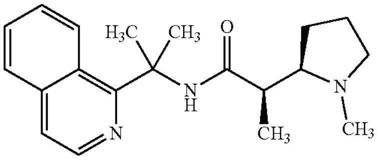

and

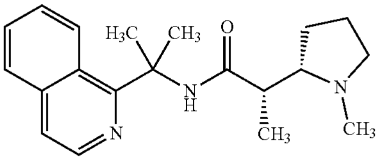

To a vial were added 2-(1-methylpyrrolidin-2-yl)propanoic acid (68 mg, 0.433 mmol), 2-(isoquinolin-1-yl)propan-2-amine (81 mg, 0.433 mmol), HATU (164 mg, 0.433 mmol) and $Et_3N$ (121 μL, 0.865 mmol) in DMF (2 mL). The reaction mixture was stirred at room temperature for several hours and then was purified by preparative HPLC (Phenomenex Gemini® C18, 5 μm, ID 30 mm×150 mm) using a gradient of 10-100% water/ACN in water (basic mode). The first eluting compound was re-purified by preparative HPLC (Phenomenex Gemini® C18, 5 μm, ID 30 mm×150 mm) using a gradient of 10-100% ACN in water (acid mode) to give TFA salts of the title compounds. The early eluting compound was arbitrarily assigned to be a mixture of the title (R,S)- and (S,R)-enantiomers and was obtained as a clear oil (6 mg, 4.3%). $^1$H NMR (400 MHz, $CD_3OD$) δ ppm 1.20 (d, J=7.3 Hz, 3H), 1.59-1.80 (m, 2H), 1.85-2.00 (m, 1H), 2.03 (s, 3H), 2.07 (s, 3H), 2.12-2.26 (m, 1H), 2.73 (s, 3H), 2.90-3.14 (m, 2H), 3.37-3.54 (m, 2H), 7.93 (ddd, J=8.6, 7.1, 1.2 Hz, 1H), 8.08 (t, J=7.6 Hz, 1H), 8.22 (s, 1H), 8.22-8.25 (m, 1H), 8.43 (d, J=6.4 Hz, 1H), 8.96 (dd, J=8.8, 0.8 Hz, 1H); ESI-MS m/z $[M+H]^+$ 326.4. The late eluting compound was arbitrarily assigned to be the mixture of (R,R)- and (S,S)-enantiomers and was obtained as a yellow oil (16 mg, 11%). $^1$H NMR (400 MHz, $CD_3OD$) δ ppm 0.97 (d, J=7.2 Hz, 3H), 1.57 (dt, J=12.5, 6.8 Hz, 1H), 1.74-1.96 (m, 9H), 2.28-2.47 (m, 5H), 2.51-2.62 (m, 1H), 3.14 (dt, J=9.7, 4.6 Hz, 1H), 7.56-7.72 (m, 4H), 7.90 (s, 1H), 8.37 (d, J=5.6 Hz, 1H), 8.68 (dd, J=8.7, 0.8 Hz, 1H); ESI-MS m/z $[M+H]^+$ 326.4.

EXAMPLE 112: (S)—N-(2-(3-chloro-2-methoxyphenyl)propan-2-yl)-2-(1-methylpyrrolidin-2-yl)acetamide

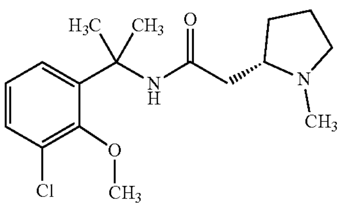 [SMILES: COc1c(Cl)cccc1C(C)(C)NC(=O)C[C@@H]1CCCN1C]

To a vial were added (S)-2-(1-methylpyrrolidin-2-yl)acetic acid (30 mg, 0.210 mmol), 2-(3-chloro-2-methoxyphenyl)propan-2-amine (41.8 mg, 0.210 mmol), HATU (80 mg, 0.210 mmol) and $Et_3N$ (58.4 μL, 0.419 mmol) in DMF (2 mL). The reaction mixture was stirred at room temperature for several hours and then was diluted with water (20 mL) and extracted with EtOAc. The organic layers were combined, dried over $Na_2SO_4$ and concentrated in vacuo. The residue was purified by preparative HPLC (Phenomenex Gemini® C18, 5 μm, ID 30 mm×150 mm) using a gradient of 10-100% ACN in water (acid mode) to give a TFA salt of the title compound as a clear oil (39 mg, 42%). $^1$H NMR (400 MHz, $CD_3OD$) δ ppm 1.74 (d, J=4.8 Hz, 6H), 1.79-2.03 (m, 2H), 2.04-2.18 (m, 1H), 2.27-2.39 (m, 1H), 2.69-2.83 (m, 2H), 2.89 (s, 3H), 3.10 (dt, J=11.5, 8.3 Hz, 1H), 3.55-3.75 (m, 2H), 3.93 (s, 3H), 7.04 (t, J=8.0 Hz, 1H), 7.28-7.36 (m, 2H); ESI-MS m/z $[M+H]^+$ 325.3.

EXAMPLE 113: (R)—N-(2-(3-chloro-2-methoxyphenyl)propan-2-yl)-2-(1-methylpyrrolidin-2-yl)acetamide

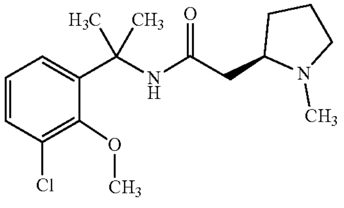 [SMILES: COc1c(Cl)cccc1C(C)(C)NC(=O)C[C@H]1CCCN1C]

A TFA salt of the title compound was prepared like EXAMPLE 112, using (R)-2-(1-methylpyrrolidin-2-yl)acetic acid (30 mg, 0.210 mmol), and was obtained as a clear oil (38 mg, 41%). $^1$H NMR (400 MHz, $CD_3OD$) δ ppm 1.74 (d, J=4.9 Hz, 6H), 1.92-2.14 (m, 2H), 2.34 (dtd, J=13.3, 8.2, 5.4 Hz, 1H), 2.69-2.83 (m, 2H), 2.89 (s, 3H), 3.10 (dt, J=11.5, 8.2 Hz, 1H), 3.55-3.75 (m, 2H), 3.93 (s, 3H), 7.04 (t, J=8.0 Hz, 1H), 7.28-7.37 (m, 2H); ESI-MS m/z $[M+H]^+$ 325.3.

EXAMPLE 114: (S)—N-(2-(3-fluoro-2-methoxyphenyl)propan-2-yl)-2-(1-methylpyrrolidin-2-yl)acetamide

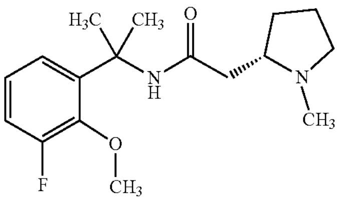 [SMILES: COc1c(F)cccc1C(C)(C)NC(=O)C[C@@H]1CCCN1C]

A TFA salt of the title compound was prepared like EXAMPLE 112, using 2-(3-fluoro-2-methoxyphenyl)propan-2-amine (38.4 mg, 0.210 mmol), and was obtained as a clear oil (44 mg, 50%). $^1$H NMR (400 MHz, $CD_3OD$) δ ppm 1.73 (d, J=5.0 Hz, 6H), 1.77-1.90 (m, 1H), 1.92-2.17 (m, 2H), 2.28-2.39 (m, 1H), 2.68-2.83 (m, 2H), 2.89 (s, 3H), 3.11 (dt, J=11.5, 8.3 Hz, 1H), 3.55-3.76 (m, 2H), 3.94 (d, J=2.3 Hz, 3H), 6.96-7.07 (m, 2H), 7.15 (d, J=7.9 Hz, 1H); ESI-MS m/z $[M+H]^+$ 309.4.

EXAMPLE 115: (R)—N-(2-(3-fluoro-2-methoxyphenyl)propan-2-yl)-2-(1-methylpyrrolidin-2-yl)acetamide

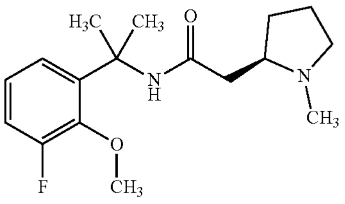 [SMILES: COc1c(F)cccc1C(C)(C)NC(=O)C[C@H]1CCCN1C]

A TFA salt of the title compound was prepared like EXAMPLE 112, using (R)-2-(1-methylpyrrolidin-2-yl)acetic acid (30 mg, 0.210 mmol) and 2-(3-fluoro-2-methoxyphenyl)propan-2-amine (38.4 mg, 0.210 mmol), and was obtained as a light-yellow oil (31 mg, 37%). $^1$H NMR (400 MHz, $CD_3OD$) δ ppm 1.73 (d, J=5.0 Hz, 6H), 1.92-2.17 (m, 2H), 2.34 (dtd, J=13.3, 8.2, 5.4 Hz, 1H), 2.69-2.82 (m, 2H), 2.89 (s, 3H), 3.11 (dt, J=11.5, 8.3 Hz, 1H), 3.55-3.71 (m, 2H), 3.95 (d, J=2.4 Hz, 3H), 6.96-7.07 (m, 2H), 7.15 (dt, J=7.6, 1.7 Hz, 1H); ESI-MS m/z $[M+H]^+$ 309.3.

EXAMPLE 116: (S)—N-(2-(2-methoxy-3-methylphenyl)propan-2-yl)-2-(1-methylpyrrolidin-2-yl) acetamide

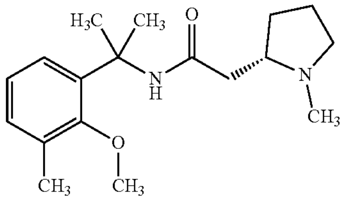 [SMILES: COc1c(C)cccc1C(C)(C)NC(=O)C[C@@H]1CCCN1C]

A TFA salt of the title compound was prepared like EXAMPLE 112, using 2-(2-methoxy-3-methylphenyl)propan-2-amine (37.6 mg, 0.210 mmol), and was obtained as a colorless oil (41 mg, 47%). $^{1}$H NMR (400 MHz, $CD_3OD$) δ ppm 1.74 (d, J=4.8 Hz, 6H), 1.80-2.03 (m, 2H), 2.03-2.18 (m, 1H), 2.25-2.37 (m, 4H), 2.68-2.82 (m, 2H), 2.88 (s, 3H), 3.10 (dt, J=11.5, 8.2 Hz, 1H), 3.55-3.70 (m, 2H), 3.78 (s, 3H), 6.95 (t, J=7.6 Hz, 1H), 7.09 (d, J=7.2 Hz, 1H), 7.20 (dd, J=7.9, 1.2 Hz, 1H); ESI-MS m/z $[M+H]^+$ 305.4.

EXAMPLE 117: (R)—N-(2-(2-methoxy-3-methylphenyl)propan-2-yl)-2-(1-methylpyrrolidin-2-yl) acetamide

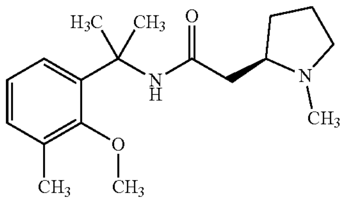 [SMILES: COc1c(C)cccc1C(C)(C)NC(=O)C[C@H]1CCCN1C]

A TFA salt of the title compound was prepared like EXAMPLE 112, using (R)-2-(1-methylpyrrolidin-2-yl)acetic acid (30 mg, 0.210 mmol) and 2-(2-methoxy-3-methylphenyl)propan-2-amine (37.6 mg, 0.210 mmol), and was obtained as a colorless oil (42 mg, 49%). $^{1}$H NMR (400 MHz, $CD_3OD$) δ ppm 1.74 (d, J=4.8 Hz, 6H), 1.79-2.03 (m, 2H), 2.03-2.19 (m, 1H), 2.26-2.38 (m, 4H), 2.69-2.82 (m, 2H), 2.88 (s, 3H), 3.10 (dt, J=11.5, 8.3 Hz, 1H), 3.55-3.70 (m, 2H), 3.78 (s, 3H), 6.92-6.98 (m, 1H), 7.09 (d, J=7.2 Hz, 1H), 7.20 (dd, J=7.9, 1.4 Hz, 1H); ESI-MS m/z $[M+H]^+$ 305.4.

EXAMPLE 118: (S)—N-(2-(3-chloro-2-methylphenyl)propan-2-yl)-2-(1-methylpyrrolidin-2-yl)acetamide

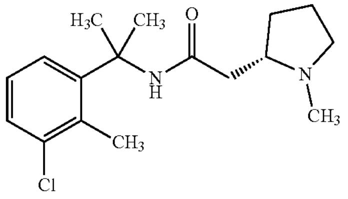 [SMILES: Cc1c(Cl)cccc1C(C)(C)NC(=O)C[C@@H]1CCCN1C]

A TFA salt of the title compound was prepared like EXAMPLE 112, using 2-(3-chloro-2-methylphenyl)propan-2-amine (38.5 mg, 0.210 mmol), and was obtained as a colorless oil (36 mg, 41%). $^{1}$H NMR (400 MHz, $CD_3OD$) δ ppm 1.74 (d, J=9.0 Hz, 6H), 1.90-2.16 (m, 2H), 2.27-2.39 (m, 1H), 2.52 (s, 3H), 2.68-2.84 (m, 2H), 2.88 (s, 3H), 3.10 (dt, J=11.5, 8.3 Hz, 1H), 3.52-3.71 (m, 2H), 7.13 (t, J=8.0 Hz, 1H), 7.29 (dd, J=7.9, 0.9 Hz, 1H), 7.40 (dd, J=8.0, 1.0 Hz, 1H); ESI-MS m/z $[M+H]^+$ 309.3.

EXAMPLE 119: (R)—N-(2-(3-chloro-2-methylphenyl)propan-2-yl)-2-(1-methylpyrrolidin-2-yl)acetamide

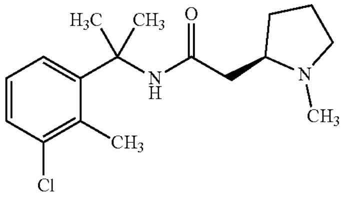 [SMILES: Cc1c(Cl)cccc1C(C)(C)NC(=O)C[C@H]1CCCN1C]

A TFA salt of the title compound was prepared like EXAMPLE 112, using (R)-2-(1-methylpyrrolidin-2-yl)acetic acid (30 mg, 0.210 mmol) and 2-(3-chloro-2-methylphenyl)propan-2-amine (38.5 mg, 0.210 mmol), and was obtained as a colorless oil (41 mg, 46%). $^{1}$H NMR (400 MHz, $CD_3OD$) δ ppm 1.74 (d, J=8.9 Hz, 6H), 1.91-2.16 (m, 2H), 2.27-2.39 (m, 1H), 2.52 (s, 3H), 2.68-2.84 (m, 2H), 2.88 (s, 3H), 3.10 (dt, J=11.5, 8.3 Hz, 1H), 3.53-3.70 (m, 2H), 7.13 (t, J=8.0 Hz, 1H), 7.29 (dd, J=7.9, 0.9 Hz, 1H), 7.40 (dd, J=8.0, 1.0 Hz, 1H); ESI-MS m/z $[M+H]^+$ 309.3.

EXAMPLE 120: 2-(1-methylpiperidin-2-yl)-N-(1-(((3-methylpyridin-2-yl)oxy)methyl)cyclopropyl) acetamide

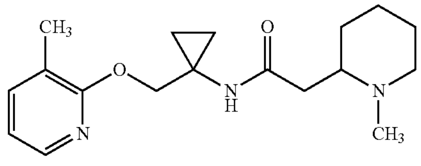 [SMILES: Cc1cccnc1OCC1(NC(=O)CC2CCCCN2C)CC1]

A mixture of 1-(((3-methylpyridin-2-yl)oxy)methyl)cyclopropan-1-amine (20.0 mg, 0.112 mmol), 2-(1-methylpiperidin-2-yl)acetic acid (17.6 mg, 0.112 mmol), DIPEA (0.049 mL, 0.28 mmol) and HATU (51.2 mg, 0.135 mmol) in DMA (1.0 mL) was stirred at room temperature for 4 hours. The product was purified by preparative HPLC (Phenomenex Gemini® C18, 5 μm, ID 30 mm×150 mm) using a gradient of 10-40% ACN in water (acid mode). The pure fractions were combined and dried in a GeneVac™ evaporator to afford a TFA salt of the title compound as a pale-yellow film (25 mg, 70%). ESI-MS m/z $[M+H]^+$ 318.2.

EXAMPLE 121: (R)—N-(1-(((3-methylpyridin-2-yl)oxy)methyl)cyclopropyl)-2-(1-methylpyrrolidin-2-yl)acetamide

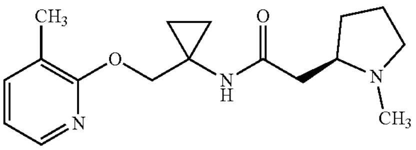 [SMILES: Cc1cccnc1OCC1(NC(=O)C[C@H]2CCCN2C)CC1]

A mixture of 1-(((3-methylpyridin-2-yl)oxy)methyl)cyclopropan-1-amine (20.0 mg, 0.112 mmol), (R)-2-(1-methylpyrrolidin-2-yl)acetic acid (16.1 mg, 0.112 mmol), DIPEA (0.049 mL, 0.28 mmol) and HATU (51.2 mg, 0.135 mmol) in DMA (1.0 mL) was stirred at RT for 4 hours. The product was purified by preparative HPLC (Phenomenex Gemini® C18, 5 μm, ID 30 mm×150 mm) using a gradient of 10-40% ACN in water (acid mode). The pure fractions were combined and dried in a GeneVac™ evaporator to afford a TFA salt of the title compound as a pale-yellow film (37.7 mg, 81%). ESI-MS m/z $[M+H]^+$ 304.2.

EXAMPLE 122: (S)—N-(1-(furo[2,3-c]pyridin-7-yloxy)-2-methylpropan-2-yl)-2-(1-methylpyrrolidin-2-yl)acetamide

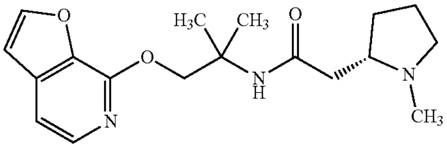 [SMILES: CN1CCC[C@H]1CC(=O)NC(C)(C)COc1nccc2ccoc12]

To a solution of (S)—N-(1-hydroxy-2-methylpropan-2-yl)-2-(1-methylpyrrolidin-2-yl)acetamide (25.0 mg, 0.117 mmol) in DMF (0.5 mL) was added sodium hydride (60 wt %, 7.0 mg, 0.175 mmol). The reaction mixture was stirred at room temperature for 50 minutes. Next, 7-chlorofuro[2,3-c]pyridine (20 mg, 0.128 mmol) was added. The reaction mixture was stirred at room temperature for 2 hours at which time cesium carbonate (54 mg, 0.166 mmol) was added. The reaction mixture was stirred at room temperature overnight and then was quenched with aqueous 1 N HCl (0.15 mL). The product was purified by preparative HPLC (Phenomenex Gemini® C18, 5 μm, ID 30 mm×150 mm) using a gradient of 10-70% water/ACN in water (basic mode). The pure fractions were combined and dried in a GeneVac™ evaporator to afford the title compound as a pale yellow solid (1.1 mg, 2.8%). ESI-MS m/z $[M+H]^+$ 332.2.

EXAMPLE 123: (S)—N-(2-methyl-1-(pyridin-2-yloxy)propan-2-yl)-2-(1-methylpyrrolidin-2-yl)acetamide

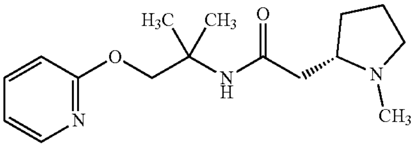 [SMILES: CN1CCC[C@H]1CC(=O)NC(C)(C)COc1ccccn1]

The title compound was prepared like EXAMPLE 122, using 2-fluoropyridine (12.5 mg, 0.128 mmol), and was obtained as a pale yellow solid (23.5 mg, 69%). ESI-MS m/z $[M+H]^+$ 292.2.

EXAMPLE 124: (S)—N-(1-((3-chloro-5-methylpyridin-2-yl)oxy)-2-methylpropan-2-yl)-2-(1-methylpyrrolidin-2-yl)acetamide

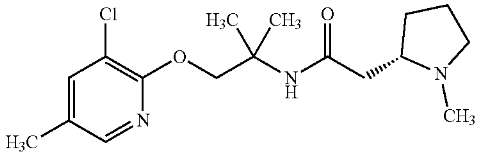 [SMILES: Cc1cnc(OCC(C)(C)NC(=O)C[C@@H]2CCCN2C)c(Cl)c1]

The title compound was prepared like EXAMPLE 122, using 2,3-dichloro-5-methylpyridine (20.8 mg, 0.128 mmol), and was obtained as a pale yellow solid (16.6 mg, 42%). $^1$H NMR (400 MHz, DMSO-$d_6$) δ ppm 1.32 (d, J=2.3 Hz, 6H), 1.37-1.47 (m, 1H), 1.53-1.61 (m, 2H), 1.71-1.78 (m, 1H), 2.01-2.07- (m, 2H), 2.16 (s, 3H), 2.21 (s, 3H), 2.22-2.36 (m, 2H), 2.84-2.88 (m, 1H), 4.32-4.41 (m, 2H), 7.73 (s, 1H), 7.89 (s, 1H), 7.91 (dd, J=2.1, 0.8 Hz, 1H); ESI-MS m/z $[M+H]^+$ 340.2.

EXAMPLE 125: (S)—N-(1-(furo[3,2-c]pyridin-4-yloxy)-2-methylpropan-2-yl)-2-(1-methylpyrrolidin-2-yl)acetamide

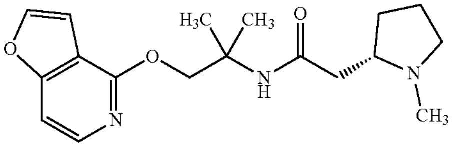 [SMILES: CN1CCC[C@H]1CC(=O)NC(C)(C)COc1nccc2occc12]

The title compound was prepared like EXAMPLE 122, using 4-chlorofuro[3,2-c]pyridine (19.7 mg, 0.128 mmol), and was obtained as a pale yellow solid (5 mg, 13%). ESI-MS m/z $[M+H]^+$ 332.2.

EXAMPLE 126: (S)—N-(1-(((3-methylpyridin-2-yl)oxy)methyl)cyclopropyl)-2-((R)-1-methylpyrrolidin-2-yl)propanamide

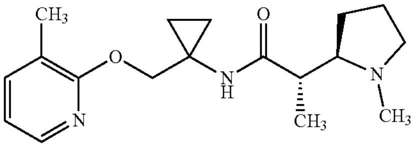 [SMILES: Cc1cccnc1OCC1(NC(=O)[C@@H](C)[C@H]2CCCN2C)CC1]

EXAMPLE 127: (R)—N-(1-(((3-methylpyridin-2-yl)oxy)methyl)cyclopropyl)-2-((S)-1-methylpyrrolidin-2-yl)propanamide

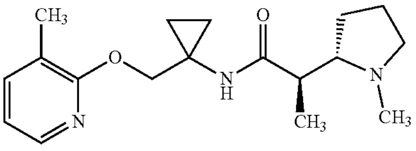 [SMILES: Cc1cccnc1OCC1(NC(=O)[C@H](C)[C@@H]2CCCN2C)CC1]

To a round bottom flask containing 2-(1-methylpyrrolidin-2-yl)propanoic acid hydrochloride (70 mg, 361 μmol) and 1-(((3-methylpyridin-2-yl)oxy)methyl)cyclopropanamine (90 mg, 505 μmol) in DMF (0.5 mL) was added HATU (206 mg, 542 μmol) and DIPEA (315 μL, 1.81 mmol). The reaction mixture was stirred at 15° C. for 2 hours and then was diluted with water (30 mL) and extracted with EtOAc (50 mL). The organic layers were dried over $Na_2SO_4$, filtered and concentrated in vacuo. The product was purified by preparative HPLC (Phenomenex Gemini® C18, 10 μm, ID 25 mm×150 mm) using a gradient of 40-70% water (with 0.05% $NH_4OH$) in ACN. Fractions containing the title compound as a mixture of (S,R)- and (R,S)-enantiomers were combined and lyophilized to afford a yellow oil (39.0 mg, 32%). $^1H$ NMR (400 MHz, $CDCl_3$) δ ppm 0.76-0.84 (m, 2H), 0.88-0.97 (m, 2H), 1.10 (d, J=7.0 Hz, 3H), 1.47 (br s, 1H), 1.65 (br d, J=6.8 Hz, 2H), 1.79-1.93 (m, 1H), 2.20 (s, 5H), 2.34 (s, 3H), 2.54 (br dd, J=7.2, 3.4 Hz, 1H), 3.12 (br s, 1H), 4.34-4.47 (m, 2H), 6.76 (dd, J=7.2, 5.1 Hz, 1H), 7.36 (d, J=7.0 Hz, 1H), 7.94 (dd, J=4.9, 1.4 Hz, 1H), 9.11 (br s, 1H); ESI-MS m/z $[M+H]^+$ 318.3. The enantiomers (35 mg) were separated by preparative SFC (Daicel ChiralCel OD-H, 5 μm, ID 30 mm×250 mm) using a mobile phase of 25% MeOH (with 0.1% $NH_4OH$) in $CO_2$. The stereochemical configurations of the title enantiomers were arbitrarily assigned.

EXAMPLE 128: N-(2-((S)-chroman-2-yl)propan-2-yl)-2-((S)-1-methylpyrrolidin-2-yl)acetamide

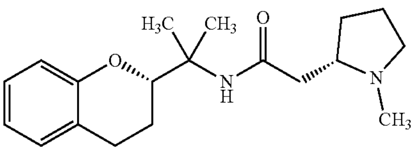 [SMILES: CN1CCC[C@H]1CC(=O)NC(C)(C)[C@@H]1CCc2ccccc2O1]

and

EXAMPLE 129: N-(2-((R)-chroman-2-yl)propan-2-yl)-2-((S)-1-methylpyrrolidin-2-yl)acetamide

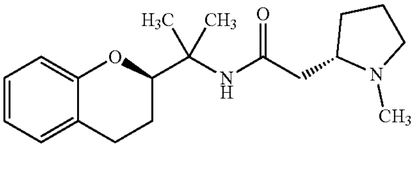 [SMILES: CN1CCC[C@H]1CC(=O)NC(C)(C)[C@H]1CCc2ccccc2O1]

To a solution of (S)-2-(1-methylpyrrolidin-2-yl)acetic acid (6.4 mg, 0.044 mmol) and HATU (16.9 mg, 0.044 mmol) in DMF (0.44 mL) was added DIPEA (19.4 μL, 0.111 mmol). The reaction mixture was stirred at room temperature for 10 minutes. Next, 2-(chroman-2-yl)propan-2-amine (10 mg, 0.044 mmol) was added and the reaction mixture was stirred at room temperature for 3 days. The product was purified by preparative HPLC (Phenomenex Gemini® C18, 5 μm, ID 30 mm×150 mm) using a gradient of 10-70% water/ACN in water (basic mode) to give the title diastereomers. The early eluting diastereomer was arbitrarily assigned as the (S,S)-diastereomer and was obtained as a white film (3.5 mg, 25%). $^1H$ NMR (400 MHz, $CD_3OD$) δ ppm 1.45 (d, J=8.2 Hz, 6H), 1.58-1.74 (m, 2H), 1.75-1.84 (m, 2H), 2.00-2.12 (m, 2H), 2.25-2.36 (m, 2H), 2.38 (s, 3H), 2.43-2.51 (m, 1H), 2.57-2.68 (m, 1H), 2.76-2.93 (m, 2H), 3.02-3.10 (m, 1H), 4.33 (dd, J=11.5, 1.8 Hz, 1H), 6.75 (dd, J=8.5, 1.1 Hz, 1H), 6.80 (td, J=7.4, 1.1 Hz, 1H), 6.99-7.09 (m, 2H); ESI-MS m/z $[M+H]^+$ 317.30. The late eluting diastereomer was arbitrarily assigned as the (R,S)-diastereomer and was obtained as a white film (2.3 mg, 16%). $^1H$ NMR (400 MHz, $CD_3OD$) δ ppm 1.45 (d, J=5.0 Hz, 6H), 1.62-1.92 (m, 4H), 1.99-2.14 (m, 2H), 2.20-2.30 (m, 1H), 2.34 (s, 3H), 2.35-2.44 (m, 2H), 2.50-2.60 (m, 1H), 2.77-2.94 (m, 2H), 2.99-3.08 (m, 1H), 4.29 (dd, J=11.4, 1.8 Hz, 1H), 6.75 (dd, J=8.5, 1.1 Hz, 1H), 6.81 (td, J=7.4, 1.1 Hz, 1H), 7.00-7.09 (m, 2H); ESI-MS m/z $[M+H]^+$ 317.30.

EXAMPLE 130: N-(2-((R)-chroman-2-yl)propan-2-yl)-2-((R)-1-methylpyrrolidin-2-yl)acetamide

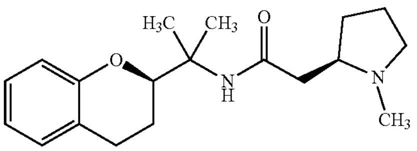 [SMILES: CN1CCC[C@@H]1CC(=O)NC(C)(C)[C@H]1CCc2ccccc2O1]

and

EXAMPLE 131: N-(2-((S)-chroman-2-yl)propan-2-yl)-2-((R)-1-methylpyrrolidin-2-yl)acetamide

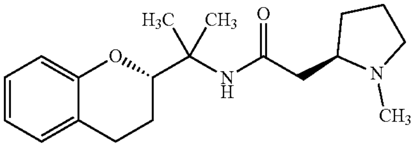 [SMILES: CN1CCC[C@@H]1CC(=O)NC(C)(C)[C@@H]1CCc2ccccc2O1]

The title diastereomers were prepared like EXAMPLE 128 and EXAMPLE 129, using (R)-2-(1-methylpyrrolidin-2-yl)acetic acid (6.4 mg, 0.044 mmol) and 2-(chroman-2-yl)propan-2-amine (10 mg, 0.044 mmol). The early eluting diastereomer was arbitrarily assigned as the (R,R)-diastereomer and was obtained as a white film (3.4 mg, 24%). $^1H$ NMR (400 MHz, $CD_3OD$) δ ppm 1.45 (d, J=8.4 Hz, 6H), 1.56-1.73 (m, 2H), 1.74-1.86 (m, 2H), 2.00-2.12 (m, 2H), 2.25-2.35 (m, 2H), 2.37 (s, 3H), 2.42-2.50 (m, 1H), 2.61 (br dd, J=6.2, 5.2 Hz, 1H), 2.76-2.95 (m, 2H), 3.01-3.10 (m, 1H), 4.32 (dd, J=11.4, 1.8 Hz, 1H), 6.75 (dd, J=8.6, 1.1 Hz, 1H), 6.80 (td, J=7.4, 1.1 Hz, 1H), 6.99-7.08 (m, 2H); ESI-MS m/z $[M+H]^+$ 317.30. The late eluting diastereomer was arbitrarily assigned as the (S,R)-diastereomer and was obtained as a white film (3.7 mg, 26%). $^1$H NMR (400 MHz, $CD_3OD$) δ ppm 1.45 (d, J=4.9 Hz, 6H), 1.61-1.75 (m, 2H), 1.75-1.94 (m, 2H), 2.01-2.13 (m, 2H), 2.24-2.35 (m, 1H), 2.37 (s, 3H), 2.38-2.46 (m, 2H), 2.52-2.66 (m, 1H), 2.76-2.95 (m, 2H), 3.02-3.10 (m, 1H), 4.30 (dd, J=11.5, 1.8 Hz, 1H), 6.75 (dd, J=8.6, 1.2 Hz, 1H), 6.81 (td, J=7.4, 1.2 Hz, 1H), 7.01-7.08 (m, 2H); ESI-MS m/z $[M+H]^+$ 317.30.

EXAMPLE 132: 3-(azetidin-1-yl)-N-(2-(2-chlorophenyl)propan-2-yl)-2-methylpropanamide

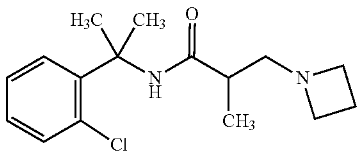 [SMILES: CC(CN1CCC1)C(=O)NC(C)(C)c1ccccc1Cl]

To a vial equipped with stir bar were added N-(2-(2-chlorophenyl)propan-2-yl)methacrylamide (825.5 mg, 3.47 mmol) and azetidine (2.34 mL, 34.7 mmol). The reaction mixture was stirred at 60° C. for 48 hours. Water was added until a precipitate formed. The solid was collected and dried under vacuum to afford the title compound as a white solid (770.7 mg, 75%). $^1$H NMR (400 MHz, $CD_3OD$) δ ppm 1.04 (d, J=6.8 Hz, 3H), 1.75 (s, 3H), 1.81 (s, 3H), 2.08 (quin, J=7.1 Hz, 2H), 2.34-2.45 (m, 2H), 2.60-2.69 (m, 1H), 3.23-3.30 (m, 4H), 7.15-7.23 (m, 1H), 7.27 (td, J=7.6, 1.6 Hz, 1H), 7.33 (dd, J=7.8, 1.5 Hz, 1H), 7.56 (dd, J=8.0, 1.6 Hz, 1H); ESI-MS $[M+H]^+$ 295.3.

EXAMPLE 133: (R)-3-(azetidin-1-yl)-N-(2-(2-chlorophenyl)propan-2-yl)-2-methylpropanamide

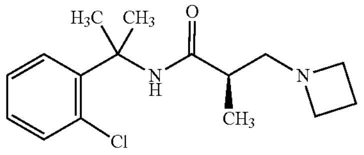 [SMILES: C[C@H](CN1CCC1)C(=O)NC(C)(C)c1ccccc1Cl]

and

EXAMPLE 134: (S)-3-(azetidin-1-yl)-N-(2-(2-chlorophenyl)propan-2-yl)-2-methylpropanamide

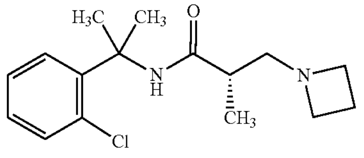 [SMILES: C[C@@H](CN1CCC1)C(=O)NC(C)(C)c1ccccc1Cl]

The title enantiomers of 3-(azetidin-1-yl)-N-(2-(2-chlorophenyl)propan-2-yl)-2-methylpropanamide (EXAMPLE 132, 770 mg, 2.61 mmol) were separated by preparative SFC (Daicel ChiralPak AD, 5 μm, ID 30 mm×250 mm) using a mobile phase of 15% EtOH (with 0.1% $NH_4OH$) in $CO_2$ and then purified by preparative HPLC (Phenomenex Gemini® C18, 5 μm, ID 30 mm×150 mm) using a gradient of 10-100% water/ACN in water (basic mode). The first eluting compound by SFC was arbitrarily assigned as the (R)-enantiomer (210.2 mg, 27%) and the second eluting compound by SFC was arbitrarily assigned as the (S)-enantiomer (239.4 mg, 31%). $^1$H NMR (400 MHz, $CD_3OD$) δ ppm 1.02 (d, J=6.8 Hz, 3H), 1.73 (s, 3H), 1.78 (s, 3H), 2.06 (quin, J=7.1 Hz, 2H), 2.31-2.43 (m, 2H), 2.57-2.68 (m, 1H), 3.21-3.27 (m, 4H), 7.13-7.20 (m, 1H), 7.21-7.28 (m, 1H), 7.31 (dd, J=7.8, 1.5 Hz, 1H), 7.54 (dd, J=8.0, 1.7 Hz, 1H); ESI-MS m/z $[M+H]^+$ 295.20.

EXAMPLE 135: N-(2-(2-chlorophenyl)propan-2-yl)-2-methyl-3-(pyrrolidin-1-yl)propanamide

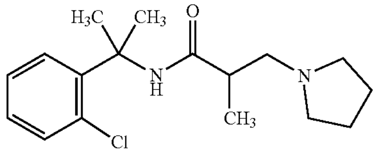 [SMILES: CC(CN1CCCC1)C(=O)NC(C)(C)c1ccccc1Cl]

To a vial equipped with stir bar were added N-(2-(2-chlorophenyl)propan-2-yl)methacrylamide (875.9 mg, 3.68 mmol) and pyrrolidine (4.57 mL, 55.3 mmol). The reaction mixture was stirred at 60° C. for 48 hours and then was concentrated under reduced pressure. The residue was taken up in methanol and filtered through a hydrophilic PTFE 0.45 m Millipore® filter, rinsing with MeOH. The filtrate was purified by preparative HPLC (Phenomenex Gemini® C18, 5 μm, ID 30 mm×150 mm) using a gradient of 10-50% ACN in water (acid mode). Fractions containing the desired product were evaporated, taken up in methanol and filtered through Agilent Stratospheres SPE (PL-$HCO_3$ MP) resin to remove TFA. The filtrate was evaporated to afford the title compound as a white solid (505.7 mg, 44%). $^1$H NMR (400 MHz, $CD_3OD$) δ ppm 1.26 (d, J=7.2 Hz, 3H), 1.79 (app d, J=1.8 Hz, 6H), 1.90-2.03 (m, 2H), 2.04-2.18 (m, 2H), 2.88 (dqd, J=9.4, 7.1, 4.6 Hz, 1H), 2.93-3.03 (m, 1H), 3.04-3.14 (m, 2H), 3.36-3.42 (m, 1H), 3.50-3.61 (m, 2H), 7.17-7.24 (m, 1H), 7.28 (td, J=7.6, 1.5 Hz, 1H), 7.34 (dd, J=7.8, 1.5 Hz, 1H), 7.56 (dd, J=7.9, 1.6 Hz, 1H), 8.52 (br s, 1H); ESI-MS $[M+H]^+$ 309.30.

EXAMPLE 136: (R)—N-(2-(2-chlorophenyl)propan-2-yl)-2-methyl-3-(pyrrolidin-1-yl)propanamide

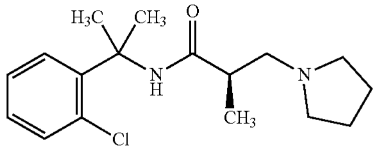 [SMILES: C[C@H](CN1CCCC1)C(=O)NC(C)(C)c1ccccc1Cl]

and

EXAMPLE 137: (S)—N-(2-(2-chlorophenyl)propan-2-yl)-2-methyl-3-(pyrrolidin-1-yl)propanamide

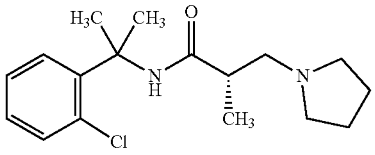 [SMILES: C[C@@H](CN1CCCC1)C(=O)NC(C)(C)c1ccccc1Cl]

The title enantiomers of N-(2-(2-chlorophenyl)propan-2-yl)-2-methyl-3-(pyrrolidin-1-yl)propanamide (EXAMPLE 135, 505.7 mg, 1.64 mmol) were separated by preparative SFC (Whelk O1(S,S), 5 μm, ID 30 mm×250 mm) using a mobile phase of 45% isopropanol (with 0.1% $NH_4OH$) in $CO_2$ and then purified by preparative HPLC (Phenomenex Gemini® C18, 5 μm, ID 30 mm×150 mm) using a gradient of 10-100% water/ACN in water (basic mode). The first eluting compound by SFC was arbitrarily assigned as the (R)-enantiomer (107.2 mg, 21%) and the second eluting compound by SFC was arbitrarily assigned as the (S)-enantiomer (30.6 mg, 6.0%). $^1H$ NMR (400 MHz, $CD_3OD$) δ ppm 1.05 (d, J=7.0 Hz, 3H), 1.74 (s, 3H), 1.75-1.82 (m, 7H), 2.40 (dd, J=12.1, 5.1 Hz, 1H), 2.47-2.64 (m, 5H), 2.73 (dd, J=12.0, 9.0 Hz, 1H), 7.13-7.20 (m, 1H), 7.24 (td, J=7.6, 1.6 Hz, 1H), 7.31 (dd, J=7.8, 1.4 Hz, 1H), 7.55 (dd, J=8.0, 1.7 Hz, 1H); ESI-MS m/z $[M+H]^+$ 309.30.

EXAMPLE 138: (R)-3-(azetidin-1-yl)-N-(2-(4-methoxyphenyl)propan-2-yl)-2-methylpropanamide

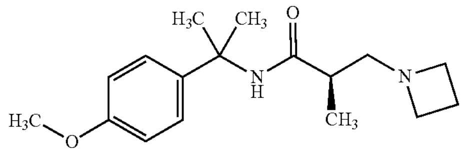 [SMILES: COc1ccc(C(C)(C)NC(=O)[C@H](C)CN2CCC2)cc1]

and

EXAMPLE 139: (S)-3-(azetidin-1-yl)-N-(2-(4-methoxyphenyl)propan-2-yl)-2-methylpropanamide

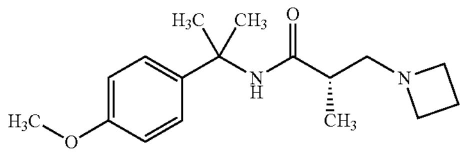 [SMILES: COc1ccc(C(C)(C)NC(=O)[C@@H](C)CN2CCC2)cc1]

STEP A: N-(2-(4-methoxyphenyl)propan-2-yl)methacrylamide

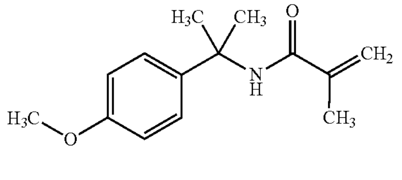 [SMILES: C=C(C)C(=O)NC(C)(C)c1ccc(OC)cc1]

To a mixture of 2-(4-methoxyphenyl)propan-2-amine hydrochloride (0.500 g, 2.48 mmol), methacrylic acid (0.213 mL, 2.48 mmol) and $Et_3N$ (1.04 mL, 7.44 mmol) in DMF (20 mL) was added HATU (1.414 g, 3.72 mmol). The reaction mixture was stirred at room temperature overnight and then was diluted with water (100 mL) and extracted with EtOAc (3×20 mL). The combined organic layers were washed with brine, dried over $MgSO_4$, filtered and concentrated under reduced pressure. The residue was purified by automated flash silica column chromatography to give the title compound (1.0 g) as a mixture of desired product and an unknown intermediate, which was carried forward without additional purification. ESI-MS m/z $[M+H]^+$ 234.3.

STEP B: (R)-3-(azetidin-1-yl)-N-(2-(4-methoxyphenyl)propan-2-yl)-2-methylpropanamide and (S)-3-(azetidin-1-yl)-N-(2-(4-methoxyphenyl)propan-2-yl)-2-methylpropanamide To a solution of crude N-(2-(4-methoxyphenyl)propan-2-yl)methacrylamide (1.0 g) in methanol (10 mL) and water (10 mL) was added azetidine (1.44 mL, 21.4 mmol). The reaction mixture was heated at 100° C. in a microwave reactor for 2 hours and then was concentrated and purified by automated flash silica column chromatography using a gradient of 0-100% EtOAc in heptanes. The title enantiomers were separated by preparative SFC (ChiralPak IC, 5 μm, ID 30 mm×250 mm) using a mobile phase of iPrOH (with 0.1% $NH_4OH$) in $CO_2$ and then purified by preparative HPLC (Phenomenex Gemini® C18, 5 μm, ID 30 mm×150 mm) using a gradient of 10-100% ACN in water (acid mode) to give a TFA salt of each enantiomer. The early eluting compound by SFC was arbitrarily assigned as the (S)-enantiomer (17 mg, 2.6%) and the late eluting compound by SFC was arbitrarily assigned as the (R)-enantiomer (33 mg, 5.0%). $^1H$ NMR (400 MHz, DMSO-$d_6$) δ ppm 1.19 (d, J=7.2 Hz, 3H), 1.61 (s, 3H), 1.66 (s, 3H), 2.26-2.41 (m, 1H), 2.47-2.61 (m, 1H), 2.54-2.61 (m, 1H), 2.67-2.77 (m, 1H), 3.11 (dd, J=12.8, 4.5 Hz, 1H), 3.37 (dd, J=12.8, 8.8 Hz, 1H), 3.73-3.78 (m, 3H), 3.98-4.18 (m, 4H), 6.81-6.88 (m, 2H), 7.26-7.33 (m, 2H); ESI-MS m/z $[M+H]^+$ 291.4.

EXAMPLE 140: (R)-3-(azetidin-1-yl)-2-methyl-N-(2-(o-tolyl)propan-2-yl)propanamide

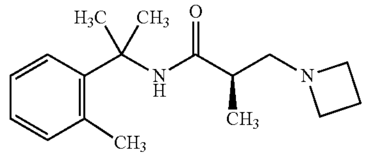 [SMILES: Cc1ccccc1C(C)(C)NC(=O)[C@H](C)CN1CCC1]

and

EXAMPLE 141: (S)-3-(azetidin-1-yl)-2-methyl-N-(2-(o-tolyl)propan-2-yl)propanamide

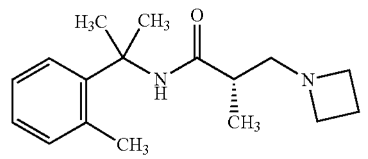 [SMILES: Cc1ccccc1C(C)(C)NC(=O)[C@@H](C)CN1CCC1]

The title enantiomers were prepared like EXAMPLE 138 and EXAMPLE 139 using 2-(o-tolyl)propan-2-amine hydrochloride (1.00 g, 5.39 mmol), but without the final HPLC re-purification. The first eluting compound by SFC was arbitrarily assigned as the (R)-enantiomer and was obtained as a white solid (165 mg, 11%) and the second eluting compound by SFC was arbitrarily assigned as the (S)-enantiomer and was obtained as a white solid (152 mg, 10%). $^1$H NMR (400 MHz, $CD_3OD$) δ ppm 1.22 (d, J=7.2 Hz, 3H), 1.67-1.79 (m, 6H), 2.29-2.42 (m, 1H), 2.46-2.64 (m, 4H), 2.69-2.80 (m, 1H), 3.14 (dd, J=12.9, 4.7 Hz, 1H), 3.38 (dd, J=12.9, 8.5 Hz, 1H), 4.02-4.21 (m, 4H), 7.08-7.20 (m, 3H), 7.41 (d, J=6.9 Hz, 1H); ESI-MS m/z $[M+H]^+$ 275.4.

EXAMPLE 142: (R)-3-(azetidin-1-yl)-N-(2-(3-fluoro-2-methylphenyl)propan-2-yl)-2-methylpropanamide

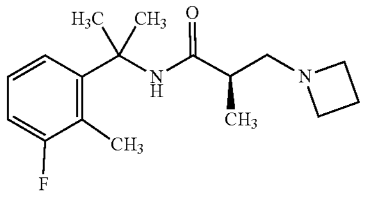 [SMILES: Cc1c(F)cccc1C(C)(C)NC(=O)[C@H](C)CN1CCC1]

and

EXAMPLE 143: (S)-3-(azetidin-1-yl)-N-(2-(3-fluoro-2-methylphenyl)propan-2-yl)-2-methylpropanamide

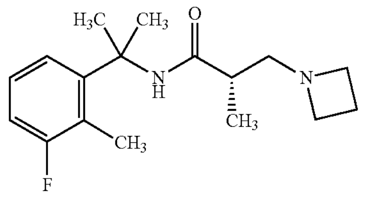 [SMILES: Cc1c(F)cccc1C(C)(C)NC(=O)[C@@H](C)CN1CCC1]

The title enantiomers were prepared like EXAMPLE 138 and EXAMPLE 139 using 2-(3-fluoro-2-methylphenyl)propan-2-amine (1.30 g, 7.77 mmol), but without the final HPLC re-purification. The first eluting compound by SFC was arbitrarily assigned as the (R)-enantiomer and was obtained as a white solid (258 mg, 11%) and the second eluting compound by SFC was arbitrarily assigned as the (S)-enantiomer and was obtained as a white solid (237 mg, 10%). $^1$H NMR (400 MHz, $CD_3OD$) δ ppm 1.05 (d, J=6.8 Hz, 3H), 1.70 (s, 3H), 1.74 (s, 3H), 2.05-2.12 (m, 2H), 2.35-2.43 (m, 5H), 2.65 (br d, J=3.9 Hz, 1H), 3.22-3.31 (m, 4H), 6.92 (t, J=8.6 Hz, 1H), 7.11-7.17 (m, 1H), 7.24 (d, J=8.0 Hz, 1H); ESI-MS m/z $[M+H]^+$ 293.0.

EXAMPLE 144: (R)-3-(azetidin-1-yl)-N-(2-(2-chloro-3-methylphenyl)propan-2-yl)-2-methylpropanamide

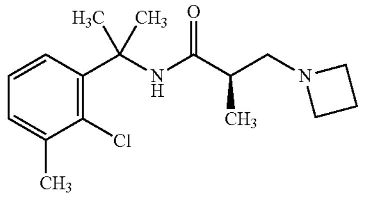 [SMILES: Cc1cccc(C(C)(C)NC(=O)[C@H](C)CN2CCC2)c1Cl]

and

EXAMPLE 145: (S)-3-(azetidin-1-yl)-N-(2-(2-chloro-3-methylphenyl)propan-2-yl)-2-methylpropanamide

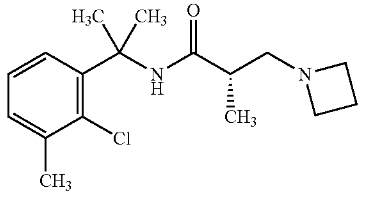 [SMILES: Cc1cccc(C(C)(C)NC(=O)[C@@H](C)CN2CCC2)c1Cl]

The title enantiomers were prepared like EXAMPLE 138 and EXAMPLE 139 using 2-(2-chloro-3-methylphenyl)propan-2-amine (2.00 g, 10.9 mmol), but without the final HPLC re-purification. The first eluting compound by SFC was arbitrarily assigned as the (R)-enantiomer and was obtained as a white solid (324 mg, 10%) and the second eluting compound by SFC was arbitrarily assigned as the (S)-enantiomer and was obtained as a white solid (327 mg, 10%). $^1$H NMR (400 MHz, $CD_3OD$) δ ppm 1.04 (d, J=6.8 Hz, 3H), 1.76 (s, 3H), 1.81 (s, 3H), 2.05-2.13 (m, 2H), 2.35-2.42 (m, 5H), 2.53-2.74 (m, 1H), 3.24-3.27 (m, 1H), 3.25-3.32 (m, 3H), 7.13-7.21 (m, 2H), 7.41 (dd, J=7.3, 2.1 Hz, 1H); ESI-MS m/z $[M+H]^+$ 309.0.

EXAMPLE 146: (R)-3-(azetidin-1-yl)-N-(2-(2-methoxy-3-methylphenyl)propan-2-yl)-2-methylpropanamide

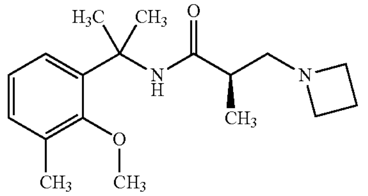 [SMILES: COc1c(C)cccc1C(C)(C)NC(=O)[C@H](C)CN1CCC1]

and

EXAMPLE 147: (S)-3-(azetidin-1-yl)-N-(2-(2-methoxy-3-methylphenyl)propan-2-yl)-2-methylpropanamide

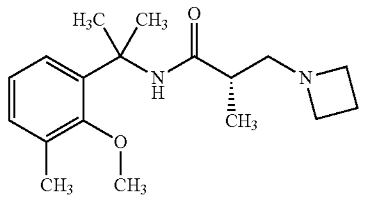 [SMILES: COc1c(C)cccc1C(C)(C)NC(=O)[C@@H](C)CN1CCC1]

The title enantiomers were prepared like EXAMPLE 138 and EXAMPLE 139 using 2-(2-methoxy-3-methylphenyl)propan-2-amine hydrochloride (2.00 g, 9.27 mmol), but without the final HPLC re-purification. The first eluting compound by SFC was arbitrarily assigned as the (R)-enantiomer and was obtained as a tan solid (720 mg, 26%) and the second eluting compound by SFC was arbitrarily assigned as the (S)-enantiomer and was obtained as a tan solid (681 mg, 24%). $^1H$ NMR (400 MHz, $CD_3OD$) δ ppm 1.06 (d, J=6.6 Hz, 3H), 1.71 (s, 3H), 1.76 (s, 3H), 2.08 (quin, J=7.1 Hz, 2H), 2.31 (s, 3H), 2.34-2.45 (m, 2H), 2.54-2.71 (m, 1H), 3.23-3.31 (m, 4H), 3.79 (s, 3H), 6.93 (t, J=7.7 Hz, 1H), 7.07 (dd, J=7.5, 0.9 Hz, 1H), 7.22 (dd, J=7.9, 1.2 Hz, 1H); ESI-MS m/z $[M+H]^+$ 305.2.

EXAMPLE 148: (R)-3-(azetidin-1-yl)-2-methyl-N-(2-(p-tolyl)propan-2-yl)propanamide

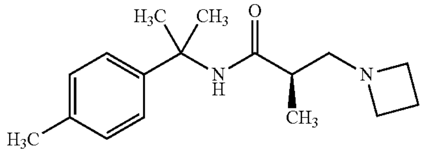 [SMILES: Cc1ccc(C(C)(C)NC(=O)[C@H](C)CN2CCC2)cc1]

and

EXAMPLE 149: (S)-3-(azetidin-1-yl)-2-methyl-N-(2-(p-tolyl)propan-2-yl)propanamide

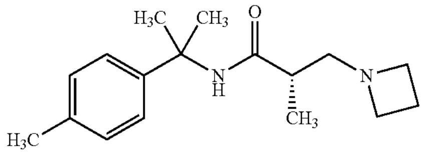 [SMILES: Cc1ccc(C(C)(C)NC(=O)[C@@H](C)CN2CCC2)cc1]

The title enantiomers were prepared like EXAMPLE 138 and EXAMPLE 139 using 2-(p-tolyl)propan-2-amine hydrochloride (2.00 g, 10.8 mmol), but without the final HPLC re-purification. The first eluting compound by SFC was arbitrarily assigned as the (R)-enantiomer and was obtained as a white solid (871 mg, 29%) and the second eluting compound by SFC was arbitrarily assigned as the (S)-enantiomer and was obtained as a white solid (864 mg, 29%). $^1H$ NMR (400 MHz, $CD_3OD$) δ ppm 1.06 (d, J=6.8 Hz, 3H), 1.61 (s, 3H), 1.66 (s, 3H), 2.09 (quin, J=7.1 Hz, 2H), 2.30 (s, 3H), 2.35-2.45 (m, 2H), 2.67 (d, J=3.5 Hz, 1H), 3.23-3.31 (m, 4H), 7.11 (d, J=7.9 Hz, 2H), 7.28 (d, J=7.6 Hz, 2H); ESI-MS m/z $[M+H]^+$ 275.1.

EXAMPLE 150: (R)-3-(azetidin-1-yl)-N-(1-(2-fluorophenyl)cyclopropyl)-2-methylpropanamide

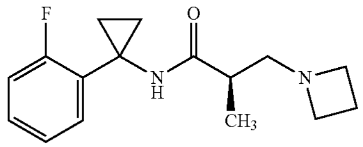 [SMILES: C[C@H](CN1CCC1)C(=O)NC1(c2ccccc2F)CC1]

and

EXAMPLE 151: (S)-3-(azetidin-1-yl)-N-(1-(2-fluorophenyl)cyclopropyl)-2-methylpropanamide

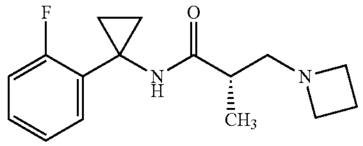 [SMILES: C[C@@H](CN1CCC1)C(=O)NC1(c2ccccc2F)CC1]

The title enantiomers were prepared like EXAMPLE 138 and EXAMPLE 139 using 1-(2-fluorophenyl)cyclopropan-1-amine hydrochloride (0.809 g, 4.31 mmol), but without the final HPLC re-purification. The first eluting compound by SFC was arbitrarily assigned as the (R)-enantiomer and was obtained as a white solid (393 mg, 33%) and the second eluting compound by SFC was arbitrarily assigned as the (S)-enantiomer and was obtained as a white solid (380 mg, 32%). $^1H$ NMR (400 MHz, $CDCl_3$) δ ppm 0.99 (d, J=7.1 Hz, 3H), 1.08-1.19 (m, 4H), 2.08 (quin, J=7.0 Hz, 3H), 2.32 (dd, J=12.0, 3.8 Hz, 1H), 2.48 (br d, J=10.4 Hz, 1H), 3.12-3.25 (m, 4H), 6.97 (t, J=9.4 Hz, 1H), 7.05 (t, J=7.3 Hz, 1H), 7.15-7.21 (m, 1H), 7.57 (td, J=7.7, 1.8 Hz, 1H); ESI-MS m/z $[M+H]^+$ 277.0.

EXAMPLE 152: (R)-3-(azetidin-1-yl)-N-(2-(3-fluorophenyl)propan-2-yl)-2-methylpropanamide

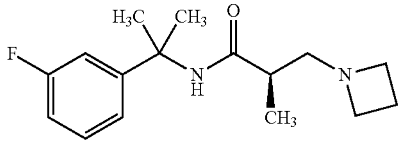 [SMILES: C[C@H](CN1CCC1)C(=O)NC(C)(C)c1cccc(F)c1]

and

EXAMPLE 153: (S)-3-(azetidin-1-yl)-N-(2-(3-fluorophenyl)propan-2-yl)-2-methylpropanamide

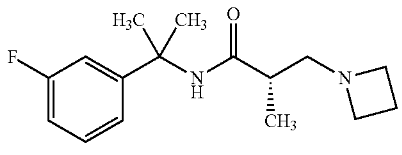 [SMILES: C[C@@H](CN1CCC1)C(=O)NC(C)(C)c1cccc(F)c1]

The title enantiomers were prepared like EXAMPLE 138 and EXAMPLE 139 using 2-(3-fluorophenyl)propan-2-amine hydrochloride (1.00 g, 5.27 mmol), but without the final HPLC re-purification. The first eluting compound by SFC was arbitrarily assigned as the (R)-enantiomer and was obtained as a white solid (0.215 g, 30%) and the second eluting compound by SFC was arbitrarily assigned as (S)-enantiomer and was obtained as a white solid (0.243 g, 34%). $^1$H NMR (400 MHz, $CDCl_3$) δ ppm 1.08 (d, J=7.2 Hz, 3H), 1.69 (d, J=0.9 Hz, 6H), 2.07-2.16 (m, 2H), 2.24 (dqd, J=10.5, 7.0, 3.6 Hz, 1H), 2.47 (dd, J=12.2, 3.6 Hz, 1H), 2.64-2.73 (m, 1H), 3.23-3.40 (m, 4H), 6.91 (tdd, J=8.3, 8.3, 2.6, 1.0 Hz, 1H), 7.09-7.21 (m, 2H), 7.25-7.32 (m, 1H), 8.88 (br s, 1H); ESI-MS m/z $[M+H]^+$ 279.4.

EXAMPLE 154: (R)-3-(azetidin-1-yl)-N-(2-(4-chlorophenyl)propan-2-yl)-2-methylpropanamide

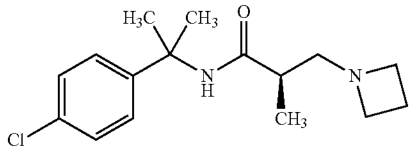 [SMILES: C[C@H](CN1CCC1)C(=O)NC(C)(C)c1ccc(Cl)cc1]

and

EXAMPLE 155: (S)-3-(azetidin-1-yl)-N-(2-(4-chlorophenyl)propan-2-yl)-2-methylpropanamide

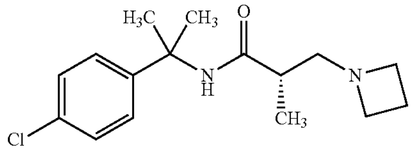 [SMILES: C[C@@H](CN1CCC1)C(=O)NC(C)(C)c1ccc(Cl)cc1]

The title enantiomers were prepared like EXAMPLE 138 and EXAMPLE 139 using 2-(4-chlorophenyl)propan-2-amine hydrochloride (1.00 g, 4.85 mmol), but with HPLC (acid mode) re-purification of the second eluting enantiomer only. The first eluting compound by SFC was arbitrarily assigned as the (R)-enantiomer and was obtained as a white solid (0.157 g, 34%) and the second eluting compound by SFC was arbitrarily assigned as the (S)-enantiomer. The TFA salt of the (S)-enantiomer was obtained as a colorless oil (0.140 g, 30%) and. $^1$H NMR (400 MHz, $CDCl_3$) δ ppm 0.97 (d, J=7.2 Hz, 3H), 1.58 (d, J=1.8 Hz, 6H), 2.00 (quin, J=7.0 Hz, 2H), 2.09 (dqd, J=10.4, 7.1, 3.6 Hz, 1H), 2.35 (dd, J=12.1, 3.7 Hz, 1H), 2.56 (dd, J=12.1, 10.2 Hz, 1H), 3.09-3.27 (m, 4H), 7.15-7.29 (m, 4H), 8.82 (brs, 1H); ESI-MS m/z $[M+H]^+$ 295.3.

EXAMPLE 156: (R)-3-(azetidin-1-yl)-N-(2-(2-fluorophenyl)propan-2-yl)-2-methylpropanamide

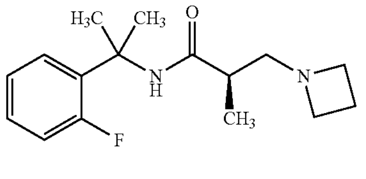 [SMILES: C[C@H](CN1CCC1)C(=O)NC(C)(C)c1ccccc1F]

and

EXAMPLE 157: (S)-3-(azetidin-1-yl)-N-(2-(2-fluorophenyl)propan-2-yl)-2-methylpropanamide

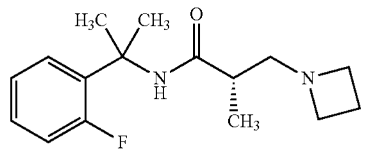 [SMILES: C[C@@H](CN1CCC1)C(=O)NC(C)(C)c1ccccc1F]

The title enantiomers were prepared like EXAMPLE 138 and EXAMPLE 139 using 2-(2-fluorophenyl)propan-2-amine (0.880 g, 5.74 mmol), but without the final HPLC re-purification. The first eluting compound by SFC was arbitrarily assigned as the (R)-enantiomer and was obtained as a white solid (0.328 g, 21%) and the second eluting compound by SFC was arbitrarily assigned as the (S)-enantiomer and was obtained as a white solid (0.259 g, 16%). $^1$H NMR (400 MHz, $CDCl_3$) δ ppm 1.05 (d, J=7.3 Hz, 3H), 1.76 (s, 6H), 2.02-2.24 (m, 3H), 2.42 (dd, J=12.0, 3.8 Hz, 1H), 2.65 (dd, J=12.0, 9.9 Hz, 1H), 3.20-3.34 (m, 4H), 6.99 (ddd, J=12.6, 8.1, 1.4 Hz, 1H), 7.06-7.13 (m, 1H), 7.16-7.24 (m, 1H), 7.40 (td, J=8.2, 1.8 Hz, 1H), 9.05 (br s, 1H); ESI-MS m/z $[M+H]^+$ 279.4.

EXAMPLE 158: 2-((S)-1-methylpyrrolidin-2-yl)-N-(2,2,2-trifluoro-1-(p-tolyl)ethyl)acetamide

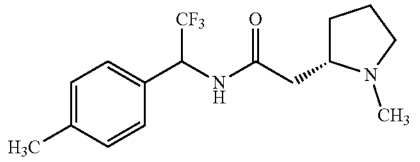 [SMILES: Cc1ccc(C(NC(=O)C[C@@H]2CCCN2C)C(F)(F)F)cc1]

To a solution of 2-((S)-pyrrolidin-2-yl)-N-(2,2,2-trifluoro-1-(p-tolyl)ethyl)acetamide (50 mg, 0.17 mmol) in DCM (1 mL) and MeOH (0.5 mL) were added $Et_3N$ (51 mg, 0.50 mmol) and formaldehyde (41 mg, 0.50 mmol). The mixture was stirred at room temperature for 15 minutes. Next, sodium triacetoxyborohydride (106 mg, 0.499 mmol) was added in one portion. The reaction mixture was stirred at room temperature overnight and then was filtered and purified by preparative HPLC (Phenomenex Gemini® C18, 5 μm, ID 30 mm×150 mm) using a gradient of 20-30% ACN in water (acid mode). The pure fractions were combined and evaporated to afford a TFA salt of the title compound as a clear oil (38 mg, 73%). $^1$H NMR (400 MHz, $CD_3OD$) δ ppm 1.67-1.88 (m, 1H), 1.92-2.19 (m, 2H), 2.28-2.40 (m, 4 H), 2.78-2.99 (m, 5H), 3.08-3.21 (m, 1H), 3.62-3.77 (m, 2H), 5.63-5.74 (m, 1H), 7.19-7.27 (m, 2H), 7.32-7.39 (m, 2H); ESI-MS m/z $[M+H]^+$ 315.4.

EXAMPLE 159: (R)—N-(2-(2-fluorophenyl)propan-2-yl)-2-(1-methylpyrrolidin-2-yl)acetamide

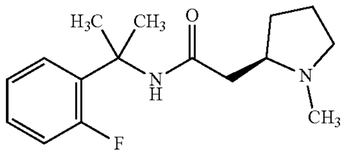 [SMILES: CN1CCC[C@@H]1CC(=O)NC(C)(C)c1ccccc1F]

To a solution of (R)—N-(2-(2-fluorophenyl)propan-2-yl)-2-(pyrrolidin-2-yl)acetamide TFA salt (30 mg, 0.079 mmol) in DCM (793 μL) were added $Et_3N$ (33.2 μL, 0.238 mmol) and aqueous formaldehyde (37 wt %, 17.7 μL, 0.238 mmol). The solution was stirred at room temperature for 30 minutes. Next, sodium triacetoxyborohydride (52.0 mg, 0.238 mmol) was added in one portion. The reaction mixture was stirred at room temperature overnight and then was diluted with MeOH and filtered through a hydrophilic PTFE 0.45 m Millipore® filter. The filtrate was purified by HPLC (Phenomenex Gemini® C18, 5 μm, ID 30 mm×150 mm) using a gradient of 10-100% ACN in water (acid mode). The product-containing fractions were evaporated to give a TFA salt of the title compound as a white solid (30 mg, 96%). $^1H$ NMR (400 MHz, $CDCl_3$) δ ppm 1.75 (app d, J=12.3 Hz, 6H), 1.84-1.96 (m, 1H), 1.97-2.08 (m, 1H), 2.09-2.21 (m, 1H), 2.24-2.36 (m, 1H), 2.64 (dd, J=15.4, 5.4 Hz, 1H), 2.79 (d, J=4.3 Hz, 3H), 2.81-2.91 (m, 1H), 3.10 (dd, J=15.6, 8.0 Hz, 1H), 3.54-3.67 (m, 1H), 3.82-3.93 (m, 1H), 6.98 (ddd, J=12.6, 8.1, 1.4 Hz, 1H), 7.08-7.13 (m, 2H), 7.19-7.25 (m, 1H), 7.38 (td, J=8.1, 1.6 Hz, 1H), 12.02-12.28 (m, 1H); ESI-MS m/z $[M+H]^+$ 279.2.

EXAMPLE 160: (S)—N-(2-(2-fluorophenyl)propan-2-yl)-2-(1-methylpyrrolidin-2-yl)acetamide

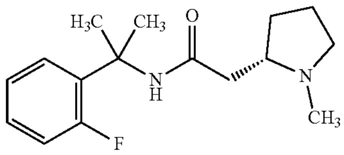 [SMILES: CN1CCC[C@H]1CC(=O)NC(C)(C)c1ccccc1F]

A TFA salt of the title compound was prepared like EXAMPLE 159, using (S)—N-(2-(2-fluorophenyl)propan-2-yl)-2-(pyrrolidin-2-yl)acetamide (150 mg, 0.396 mmol), $Et_3N$ (166 μL, 1.19 mmol), aqueous formaldehyde (37 wt %, 89 μL, 1.19 mmol) and sodium triacetoxyborohydride (260 mg, 1.19 mmol), and was obtained as a white solid (105 mg, 68%). $^1H$ NMR (400 MHz, $CDCl_3$) δ ppm 1.75 (app d, J=13.0 Hz, 6H), 1.85-1.97 (m, 1H), 1.97-2.08 (m, 1H), 2.10-2.22 (m, 1H), 2.24-2.36 (m, 1H), 2.62 (dd, J=15.3, 5.3 Hz, 1H), 2.78 (d, J=3.8 Hz, 3H), 2.80-2.90 (m, 1H), 3.11 (dd, J=15.3, 8.0 Hz, 1H), 3.60 (dq, J=14.4, 7.4 Hz, 1H), 3.83-3.93 (m, 1H), 6.98 (ddd, J=12.6, 8.1, 1.4 Hz, 1H), 7.10 (td, J=7.6, 1.4 Hz, 2H), 7.18-7.25 (m, 1H), 7.38 (td, J=8.2, 1.6 Hz, 1H), 12.34-12.49 (m, 1H); ESI-MS m/z $[M+H]^+$ 279.4.

EXAMPLE 161: 3-(azetidin-1-yl)-N-(2-(2-chloro-3-methylphenyl)propan-2-yl)propanamide

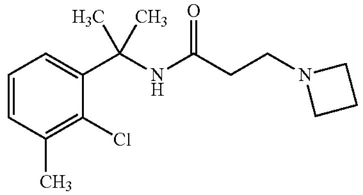 [SMILES: Cc1cccc(C(C)(C)NC(=O)CCN2CCC2)c1Cl]

To a mixture of 2-(2-chloro-3-methylphenyl)propan-2-amine hydrochloride (0.080 g, 0.36 mmol), lithium 3-(azetidin-1-yl)propanoate (0.049 g, 0.36 mmol) and $Et_3N$ (0.203 mL, 1.45 mmol) in DMF (3 mL) was added HATU (0.207 g, 0.545 mmol).The reaction mixture was stirred at RT overnight and then directly purified by preparative HPLC (Phenomenex Gemini® C18, 5 μm, ID 30 mm×150 mm) using a gradient of 10-50% ACN in water (acid mode) to give a TFA salt of the title compound as a clear oil (0.061 g, 57%). $^1H$ NMR (400 MHz, $CD_3OD$) δ ppm 1.76 (s, 6H), 2.31-2.40 (m, 4H), 2.51-2.60 (m, 3H), 3.33-3.37 (m, 2H), 3.98-4.07 (m, 2H), 4.12-4.20 (m, 2H), 7.14-7.21 (m, 2H), 7.40 (dd, J=6.9, 2.6 Hz, 1H); ESI-MS m/z $[M+H]^+$ 295.3.

EXAMPLE 162: 3-(azetidin-1-yl)-N-(2-(m-tolyl)propan-2-yl)propanamide

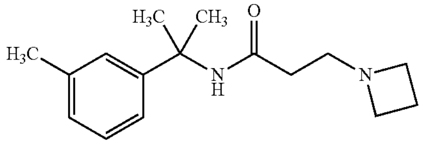 [SMILES: Cc1cccc(C(C)(C)NC(=O)CCN2CCC2)c1]

To a mixture of 2-(m-tolyl)propan-2-amine hydrochloride (0.058 g, 0.39 mmol), lithium 3-(azetidin-1-yl)propanoate (0.050 g, 0.39 mmol) and $Et_3N$ (0.216 mL, 1.55 mmol) in DMF (3 mL) was added HATU (0.221 g, 0.581 mmol). The reaction mixture was stirred at room temperature overnight and then was directly purified by preparative HPLC (Phenomenex Gemini® C18, 5 μm, ID 30 mm×150 mm) using a gradient of 10-50% ACN in water (acid mode) to give the TFA salt of the title compound as a white solid (0.088 g, 63%). $^1H$ NMR (400 MHz, $CD_3OD$) δ ppm 1.63 (s, 6H), 2.26-2.41 (m, 4H), 2.43-2.59 (m, 3H), 3.31-3.37 (m, 2H), 3.93-4.04 (m, 2H), 4.09-4.21 (m, 2H), 7.01 (d, J=6.2 Hz, 1H), 7.12-7.22 (m, 3H); ESI-MS m/z $[M+H]^+$ 261.4.

EXAMPLE 163: 3-(azetidin-1-yl)-N-(2-(3-fluorophenyl)propan-2-yl)propanamide

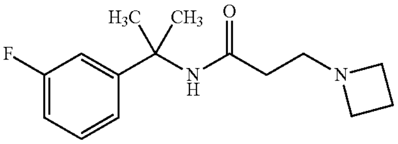 [SMILES: CC(C)(NC(=O)CCN1CCC1)c1cccc(F)c1]

A TFA salt of the title compound was prepared like EXAMPLE 162, using 2-(3-fluorophenyl)propan-2-amine (0.059 g. 0.39 mmol), and was obtained as a yellow oil (0.034 g, 39%). $^1$H NMR (400 MHz, $CD_3OD$) δ ppm 1.64 (s, 6H), 2.32-2.45 (m, 1H), 2.49-2.65 (m, 3H), 3.35-3.41 (m, 2H), 3.99-4.10 (m, 2H), 4.14-4.24 (m, 2H), 6.93 (t, J=8.3 Hz, 1H), 7.11 (d, J=10.9 Hz, 1H), 7.20 (d, J=7.6 Hz, 1H), 7.32 (td, J=8.0, 6.1 Hz, 1H); ESI-MS m/z $[M+H]^+$ 265.4.

EXAMPLE 164: 3-(azetidin-1-yl)-N-(2-(3-chlorophenyl)propan-2-yl)propanamide

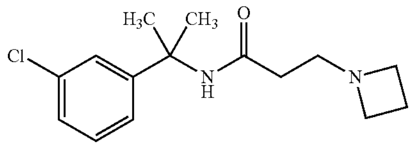 [SMILES: CC(C)(NC(=O)CCN1CCC1)c1cccc(Cl)c1]

A TFA salt of the title compound was prepared like EXAMPLE 162, using 2-(3-chlorophenyl)propan-2-amine (0.080 g, 0.39 mmol), and was obtained as a yellow oil (0.042 g, 34%). $^1$H NMR (400 MHz, $CD_3OD$) δ ppm 1.63 (s, 6H), 2.36 (dtt, J=11.8, 9.6, 4.9 Hz, 1H), 2.49-2.65 (m, 3H), 3.34-3.40 (m, 2H), 3.99-4.09 (m, 2H), 4.13-4.24 (m, 2H), 7.18-7.22 (m, 1H), 7.26-7.34 (m, 2H), 7.38 (t, J=1.6 Hz, 1H); ESI-MS m/z $[M+H]^+$ 281.3.

EXAMPLE 165: 3-(azetidin-1-yl)-N-(2-(4-chlorophenyl)propan-2-yl)propanamide

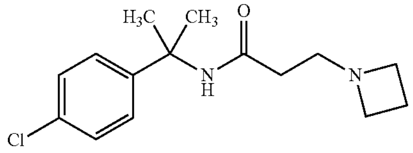 [SMILES: CC(C)(NC(=O)CCN1CCC1)c1ccc(Cl)cc1]

A TFA salt of the title compound was prepared like EXAMPLE 162, using 2-(4-chlorophenyl)propan-2-amine (0.080 g, 0.39 mmol), and was obtained as a yellow oil (0.022 g, 18%). $^1$H NMR (400 MHz, $CD_3OD$) δ ppm 1.63 (s, 6H), 2.32-2.44 (m, 1H), 2.49-2.63 (m, 3H), 3.37 (t, J=6.6 Hz, 2H), 3.99-4.10 (m, 2H), 4.13-4.24 (m, 2H), 7.25-7.33 (m, 2H), 7.33-7.39 (m, 2H); ESI-MS m/z $[M+H]^+$ 281.3.

EXAMPLE 166: 3-(azetidin-1-yl)-N-(2-(3-fluoro-2-methylphenyl)propan-2-yl)propanamide

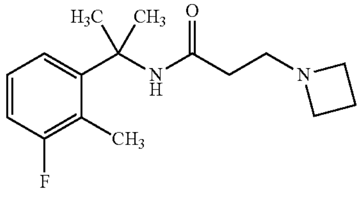 [SMILES: Cc1c(F)cccc1C(C)(C)NC(=O)CCN1CCC1]

A TFA salt of the title compound was prepared like EXAMPLE 162, using 2-(3-fluoro-2-methylphenyl)propan-2-amine hydrochloride (0.079 g, 0.39 mmol), and was obtained as a yellow oil (4.9 mg, 5%). $^1$H NMR (400 MHz, $CD_3OD$) δ ppm 1.71 (s, 6H), 2.34 (d, J=3.0 Hz, 4H), 2.48-2.60 (m, 3H), 3.34-3.38 (m, 2H), 4.00-4.10 (m, 2H), 4.13-4.23 (m, 2H), 6.93 (t, J=8.7 Hz, 1H), 7.15 (td, J=7.9, 6.3 Hz, 1H), 7.20-7.26 (m, 1H); ESI-MS m/z $[M+H]^+$ 279.4.

EXAMPLE 167: 3-(azetidin-1-yl)-N-(1-(2,5-difluorophenyl)-2,2-difluoroethyl)propanamide

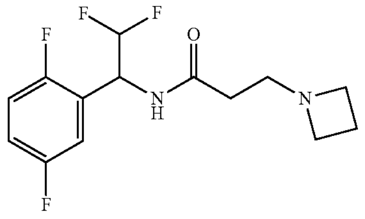 [SMILES: O=C(CCN1CCC1)NC(c1cc(F)ccc1F)C(F)F]

STEP A: N-(1-(2,5-difluorophenyl)-2,2-difluoroethyl)acrylamide

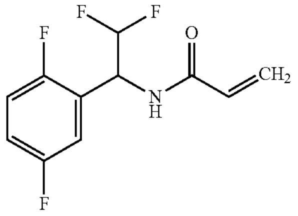 [SMILES: C=CC(=O)NC(c1cc(F)ccc1F)C(F)F]

To a mixture of acrylic acid (0.355 mL, 5.18 mmol), 1-(2,5-difluorophenyl)-2,2-difluoroethan-1-amine (1.00 g, 5.18 mmol) and DIPEA (3.62 mL, 20.7 mmol) in DMF (20 mL) was added HATU (2.95 g, 7.77 mmol). The reaction mixture was stirred at RT overnight and then was diluted with water (10 mL) and extracted with EtOAc. The organic layers were concentrated and purified by automated flash silica column chromatography, using a gradient of 0-60% EtOAc in heptanes, to give the title compound (1.10 g, 86%). ESI-MS $[M+H]^+$ 248.3.

STEP B: 3-(azetidin-1-yl)-N-(1-(2,5-difluorophenyl)-2,2-difluoroethyl)propanamide A mixture of N-(1-(2,5-difluorophenyl)-2,2-difluoroethyl)acrylamide (1.10 g, 4.45 mmol) and azetidine (0.600 mL, 8.90 mmol) in MeOH (5 mL) and water (5 mL) was heated at 100° C. overnight. The reaction mixture was then concentrated under reduced pressure and purified by automated flash silica column chromatography, using a gradient of 0-40% EtOAc (with 2% $Et_3N$) in heptanes to give the title compound as a white solid (0.789 g, 58%). $^1$H NMR (400 MHz, $CD_3OD$) δ ppm 2.07 (quin, J=7.2 Hz, 2H), 2.35 (td, J=7.1, 1.8 Hz, 2H), 2.71 (td, J=7.1, 2.1 Hz, 2H), 3.20-3.28 (m, 4H), 5.69 (td, J=14.1, 3.1 Hz, 1H), 5.99 (d, J=3.0 Hz, 1H), 6.27 (d, J=3.0 Hz, 1H), 6.13 (d, J=3.1 Hz, 1H), 7.09-7.20 (m, 2H), 7.27 (ddd, J=8.8, 5.6, 3.0 Hz, 1H); ESI-MS $[M+H]^+$ 305.3.

EXAMPLE 168: (S)-3-(azetidin-1-yl)-N-(1-(2,5-difluorophenyl)-2,2-difluoroethyl)propanamide

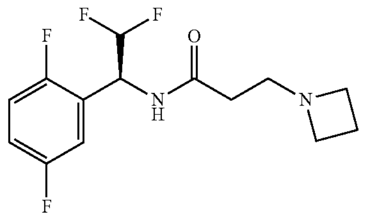 [SMILES: O=C(CCN1CCC1)N[C@@H](c1cc(F)ccc1F)C(F)F]

and

EXAMPLE 169: (R)-3-(azetidin-1-yl)-N-(1-(2,5-difluorophenyl)-2,2-difluoroethyl)propanamide

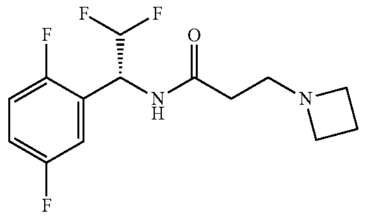 [SMILES: O=C(CCN1CCC1)N[C@H](c1cc(F)ccc1F)C(F)F]

The title enantiomers of 3-(azetidin-1-yl)-N-(1-(2,5-difluorophenyl)-2,2-difluoroethyl)propanamide (EXAMPLE 167) were separated by preparative SFC (ChiralPak AS, 5 μm, ID 30 mm×250 mm) and then purified by preparative HPLC (Phenomenex Gemini® C18, 5 μm, ID 30 mm×150 mm) using a gradient of 20-80% water/ACN in water (basic mode). The first eluting compound by SFC was arbitrarily assigned as the (S)-enantiomer (13.3 mg) and the second eluting compound by SFC was arbitrarily assigned as the (R)-enantiomer (31.2 mg). $^1$H NMR (400 MHz, $CD_3OD$) δ ppm 1.98 (quin, J=7.2 Hz, 2H), 2.23 (td, J=7.2, 2.0 Hz, 2H), 2.60 (td, J=7.2, 1.8 Hz, 2H), 3.10-3.18 (m, 4H), 5.55 (td, J=14.1, 3.1 Hz, 1H), 5.85-6.18 (m, 1H), 6.96-7.22 (m, 3H); ESI-MS $[M+H]^+$ 305.30.

EXAMPLE 170: 3-(azetidin-1-yl)-N-(2-(3-fluoro-2-methoxyphenyl)propan-2-yl)-2-methylpropanamide

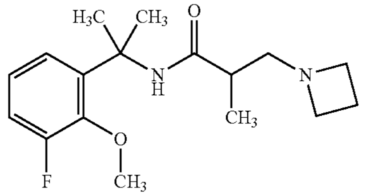 [SMILES: COc1c(F)cccc1C(C)(C)NC(=O)C(C)CN1CCC1]

The title compound was prepared like EXAMPLE 167, using 2-(3-fluoro-2-methoxyphenyl)propan-2-amine hydrochloride (0.600 g, 2.73 mmol), methacrylic acid (0.235 mL, 2.73 mmol), DIPEA (1.91 mL, 10.9 mmol) and HATU (1.56 g, 4.10 mmol) in DMF and a gradient of 40-100% EtOAc in heptanes for the purification in STEP B, and was obtained as a white solid (520 mg, 62% over two steps). $^1$H NMR (400 MHz, $CD_3OD$) δ ppm 1.06 (d, J=6.6 Hz, 3H), 1.70 (s, 3H), 1.75 (s, 3H), 2.09 (quin, J=7.1 Hz, 2H), 2.36-2.44 (m, 2H), 2.62-2.70 (m, 1H), 3.24-3.31 (m, 4H), 3.95 (d, J=2.5 Hz, 3H), 6.94-7.04 (m, 2H), 7.17 (d, J=7.4 Hz, 1H); ESI-MS $[M+H]^+$ 309.4.

EXAMPLE 171: (R)-3-(azetidin-1-yl)-N-(2-(3-fluoro-2-methoxyphenyl)propan-2-yl)-2-methylpropanamide

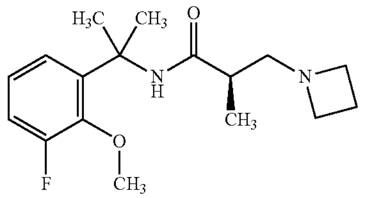 [SMILES: COc1c(F)cccc1C(C)(C)NC(=O)[C@H](C)CN1CCC1]

and

EXAMPLE 172: (S)-3-(azetidin-1-yl)-N-(2-(3-fluoro-2-methoxyphenyl)propan-2-yl)-2-methylpropanamide

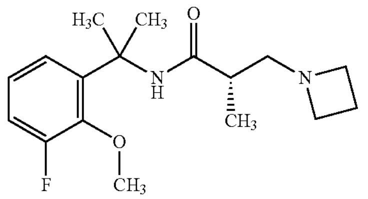 [SMILES: COc1c(F)cccc1C(C)(C)NC(=O)[C@@H](C)CN1CCC1]

The title enantiomers of 3-(azetidin-1-yl)-N-(2-(3-fluoro-2-methoxyphenyl)propan-2-yl)-2-methylpropanamide (EXAMPLE 170, 520 mg, 1.69 mmol) were separated by preparative SFC (ChiralPak IC, 5 μm, ID 30 mm×250 mm) using a mobile phase of 30% EtOH (with 0.1% $NH_4OH$) in $CO_2$. The first eluting compound was arbitrarily assigned as the (R)-enantiomer (137.1 mg, 26%) and the second eluting compound was arbitrarily assigned as the (S)-enantiomer (132.1 mg, 25%). ESI-MS $[M+H]^+$ 309.2.

EXAMPLE 173: 3-(azetidin-1-yl)-N-(2-fluoro-1-(p-tolyl)ethyl)propanamide

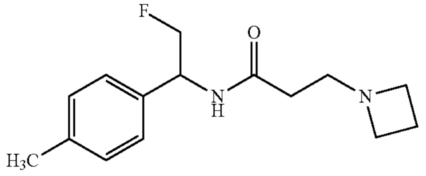 [SMILES: Cc1ccc(C(CF)NC(=O)CCN2CCC2)cc1]

The title compound was prepared like EXAMPLE 167, using 2-fluoro-1-(p-tolyl)ethan-1-amine hydrochloride (1.00 g, 5.27 mmol), acrylic acid (0.362 mL, 5.27 mmol), DIPEA (3.68 mL, 21.1 mmol) and HATU (2.41 g, 6.33 mmol) in DMA (20 mL) and a gradient of 40-100% EtOAc in heptanes for the purification in STEP B, and was obtained as a white solid (221 mg, 16% over two steps). $^1$H NMR (400 MHz, $CD_3OD$) δ ppm 2.10 (quin, J=7.2 Hz, 2H), 2.28-2.38 (m, 5H), 2.73 (td, J=7.3, 1.6 Hz, 2H), 3.24-3.31 (m, 4H), 4.45-4.54 (m, 1H), 4.57-4.66 (m, 1H), 5.13-5.23 (m, 1H), 7.15-7.27 (m, 4H); ESI-MS $[M+H]^+$ 263.4.

EXAMPLE 174: (S)-3-(azetidin-1-yl)-N-(2-fluoro-1-(p-tolyl)ethyl)propanamide

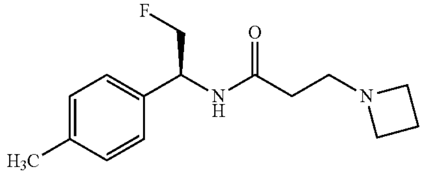 [SMILES: Cc1ccc([C@@H](CF)NC(=O)CCN2CCC2)cc1]

and

EXAMPLE 175: (R)-3-(azetidin-1-yl)-N-(2-fluoro-1-(p-tolyl)ethyl)propanamide

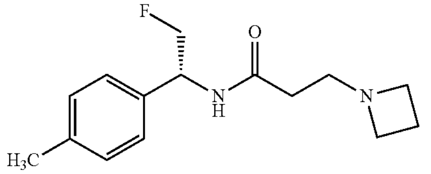

The title enantiomers of 3-(azetidin-1-yl)-N-(2-fluoro-1-(p-tolyl)ethyl)propanamide (EXAMPLE 173, 221 mg, 0.836 mmol) were separated by preparative SFC (Whelk O1(S,S), 5 μm, ID 30 mm×250 mm) using a mobile phase of 40% EtOH (with 0.1% $NH_4OH$) in $CO_2$. The first eluting compound was arbitrarily assigned as the (S)-enantiomer (88.5 mg, 40%) and the second eluting compound was arbitrarily assigned as the (R)-enantiomer (86.7 mg, 39%). ESI-MS $[M+H]^+$ 265.0.

EXAMPLE 176: (S)—N-(1-(((3-methylpyridin-2-yl)oxy)methyl)cyclopropyl)-2-((S)-1-methylpyrrolidin-2-yl)propanamide

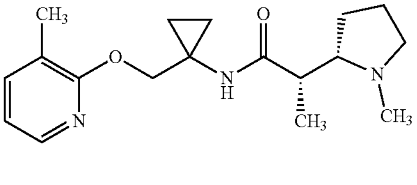 [SMILES: Cc1cccnc1OCC1(NC(=O)[C@@H](C)[C@@H]2CCCN2C)CC1]

and

EXAMPLE 177: (R)—N-(1-(((3-methylpyridin-2-yl)oxy)methyl)cyclopropyl)-2-((R)-1-methylpyrrolidin-2-yl)propanamide

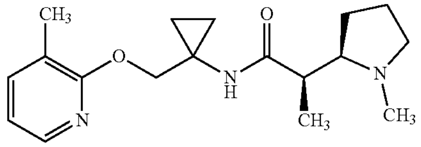 [SMILES: Cc1cccnc1OCC1(NC(=O)[C@H](C)[C@H]2CCCN2C)CC1]

To a round bottom flask containing 2-(1-methylpyrrolidin-2-yl)propanoic acid hydrochloride (0.100 g, 516 μmol) and 1-(((3-methylpyridin-2-yl)oxy)methyl)cyclopropanamine (92.0 mg, 516 μmol) in ACN (2 mL) was added DIPEA (450 μL, 2.58 mmol) and T3P (50% in EtOAc, 461 μL, 775 μmol). The reaction mixture was stirred at 60° C. for 16 hours and then was diluted with water (15 mL) and extracted with EtOAc (30 mL). The organic layer was dried over $Na_2SO_4$, filtered and concentrated in vacuo. The product was purified by preparative HPLC (Xtimate™ C18, 10 μm, ID 50 mm×250 mm) using a gradient of 27-57% water (with 0.04% $NH_4OH$+10 mM $NH_4HCO_3$) in ACN. The product-containing fractions were combined and lyophilized to afford a white semi-solid (22.0 mg, 12%). The title enantiomers were separated by preparative SFC (Daicel ChiralCel OD-H, 5 μm, ID 30 mm×250 mm) using a mobile phase of 25% MeOH (with 0.1% $NH_4OH$) in $CO_2$ to give the title enantiomers whose stereochemical configurations were arbitrarily assigned. $^1$H NMR (400 MHz, $CDCl_3$) δ ppm 0.87 (br d, J=9.0 Hz, 2H), 0.94-1.00 (m, 2H), 1.14 (d, J=7.3 Hz, 3H), 1.53-1.60 (m, 1H), 1.64-1.68 (m, 1H), 1.90-1.96 (m, 2H), 2.21 (s, 3H), 2.25-2.38 (m, 5H), 2.46-2.56 (m, 1H), 3.07 (ddd, J=9.7, 6.3, 3.8 Hz, 1H), 4.42 (q, J=11.3 Hz, 2H), 6.76 (dd, J=7.2, 5.1 Hz, 1H), 7.37 (dd, J=7.2, 0.9 Hz, 1H), 7.52 (br s, 1H), 7.91-7.96 (m, 1H); ESI-MS m/z $[M+H]^+$ 318.3.

EXAMPLE 178: (S)-2-(azetidin-1-ylmethyl)-N—((S)-2,2-difluoro-1-phenylethyl)-3-methylbutanamide

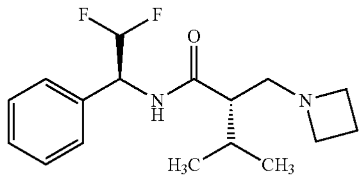 [SMILES: CC(C)[C@@H](CN1CCC1)C(=O)N[C@@H](c1ccccc1)C(F)F]

To a suspension of (S)-2-(azetidin-1-ylmethyl)-3-methylbutanoic acid, lithium salt (100 mg, 0.561 mmol) and (S)-2,2-difluoro-1-phenylethan-1-amine hydrochloride (130 mg, 0.673 mmol) in DMA (4 mL) was added $Et_3N$ (235 μL, 1.68 mmol) followed by HATU (256 mg, 0.673 mmol). The reaction mixture was stirred at RT for 3 hours and then was diluted with EtOAc (10 mL) and washed with water (2×5 mL) followed by brine (5 mL). The organic phase was collected, dried over sodium sulfate and concentrated to an oil, which was purified by preparative HPLC (Phenomenex Gemini® C18, 5 μm, ID 30 mm×150 mm) using a gradient of 30-100% water/ACN in water (basic mode). The pure fractions were combined and lyophilized to afford the title compound as a white solid (48.1 mg, 28%). $^1$H NMR (400 MHz, $CD_3CN$) δ ppm 0.85 (dd, J=6.6, 1.4 Hz, 6H), 1.95-2.06 (m, 4H), 2.43 (dd, J=11.9, 3.3 Hz, 1H), 2.70 (dd, J=11.9, 10.0 Hz, 1H), 3.09-3.26 (m, 4H), 5.34 (tdd, J=15.1, 8.8, 2.9 Hz, 1H), 5.88-6.25 (m, 1H), 7.31-7.50 (m, 5H), 8.63 (br d, J=7.3 Hz, 1H); ESI-MS m/z $[M+H]^+$ 311.4.

EXAMPLE 179: (S)-2-(azetidin-1-ylmethyl)-N—((R)-2,2-difluoro-1-phenylethyl)-3-methylbutanamide

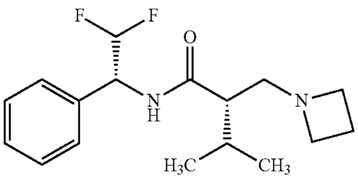 [SMILES: CC(C)[C@@H](CN1CCC1)C(=O)N[C@H](c1ccccc1)C(F)F]

The title compound was prepared like EXAMPLE 178, using (R)-2,2-difluoro-1-phenylethan-1-amine hydrochloride (130 mg, 0.673 mmol), (S)-2-(azetidin-1-ylmethyl)-3-methylbutanoic acid lithium salt (100 mg, 0.561 mmol), HATU (256 mg, 0.673 mmol) and $Et_3N$ (0.235 mL, 1.68 mmol) in DMA (1.87 mL), and was obtained as a white solid (83 mg, 48%). $^1$H NMR (400 MHz, $CD_3CN$) δ ppm 0.90 (dd, J=10.7, 6.7 Hz, 6H), 1.94-1.98 (m, 3H), 2.00-2.05 (m, 1H), 2.41 (dd, J=11.7, 3.51 Hz, 1H), 2.65 (dd, J=11.7, 10.3 Hz, 1H), 3.01-3.10 (m, 2H), 3.12-3.23 (m, 2H), 5.27-5.50 (m, 1H), 5.92-6.28 (m, 1H), 7.31-7.50 (m, 5H), 8.34 (br d, J=7.5 Hz, 1H); ESI-MS m/z $[M+H]^+$ 311.4.

EXAMPLE 180: (S)-2-(azetidin-1-ylmethyl)-N—((R)-2,2-difluoro-1-phenylethyl)butanamide

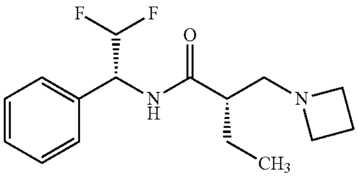 [SMILES: CC[C@@H](CN1CCC1)C(=O)N[C@H](c1ccccc1)C(F)F]

The title compound was prepared like EXAMPLE 178, using (R)-2,2-difluoro-1-phenylethan-1-amine hydrochloride (248 mg, 1.28 mmol), (S)-2-(azetidin-1-ylmethyl)butanoic acid lithium salt (210 mg, 1.28 mmol), HATU (584 mg, 1.54 mmol) and $Et_3N$ (0.535 mL, 3.84 mmol) in DMA (6.4 mL), and was obtained as a white solid (171 mg, 45%). $^1$H NMR (400 MHz, $CD_3CN$) δ ppm 0.90 (t, J=7.5 Hz, 3H), 1.39-1.52 (m, 1H), 1.54-1.67 (m, 1H), 1.99-2.07 (m, 2H), 2.16-2.23 (m, 1H), 2.40 (dd, J=11.8, 4.1 Hz, 1H), 2.62 (dd, J=11.9, 9.9 Hz, 1H), 3.10-3.17 (m, 2H), 3.20-3.27 (m, 2H), 5.40 (dddd, J=15.6, 14.6, 8.9, 2.8 Hz, 1H), 5.92-6.30 (m, 1H), 7.31-7.55 (m, 5H), 8.65 (br d, J=6.9 Hz, 1H); ESI-MS m/z $[M+H]^+$ 297.4.

EXAMPLE 181: (R)-3-(azetidin-1-yl)-N—((R)-2,2-difluoro-1-phenylethyl)-2-methylpropanamide

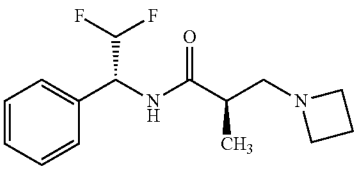 [SMILES: C[C@H](CN1CCC1)C(=O)N[C@H](c1ccccc1)C(F)F]

The title compound was prepared like EXAMPLE 178, using (R)-2,2-difluoro-1-phenylethan-1-amine hydrochloride (284 mg, 1.467 mmol), (R)-3-(azetidin-1-yl)-2-methylpropanoic acid (arbitrarily assigned, 210 mg, 1.47 mmol), HATU (669 mg, 1.76 mmol) and $Et_3N$ (613 μL, 4.40 mmol) in DMA (7.33 mL), and was obtained as a tan solid (186 mg, 45%). $^1$H NMR (400 MHz, $CD_3CN$) δ ppm 1.01 (d, J=7.0 Hz, 3H), 2.05 (quin, J=7.0 Hz, 2H), 2.26-2.43 (m, 2H), 2.52-2.61 (m, 1H), 3.14-3.21 (m, 2H), 3.23-3.31 (m, 2H), 5.33 (tdd, J=15.1, 8.8, 2.8 Hz, 1H), 5.90-6.27 (m, 1H), 7.30-7.48 (m, 5H), 9.37 (br d, J=5.9 Hz, 1H); ESI-MS m/z $[M+H]^+$ 283.3.

EXAMPLE 182: (R)-2-(azetidin-1-ylmethyl)-N-(2-(4-fluorophenyl)propan-2-yl)butanamide

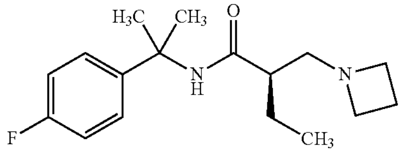 [SMILES: CC[C@H](CN1CCC1)C(=O)NC(C)(C)c1ccc(F)cc1]

and

EXAMPLE 183: (S)-2-(azetidin-1-ylmethyl)-N-(2-(4-fluorophenyl)propan-2-yl)butanamide

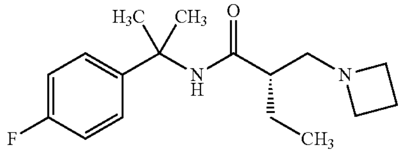 [SMILES: CC[C@@H](CN1CCC1)C(=O)NC(C)(C)c1ccc(F)cc1]

To a suspension of 2-(4-fluorophenyl)propan-2-amine (0.883 g, 5.76 mmol) and 2-(azetidin-1-ylmethyl)butanoic acid (1.13 g, 5.24 mmol) in DMA (26.2 mL) was added $Et_3N$ (1.46 mL, 10.5 mmol) followed by HATU (2.39 g, 6.29 mmol). The reaction mixture was stirred at RT for 3 hours and then was diluted with isopropyl acetate (100 mL) and washed with water (100 mL) followed by brine (50 mL). The organic phase was collected, dried over sodium sulfate and concentrated to an oil, which was purified by preparative HPLC (Phenomenex Gemini® C18, 5 μm, ID 30 mm×150 mm) using a gradient of 10-100% water/ACN in water (basic mode). The pure fractions were combined and lyophilized to afford a mixture of the title compounds as a white solid (0.704 g). The title enantiomers were separated by preparative SFC (Daicel ChiralPak IC, 5 μm, ID 30 mm×250 mm) using isopropanol (with 0.1% $NH_4OH$) in $CO_2$ as the mobile phase. The first eluting compound was arbitrarily assigned as the (R)-enantiomer and was obtained as a white solid (0.229 g, 36%) and the second eluting compound was arbitrarily assigned as the (S)-enantiomer and was obtained as a white solid (0.266 g, 42%). $^1$H NMR (400 MHz, $CDCl_3$) δ ppm 0.89 (t, J=7.4 Hz, 3H), 1.35-1.54 (m, 1H), 1.68 (m, 7H), 1.92-2.13 (m, 3H), 2.45 (dd, J=12.2, 3.6 Hz, 1H), 2.68 (dd, J=12.2, 9.5 Hz, 1H), 3.17-3.31 (m, 4H), 6.98 (t, J=8.7 Hz, 2H), 7.32-7.45 (m, 2H), 8.25 (br s, 1H); ESI-MS m/z $[M+H]^+$ 293.4.

EXAMPLE 184: (R)-2-(azetidin-1-ylmethyl)-N-(2-(3-fluorophenyl)propan-2-yl)butanamide

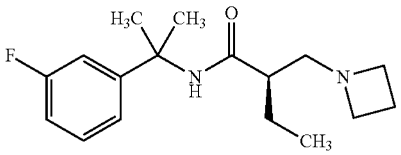 [SMILES: CC[C@H](CN1CCC1)C(=O)NC(C)(C)c1cccc(F)c1]

and

EXAMPLE 185: (S)-2-(azetidin-1-ylmethyl)-N-(2-(3-fluorophenyl)propan-2-yl)butanamide

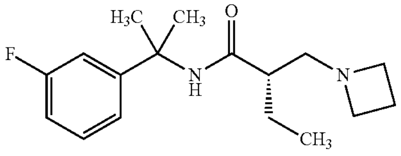 [SMILES: CC[C@@H](CN1CCC1)C(=O)NC(C)(C)c1cccc(F)c1]

The title enantiomers were prepared like EXAMPLE 182 and EXAMPLE 183, using 2-(3-fluorophenyl)propan-2-amine (0.965 g, 6.30 mmol), 2-(azetidin-1-ylmethyl)butanoic acid (0.900 g, 5.72 mmol), HATU (2.61 g, 6.87 mmol) and $Et_3N$ (2.39 mL, 17.2 mmol) in DMA (6 mL). The first eluting compound was arbitrarily assigned as the (R)-enantiomer and was obtained as a white solid (308 mg, 18%) and the second eluting compound was arbitrarily assigned as the (S)-enantiomer and was obtained as a white solid (315 mg, 19%). $^1$H NMR (400 MHz, $CD_3CN$) δ ppm 0.86 (t, J=7.5 Hz, 3H), 1.32-1.51 (m, 2H), 1.52-1.66 (m, 6H), 2.03 (quin, J=7.0 Hz, 3H), 2.30 (dd, J=11.7, 4.5 Hz, 1H), 2.57 (dd, J=11.7, 9.7 Hz, 1H), 3.08-3.28 (m, 4H), 6.80-6.99 (m, 1H), 7.18-7.35 (m, 3H), 7.50 (br s, 1H); ESI-MS m/z $[M+H]^+$ 293.4.

EXAMPLE 186: (R)-2-(azetidin-1-ylmethyl)-N-(2-(p-tolyl)propan-2-yl)butanamide

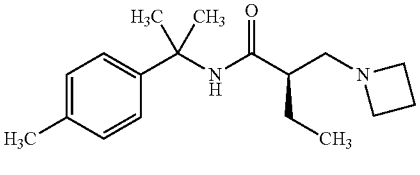 [SMILES: CC[C@H](CN1CCC1)C(=O)NC(C)(C)c1ccc(C)cc1]

and

EXAMPLE 187: (S)-2-(azetidin-1-ylmethyl)-N-(2-(p-tolyl)propan-2-yl)butanamide

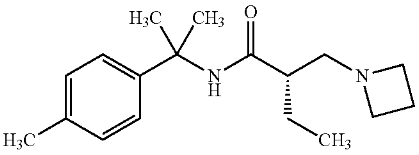 [SMILES: CC[C@@H](CN1CCC1)C(=O)NC(C)(C)c1ccc(C)cc1]

The title enantiomers were prepared like EXAMPLE 182 and 183, using 2-(p-tolyl)propan-2-amine hydrochloride (1.42 g, 7.65 mmol), 2-(azetidin-1-ylmethyl)butanoic acid (1.50 g, 6.96 mmol), HATU (3.17 g, 8.35 mmol) and $Et_3N$ (2.91 mL, 20.9 mmol) in DMA (34.8 mL). The first eluting compound was arbitrarily assigned as the (R)-enantiomer and was obtained as a white solid (347 mg, 17%) and the second eluting compound was arbitrarily assigned as the (S)-enantiomer and was obtained as a white solid (298 mg, 15%). $^1$H NMR (400 MHz, $CD_3CN$) δ ppm 0.86 (t, J=7.4 Hz, 3H), 1.33-1.51 (m, 2H), 1.56 (s, 3H), 1.60 (s, 3H), 1.97-2.07 (m, 3H), 2.26-2.35 (m, 4H), 2.57 (dd, J=11.7, 9.2 Hz, 1H), 3.09-3.28 (m, 4H), 7.05-7.17 (m, 2H), 7.33 (d, J=8.3 Hz, 2H), 7.53 (br s, 1H); ESI-MS m/z $[M+H]^+$ 289.4.

EXAMPLE 188: (S)-2-(azetidin-1-ylmethyl)-N—((R)-2,2-difluoro-1-(2-methoxyphenyl)ethyl)-3-methylbutanamide

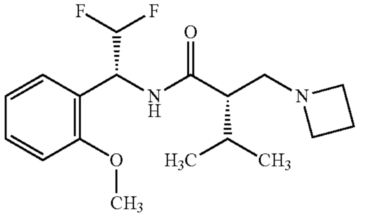 [SMILES: COc1ccccc1[C@@H](NC(=O)[C@H](CN1CCC1)C(C)C)C(F)F]

To a solution of (R)-2,2-difluoro-1-(2-methoxyphenyl)ethan-1-amine hydrochloride (55.9 mg, 0.250 mmol) and (S)-2-(azetidin-1-ylmethyl)-3-methylbutanoic acid (42.8 mg, 0.250 mmol) in DMA (1.25 mL) were added DIPEA (131 μL, 0.750 mmol) and HATU (114 mg, 0.300 mmol). The reaction mixture was stirred at room temperature overnight and then was diluted with water and extracted with EtOAc. The organic phase was washed with saturated aqueous NaCl, dried with $Na_2SO_4$, filtered and concentrated under reduced pressure. The residue was purified by automated flash silica column chromatography using a gradient of 0-100% EtOAc (with 2% $Et_3N$) in heptanes. The product-containing fractions were taken up in methanol and filtered through a hydrophilic PTFE 0.45 m Millipore® filter, rinsing with methanol. The filtrate was purified by preparative HPLC (Phenomenex Gemini® C18, 5 μm, ID 30 mm×150 mm) using a gradient of 10-70% water/ACN in water (basic mode). The pure fractions were evaporated and lyophilized to afford the title compound as a white solid (42.0 mg, 49%). $^1$H NMR (400 MHz, $CD_3OD$) δ ppm 0.98 (dd, J=6.8, 4.5 Hz, 6H), 1.75-1.87 (m, 1H), 1.92 (quin, J=7.1 Hz, 2H), 2.17 (ddd, J=10.3, 7.8, 3.5 Hz, 1H), 2.55 (dd, J=11.9, 3.5 Hz, 1H), 2.71 (dd, J=11.9, 10.4 Hz, 1H), 3.04 (q, J=7.0 Hz, 2H), 3.13 (q, J=7.1 Hz, 2H), 3.91 (s, 3H), 5.78 (ddd, J=19.4, 8.9, 3.3 Hz, 1H), 5.92-6.24 (m, 1H), 7.00 (td, J=7.5, 1.0 Hz, 1H), 7.02-7.07 (m, 1H), 7.35 (ddd, J=8.3, 7.4, 1.7 Hz, 1H), 7.43 (dd, J=7.6, 1.6 Hz, 1H); ESI-MS $[M+H]^+$ 341.30.

EXAMPLE 189: (S)-2-(azetidin-1-ylmethyl)-N—((R)-2,2-difluoro-1-(2-methoxyphenyl)ethyl)butanamide

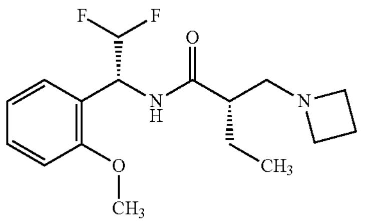 [SMILES: CC[C@@H](CN1CCC1)C(=O)N[C@H](c1ccccc1OC)C(F)F]

To a solution of (R)-2,2-difluoro-1-(2-methoxyphenyl)ethan-1-amine hydrochloride (55.9 mg, 0.250 mmol) and (S)-2-(azetidin-1-ylmethyl)butanoic acid (39.3 mg, 0.250 mmol) in DMA (1.25 mL) were added DIPEA (131 μL, 0.750 mmol) and HATU (114 mg, 0.300 mmol). The reaction mixture was stirred at room temperature overnight and then was filtered through a hydrophilic PTFE 0.45 m Millipore® filter, rinsing with methanol. The filtrate was purified by preparative HPLC (Phenomenex Gemini® C18, 5 μm, ID 30 mm×150 mm) using a gradient of 10-100% ACN in water (acid mode) followed by a gradient of 10-70% water/ACN in water (basic mode). Fractions containing the desired product were evaporated and lyophilized to afford the title compound as a white solid (13.3 mg, 16%). $^1H$ NMR (400 MHz, $CD_3OD$) δ ppm 0.83 (t, J=7.5 Hz, 3H), 1.31-1.53 (m, 2H), 1.85 (quin, J=7.1 Hz, 2H), 2.19-2.29 (m, 1H), 2.29-2.37 (m, 1H), 2.54 (dd, J=11.9, 9.2 Hz, 1H), 2.92-3.01 (m, 2H), 3.01-3.11 (m, 2H), 3.80 (s, 3H), 5.66 (ddd, J=19.4, 8.8, 3.3 Hz, 1H), 5.81-6.14 (m, 1H), 6.88 (td, J=7.5, 1.0 Hz, 1H), 6.93 (dd, J=8.3, 0.8 Hz, 1H), 7.24 (ddd, J=8.2, 7.5, 1.7 Hz, 1H), 7.30 (dd, J=7.6, 1.6 Hz, 1H); ESI-MS $[M+H]^+$ 327.30.

EXAMPLE 190: (S)-3-(azetidin-1-yl)-N-(2,2,2-trifluoro-1-(4-fluorophenyl)ethyl)propanamide

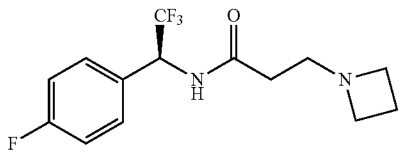 [SMILES: O=C(CCN1CCC1)N[C@@H](c1ccc(F)cc1)C(F)(F)F]

STEP A: (R)-2-methyl-N—((S)-2,2,2-trifluoro-1-(4-fluorophenyl)ethyl)propane-2-sulfinamide

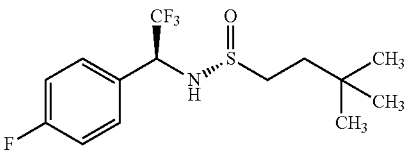 [SMILES: CC(C)(C)CC[S@@](=O)N[C@@H](c1ccc(F)cc1)C(F)(F)F]

To a solution of 2,2,2-trifluoro-1-(4-fluorophenyl)ethan-1-one (1.00 g, 5.21 mmol) in dry ethyl ether (30 mL) was added (R)-2-methylpropane-2-sulfinamide (0.946 g, 7.81 mmol) followed by titanium(IV) isopropoxide (2.29 mL, 7.81 mmol) at 0° C. The reaction mixture was stirred at room temperature overnight and then was cooled to −40° C. Next, $NaBH_4$ (0.591 g, 15.6 mmol) was added and the mixture was stirred at −40° C. for 3 hours and then warmed to room temperature. The reaction mixture was quenched by the slow addition of saturated aqueous $NH_4Cl$ (100 mL). The aqueous layer was extracted with DCM and the combined organic layers were dried over $MgSO_4$, concentrated and purified by flash silica column chromatography using a gradient of 0-50% EtOAc in heptanes. Fractions containing the major diastereomer were collected and concentrated to give the title compound as a white solid (0.653 g, 42%). The stereochemical configuration of the newly formed chiral center was arbitrarily assigned. ESI-MS m/z $[M+H]^+$ 298.2.

STEP B: (S)-2,2,2-trifluoro-1-(4-fluorophenyl)ethan-1-amine

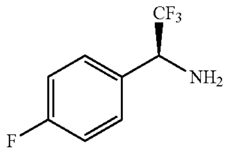 [SMILES: N[C@@H](c1ccc(F)cc1)C(F)(F)F]

To a stirred solution of (R)-2-methyl-N—((S)-2,2,2-trifluoro-1-(4-fluorophenyl)ethyl)propane-2-sulfinamide (0.653 g, 2.196 mmol) in methanol (5 mL) was added dropwise 4 M HCl in dioxane (1.65 mL, 6.59 mmol). The reaction mixture was stirred at room temperature overnight and then was concentrated under reduced pressure. The residue was taken up in diethyl ether (10 mL) and the resulting precipitate was collected by filtration to give an HCl salt of the title compound as a white solid (0.457 g, 91%). ESI-MS m/z $[M+H]^+$ 194.2.

STEP C: (S)—N-(2,2,2-trifluoro-1-(4-fluorophenyl)ethyl)acrylamide

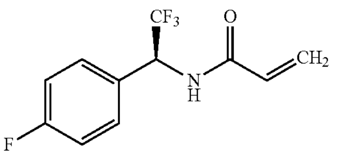 [SMILES: C=CC(=O)N[C@@H](c1ccc(F)cc1)C(F)(F)F]

To a mixture of (S)-2,2,2-trifluoro-1-(4-fluorophenyl)ethan-1-amine hydrochloride (0.278 g, 1.21 mmol), acrylic acid (0.099 mL, 1.45 mmol) and $Et_3N$ (0.675 mL, 4.84 mmol) in DMF (5 mL) was added HATU (0.691 g, 1.816 mmol). The reaction mixture was stirred at room temperature overnight and then was diluted with water (20 mL) and extracted with EtOAc (3×10 mL). The organic layers were combined, dried over $MgSO_4$ and concentrated under reduced pressure. The crude residue was purified by flash silica column chromatography using a gradient of 0-50% EtOAc in heptanes to give the title compound as a white solid (0.14 g, 47%).

STEP D: (S)-3-(azetidin-1-yl)-N-(2,2,2-trifluoro-1-(4-fluorophenyl)ethyl)propanamide A mixture of (S)—N-(2,2,2-trifluoro-1-(4-fluorophenyl) ethyl)acrylamide (0.14 g, 0.566 mmol) and azetidine (0.202 mL, 2.83 mmol) in methanol (2 mL) and water (2 mL) was heated at 100° C. for 30 minutes in a microwave reactor. The reaction mixture was concentrated and purified by preparative HPLC (Phenomenex Gemini® C18, 5 μm, ID 30 mm×150 mm) using a gradient of 10-50% ACN in water (acid mode) to give a TFA salt of the title compound as a clear oil (0.103 g, 43% yield, 74% ee). The stereochemical configuration of the title compound was arbitrarily assigned. $^1$H NMR (400 MHz, $CDCl_3$) δ ppm 2.25-2.41 (m, 1H), 2.54-2.65 (m, 1H), 2.67-2.85 (m, 2H), 3.35-3.52 (m, 2H), 3.74-3.97 (m, 2H), 4.11 (br s, 1H), 4.29 (br s, 1H), 5.62 (quin, J=8.3 Hz, 1H), 7.00-7.11 (m, 2H), 7.45 (dd, J=8.5, 5.1 Hz, 2H), 8.96 (br d, J=9.4 Hz, 1H); ESI-MS m/z [M+H]$^+$ 305.3.

EXAMPLE 191: (S)-3-(azetidin-1-yl)-N-(1-(3-chlorophenyl)-2,2,2-trifluoroethyl)propanamide

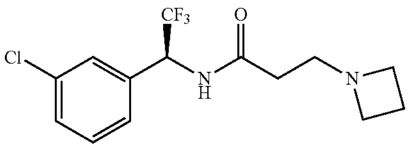 [SMILES: O=C(CCN1CCC1)N[C@@H](c1cccc(Cl)c1)C(F)(F)F]

A TFA salt of the title compound was prepared like EXAMPLE 190, using 2,2,2-trifluoro-1-(3-chlorophenyl) ethan-1-one (1.00 g, 4.79 mmol), and was obtained as a clear oil (62 mg, 3% yield over four steps, 92% ee). The stereochemical configuration of the title compound was arbitrarily assigned. $^1$H NMR (400 MHz, $CDCl_3$) δ ppm 2.26-2.41 (m, 1H), 2.56-2.76 (m, 2H), 2.79-2.87 (m, 1H), 3.35-3.52 (m, 2H), 3.75-3.98 (m, 2H), 4.14 (br s, 1H), 4.30 (br s, 1H), 5.62 (quin, J=8.3 Hz, 1H), 7.26-7.40 (m, 3H), 7.47 (s, 1H), 9.05 (br d, J=9.3 Hz, 1H); ESI-MS m/z [M+H]$^+$ 321.3.

EXAMPLE 192: (R)-3-(azetidin-1-yl)-N-(1-(3-chlorophenyl)-2,2,2-trifluoroethyl)propanamide

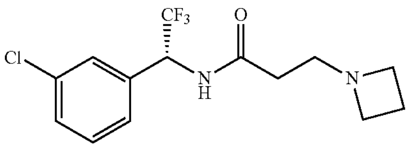 [SMILES: O=C(CCN1CCC1)N[C@H](c1cccc(Cl)c1)C(F)(F)F]

A TFA salt of the title compound was prepared like EXAMPLE 190, using 2,2,2-trifluoro-1-(3-chlorophenyl) ethan-1-one (1.00 g, 4.79 mmol) and (S)-2-methylpropane-2-sulfinamide (0.872 g, 7.19 mmol), and was obtained as a clear oil (0.048 g, 2.3% yield over four steps, 91% ee). The stereochemical configuration of the title compound was arbitrarily assigned. $^1$H NMR (400 MHz, $CDCl_3$) δ ppm 2.26-2.41 (m, 1H), 2.55-2.77 (m, 2H), 2.79-2.89 (m, 1H), 3.35-3.52 (m, 2H), 3.75-3.97 (m, 2H), 4.13 (br s, 1H), 4.30 (br s, 1H), 5.62 (quin, J=8.3 Hz, 1H), 7.28-7.41 (m, 3H), 7.47 (s, 1H), 9.03 (br d, J=9.4 Hz, 1H); ESI-MS m/z [M+H]$^+$ 321.2.

EXAMPLE 193: (R)-3-(azetidin-1-yl)-N-(2,2,2-trifluoro-1-(3-fluorophenyl)ethyl)propanamide

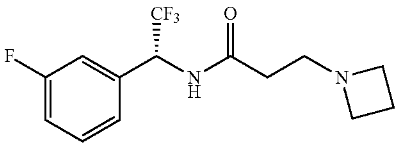 [SMILES: O=C(CCN1CCC1)N[C@H](c1cccc(F)c1)C(F)(F)F]

A TFA salt of the title compound was prepared like EXAMPLE 190, using 2,2,2-trifluoro-1-(3-fluorophenyl) ethan-1-one (1.00 g, 5.21 mmol) and (S)-2-methylpropane-2-sulfinamide (0.946 g, 7.81 mmol), and was obtained as a clear oil (0.011 g, 0.05% yield over four steps, 85% ee). The stereochemical configuration of the title compound was arbitrarily assigned. $^1$H NMR (400 MHz, $CDCl_3$) δ ppm 2.29-2.43 (m, 1H), 2.57-2.79 (m, 2H), 2.82-2.90 (m, 1H), 3.38-3.55 (m, 2H), 3.76-3.94 (m, 2H), 4.14 (br s, 1H), 4.33 (br s, 1H), 5.61-5.71 (m, 1H), 7.09 (t, J=8.2 Hz, 1H), 7.20-7.30 (m, 1H), 7.20-7.25 (m, 1H), 7.38 (td, J=8.0, 5.8 Hz, 1H), 8.94 (br d, J=9.4 Hz, 1H); ESI-MS m/z [M+H]$^+$ 305.3.

EXAMPLE 194: (S)-2-(azetidin-1-ylmethyl)-N—((R)-2,2-difluoro-1-(3-fluorophenyl)ethyl)-3-methylbutanamide

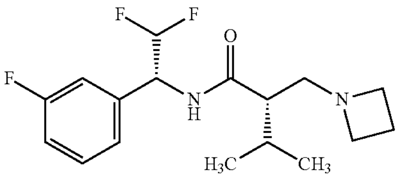 [SMILES: CC(C)[C@@H](CN1CCC1)C(=O)N[C@H](c1cccc(F)c1)C(F)F]

To a solution of (R)-2,2-difluoro-1-(3-fluorophenyl) ethan-1-amine hydrochloride (68.8 mg, 0.325 mmol) and (S)-2-(azetidin-1-ylmethyl)-3-methylbutanoic acid (42.8 mg, 0.250 mmol) in DMA (1.25 mL) were added DIPEA (131 μL, 0.750 mmol) and HATU (114 mg, 0.300 mmol). The reaction mixture was stirred at room temperature overnight and then was filtered through a hydrophilic PTFE 0.45 m Millipore® filter, rinsing with methanol. The filtrate was purified by preparative HPLC (Phenomenex Gemini® C18, 5 μm, ID 30 mm×150 mm) using a gradient of 10-50% ACN in water (acid mode). The product-containing fractions were evaporated, taken up in methanol and filtered through Agilent Stratospheres SPE (PL-$HCO_3$ MP) resin to remove TFA. The filtrate was evaporated, and the residue was transferred to a vial and lyophilized to afford the title compound as a white solid (35.8 mg, 44%). $^1$H NMR (400 MHz, $CD_3OD$) δ ppm 0.96 (dd, J=8.0, 6.8 Hz, 6H), 1.71-1.87 (m, 1H), 1.93 (quin, J=7.1 Hz, 2H), 2.14 (ddd, J=10.8, 7.7, 3.5 Hz, 1H), 2.51 (dd, J=11.9, 3.6 Hz, 1H), 2.73 (dd, J=11.7, 10.6 Hz, 1H), 3.03 (q, J=7.0 Hz, 2H), 3.14 (q, J=7.1 Hz, 2 H), 5.42 (ddd, J=15.9, 12.8, 3.2 Hz, 1H), 5.91-6.25 (m, 1H), 7.04-7.13 (m, 1H), 7.28 (d, J=7.4 Hz, 2H), 7.36-7.45 (m, 1H); ESI-MS [M+H]$^+$ 329.30.

EXAMPLE 195: (S)-2-(azetidin-1-ylmethyl)-N—((R)-2,2-difluoro-1-(3-fluorophenyl)ethyl)butanamide

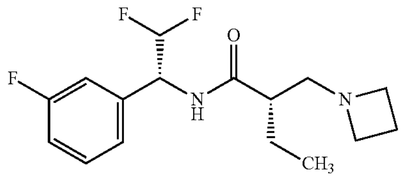 [SMILES: CC[C@@H](CN1CCC1)C(=O)N[C@H](c1cccc(F)c1)C(F)F]

The title compound was prepared like EXAMPLE 194, using (R)-2,2-difluoro-1-(3-fluorophenyl)ethan-1-amine hydrochloride (68.8 mg, 0.325 mmol), (S)-2-(azetidin-1-ylmethyl)butanoic acid (39.3 mg, 0.250 mmol), DIPEA (131 μL, 0.750 mmol) and HATU (114 mg, 0.300 mmol) in DMA (1.25 mL), and was obtained as a white solid (25.2 mg, 32%). $^1$H NMR (400 MHz, $CD_3OD$) δ ppm 0.93 (t, J=7.4 Hz, 3H), 1.41-1.63 (m, 2H), 1.97 (quin, J=7.1 Hz, 2H), 2.33 (tt, J=9.3, 4.8 Hz, 1H), 2.39-2.47 (m, 1H), 2.67 (dd, J=11.8, 9.4 Hz, 1H), 3.08 (q, J=6.9 Hz, 2H), 3.17 (q, J=7.1 Hz, 2H), 5.41 (ddd, J=15.8, 12.9, 3.2 Hz, 1H), 5.91-6.26 (m, 1H), 7.03-7.14 (m, 1H), 7.21-7.31 (m, 2H), 7.41 (td, J=8.1, 6.0 Hz, 1H); ESI-MS $[M+H]^+$ 315.30.

EXAMPLE 196: (S)-2-(azetidin-1-ylmethyl)-N—((R)-2,2-difluoro-1-(4-fluorophenyl)ethyl)-3-methylbutanamide

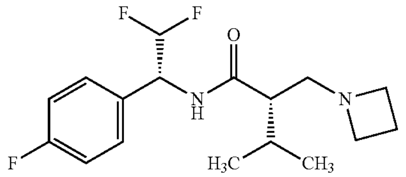 [SMILES: CC(C)[C@@H](CN1CCC1)C(=O)N[C@H](c1ccc(F)cc1)C(F)F]

The title compound was prepared like EXAMPLE 194, using (R)-2,2-difluoro-1-(4-fluorophenyl)ethan-1-amine hydrochloride (48.7 mg, 0.230 mmol), (S)-2-(azetidin-1-ylmethyl)-3-methylbutanoic acid (39.4 mg, 0.230 mmol), DIPEA (121 μL, 0.690 mmol) and HATU (105 mg, 0.276 mmol) in DMA (1.15 mL), and was obtained as a white solid (23.5 mg, 31%). $^1$H NMR (400 MHz, $CD_3OD$) δ ppm 0.93-1.01 (m, 6H), 1.75-1.88 (m, 1H), 1.94 (quin, J=7.1 Hz, 2H), 2.10-2.19 (m, 1H), 2.53 (dd, J=11.9, 3.5 Hz, 1H), 2.75 (dd, J=11.8, 10.5 Hz, 1H), 3.04 (q, J=7.0 Hz, 2H), 3.14 (q, J=7.2 Hz, 2H), 5.34-5.47 (m, 1H), 5.90-6.27 (m, 1H), 7.09-7.20 (m, 2H), 7.46-7.56 (m, 2H); ESI-MS $[M+H]^+$ 329.30.

EXAMPLE 197: (S)—N-(1-(3-chlorophenyl)-2,2-difluoroethyl)-3-(pyrrolidin-1-yl)propanamide

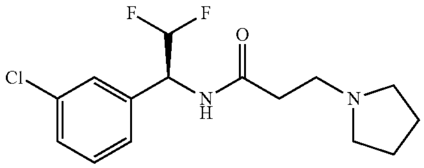 [SMILES: O=C(CCN1CCCC1)N[C@@H](c1cccc(Cl)c1)C(F)F]

and

EXAMPLE 198: (R)—N-(1-(3-chlorophenyl)-2,2-difluoroethyl)-3-(pyrrolidin-1-yl)propanamide

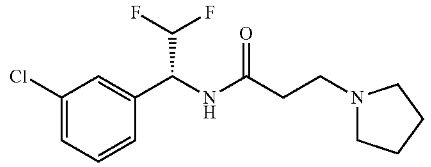 [SMILES: O=C(CCN1CCCC1)N[C@H](c1cccc(Cl)c1)C(F)F]

To a mixture of 3-(pyrrolidin-1-yl)propanoic acid hydrochloride (0.938 g, 5.22 mmol), 1-(3-chlorophenyl)-2,2-difluoroethan-1-amine (1.00 g, 5.22 mmol, enantiopurity unknown) and DIPEA (3.65 mL, 20.9 mmol) in DMF (20 mL) was added HATU (2.98 g, 7.83 mmol). The reaction mixture was stirred at room temperature overnight and then was diluted with water (10 mL) and extracted with EtOAc. The organic phase was concentrated and purified by flash silica column chromatography using a gradient of 40-100% EtOAc (with 2% $Et_3N$) in heptanes to give a mixture of the title enantiomers as a yellow oil (0.964 g). The title enantiomers were separated by preparative chiral SFC in which the first eluting compound was arbitrarily assigned as the (S)-enantiomer and was obtained as a yellow oil (757 mg, 46%) and the second eluting compound was arbitrarily assigned as the (R)-enantiomer was obtained as a yellow oil (83 mg, 5%). $^1$H NMR (400 MHz, $CDCl_3$) δ ppm 1.81-1.93 (m, 4H), 2.36-2.53 (m, 2H), 2.57-2.67 (m, 4H), 2.72-2.86 (m, 2H), 5.35 (dddd, J=17.0, 13.0, 8.7, 2.0 Hz, 1H), 6.08 (d, J=2.0 Hz, 1H), 5.76-6.06 (m, 1H), 5.80 (d, J=2.0 Hz, 1H), 5.94 (dd, J=2.0, 1.0 Hz, 1H), 7.20 (d, J=6.6 Hz, 1H), 7.24-7.36 (m, 3H), 10.38 (br d, J=8.2 Hz, 1H); ESI-MS m/z $[M+H]^+$ 317.3.

EXAMPLE 199: (R)-2-(azetidin-1-ylmethyl)-N-(2-(2-fluorophenyl)propan-2-yl)butanamide

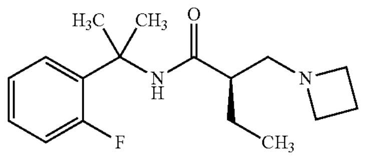 [SMILES: CC[C@H](CN1CCC1)C(=O)NC(C)(C)c1ccccc1F]

EXAMPLE 200: (S)-2-(azetidin-1-ylmethyl)-N-(2-(2-fluorophenyl)propan-2-yl)butanamide

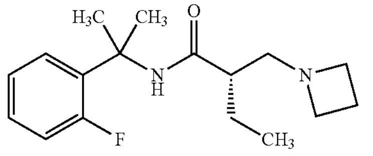 [SMILES: CC[C@@H](CN1CCC1)C(=O)NC(C)(C)c1ccccc1F]

The title enantiomers were prepared like EXAMPLE 197 and EXAMPLE 198, using 2-(azetidin-1-ylmethyl)butanoic acid trihydrochloride (1.218 g, 4.57 mmol), 2-(2-fluorophenyl)propan-2-amine (0.700 g, 4.57 mmol), DIPEA (4.79 mL, 27.4 mmol) and HATU (2.61 g, 6.85 mmol) in DMF (20 mL). The first eluting compound by SFC was arbitrarily assigned as the (R)-enantiomer and was obtained as a light pink solid (126 mg, 9.4%) and the second eluting compound by SFC was arbitrarily assigned as the (S)-enantiomer and was obtained as a light pink solid (169 mg, 13%). $^{1}$H NMR (400 MHz, $CD_3OD$) δ ppm 0.89 (t, J=7.5 Hz, 3H), 1.41-1.51 (m, 2H), 1.74 (d, J=5.9 Hz, 6H), 2.08 (quin, J=7.1 Hz, 2H), 2.22 (ddd, J=8.3, 5.6, 2.8 Hz, 1H), 2.42 (dd, J=12.4, 5.1 Hz, 1H), 2.64 (dd, J=11.9, 8.4 Hz, 1H), 3.23-3.31 (m, 4H), 7.01 (ddd, J=12.7, 8.2, 1.3 Hz, 1H), 7.09-7.14 (m, 1H), 7.21-7.27 (m, 1H), 7.49 (td, J=8.2, 1.7 Hz, 1H); ESI-MS m/z $[M+H]^+$ 293.4.

EXAMPLE 201: (R)-3-(azetidin-1-yl)-N-(2,2-difluoro-1-phenylethyl)propanamide

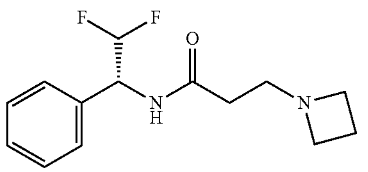 [SMILES: O=C(CCN1CCC1)N[C@H](c1ccccc1)C(F)F]

STEP A: N-(2,2-difluoro-1-phenylethyl)acrylamide

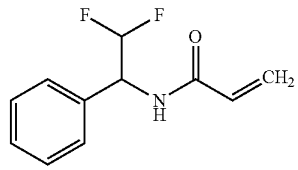

To a mixture of acrylic acid (0.294 mL, 4.29 mmol), 2,2-difluoro-1-phenylethan-1-amine hydrochloride (0.830 g, 4.29 mmol) and DIPEA (2.99 mL, 17.2 mmol) in DMF (20 mL) was added HATU (2.44 g, 6.43 mmol). The reaction mixture was stirred at room temperature overnight and then was diluted with water (10 mL) and extracted with EtOAc. The organic phase was concentrated and purified by flash silica column chromatography using a gradient of 0-50% EtOAc in heptanes to give the title compound (0.82 g, 91%).

STEP B: (R)-3-(azetidin-1-yl)-N-(2,2-difluoro-1-phenylethyl)propanamide

A mixture of N-(2,2-difluoro-1-phenylethyl)acrylamide (0.82 g, 3.88 mmol) and azetidine (0.523 mL, 7.76 mmol) in methanol (5 mL) and water (5 mL) was heated at 100° C. The reaction mixture was concentrated and purified by flash silica column chromatography using a gradient of 40-100% EtOAc (with 2% $Et_3N$) in heptanes to give a racemic mixture of 3-(azetidin-1-yl)-N-(2,2-difluoro-1-phenylethyl)propanamide as a colorless oil (0.341 g). The enantiomers were separated via preparative chiral SFC. The first eluting compound was impure and was not collected. The second eluting compound, which was arbitrarily assigned as the (R)-enantiomer, was re-purified by flash silica column chromatography using a gradient of 40-100% EtOAc (with 2% $Et_3N$) in heptanes and was obtained as a clear oil (40 mg, 3.8%). $^{1}$HNMR (400 MHz, $CD_3OD$) δ ppm 2.07 (quin, J=7.2 Hz, 2H), 2.26-2.41 (m, 2H), 2.64-2.76 (m, 2H), 3.19-3.22 (m, 1H), 3.25-3.32 (m, 2H), 5.32 (ddd, J=15.1, 14.1, 3.1 Hz, 1H), 5.92 (d, J=3.1 Hz, 1H), 5.90-6.23 (m, 1H), 6.06 (d, J=3.1 Hz, 1H), 6.20 (d, J=3.1 Hz, 1H), 7.31-7.42 (m, 5H); ESI-MS m/z $[M+H]^+$ 269.3.

EXAMPLE 202: (R)-3-(azetidin-1-yl)-N-(1-(3-chlorophenyl)-2,2-difluoroethyl)propanamide

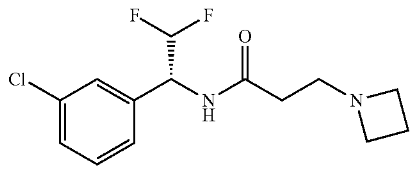 [SMILES: O=C(CCN1CCC1)N[C@H](c1cccc(Cl)c1)C(F)F]

STEP A: (R)—N-(1-(3-chlorophenyl)-2,2-difluoroethyl)acrylamide

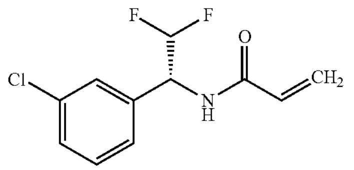 [SMILES: C=CC(=O)N[C@H](c1cccc(Cl)c1)C(F)F]

To a mixture of acrylic acid (0.060 mL, 0.877 mmol), (R)-1-(3-chlorophenyl)-2,2-difluoroethan-1-amine hydrochloride (0.200 g, 0.877 mmol) and DIPEA (0.613 mL, 3.51 mmol) in DMF (20 mL) was added HATU (0.500 g, 1.315 mmol). The reaction mixture was stirred at room temperature overnight and then was diluted with water (10 mL) and extracted with EtOAc. The organic phase was concentrated and purified by flash silica column chromatography using a gradient of 0-60% EtOAc in heptanes to give the title compound (0.130 g, 60%). ESI-MS m/z $[M+H]^+$ 246.2.

STEP B: (R)-3-(azetidin-1-yl)-N-(1-(3-chlorophenyl)-2,2-difluoroethyl)propanamide A mixture of (R)—N-(1-(3-chlorophenyl)-2,2-difluoroethyl)acrylamide (0.130 g, 0.529 mmol) and azetidine (0.071 mL, 1.058 mmol) in methanol (1 mL) and water (1 mL) was heated at 100° C. overnight. The reaction mixture was concentrated and purified by flash silica column chromatography using a gradient of 40-100% EtOAc (with 2% $Et_3N$) in heptanes to give the title compound as a white solid (88 mg, 55%). $^{1}$HNMR (400 MHz, $CD_3OD$) δ ppm 2.09 (quin, J=7.2 Hz, 2H), 2.34 (td, J=7.2, 1.8 Hz, 2H), 2.69-2.77 (m, 2H), 3.23-3.29 (m, 4H), 5.33 (td, J=14.6, 3.0 Hz, 1H), 5.92-6.25 (m, 1H), 5.94 (d, J=3.0 Hz, 1H), 6.08 (d, J=3.0 Hz, 1H), 6.22 (d, J=3.1 Hz, 1H), 7.32-7.39 (m, 3H), 7.45 (s, 1H); ESI-MS m/z $[M+H]^+$ 303.3.

EXAMPLE 203: N-(2-(isoquinolin-1-yl)propan-2-yl)-2-(1-methylpyrrolidin-2-yl)acetamide

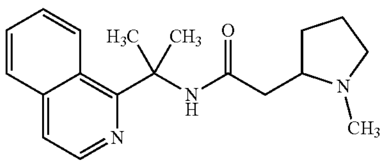 [SMILES: CN1CCCC1CC(=O)NC(C)(C)c1nccc2ccccc12]

To a vial containing 2-(1-methylpyrrolidin-2-yl)acetic acid HCl (150 mg, 0.835 mmol) and DIPEA (436 μl, 2.505 mmol) in DMF (835 μL) and EtOAc (3340 μL) was added HATU (349 mg, 0.918 mmol). The reaction mixture was stirred at room temperature for 15 minutes. Next, 2-(isoquinolin-1-yl)propan-2-amine bis HCl (216 mg, 0.835 mmol) was added and the reaction mixture was stirred at room temperature overnight. Additional HATU (150 mg) was added. The reaction mixture was heated to 45° C. for 2 hours and then was partitioned between saturated aqueous $NaHCO_3$ and EtOAc. The aqueous layer was extracted with EtOAc (2×). The organic layers were combined, washed with brine/$NaHCO_3$ (1:1), dried over $MgSO_4$, filtered and concentrated. The crude product was purified by flash silica column chromatography (NH silica, 60 μm, 30 grams) using a gradient of 0.5-10% MeOH in EtOAc to give the title compound as a white solid (112 mg, 43%). $^1H$ NMR (400 MHz, $CD_3CN$) δ ppm 1.47-1.60 (m, 1H), 1.63-1.89 (m, 10H), 2.09-2.29 (m, 4H), 2.30-2.40 (m, 4H), 3.07 (ddd, J=9.4, 7.2, 2.3 Hz, 1H), 7.51-7.61 (m, 2H), 7.66 (ddd, J=8.2, 6.9, 1.2 Hz, 1H), 7.83-7.95 (m, 1H), 8.37 (d, J=5.6 Hz, 1H), 8.64-8.72 (m, 1H), 8.73-8.87 (m, 1H).

EXAMPLE 204: (S)-2-(azetidin-1-ylmethyl)-N—((R)-2,2-difluoro-1-(4-fluorophenyl)ethyl)butanamide

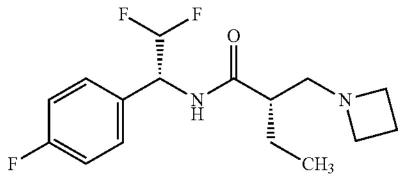 [SMILES: CC[C@@H](CN1CCC1)C(=O)N[C@H](c1ccc(F)cc1)C(F)F]

To a solution of (R)-2,2-difluoro-1-(4-fluorophenyl)ethan-1-amine hydrochloride (63 mg, 0.30 mmol) and (S)-2-(azetidin-1-ylmethyl)butanoic acid (47 mg, 0.30 mmol) in DMA (1.5 mL) were added DIPEA (157 μL, 0.900 mmol) and HATU (137 mg, 0.360 mmol). The reaction mixture was stirred at room temperature overnight and then was filtered through a hydrophilic PTFE 0.45 m Millipore® filter, rinsing with methanol. The filtrate was purified by preparative HPLC (Phenomenex Gemini® C18, 5 μm, ID 30 mm×150 mm) using a gradient of 10-50% ACN in water (acid mode). The product-containing fractions were evaporated and further purified by semi-preparative SFC (Amylose-1, 5 μm, ID 21 mm×150 mm) using a gradient of 1-50% methanol (with 0.1% $NH_4OH$) in $CO_2$. The pure fractions were evaporated and lyophilized to afford the title compound as a white solid (7.2 mg, 7.6%). $^1H$ NMR (400 MHz, $CD_3OD$) δ ppm 0.93 (t, J=7.4 Hz, 3H), 1.42-1.63 (m, 2H), 1.97 (quin, J=7.2 Hz, 2H), 2.33 (tt, J=9.3, 4.8 Hz, 1H), 2.45 (dd, J=11.9, 4.5 Hz, 1H), 2.64-2.74 (m, 1H), 3.03-3.23 (m, 4H), 5.30-5.46 (m, 1H), 5.86-6.27 (m, 1H), 7.05-7.21 (m, 2H), 7.43-7.54 (m, 2H); ESI-MS $[M+H]^+$ 315.30.

EXAMPLE 205: (R)-3-(azetidin-1-yl)-N—((R)-2-fluoro-1-phenylethyl)-2-methylpropanamide

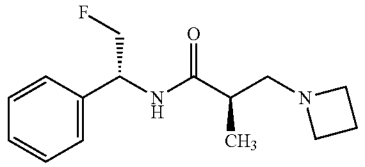 [SMILES: C[C@H](CN1CCC1)C(=O)N[C@@H](CF)c1ccccc1]

EXAMPLE 206: (S)-3-(azetidin-1-yl)-N—((R)-2-fluoro-1-phenylethyl)-2-methylpropanamide

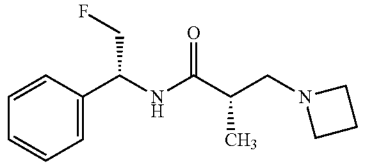 [SMILES: C[C@@H](CN1CCC1)C(=O)N[C@@H](CF)c1ccccc1]

To a mixture of 3-(azetidin-1-yl)-2-methylpropanoic acid (0.341 g, 2.38 mmol), (R)-2-fluoro-1-phenylethan-1-amine hydrochloride (0.418 g, 2.38 mmol) and DIPEA (1.66 mL, 9.52 mmol) in DMF was added HATU (1.36 g, 3.57 mmol). The reaction mixture was stirred at RT overnight and then was diluted with water and extracted with EtOAc. The organic phase was concentrated and purified by automated flash silica column chromatography using a gradient of 40-100% EtOAc with 2% $Et_3N$ in heptanes to give a mixture of the title diastereomers as an off-white solid (210 mg). The diastereomers were separated by preparative SFC (Cellulose-2, 5 μm, ID 30 mm×250 mm) using a mobile phase of 35% EtOH (with 0.1% $NH_4OH$) in $CO_2$. The first eluting compound was arbitrarily assigned as the (R,R)-diastereomer (64.6 mg, 10%) and the second eluting compound was arbitrarily assigned as the (S,R)-diastereomer (50.7 mg, 8.1%). ESI-MS $[M+H]^+$ 265.0.

EXAMPLE 207: (S)-3-(azetidin-1-yl)-N-(2,2,2-trifluoro-1-(p-tolyl)ethyl)propanamide

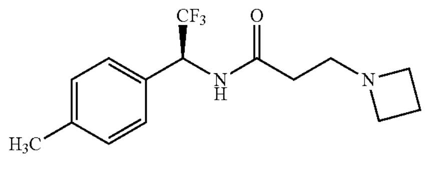 [SMILES: Cc1ccc([C@H](NC(=O)CCN2CCC2)C(F)(F)F)cc1]

STEP A: (R)-2-methyl-N—((S)-2,2,2-trifluoro-1-(p-tolyl)ethyl)propane-2-sulfinamide

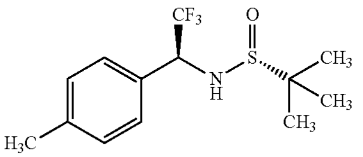 [SMILES: Cc1ccc([C@H](N[S@](=O)C(C)(C)C)C(F)(F)F)cc1]

To a solution of 2,2,2-trifluoro-1-(p-tolyl)ethan-1-one (1.00 g, 5.31 mmol) in dry diethyl ether (30 mL) was added (R)-2-methylpropane-2-sulfinamide (0.966 g, 7.97 mmol) followed by titanium(IV) isopropoxide (2.34 mL, 7.97 mmol) at 0° C. The reaction mixture was stirred at room temperature overnight and then was cooled to −40° C. Next, $NaBH_4$ (0.603 g, 15.9 mmol) was added. The reaction mixture was stirred at −40° C. for 3 hours and then was warmed to room temperature and quenched by the slow addition of saturated aqueous $NH_4Cl$ (100 mL). The aqueous and organic layers were separated. The aqueous layer was extracted with DCM, and the organic layers were combined, dried over $MgSO_4$, concentrated and purified by flash silica column chromatography using a gradient of 0-50% EtOAc in heptanes. Fractions containing the major diastereomer were collected and concentrated to give the title compound as a clear oil (0.406 g, 26%). The stereochemical configuration of the newly formed chiral center was arbitrarily assigned. ESI-MS m/z $[M+H]^+$ 294.2.

STEP B: (S)-2,2,2-trifluoro-1-(p-tolyl)ethan-1-amine

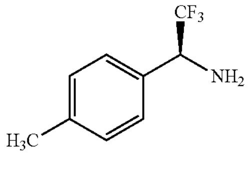

To a stirred solution of (R)-2-methyl-N—((S)-2,2,2-trifluoro-1-(p-tolyl)ethyl)propane-2-sulfinamide (0.406 g, 1.384 mmol) in methanol (5 mL) was added dropwise 4 M HCl in dioxane (1.04 mL, 4.15 mmol). The reaction mixture was stirred at room temperature overnight and then was concentrated under reduced pressure. The resulting residue was taken up in diethyl ether (10 mL) and the resulting precipitate was collected by filtration to give an HCl salt of the title compound as a white solid (0.27 g, 86%). The stereochemical configuration of the title compound was arbitrarily assigned. ESI-MS m/z $[M+H]^+$ 173.1.

STEP C: (S)-3-(azetidin-1-yl)-N-(2,2,2-trifluoro-1-(p-tolyl)ethyl)propanamide

To a mixture of (S)-2,2,2-trifluoro-1-(p-tolyl)ethan-1-amine hydrochloride (0.15 g, 0.665 mmol), 3-(azetidin-1-yl)propanoic acid hydrochloride (0.110 g, 0.665 mmol) and $Et_3N$ (0.371 mL, 2.66 mmol) in DMF (5 mL) was added HATU (0.379 g, 0.997 mmol). The reaction mixture was stirred at room temperature overnight and then was directly purified by preparative HPLC (Phenomenex Gemini® C18, 5 μm, ID 30 mm×150 mm) using a gradient of 10-100% water/ACN in water (basic mode) to give the title compound as a white solid (0.025 g, 13%). $^1H$ NMR (400 MHz, $CDCl_3$) δ ppm 2.13-2.20 (m, 2H), 2.22-2.35 (m, 2H), 2.38 (s, 3H), 2.62-2.78 (m, 2H), 3.25-3.35 (m, 4H), 5.59-5.70 (m, 1H), 7.20-7.26 (m, 2H), 7.29-7.34 (m, 2H), 10.34 (br d, J=9.2 Hz, 1H); ESI-MS m/z $[M+H]^+$ 301.3.

EXAMPLE 208: (S)-3-(azetidin-1-yl)-N-(2,2,2-trifluoro-1-(3-fluorophenyl)ethyl)propanamide

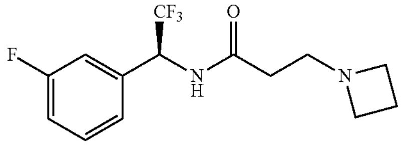 [SMILES: O=C(CCN1CCC1)N[C@@H](c1cccc(F)c1)C(F)(F)F]

The title compound was prepared like EXAMPLE 207, using 2,2,2-trifluoro-1-(3-fluorophenyl)ethan-1-one (1.00 g, 5.21 mmol), and was obtained as a white solid (0.03 g). The stereochemical configuration of the title compound was arbitrarily assigned. $^1H$ NMR (400 MHz, $CDCl_3$) δ ppm 2.18 (quin, J=7.1 Hz, 2H), 2.24-2.38 (m, 2H), 2.65-2.78 (m, 2H), 3.31 (sxt, J=7.0 Hz, 4H), 5.64-5.74 (m, 1H), 7.06-7.16 (m, 2H), 7.21 (d, J=7.6 Hz, 1H), 7.39 (td, J=8.0, 5.8 Hz, 1H), 10.53 (br d, J=8.8 Hz, 1H); ESI-MS m/z $[M+H]^+$ 305.3.

EXAMPLE 209: (S)-3-(azetidin-1-yl)-N-(2,2,2-trifluoro-1-(2-fluorophenyl)ethyl)propanamide

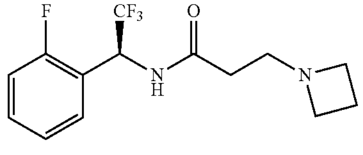 [SMILES: O=C(CCN1CCC1)N[C@@H](c1ccccc1F)C(F)(F)F]

The title compound was prepared like EXAMPLE 207, using 2,2,2-trifluoro-1-(2-fluorophenyl)ethan-1-one (1.00 g, 5.21 mmol), and was obtained as a white solid (0.02 g). The stereochemical configuration of the title compound was arbitrarily assigned. $^1H$ NMR (400 MHz, $CDCl_3$) δ ppm 2.17 (quin, J=7.1 Hz, 2H), 2.30 (ddd, J=14.3, 7.6, 4.0 Hz, 2H), 2.63-2.76 (m, 2H), 3.30 (sxt, J=6.8 Hz, 4H), 5.94-6.05 (m, 1H), 7.11-7.23 (m, 2H), 7.35-7.43 (m, 2H), 10.55 (br d, J=9.0 Hz, 1H); ESI-MS m/z $[M+H]^+$ 305.3.

EXAMPLE 210: (S)-3-(azetidin-1-yl)-N-(2,2,2-trifluoro-1-(o-tolyl)ethyl)propanamide

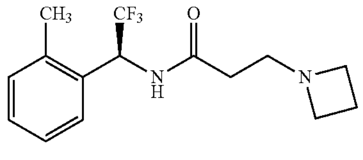 [SMILES: Cc1ccccc1[C@H](NC(=O)CCN1CCC1)C(F)(F)F]

The title compound was prepared like EXAMPLE 207, using 2,2,2-trifluoro-1-(o-tolyl)ethan-1-one (1.00 g, 5.31 mmol), and was obtained as a clear oil (0.03 g). The stereochemical configuration of the title compound was arbitrarily assigned. $^1$H NMR (400 MHz, $CDCl_3$) δ ppm 2.12-2.20 (m, 2H), 2.20-2.36 (m, 2H), 2.49 (s, 3H), 2.60-2.76 (m, 2H), 3.22-3.37 (m, 4H), 5.95-6.05 (m, 1H), 7.16-7.43 (m, 4H), 10.39 (br d, J=9.0 Hz, 1H); ESI-MS m/z $[M+H]^+$ 301.3.

Table 1 lists biological assay data (SSTR4 activity, SSTR4 binding, and SSTR1 binding) for some of the compounds shown in the examples, where larger $pEC_{50}$ and $pIC_{50}$ values represent higher activity or potency. The compounds shown in Table 1 were tested in accordance with a cell-based assay which measures the inhibition of forskolin stimulated cAMP in cells overexpressing SSTR4 (reported as $pEC_{50}$). Many of the compounds shown in Table 1 were also tested in accordance with membrane-based assays which measure competitive binding of the compounds to SSTR4 and SSTR1 (reported as $pIC_{50}$). These assays are described in the section entitled Biological Activity, above.

TABLE 1

Biological Assay Data

| EXAMPLE No. | SSTR4 Activity $pEC_{50}$ | SSTR4 Binding $pIC_{50}$ | SSTR1 Binding $pIC_{50}$ |
|---|---|---|---|
| 1 | 8.2 | 7.2 | 5.0 |
| 2 | 8.2 | 7.2 | 5.5 |
| 3 | 7.6 | 6.7 | 5.3 |
| 4 | 7.6 | 6.8 | 5.0 |
| 5 | 8.4 | 7.3 | 5.3 |
| 6 | 8.8 | 7.6 | 5.6 |
| 7 | 8.4 | 7.1 | 5.3 |
| 8 | 8.6 | 7.3 | 5.4 |
| 9 | 7.9 | 6.9 | 5.1 |
| 10 | 6.7 | — | — |
| 11 | 7.4 | 6.7 | 4.6 |
| 12 | 6.9 | — | — |
| 13 | 7.7 | 6.9 | 4.3 |
| 14 | 8.2 | 7.1 | 4.6 |
| 15 | 7.6 | 6.5 | 4.3 |
| 16 | 7.9 | 7.0 | 5.5 |
| 17 | 8.4 | 7.0 | 5.3 |
| 18 | 8.1 | 7.0 | 5.1 |
| 19 | 7.9 | 6.9 | 5.0 |
| 20 | 5.7 | — | — |
| 21 | 7.9 | 7.1 | 4.6 |
| 22 | 8.1 | 7.2 | 5.6 |
| 23 | 7.6 | 6.0 | 5.1 |
| 24 | 7.9 | 6.7 | 5.2 |
| 25 | 7.1 | — | — |
| 26 | 5.6 | — | — |
| 27 | 7.5 | 6.3 | <4.3 |
| 28 | 7.7 | 6.6 | 4.8 |
| 29 | 7.0 | — | — |
| 30 | 7.5 | 6.9 | 4.5 |
| 31 | 6.5 | — | — |
| 32 | 6.3 | — | — |
| 33 | 7.1 | — | — |
| 34 | 7.0 | 6.5 | <4.3 |
| 35 | 7.2 | 6.5 | 4.9 |
| 36 | 6.3 | — | — |
| 37 | 6.0 | — | — |
| 38 | 7.2 | 6.5 | 4.6 |
| 39 | 7.3 | 6.1 | <4.3 |
| 40 | 7.3 | 6.7 | 4.7 |
| 41 | 8.5 | 7.2 | 5.2 |
| 42 | 9.1 | 8.5 | 6.2 |
| 43 | 8.7 | 7.7 | 5.4 |
| 44 | 8.2 | 7.2 | 4.9 |
| 45 | 7.6 | 6.8 | 5.1 |
| 46 | 7.9 | 6.4 | 4.6 |
| 47 | 7.9 | 6.4 | 4.6 |
| 48 | 7.6 | 6.5 | 4.8 |
| 49 | 7.6 | 6.7 | 4.8 |
| 50 | 7.8 | 6.9 | 4.9 |
| 51 | 6.9 | — | — |

TABLE 1-continued

Biological Assay Data

| EXAMPLE No. | SSTR4 Activity $pEC_{50}$ | SSTR4 Binding $pIC_{50}$ | SSTR1 Binding $pIC_{50}$ |
|---|---|---|---|
| 52 | 6.3 | — | — |
| 53 | 7.2 | — | — |
| 54 | 6.6 | — | — |
| 55 | 7.0 | 6.0 | 4.4 |
| 56 | 6.7 | — | — |
| 57 | 8.4 | 7.0 | 4.9 |
| 58 | 7.4 | — | — |
| 59 | 7.8 | — | — |
| 60 | 7.0 | 6.3 | 4.6 |
| 61 | 6.8 | — | — |
| 62 | 7.6 | 6.6 | 4.6 |
| 63 | 7.2 | 5.8 | 4.3 |
| 64 | 7.0 | — | — |
| 65 | 6.6 | — | — |
| 66 | 7.8 | — | — |
| 67 | 8.8 | — | — |
| 68 | 7.6 | — | — |
| 69 | 7.6 | — | — |
| 70 | 8.3 | 7.1 | 5.9 |
| 71 | 7.5 | 6.6 | 4.6 |
| 72 | 7.7 | — | — |
| 73 | 7.4 | — | — |
| 74 | 7.5 | — | — |
| 75 | 8.6 | 7.5 | 5.0 |
| 76 | 6.2 | — | — |
| 77 | 7.1 | 5.5 | <4.3 |
| 78 | 6.6 | 5.0 | <4.3 |
| 79 | 6.4 | — | — |
| 80 | 7.6 | 6.5 | 4.7 |
| 81 | 6.4 | — | — |
| 82 | 6.5 | — | — |
| 83 | 6.6 | — | — |
| 84 | 7.0 | — | — |
| 85 | 6.7 | — | — |
| 86 | 6.6 | — | — |
| 87 | 6.5 | — | — |
| 88 | 7.2 | 6.4 | 4.4 |
| 89 | 6.9 | — | — |
| 90 | 7.2 | — | — |
| 91 | 7.4 | 6.4 | 4.6 |
| 92 | 7.2 | 6.0 | <4.3 |
| 93 | 7.2 | — | — |
| 94 | 7.2 | 6.4 | <4.3 |
| 95 | 6.1 | — | — |
| 96 | 7.8 | 6.7 | 4.8 |
| 97 | 6.0 | — | — |
| 98 | 6.8 | — | — |
| 99 | 5.4 | — | — |
| 100 | 6.7 | 6.0 | <4.3 |
| 101 | 7.0 | 6.2 | <4.3 |
| 102 | 6.2 | — | — |
| 103 | 6.3 | — | — |
| 104 | 7.0 | 5.7 | 4.4 |
| 105 | 6.1 | — | — |
| 106 | 7.7 | — | — |
| 107 | 6.7 | — | — |
| 108 | 7.7 | — | — |
| 109 | 6.2 | — | — |
| 110 | 8.4 | 7.1 | 4.9 |
| 111 | 8.5 | 7.6 | 5.4 |
| 112 | 7.1 | 6.3 | <4.3 |
| 113 | 7.1 | — | — |
| 114 | 6.6 | — | — |
| 115 | 6.7 | — | — |
| 116 | 7.1 | — | — |
| 117 | 6.8 | — | — |
| 118 | 7.1 | 6.4 | 4.4 |
| 119 | 7.8 | 6.6 | 4.7 |
| 120 | 6.6 | — | — |
| 121 | 6.2 | — | — |
| 122 | 6.5 | — | — |
| 123 | 6.8 | — | — |
| 124 | 7.4 | — | — |
| 125 | 6.9 | — | — |
| 126 | 6.4 | — | — |

TABLE 1-continued

| Biological Assay Data | | | |
|---|---|---|---|
| EXAMPLE No. | SSTR4 Activity $pEC_{50}$ | SSTR4 Binding $pIC_{50}$ | SSTR1 Binding $pIC_{50}$ |
| 127 | 8.1 | 6.9 | 5.1 |
| 128 | 7.4 | 6.5 | 5.0 |
| 129 | 6.4 | — | — |
| 130 | 6.5 | — | — |
| 131 | 7.3 | 6.6 | 4.9 |
| 132 | 8.1 | 7.1 | 4.7 |
| 133 | 6.7 | — | — |
| 134 | 8.9 | 7.3 | 5.2 |
| 135 | 8.0 | 6.8 | 4.8 |
| 136 | 8.2 | 6.9 | 5.0 |
| 137 | 6.5 | — | — |
| 138 | 7.9 | 6.9 | 4.8 |
| 139 | 5.9 | — | — |
| 140 | 8.2 | 7.3 | 4.9 |
| 141 | 6.4 | — | — |
| 142 | 8.8 | 7.8 | 5.7 |
| 143 | 6.7 | — | — |
| 144 | 7.0 | — | — |
| 145 | 9.1 | 7.7 | 5.9 |
| 146 | 8.6 | 7.7 | 5.6 |
| 147 | 7.2 | 5.8 | 4.3 |
| 148 | 6.3 | — | — |
| 149 | 8.5 | 7.3 | 5.2 |
| 150 | — | — | — |
| 151 | 8.1 | 7.0 | 5.1 |
| 152 | 6.0 | — | — |
| 153 | 8.4 | 7.1 | 5.2 |
| 154 | 5.9 | — | — |
| 155 | 8.6 | 7.4 | 5.5 |
| 156 | 8.1 | 7.0 | 4.7 |
| 157 | 5.6 | — | — |
| 158 | 6.4 | — | — |
| 159 | 6.4 | — | — |
| 160 | 6.8 | 6.0 | <4.3 |
| 161 | 8.4 | 7.3 | 5.2 |
| 162 | 8.1 | 7.1 | 4.6 |
| 163 | 7.6 | 6.4 | <4.3 |
| 164 | 7.9 | 7.4 | 4.5 |
| 165 | 8.0 | 7.1 | 4.6 |
| 166 | 7.9 | 7.3 | 4.4 |
| 167 | 7.6 | 6.6 | <4.3 |
| 168 | <5.3 | — | — |
| 169 | 8.6 | 6.5 | 4.4 |
| 170 | 9.1 | 7.6 | 5.3 |
| 171 | 8.7 | 7.8 | 5.4 |
| 172 | 6.6 | — | — |
| 173 | 7.7 | 6.7 | <4.3 |
| 174 | <5.0 | — | — |
| 175 | 7.7 | 6.8 | 4.5 |
| 176 | 6.9 | — | — |
| 177 | <5.0 | — | — |
| 178 | 7.4 | 7.4 | 5.2 |
| 179 | 9.7 | 8.7 | 6.6 |
| 180 | 9.9 | 8.5 | 6.2 |
| 181 | 9.8 | 8.2 | 5.8 |
| 182 | 8.8 | 7.9 | 6.0 |
| 183 | 7.3 | 6.3 | 4.7 |
| 184 | 9.2 | 7.8 | 5.7 |
| 185 | 7.1 | — | — |
| 186 | 6.7 | — | — |
| 187 | 9.1 | 7.7 | 5.8 |
| 188 | 9.3 | 8.7 | 6.9 |
| 189 | 9.0 | 8.1 | 6.2 |
| 190 | 8.7 | 7.7 | 5.5 |
| 191 | 8.7 | 8.0 | 5.6 |
| 192 | 7.8 | 6.9 | 4.5 |
| 193 | 7.8 | 6.7 | 4.5 |
| 194 | 9.1 | 8.6 | 6.2 |
| 195 | 8.7 | 8.6 | 6.0 |
| 196 | 9.7 | 8.5 | 6.3 |
| 197 | 5.7 | — | — |
| 198 | 8.2 | 7.7 | 5.1 |
| 199 | <5.0 | — | — |
| 200 | 8.7 | 7.6 | 5.3 |
| 201 | 7.5 | 7.2 | 4.6 |
| 202 | 9.1 | 7.7 | 5.2 |
| 203 | 8.4 | 6.8 | 5.4 |
| 204 | 10.0 | 8.5 | 6.2 |
| 205 | 8.9 | 7.6 | 5.6 |
| 206 | 6.7 | — | — |
| 207 | 8.8 | 7.4 | 5.3 |
| 208 | 8.5 | 7.4 | 4.8 |
| 209 | 8.9 | 6.9 | 4.7 |
| 210 | 8.0 | 7.5 | 5.4 |

As used in this specification and the appended claims, singular articles such as "a," "an," and "the," may refer to a single object or to a plurality of objects unless the context clearly indicates otherwise. Thus, for example, reference to a composition containing "a compound" may include a single compound or two or more compounds. The above description is intended to be illustrative and not restrictive. Many embodiments will be apparent to those of skill in the art upon reading the above description. Therefore, the scope of the invention should be determined with reference to the appended claims and includes the full scope of equivalents to which such claims are entitled. The disclosures of all articles and references cited in the disclosure, including patents, patent applications and publications, are herein incorporated by reference in their entirety and for all purposes.

What is claimed is:

1. A compound of Formula 1,

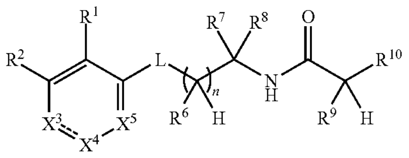

1 or a pharmaceutically acceptable salt thereof in which:

(a) $X^3$ is selected from $NR^{3N}$ and O, $X^4$ is a single bond, and $X^5$ is selected from N and $CR^5$; and $R^1$ and $R^2$, together with the carbon atoms to which they are attached, form a fused ring which is benzene, wherein each non-fusion carbon atom of the fused ring is unsubstituted or is substituted with an optional substituent independently selected from:

(i) halo, hydroxy, and cyano; and (ii) $C_{1-4}$ alkyl, $C_{3-6}$ cycloalkyl, and $C_{1-4}$ alkoxy, each optionally substituted with up to 3 substituents independently selected from halo; or (b) $X^3$ is $CR^{3C}$, $X^4$ is selected from N and $CR^4$, and $X^5$ is selected from N and $CR^5$; and $R^1$ and $R^2$ are each independently selected from:

(i) hydrogen, halo, hydroxy, and cyano; and (ii) $C_{1-4}$ alkyl, $C_{3-6}$ cycloalkyl, and $C_{1-4}$ alkoxy, each optionally substituted with up to 3 substituents independently selected from halo; or $R^1$ and $R^2$, together with the carbon atoms to which they are attached, form a fused ring selected from furan, pyrazole, and benzene, wherein one of the nitrogen atoms of the pyrazole ring is substituted with hydrogen, $C_{1-4}$ alkyl or $C_{3-6}$ cycloalkyl, and each non-fusion carbon atom of the fused ring is unsubstituted or is substituted with an optional substituent independently selected from:
(i) halo, hydroxy, and cyano; and
(ii) $C_{1-4}$ alkyl, $C_{3-6}$ cycloalkyl, and $C_{1-4}$ alkoxy, each optionally substituted with up to 3 substituents independently selected from halo;
L is O and n is 1; or
L is a single bond and n is 0 or 1;
$R^{3N}$ is selected from hydrogen, $C_{1-4}$ alkyl and $C_{3-6}$ cycloalkyl;
$R^{3C}$ and $R^4$ are each independently selected from:
(i) hydrogen, halo, hydroxy, and cyano; and
(ii) $C_{1-4}$ alkyl, $C_{3-6}$ cycloalkyl, and $C_{1-4}$ alkoxy, each optionally substituted with up to 3 substituents independently selected from halo;
$R^5$ is selected from:
(i) hydrogen, halo, hydroxy, and cyano; and
(ii) $C_{1-4}$ alkyl and $C_{1-4}$ alkoxy, each optionally substituted with up to 3 substituents independently selected from halo; and
$R^6$ is hydrogen; or
$R^5$ and $R^6$ together form an ethane-1,2-diyl bridging the carbon atoms to which they are attached;
$R^7$ and $R^8$ are each independently selected from hydrogen and $C_{1-4}$ alkyl which is optionally substituted with up to 3 substituents independently selected from halo, wherein at least one of $R^7$ and $R^8$ is not hydrogen, or $R^7$ and $R^8$, together with the carbon atom to which they are attached, form a $C_{3-6}$ cycloalkylidene;
$R^9$ is selected from hydrogen and $C_{1-4}$ alkyl which is optionally substituted with up to 3 substituents independently selected from halo; and
$R^{10}$ is azetidin-1-ylmethyl.

2. The compound or pharmaceutically acceptable salt thereof according to claim 1, wherein $X^3$ is selected from $NR^{3N}$ and O, $X^4$ is a single bond, and $X^5$ is selected from N and $CR^5$.

3. The compound or pharmaceutically acceptable salt thereof according to claim 2, wherein each non-fusion carbon atom of the fused ring formed by $R^1$ and $R^2$ is unsubstituted or is substituted with an optional substituent independently selected from halo and $C_{1-3}$ alkyl which is optionally substituted with up to 3 substituents independently selected from halo.

4. The compound or pharmaceutically acceptable salt thereof according to claim 2, wherein $X^3$ is selected from $NR^{3N}$ and O, $X^4$ is a single bond, and $X^5$ is N.

5. The compound or pharmaceutically acceptable salt thereof according to claim 2, wherein L is a single bond and n is 0.

6. The compound or pharmaceutically acceptable salt thereof according to claim 1, wherein $X^3$ is $CR^{3C}$, $X^4$ is selected from N and $CR^4$, and $X^5$ is selected from N and $CR^5$.

7. The compound or pharmaceutically acceptable salt thereof according to claim 6, wherein $R^1$ and $R^2$ are each independently selected from:
(i) hydrogen, halo, hydroxy, and cyano; and
(ii) $C_{1-4}$ alkyl, $C_{3-6}$ cycloalkyl, and $C_{1-4}$ alkoxy, each optionally substituted with up to 3 substituents independently selected from halo.

8. The compound or pharmaceutically acceptable salt thereof according to claim 6, wherein $R^1$ and $R^2$, together with the carbon atoms to which they are attached, form a fused ring selected from furan, pyrazole, and benzene, wherein one of the nitrogen atoms of the pyrazole ring is substituted with hydrogen, $C_{1-4}$ alkyl or $C_{3-6}$ cycloalkyl, and each non-fusion carbon atom of the fused ring is unsubstituted or is substituted with an optional substituent independently selected from:
(i) halo, hydroxy, and cyano; and
(ii) $C_{1-4}$ alkyl, $C_{3-6}$ cycloalkyl, and $C_{1-4}$ alkoxy, each optionally substituted with up to 3 substituents independently selected from halo.

9. The compound or pharmaceutically acceptable salt thereof according to claim 6, wherein $R^{3C}$ and $R^4$ are each independently selected from:
(i) hydrogen and halo; and
(ii) $C_{1-4}$ alkyl, $C_{3-6}$ cycloalkyl, and $C_{1-4}$ alkoxy, each optionally substituted with up to 3 substituents independently selected from halo.

10. The compound or pharmaceutically acceptable salt thereof according to claim 6, wherein $R^5$ is selected from:
(i) hydrogen and halo; and
(ii) $C_{1-4}$ alkyl and $C_{1-4}$ alkoxy, each optionally substituted with up to 3 substituents independently selected from halo.

11. The compound or pharmaceutically acceptable salt thereof according to claim 1, wherein $R^7$ and $R^8$ are each independently selected from hydrogen and $C_{1-4}$ alkyl which is optionally substituted with up to 3 substituents independently selected from halo, wherein at least one of $R^7$ and $R^8$ is not hydrogen.

12. The compound or pharmaceutically acceptable salt thereof according to claim 1, wherein $R^7$ and $R^8$, together with the carbon atom to which they are attached, form a cyclopropylidene, cyclobutylidene, and cyclopentylidene.

13. The compound or pharmaceutically acceptable salt thereof according to claim 1, wherein $R^9$ is selected from hydrogen, methyl, ethyl, and isopropyl.

14. The compound according to claim 1, which is selected from the following compounds:
3-(azetidin-1-yl)-N-(2-(2-chlorophenyl)propan-2-yl)-2-methylpropanamide;
(R)-3-(azetidin-1-yl)-N-(2-(2-chlorophenyl)propan-2-yl)-2-methylpropanamide;
(S)-3-(azetidin-1-yl)-N-(2-(2-chlorophenyl)propan-2-yl)-2-methylpropanamide;
(R)-3-(azetidin-1-yl)-N-(2-(4-methoxyphenyl)propan-2-yl)-2-methylpropanamide;
(S)-3-(azetidin-1-yl)-N-(2-(4-methoxyphenyl)propan-2-yl)-2-methylpropanamide;
(R)-3-(azetidin-1-yl)-2-methyl-N-(2-(o-tolyl)propan-2-yl)propanamide;
(S)-3-(azetidin-1-yl)-2-methyl-N-(2-(o-tolyl)propan-2-yl)propanamide;
(R)-3-(azetidin-1-yl)-N-(2-(3-fluoro-2-methylphenyl)propan-2-yl)-2-methylpropanamide;
(S)-3-(azetidin-1-yl)-N-(2-(3-fluoro-2-methylphenyl)propan-2-yl)-2-methylpropanamide;
(R)-3-(azetidin-1-yl)-N-(2-(2-chloro-3-methylphenyl)propan-2-yl)-2-methylpropanamide;
(S)-3-(azetidin-1-yl)-N-(2-(2-chloro-3-methylphenyl)propan-2-yl)-2-methylpropanamide;
(R)-3-(azetidin-1-yl)-N-(2-(2-methoxy-3-methylphenyl)propan-2-yl)-2-methylpropanamide;
(S)-3-(azetidin-1-yl)-N-(2-(2-methoxy-3-methylphenyl)propan-2-yl)-2-methylpropanamide;
(R)-3-(azetidin-1-yl)-2-methyl-N-(2-(p-tolyl)propan-2-yl)propanamide;
(S)-3-(azetidin-1-yl)-2-methyl-N-(2-(p-tolyl)propan-2-yl)propanamide;

(R)-3-(azetidin-1-yl)-N-(1-(2-fluorophenyl)cyclopropyl)-2-methylpropanamide;
(S)-3-(azetidin-1-yl)-N-(1-(2-fluorophenyl)cyclopropyl)-2-methylpropanamide;
(R)-3-(azetidin-1-yl)-N-(2-(3-fluorophenyl)propan-2-yl)-2-methylpropanamide;
(S)-3-(azetidin-1-yl)-N-(2-(3-fluorophenyl)propan-2-yl)-2-methylpropanamide;
(R)-3-(azetidin-1-yl)-N-(2-(4-chlorophenyl)propan-2-yl)-2-methylpropanamide;
(S)-3-(azetidin-1-yl)-N-(2-(4-chlorophenyl)propan-2-yl)-2-methylpropanamide;
(R)-3-(azetidin-1-yl)-N-(2-(2-fluorophenyl)propan-2-yl)-2-methylpropanamide;
(S)-3-(azetidin-1-yl)-N-(2-(2-fluorophenyl)propan-2-yl)-2-methylpropanamide;
3-(azetidin-1-yl)-N-(2-(2-chloro-3-methylphenyl)propan-2-yl)propanamide;
3-(azetidin-1-yl)-N-(2-(m-tolyl)propan-2-yl)propanamide;
3-(azetidin-1-yl)-N-(2-(3-fluorophenyl)propan-2-yl)propanamide;
3-(azetidin-1-yl)-N-(2-(3-chlorophenyl)propan-2-yl)propanamide;
3-(azetidin-1-yl)-N-(2-(4-chlorophenyl)propan-2-yl)propanamide;
3-(azetidin-1-yl)-N-(2-(3-fluoro-2-methylphenyl)propan-2-yl)propanamide;
3-(azetidin-1-yl)-N-(1-(2,5-difluorophenyl)-2,2-difluoroethyl)propanamide;
(S)-3-(azetidin-1-yl)-N-(1-(2,5-difluorophenyl)-2,2-difluoroethyl)propanamide;
(R)-3-(azetidin-1-yl)-N-(1-(2,5-difluorophenyl)-2,2-difluoroethyl)propanamide;
3-(azetidin-1-yl)-N-(2-(3-fluoro-2-methoxyphenyl)propan-2-yl)-2-methylpropanamide;
(R)-3-(azetidin-1-yl)-N-(2-(3-fluoro-2-methoxyphenyl)propan-2-yl)-2-methylpropanamide;
(S)-3-(azetidin-1-yl)-N-(2-(3-fluoro-2-methoxyphenyl)propan-2-yl)-2-methylpropanamide;
3-(azetidin-1-yl)-N-(2-fluoro-1-(p-tolyl)ethyl)propanamide;
(S)-3-(azetidin-1-yl)-N-(2-fluoro-1-(p-tolyl)ethyl)propanamide;
(R)-3-(azetidin-1-yl)-N-(2-fluoro-1-(p-tolyl)ethyl)propanamide;
(S)-2-(azetidin-1-ylmethyl)-N—((S)-2,2-difluoro-1-phenylethyl)-3-methylbutanamide;
(S)-2-(azetidin-1-ylmethyl)-N—((R)-2,2-difluoro-1-phenylethyl)-3-methylbutanamide;
(S)-2-(azetidin-1-ylmethyl)-N—((R)-2,2-difluoro-1-phenylethyl)butanamide;
(R)-3-(azetidin-1-yl)-N—((R)-2,2-difluoro-1-phenylethyl)-2-methylpropanamide;
(R)-2-(azetidin-1-ylmethyl)-N-(2-(4-fluorophenyl)propan-2-yl)butanamide;
(S)-2-(azetidin-1-ylmethyl)-N-(2-(4-fluorophenyl)propan-2-yl)butanamide;
(R)-2-(azetidin-1-ylmethyl)-N-(2-(3-fluorophenyl)propan-2-yl)butanamide;
(S)-2-(azetidin-1-ylmethyl)-N-(2-(3-fluorophenyl)propan-2-yl)butanamide;
(R)-2-(azetidin-1-ylmethyl)-N-(2-(p-tolyl)propan-2-yl)butanamide;
(S)-2-(azetidin-1-ylmethyl)-N-(2-(p-tolyl)propan-2-yl)butanamide;
(S)-2-(azetidin-1-ylmethyl)-N—((R)-2,2-difluoro-1-(2-methoxyphenyl)ethyl)-3-methylbutanamide;
(S)-2-(azetidin-1-ylmethyl)-N—((R)-2,2-difluoro-1-(2-methoxyphenyl)ethyl)butanamide;
(S)-3-(azetidin-1-yl)-N-(2,2,2-trifluoro-1-(4-fluorophenyl)ethyl)propanamide;
(S)-3-(azetidin-1-yl)-N-(1-(3-chlorophenyl)-2,2,2-trifluoroethyl)propanamide;
(R)-3-(azetidin-1-yl)-N-(1-(3-chlorophenyl)-2,2,2-trifluoroethyl)propanamide;
(R)-3-(azetidin-1-yl)-N-(2,2,2-trifluoro-1-(3-fluorophenyl)ethyl)propanamide;
(S)-2-(azetidin-1-ylmethyl)-N—((R)-2,2-difluoro-1-(3-fluorophenyl)ethyl)-3-methylbutanamide;
(S)-2-(azetidin-1-ylmethyl)-N—((R)-2,2-difluoro-1-(3-fluorophenyl)ethyl)butanamide;
(S)-2-(azetidin-1-ylmethyl)-N—((R)-2,2-difluoro-1-(4-fluorophenyl)ethyl)-3-methylbutanamide;
(R)-2-(azetidin-1-ylmethyl)-N-(2-(2-fluorophenyl)propan-2-yl)butanamide;
(S)-2-(azetidin-1-ylmethyl)-N-(2-(2-fluorophenyl)propan-2-yl)butanamide;
(R)-3-(azetidin-1-yl)-N-(2,2-difluoro-1-phenylethyl)propanamide;
(R)-3-(azetidin-1-yl)-N-(1-(3-chlorophenyl)-2,2-difluoroethyl)propanamide;
(S)-2-(azetidin-1-ylmethyl)-N—((R)-2,2-difluoro-1-(4-fluorophenyl)ethyl)butanamide;
(R)-3-(azetidin-1-yl)-N—((R)-2-fluoro-1-phenylethyl)-2-methylpropanamide;
(S)-3-(azetidin-1-yl)-N—((R)-2-fluoro-1-phenylethyl)-2-methylpropanamide;
(S)-3-(azetidin-1-yl)-N-(2,2,2-trifluoro-1-(p-tolyl)ethyl)propanamide;
(S)-3-(azetidin-1-yl)-N-(2,2,2-trifluoro-1-(3-fluorophenyl)ethyl)propanamide;
(S)-3-(azetidin-1-yl)-N-(2,2,2-trifluoro-1-(2-fluorophenyl)ethyl)propanamide;
(S)-3-(azetidin-1-yl)-N-(2,2,2-trifluoro-1-(o-tolyl)ethyl)propanamide; and
a pharmaceutically acceptable salt of any one of the aforementioned compounds.

15. The compound according to claim 1, wherein the compound is (S)-2-(azetidin-1-ylmethyl)-N—((R)-2,2-difluoro-1-phenylethyl)butanamide, or a pharmaceutically acceptable salt thereof.

16. The compound according to claim 1, wherein the compound is(S)-2-(azetidin-1-ylmethyl)-N—((R)-2,2-difluoro-1-(3-fluorophenyl)ethyl)-3-methylbutanamide, or a pharmaceutically acceptable salt thereof.

17. A pharmaceutical composition comprising:
a compound or pharmaceutically acceptable salt as defined in claim 1; and
a pharmaceutically acceptable excipient.

* * * * *